(12) United States Patent
Follmann et al.

(10) Patent No.: US 9,096,592 B2
(45) Date of Patent: Aug. 4, 2015

(54) BICYCLIC AZA HETEROCYCLES, AND USE THEREOF

(75) Inventors: Markus Follmann, Köln (DE); Johannes-Peter Stasch, Solingen (DE); Gorden Redlich, Bochum (DE); Jens Ackerstaff, Berlin (DE); Nils Griebenow, Dormagen (DE); Andreas Knorr, Erkrath (DE); Frank Wunder, Wuppertal (DE); Volkhart Min-Jian Li, Velbert (DE); Lars Bärfacker, Oberhausen (DE); Stefan Weigand, Penzberg (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 24 days.

(21) Appl. No.: 13/819,337

(22) PCT Filed: Aug. 31, 2011

(86) PCT No.: PCT/EP2011/065006
§ 371 (c)(1),
(2), (4) Date: Apr. 5, 2013

(87) PCT Pub. No.: WO2012/028647
PCT Pub. Date: Mar. 8, 2012

(65) Prior Publication Data
US 2014/0148433 A1    May 29, 2014

(30) Foreign Application Priority Data
Sep. 3, 2010  (DE) .................. 10 2010 040 233

(51) Int. Cl.
| | | |
|---|---|---|
| *A01N 43/00* | (2006.01) | |
| *A61K 31/00* | (2006.01) | |
| *C07D 471/04* | (2006.01) | |
| *C07D 487/04* | (2006.01) | |
| *C07D 519/00* | (2006.01) | |
| *A61K 31/517* | (2006.01) | |
| *A61K 31/519* | (2006.01) | |
| *A61K 31/522* | (2006.01) | |
| *A61K 31/5377* | (2006.01) | |
| *A61K 31/551* | (2006.01) | |
| *A61K 45/06* | (2006.01) | |
| *C07D 473/28* | (2006.01) | |
| *C07D 475/06* | (2006.01) | |
| *C07D 495/04* | (2006.01) | |
| *C07D 498/04* | (2006.01) | |
| *C07D 513/04* | (2006.01) | |

(52) U.S. Cl.
CPC ............ *C07D 471/04* (2013.01); *A61K 31/517* (2013.01); *A61K 31/519* (2013.01); *A61K 31/522* (2013.01); *A61K 31/5377* (2013.01); *A61K 31/551* (2013.01); *A61K 45/06* (2013.01); *C07D 473/28* (2013.01); *C07D 475/06* (2013.01); *C07D 487/04* (2013.01); *C07D 495/04* (2013.01); *C07D 498/04* (2013.01); *C07D 513/04* (2013.01); *C07D 519/00* (2013.01)

(58) Field of Classification Search
CPC . A61K 31/517; A61K 31/519; A61K 31/522; A61K 31/5377; A61K 31/551; A61K 45/06; C07D 471/04; C07D 473/28; C07D 475/06; C07D 487/04; C07D 495/04; C07D 498/04; C07D 513/04; C07D 519/00
USPC ................ 514/221, 249, 260.1, 261.1, 262.1, 514/263.22, 266.21; 544/254, 255, 258, 544/262, 276, 278, 284; 540/568
See application file for complete search history.

(56) References Cited

U.S. PATENT DOCUMENTS

| | | |
|---|---|---|
| 5,976,523 A | 11/1999 | Awaya et al. |
| 6,166,027 A | 12/2000 | Straub et al. |
| 6,180,656 B1 | 1/2001 | Fürstner et al. |
| 6,451,805 B1 | 9/2002 | Straub et al. |
| 6,743,798 B1 * | 6/2004 | Straub et al. .................. 514/256 |
| 6,903,089 B1 | 6/2005 | Stasch et al. |
| 7,410,973 B2 | 8/2008 | Fuerer et al. |
| 7,414,136 B2 | 8/2008 | Matsumura et al. |
| 8,242,272 B2 | 8/2012 | Jimenez et al. |
| 8,309,551 B2 | 11/2012 | Schirok et al. |
| 2004/0235863 A1 | 11/2004 | Feurer et al. |
| 2011/0218202 A1 | 9/2011 | Brockunier et al. |
| 2011/0224197 A1 | 9/2011 | Henkel et al. |

(Continued)

FOREIGN PATENT DOCUMENTS

| | | |
|---|---|---|
| CA | 2804470 | 1/2012 |
| CA | 2833698 | 10/2012 |

(Continued)

OTHER PUBLICATIONS

Becker et al.,"NO-Independent Regulatory Site of Direct sGC Stimulators like YC-1 and BAY 41-2272," BMC Pharmacology, 2001, 1: 13 *.

Cheng et al., "Potential Purine Antagonists VII. Synthesis of 6-Alkylpyrazolo-[3,4-d]pyrimidines," J. Org. Chem., 1958, 23:191-200.

Evgenov et al.,"NO-independent stimulators and activators of soluble guanylate cyclase: discovery and therapeutic potential," Nat. Rev. Drug. Disc, Sep. 2006, 5:755-768.

(Continued)

*Primary Examiner* — Jennifer M Kim
*Assistant Examiner* — Jean Cornet
(74) *Attorney, Agent, or Firm* — Buchanan Ingersoll & Rooney PC

(57) ABSTRACT

The present application relates to novel bicyclic azaheterocycles, to processes for preparation thereof, to the use thereof, alone or in combinations, for treatment and/or prophylaxis of diseases and to the use thereof for production of medicaments for treatment and/or prophylaxis of diseases, especially for treatment and/or prophylaxis of cardiovascular disorders.

6 Claims, No Drawings

(56) References Cited

U.S. PATENT DOCUMENTS

| | | |
|---|---|---|
| 2013/0072492 A1 | 3/2013 | Raghavan et al. |
| 2013/0172372 A1 | 7/2013 | Follmann et al. |
| 2013/0178475 A1 | 7/2013 | Moore et al. |

FOREIGN PATENT DOCUMENTS

| | | |
|---|---|---|
| CA | 2834901 | 11/2012 |
| CN | 1613849 | 5/2005 |
| EP | 0634413 | 1/1995 |
| WO | 0183490 | 11/2001 |

OTHER PUBLICATIONS

Glass et al., "Stimulation of Human Platelet Guanylate Cyclase by Fatty Acids," J. Biol. Chem., Feb. 25, 1977, 252 (4):1279-1285 Listed on some IDS's as Goldberg.

Hassan et al.,"Aryl-Aryl Bond Formation One Century after the Discovery of the Ullmann Reaction," Chem. Rev. 2002, 102: 1359-1469.

Ko et al., "YC-1, a Novel Activator of Platelet Guanylate Cyclase," Blood, Dec. 1994, 84(12): 4226-4233.

Mittendorf et al., "Discovery of Riociguat (BAY 63/2521): A Potent, Oral Stimulator of Soluble Guanylate Cyclase for the Treatment of Pulmonary Hypertension," Chem. Med. Chem., 2009, 4: 853-865.

Mülsch et al., "Effect of YC-1, an NO-independent, superoxide-sensitive stimulator of soluble guanylyl cyclase, on smooth muscle responsiveness to nitrovasodilators," Brit. J. Pharm., 1997, 120: 681-689.

Pettibone et al., "A Structurally Novel Stimulator of Guanylate Cyclase with Long-Lasting Hypotensive Activity in the Dog," Euro. J. of Pharmacology, 1985, 116: 307-312.

Sharkovska et al.,"Nitric oxide-independent stimulation of soluble guanylate cyclase reduces organ damage in experimental low-renin and high-renin models," J. Hypertnesion, 2010, 28(8):1666-1675.

Stasch et al.,"Soluble Guanylate Cyclase as an Emerging Therapeutic Target in Cardiopulmonary Disease," Circulation, May 2011, 123: 2263-2273.

Winn et al., "2-(Alkylamino)nicotinic Acid and Analogs. Potent Angiotensin II Antagonists," J. Med. Chem 1993, 36: 2676-2688.

Witte et al.,"Experimental heart failure in rats: effects on cardiovascular circadian rhythms and on myocardial β-adrenergic signaling," Cardiovascular Research, 2000, 47: 350-358.

Wu et al., "YC-1 inhibited human platelet aggregation through NO-independent activation of soluble guanylate cyclase," Br J. Pharmacol. Oct. 1995, 116(3):1973-1978.

Wunder et al., "A cell-based cGMP assay useful for ultra-high-throughput screening and identification of modulators of the nitric oxide/cGMP pathway," Anal. Biochem., 2005, 339:104-112.

Yu et al., "Vasorelaxant Effect of Isoliquiritigenin, A novel soluble guanylate cyclase activator, in rat aorta," Brit. J. of Pharmacology, 1995, 114: 1587-1594.

\* cited by examiner

BICYCLIC AZA HETEROCYCLES, AND USE THEREOF

The present application relates to novel bicyclic azaheterocycles, to processes for preparation thereof, to the use thereof, alone or in combinations, for treatment and/or prophylaxis of diseases and to the use thereof for production of medicaments for treatment and/or prophylaxis of diseases, especially for treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. This is of central importance for the activation mechanism. NO can bind to the iron atom of heme and thus markedly increase the activity of the enzyme. Heme-free preparations cannot, by contrast, be stimulated by NO. Carbon monoxide (CO) is also able to bind to the central iron atom of heme, but the stimulation by CO is much less than that by NO.

Through the formation of cGMP and the resulting regulation of phosphodiesterases, ion channels and protein kinases, guanylate cyclase plays a crucial role in different physiological processes, more particularly in the relaxation and proliferation of smooth muscle cells, in platelet aggregation and platelet adhesion, and in neuronal signal transmission, and also in the event of disorders based on disruption of the abovementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Therapeutic stimulation of soluble guanylate cyclase has to date been accomplished using exclusively compounds such as organic nitrates, the effect of which is based on NO. This is formed by bioconversion and activates soluble guanylate cyclase by attack at the central iron atom of heme. In addition to the side effects, the development of tolerance is one of the crucial disadvantages of this mode of treatment.

In the last few years, there have been descriptions of some compounds which stimulate soluble guanylate cyclase directly, i.e. without prior release of NO, for example 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223).

As stimulators of soluble guanylate cyclase, WO 00/06569 discloses fused pyrazole derivatives, and WO 01/083490 a fused aminopyridine derivative. WO 2010/065275 discloses pyrrolopyrimidones as activators of soluble guanylate cyclase.

It was an object of the present invention to provide novel substances which act as very potent stimulators of soluble guanylate cyclase and are therefore suitable for treatment and/or prophylaxis of cardiovascular disorders.

The present invention provides compounds of the general formula (I)

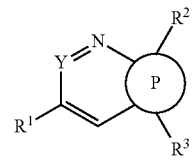

in which
the ring P is a group of the formula

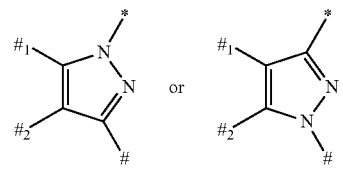

where
* is the attachment site to $R^2$,
# is the attachment site to $R^3$,
$\#_1$ is the attachment site to the nitrogen atom,
$\#_2$ is the attachment site to the carbon atom,
Y is CH or N,
$R^1$ is hydrogen or fluorine,
$R^2$ is $(C_1-C_6)$-alkyl or benzyl,
 where $(C_1-C_6)$-alkyl is substituted by one trifluoromethyl substituent,
 where $(C_1-C_6)$-alkyl may be substituted by 1 to 3 fluorine substituents,
 and
 where benzyl is substituted by 1 to 3 fluorine substituents,
$R^3$ is a group of the formula

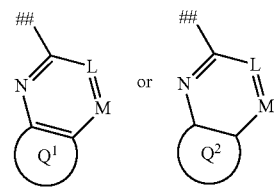

where
## is the attachment site to the ring P,
L is CH or N,
M is $CR^4$ or N,
 in which
 $R^4$ is hydrogen, halogen, cyano, $(C_1-C_4)$-alkyl, $(C_2-C_4)$-alkynyl, hydroxyl, $(C_1-C_4)$-alkoxy, $(C_1-C_4)$-alkylcarbonyl, $(C_1-C_4)$-alkoxycarbonyl, amino, mono-$(C_1-C_4)$-alkylamino, di-$(C_1-C_4)$-alkylamino or azetidinyl,
 in which $(C_1-C_4)$-alkyl, $(C_2-C_4)$-alkynyl, $(C_1-C_4)$-alkoxy, mono-$(C_1-C_4)$— alkylamino and di-$(C_1$-

$C_4$)-alkylamino may themselves be substituted by 1 or 2 substituents each independently selected from the group of fluorine, hydroxyl and amino, the ring $Q^1$ is 5- to 7-membered heterocyclyl, phenyl or 5- or 6-membered heteroaryl,
  in which 5- to 7-membered heterocyclyl, phenyl and 5- or 6-membered heteroaryl may be substituted by 1 to 3 substituents each independently selected from the group of halogen, difluoromethyl, trifluoromethyl, trideuteromethyl, ($C_1$-$C_6$)-alkyl, ($C_2$-$C_6$)-alkenyl, ($C_3$-$C_7$)-cycloalkyl, oxo, hydroxyl, ($C_1$-$C_4$)-alkoxy, ($C_1$-$C_4$)-alkoxycarbonyl, ($C_3$-$C_7$)-cycloalkoxycarbonyl, amino, mono-($C_1$-$C_4$)-alkylamino, di-($C_1$-$C_4$)-alkylamino, thiooxo, ($C_1$-$C_4$)-alkylthio, aminosulfonyl, mono-($C_1$-$C_4$)-alkylaminosulfonyl, di-($C_1$-$C_4$)-alkylaminosulfonyl, 4- to 7-membered heterocyclyl, phenyl and benzyl,
    in which ($C_1$-$C_6$)-alkyl, ($C_3$-$C_7$)-cycloalkyl, ($C_1$-$C_4$)-alkoxy, ($C_1$-$C_4$)-alkoxycarbonyl and ($C_1$-$C_4$)-alkylthio may themselves be substituted by 1 to 3 substituents each independently selected from the group of halogen, trifluoromethyl, ($C_3$-$C_7$)-cycloalkyl, hydroxyl, ($C_1$-$C_4$)-alkoxy, ($C_1$-$C_4$)-alkylsulfonyl and 4- to 7-membered heterocyclyl,
      in which 4- to 7-membered heterocyclyl in turn may itself be substituted by 1 or 2 substituents each independently selected from the group of halogen, trifluoromethyl, ($C_1$-$C_4$)-alkyl and ($C_3$-$C_7$)-cycloalkyl,
        in which ($C_1$-$C_4$)-alkyl may additionally itself be substituted by 1 or 2 substituents each independently selected from the group of fluorine, trifluoromethyl, ($C_3$-$C_7$)-cycloalkyl, hydroxyl and ($C_1$-$C_4$)-alkoxy,
    in which 4- to 7-membered heterocyclyl may itself be substituted by 1 or 2 substituents each independently selected from the group of halogen, trifluoromethyl, ($C_1$-$C_4$)-alkyl and ($C_3$-$C_7$)-cycloalkyl,
      in which ($C_1$-$C_4$)-alkyl in turn may itself be substituted by 1 or 2 substituents each independently selected from the group of fluorine, trifluoromethyl, ($C_3$-$C_7$)-cycloalkyl, hydroxyl and ($C_1$-$C_4$)-alkoxy,
    and
    in which phenyl and benzyl may themselves be substituted by 1 to 3 halogen, cyano, trifluoromethyl, ($C_1$-$C_4$)-alkyl, ($C_1$-$C_4$)-alkoxy and ($C_1$-$C_4$)-alkylsulfonyl substituents, the ring $Q^2$ is 5-membered heteroaryl,
  in which 5-membered heteroaryl may be substituted by 1 to 3 substituents each independently selected from the group of halogen, difluoromethyl, trifluoromethyl, trideuteromethyl, ($C_1$-$C_6$)-alkyl, ($C_2$-$C_6$)-alkenyl, ($C_3$-$C_7$)-cycloalkyl, hydroxyl, ($C_1$-$C_4$)-alkoxy, ($C_1$-$C_4$)-alkoxycarbonyl, ($C_3$-$C_7$)-cycloalkoxycarbonyl, amino, mono-($C_1$-$C_4$)-alkylamino, di-($C_1$-$C_4$)-alkylamino, ($C_1$-$C_4$)-alkylthio, aminosulfonyl, mono-($C_1$-$C_4$)-alkylaminosulfonyl, di-($C_1$-$C_4$)-alkylaminosulfonyl, phenyl and benzyl,
    in which ($C_1$-$C_6$)-alkyl, ($C_3$-$C_7$)-cycloalkyl, ($C_1$-$C_4$)-alkoxy, ($C_1$-$C_4$)-alkoxycarbonyl and ($C_1$-$C_4$)-alkylthio may themselves be substituted by 1 to 3 substituents each independently selected from the group of halogen, trifluoromethyl, ($C_3$-$C_7$)-cycloalkyl, hydroxyl, ($C_1$-$C_4$)-alkoxy, ($C_1$-$C_4$)-alkylsulfonyl and 4- to 7-membered heterocyclyl,
    and
    in which phenyl and benzyl may themselves be substituted by 1 to 3 halogen, trifluoromethyl, ($C_1$-$C_4$)-alkyl and ($C_1$-$C_4$)-alkoxy substituents, and the N-oxides, salts, solvates, salts of N-oxides and solvates of the N-oxides or salts thereof,
excluding the compounds:
2-[1-(2-fluorobenzyl)-1H-pyrazolo[3,4-b]pyridin-3-yl]-8-methyl-9H-purine,
2-[1-(2-fluorobenzyl)-1H-pyrazolo[3,4-b]pyridin-3-yl]-8-methyl-9H-purin-6-amine,
N-butyl-2-[1-(2-fluorobenzyl)-1H-pyrazolo[3,4-b]pyridin-3-yl]-8-methyl-9H-purin-6-amine Inventive compounds are the compounds of the formula (I) and the salts, solvates and solvates of the salts thereof, the compounds encompassed by formula (I) of the formulae specified hereinafter and the salts, solvates and solvates of the salts thereof, and the compounds encompassed by formula (I) and specified hereinafter as working examples and the salts, solvates and solvates of the salts thereof, to the extent that the compounds encompassed by formula (I) and specified hereinafter are not already salts, solvates and solvates of the salts.

Preferred salts in the context of the present invention are physiologically acceptable salts of the inventive compounds. Also encompassed are salts which are not themselves suitable for pharmaceutical applications but can be used, for example, for isolation or purification of the inventive compounds.

Physiologically acceptable salts of the inventive compounds include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the inventive compounds which, in the solid or liquid state, form a complex by coordination with solvent molecules. Hydrates are a specific form of the solvates in which the coordination is with water. Preferred solvates in the context of the present invention are hydrates.

The inventive compounds may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, more particularly HPLC chromatography on an achiral or chiral phase.

If the inventive compounds can occur in tautomeric forms, the present invention encompasses all tautomeric forms.

The present invention also encompasses all suitable isotopic variants of the inventive compounds. An isotopic variant of an inventive compound is understood here to mean a compound in which at least one atom within the inventive compound has been exchanged for another atom of the same atomic number, but with a different atomic mass than the atomic mass which usually or predominantly occurs in nature. Examples of isotopes which can be incorporated into an inventive compound are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of an inventive compound, such as, more particularly, those in which one or more radioactive isotopes have been incorporated, may be of benefit, for example, for the study of the mechanism of action or of the active ingredient distribution in the body; due to the comparative ease of preparability and detectability, compounds labeled particularly with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the inventive compounds may therefore in some cases also constitute a preferred embodiment of the present invention. Isotopic variants of the inventive compounds can be prepared by processes known to those skilled in the art, for example by the methods described below and the methods described in the working examples, by using corresponding isotopic modifications of the particular reagents and/or starting compounds therein.

In addition, the present invention also encompasses prodrugs of the inventive compounds. The term "prodrugs" here denotes compounds which may themselves be biologically active or inactive, but are converted (for example metabolically or hydrolytically) to inventive compounds during their residence time in the body.

In the context of the present invention, unless specified otherwise, the substituents are each defined as follows:

Alkyl in the context of the invention is a linear or branched alkyl radical having the number of carbon atoms specified in each case. Preferred examples include: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl, 1,4-dimethylpentyl, 4,4-dimethylpentyl and 1,4,4-trimethylpentyl.

Cycloalkyl in the context of the invention is a monocyclic saturated alkyl radical having 3 to 7 carbon atoms. Preferred examples include: cyclopropyl, cyclobutyl, cyclopentyl, cyclohexyl and cycloheptyl.

Alkenyl in the context of the invention is a linear or branched alkenyl radical having 2 to 6 carbon atoms and one or two double bonds. Preference is given to a straight-chain or branched alkenyl radical having 2 to 4 carbon atoms and one double bond. Preferred examples include: vinyl, allyl, isopropenyl and n-but-2-en-1-yl.

Alkynyl in the context of the invention is a linear or branched alkynyl radical having 2 to 4 carbon atoms and one triple bond. Preferred examples include: ethynyl, n-prop-1-yn-1-yl, n-prop-2-yn-1-yl, n-but-2-yn-1-yl and n-but-3-yn-1-yl.

Alkylcarbonyl in the context of the invention is a linear or branched alkyl radical having 1 to 6 or 1 to 4 carbon atoms and a carbonyl group attached in the 1 position. Preferred examples include: methylcarbonyl, ethylcarbonyl, n-propylcarbonyl, isopropylcarbonyl, n-butylcarbonyl, isobutylcarbonyl and tert-butylcarbonyl.

Alkoxy in the context of the invention is a linear or branched alkoxy radical having 1 to 4 carbon atoms. Preferred examples include: methoxy, ethoxy, n-propoxy, isopropoxy, 1-methylpropoxy, n-butoxy, isobutoxy and tert-butoxy.

Alkoxycarbonyl in the context of the invention is a linear or branched alkoxy radical having 1 to 6 or 1 to 4 carbon atoms and a carbonyl group attached to the oxygen. Preference is given to a linear or branched alkoxycarbonyl radical having 1 to 4 carbon atoms in the alkoxy group. Preferred examples include: methoxycarbonyl, ethoxycarbonyl, n-propoxycarbonyl, isopropoxycarbonyl and tert-butoxycarbonyl.

Cycloalkoxycarbonyl in the context of the invention is a monocyclic saturated cycloalkoxy radical having 3 to 7 carbon atoms and a carbonyl group attached to the oxygen atom. Preferred examples include: cyclopropyloxycarbonyl, cyclobutyloxycarbonyl, cyclopentyloxycarbonyl, cyclohexyloxycarbonyl and cycloheptyloxycarbonyl.

Alkylsulfonyl in the context of the invention is a linear or branched alkyl radical which has 1 to 4 carbon atoms and is bonded via a sulfonyl group. Preferred examples include: methylsulfonyl, ethylsulfonyl, n-propylsulfonyl, isopropylsulfonyl, n-butylsulfonyl and tert-butylsulfonyl.

Monoalkylamino in the context of the invention is an amino group having a linear or branched alkyl substituent having 1 to 6 carbon atoms. Preferred examples include: methylamino, ethylamino, n-propylamino, isopropylamino and tert-butylamino.

Dialkylamino in the context of the invention is an amino group having two identical or different, linear or branched alkyl substituents each having 1 to 6 carbon atoms. Preferred examples include: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

Monoalkylaminosulfonyl in the context of the invention is an amino group which is attached via a sulfonyl group and has a linear or branched alkyl substituent having 1 to 6 carbon atoms. Preferred examples include: methylaminosulfonyl, ethylaminosulfonyl, n-propylaminosulfonyl, isopropylaminosulfonyl, n-butylaminosulfonyl and tert-butylaminosulfonyl.

Dialkylaminosulfonyl in the context of the invention is an amino group which is attached via a sulfonyl group and has two identical or different, linear or branched alkyl substituents each having 1 to 6 carbon atoms. Preferred examples include: N,N-dimethylaminosulfonyl, N,N-diethylaminosulfonyl, N-ethyl-N-methylaminosulfonyl, N-methyl-N-n-propylaminosulfonyl, N-n-butyl-N-methylaminosulfonyl and N-tert-butyl-N-methylaminosulfonyl.

Alkylthio in the context of the invention is a thio group having a linear or branched alkyl substituent having 1 to 4 carbon atoms. Preferred examples include: methylthio, ethylthio, n-propylthio, isopropylthio, n-butylthio and tert-butylthio.

5- to 7-membered heterocyclyl in the context of the invention is a partly unsaturated heterocycle which has a total of 5 to 7 ring atoms and 1 or 2 double bonds and contains 1 ring nitrogen atom, and may contain 1 or 2 further ring heteroatoms from the group of N, O and/or S. Examples include:

dihydropyrazolyl, dihydroimidazolyl, dihydrooxazolyl, dihydrothiazolyl, dihydroisooxazolyl, dihydroisothiazolyl, dihydrothiadiazolyl, dihydropyridinyl, tetrahydropyridinyl, tetrahydropyridazinyl, dihydropyrimidinyl, tetrahydropyrimidinyl, dihydropyrazinyl, tetrahydropyrazinyl, dihydrotriazinyl, tetrahydrotriazinyl, dihydrooxazinyl, thiadiazinanyl, dihydrodiazepinyl and tetrahydrodiazepinyl. Preference is given to: dihydroimidazolyl, dihydrooxazolyl, dihydropyrazinyl, tetrahydropyrazinyl, dihydrotriazinyl and dihydrodiazepinyl.

4- to 7-membered heterocyclyl in the context of the invention is a saturated heterocycle which has a total of 4 to 7 ring atoms and contains 1 to 3 ring heteroatoms from the group of N, O and/or S. Examples include: azetidinyl, pyrrolidinyl, tetrahydrofuranyl, piperidinyl, tetrahydropyranyl, piperazinyl and morpholinyl.

Heteroaryl in the context of the invention is a monocyclic aromatic heterocycle (heteroaromatic) which has a total of 5 or 6 ring atoms and contains up to three identical or different ring heteroatoms from the group of N, O and/or S. Examples include: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preferred examples include: thienyl, thiazolyl, oxazolyl, isothiazolyl, isoxazolyl, pyrazolyl, imidazolyl, triazolyl, oxadiazolyl, thiadiazolyl, pyridyl, pyrimidinyl and pyrazinyl.

An oxo group in the context of the invention is an oxygen atom bonded via a double bond to a carbon atom.

A thiooxo group in the context of the invention is a sulfur atom bonded via a double bond to a carbon atom.

Halogen in the context of the invention is fluorine, chlorine, bromine and iodine.

In the formula of the group that P or $R^3$ may represent, the end point of the line marked by the symbol *, #, $\#_1$, $\#_2$ or ## does not represent a carbon atom or a $CH_2$ group but is part of the bond to the respective atom to which P or $R^3$ is bonded.

When radicals in the inventive compounds are substituted, the radicals, unless specified otherwise, may be mono- or polysubstituted. In the context of the present invention, all radicals which occur more than once are defined independently of one another. Substitution by one, two or three identical or different substituents is preferred.

Preference is given in the context of the present invention to compounds of the formula (I) in which
the ring P is a group of the formula

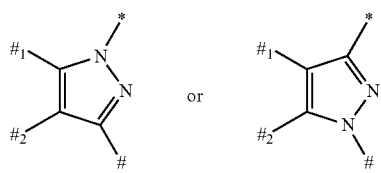

where
* is the attachment site to $R^2$,
# is the attachment site to $R^3$,
$\#_1$ is the attachment site to the nitrogen atom,
2 is the attachment site to the carbon atom,
Y is CH or N,
$R^1$ is hydrogen or fluorine,
$R^2$ is $(C_1-C_6)$-alkyl or benzyl,
where $(C_1-C_6)$-alkyl is substituted by one trifluoromethyl substituent,
where $(C_1-C_6)$-alkyl may be substituted by 1 to 3 fluorine substituents,
and
where benzyl is substituted by 1 to 3 fluorine substituents,
$R^3$ is a group of the formula

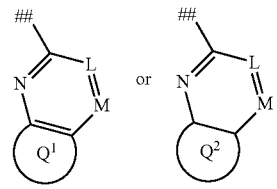

where
## is the attachment site to the ring P,
L is CH or N,
M is $CR^4$ or N,
in which
$R^4$ is hydrogen, halogen, cyano, $(C_1-C_4)$-alkyl, $(C_2-C_4)$-alkynyl, hydroxyl, $(C_1-C_4)$-alkoxy, $(C_1-C_4)$-alkylcarbonyl, $(C_1-C_4)$-alkoxycarbonyl, amino, mono-$(C_1-C_4)$-alkylamino, di-$(C_1-C_4)$-alkylamino or azetidinyl,
in which $(C_1-C_4)$-alkyl, $(C_2-C_4)$-alkynyl, $(C_1-C_4)$-alkoxy, mono-$(C_1-C_4)$-alkylamino and di-$(C_1-C_4)$-alkylamino may themselves be substituted by 1 or 2 substituents each independently selected from the group of fluorine, hydroxyl and amino,
the ring $Q^1$ is 5- to 7-membered heterocyclyl, phenyl or 5- or 6-membered heteroaryl,
in which 5- to 7-membered heterocyclyl, phenyl and 5- or 6-membered heteroaryl may be substituted by 1 to 3 substituents each independently selected from the group of halogen, difluoromethyl, trifluoromethyl, trideuteromethyl, $(C_1-C_6)$-alkyl, $(C_2-C_6)$-alkenyl, $(C_3-C_7)$-cycloalkyl, oxo, hydroxyl, $(C_1-C_4)$-alkoxy, $(C_1-C_4)$-alkoxycarbonyl, $(C_3-C_7)$-cycloalkoxycarbonyl, amino, mono-$(C_1-C_4)$-alkylamino, di-$(C_1-C_4)$-alkylamino, thiooxo, $(C_1-C_4)$-alkylthio, aminosulfonyl, mono-$(C_1-C_4)$-alkylaminosulfonyl, di-$(C_1-C_4)$-alkylaminosulfonyl, 4- to 7-membered heterocyclyl, phenyl and benzyl,
in which $(C_1-C_4)$-alkyl, $(C_3-C_7)$-cycloalkyl, $(C_1-C_4)$-alkoxy, $(C_1-C_4)$-alkoxycarbonyl and $(C_1-C_4)$-alkylthio may themselves be substituted by 1 to 3 substituents each independently selected from the group of halogen, trifluoromethyl, $(C_3-C_7)$-cycloalkyl, hydroxyl and $(C_1-C_4)$-alkoxy,
in which 4- to 7-membered heterocyclyl may itself be substituted by 1 or 2 substituents each independently selected from the group of halogen, trifluoromethyl, $(C_1-C_4)$-alkyl and $(C_3-C_7)$-cycloalkyl,
in which $(C_1-C_4)$-alkyl may itself be substituted by 1 or 2 substituents each independently selected from the group of fluorine, trifluoromethyl, $(C_3-C_7)$-cycloalkyl, hydroxyl and $(C_1-C_4)$-alkoxy,
and
in which phenyl and benzyl may themselves be substituted by 1 to 3 halogen, cyano, trifluoromethyl, $(C_1-C_4)$-alkyl, $(C_1-C_4)$-alkoxy and $(C_1-C_4)$-alkylsulfonyl substituents,
the ring $Q^2$ is 5-membered heteroaryl,
in which 5-membered heteroaryl may be substituted by 1 to 3 substituents each independently selected from the group of halogen, difluoromethyl, trifluoromethyl, trideuteromethyl, $(C_1-C_6)$-alkyl, $(C_2-C_6)$-alkenyl, $(C_3-C_7)$-cycloalkyl, hydroxyl, $(C_1-C_4)$-alkoxy, $(C_1-C_4)$-alkoxycarbonyl, $(C_3-C_7)$-cycloalkoxycarbonyl, amino, mono-$(C_1-C_4)$-alkylamino, di-$(C_1-C_4)$-alkylamino, $(C_1-C_4)$-alkylthio, aminosulfonyl, mono-$(C_1-C_4)$-alkylaminosulfonyl, di-$(C_1-C_4)$-alkylaminosulfonyl, phenyl and benzyl, in which $(C_1-C_4)$-alkyl, $(C_3-C_7)$-cycloalkyl, $(C_1-C_4)$-alkoxy, $(C_1-C_4)$-alkoxycarbonyl and $(C_1-C_4)$-alkylthio may themselves be substituted by 1 to 3 substituents each independently selected from the group of halogen, trifluoromethyl, $(C_3-C_7)$-cycloalkyl, hydroxyl and $(C_1-C_4)$-alkoxy, and in which phenyl and benzyl may themselves be substituted by 1 to 3 halogen, trifluoromethyl, $(C_1-C_4)$-alkyl and $(C_1-C_4)$-alkoxy substituents, and the N-oxides, salts, solvates, salts of N-oxides and solvates of the N-oxides or salts thereof,
excluding the compounds:
2-[1-(2-fluorobenzyl)-1H-pyrazolo[3,4-b]pyridin-3-yl]-8-methyl-9H-purine,
2-[1-(2-fluorobenzyl)-1H-pyrazolo[3,4-b]pyridin-3-yl]-8-methyl-9H-purin-6-amine,
N-butyl-2-[1-(2-fluorobenzyl)-1H-pyrazolo[3,4-b]pyridin-3-yl]-8-methyl-9H-purin-6-amine Preference is given in the context of the present invention to compounds of the formula (I) in which the ring P is a group of the formula

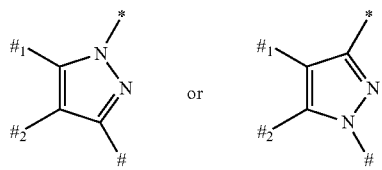

where
* is the attachment site to $R^2$,
# is the attachment site to $R^3$,
$\#_1$ is the attachment site to the nitrogen atom,
$\#_2$ is the attachment site to the carbon atom,
Y is CH,
R' is hydrogen or fluorine,
$R^2$ is 2,2,3,3,3-pentafluoroprop-1-yl or benzyl,
where benzyl is substituted by 1 or 2 fluorine substituents,
$R^3$ is a group of the formula

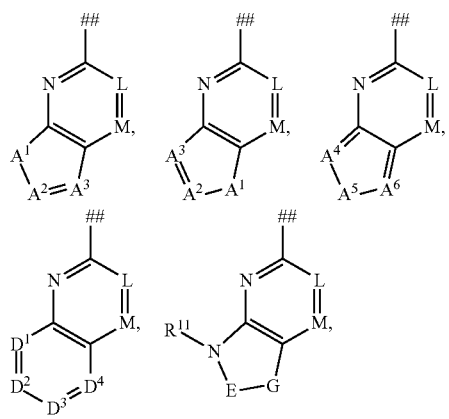

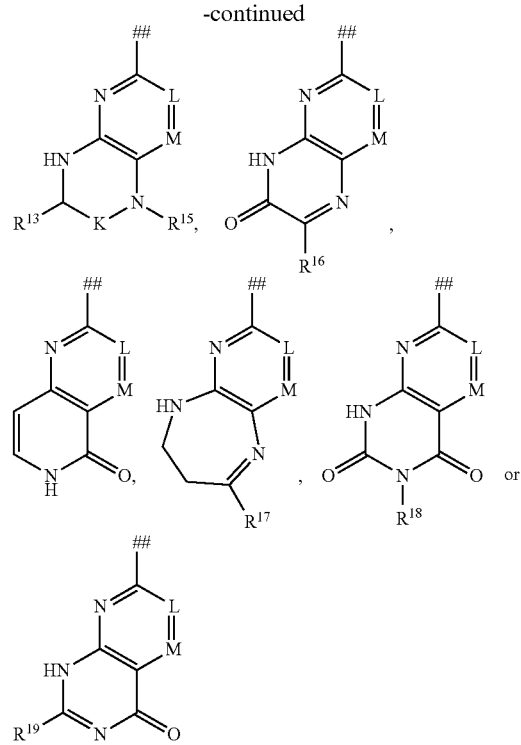

where
## is the attachment site to the ring P,
L is CH or N,
M is $CR^4$ or N,
in which
$R^4$ is hydrogen, chlorine, cyano, $(C_1-C_4)$-alkyl, $(C_2-C_4)$-alkynyl, amino, methylamino, ethylamino, dimethylamino, diethylamino or azetidinyl,
in which $(C_1-C_4)$-alkyl, $(C_2-C_4)$-alkynyl, ethylamino and diethylamino may themselves be substituted by 1 or 2 substituents selected independently from the group of fluorine, hydroxyl and amino,
$A^1$ is O, S or $NR^5$,
in which
$R^5$ is hydrogen, trifluoromethyl or $(C_1-C_4)$-alkyl, in which $(C_1-C_4)$-alkyl may itself be substituted by 1 or 2 substituents each independently selected from the group of fluorine, trifluoromethyl, hydroxyl, methoxy and ethoxy,
$A^2$ is N,
$A^3$ is N or $CR^7$,
in which
$R^7$ is hydrogen, fluorine, trifluoromethyl, $(C_1-C_4)$-alkyl, hydroxyl, $(C_1-C_4)$— alkoxy, amino, methylamino, ethylamino, dimethylamino or diethylamino,
in which $(C_1-C_4)$-alkyl and $(C_1-C_4)$-alkoxy may themselves be substituted by 1 or 2 substituents each independently selected from the group of fluorine, trifluoromethyl, hydroxyl, methoxy and ethoxy,
$A^4$ and $A^6$ are each independently N or $CR^8$,
in which
$R^8$ is hydrogen, fluorine, chlorine, trifluoromethyl, $(C_1-C_4)$-alkyl, hydroxyl, $(C_1-C_4)$-alkoxy, methylamino, ethylamino, dimethylamino or diethylamino,
in which $(C_1-C_4)$-alkyl and $(C_1-C_4)$-alkoxy may themselves be substituted by 1 or 2 substituents each independently selected from the group of fluorine, trifluoromethyl, hydroxyl, methoxy and ethoxy, $A^5$ is $NR^9$,
  in which
    $R^9$ is hydrogen or $(C_1\text{-}C_4)$-alkyl,
      in which $(C_1\text{-}C_4)$-alkyl may itself be substituted by 1 or 2 substituents each independently selected from the group of fluorine, trifluoromethyl, hydroxyl, methoxy and ethoxy, $D^1, D^2, D^3$ and $D^4$ are each independently N or $CR^{10}$,
  in which
    $R^{10}$ is hydrogen, fluorine, chlorine or trifluoromethyl,
  with the proviso that not more than two of the $D^1, D^2, D^3$ and $D^4$ groups are nitrogen,
  and
  with the proviso that at least one of the $D^1, D^2, D^3$ and $D^4$ groups is CH, E is C=O, C=S or $SO_2$, G is O or $NR^{12}$,
  in which
    $R^{12}$ is hydrogen, trideuteromethyl, $(C_1\text{-}C_6)$-alkyl, $(C_2\text{-}C_6)$-alkenyl, $(C_3\text{-}C_7)$-cycloalkyl, azetidinyl, pyrrolidinyl, piperidinyl or benzyl,
      in which $(C_1\text{-}C_6)$-alkyl may itself be substituted by 1 to 3 substituents each independently selected from the group of fluorine, trifluoromethyl, cyclopropyl, cyclobutyl, hydroxyl, methoxy, ethoxy, methylsulfonyl, ethylsulfonyl, azetidinyl, oxetanyl, pyrrolidinyl, piperidinyl and morpholinyl,
        in which azetidinyl, oxetanyl, pyrrolidinyl, piperidinyl and morpholinyl in turn may themselves be substituted by 1 or 2 substituents each independently selected from the group of fluorine, trifluoromethyl, 2,2-difluoroethyl, 2,2,2-trifluoroethyl, methyl and ethyl,
      in which azetidinyl, pyrrolidinyl and piperidinyl may themselves be substituted by 1 or 2 substituents each independently selected from the group of fluorine, trifluoromethyl, methyl, ethyl, cyclopropyl and cyclobutyl,
        in which methyl and ethyl in turn may themselves be substituted by 1 or 2 substituents each independently selected from the group of fluorine, trifluoromethyl, cyclopropyl, cyclobutyl, hydroxyl, methoxy and ethoxy,
      and
      in which benzyl may itself be substituted by 1 or 2 fluorine, chlorine, trifluoromethyl, methyl, ethyl, methylsulfonyl and ethylsulfonyl substituents, K is N or $CR^{14}$,
  in which
    $R^{14}$ is hydrogen or oxo, $R^{11}$ is hydrogen, trideuteromethyl, $(C_1\text{-}C_6)$-alkyl or $(C_2\text{-}C_6)$-alkenyl,
  in which $(C_1\text{-}C_4)$-alkyl may be substituted by 1 or 2 substituents each independently selected from the group of fluorine, trifluoromethyl, cyclopropyl, cyclobutyl, hydroxyl, methoxy and ethoxy, $R^{13}$ is hydrogen or oxo, $R^{15}$ is hydrogen, $(C_1\text{-}C_3)$-alkoxycarbonyl or aminosulfonyl, in which $(C_1\text{-}C_3)$-alkoxycarbonyl may be substituted by 1 or 2 substituents each independently selected from the group of fluorine, trifluoromethyl, hydroxyl, methoxy and ethoxy, $R^{16}$ is hydrogen, trifluoromethyl, $(C_1\text{-}C_4)$-alkyl, $(C_3\text{-}C_6)$-cycloalkyl and phenyl, in which phenyl may be substituted by 1 or 2 substituents each independently selected from the group of fluorine, chlorine, trifluoromethyl, $(C_1\text{-}C_4)$-alkyl, methoxy and ethoxy, $R^{17}$ is hydrogen, trifluoromethyl, $(C_1\text{-}C_4)$-alkyl, cyclopropyl, cyclobutyl and phenyl,
  in which phenyl may be substituted by 1 or 2 substituents each independently selected from the group of fluorine, chlorine, trifluoromethyl, methyl, ethyl, methoxy and ethoxy, $R^{18}$ is hydrogen or $(C_1\text{-}C_6)$-alkyl,
  in which $(C_1\text{-}C_6)$-alkyl may be substituted by 1 or 2 substituents each independently selected from the group of fluorine, trifluoromethyl, cyclopropyl, cyclobutyl, hydroxyl, methoxy and ethoxy, $R^{19}$ is hydrogen or $(C_1\text{-}C_6)$-alkyl,
  in which $(C_1\text{-}C_6)$-alkyl may be substituted by 1 or 2 substituents each independently selected from the group of fluorine, trifluoromethyl, cyclopropyl, cyclobutyl, hydroxyl, methoxy and ethoxy, and the salts, solvates and solvates of the salts thereof.

Preference is given in the context of the present invention to compounds of the formula (I) in which
the ring P is a group of the formula

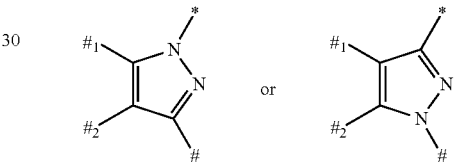

where
* is the attachment site to $R^2$,
# is the attachment site to $R^3$,
$\#_1$ is the attachment site to the nitrogen atom,
$\#_2$ is the attachment site to the carbon atom,
Y is CH,
$R^1$ is hydrogen or fluorine,
$R^2$ is 2,2,3,3,3-pentafluoroprop-1-yl or benzyl,
  where benzyl is substituted by 1 or 2 fluorine substituents,
$R^3$ is a group of the formula

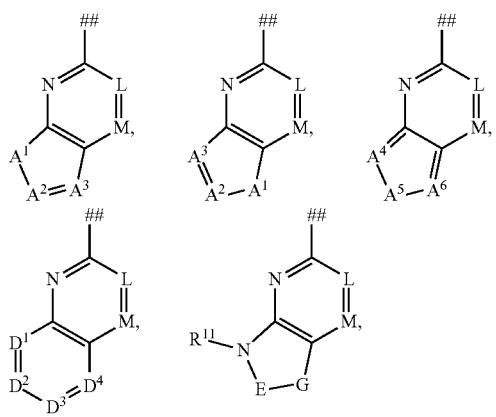

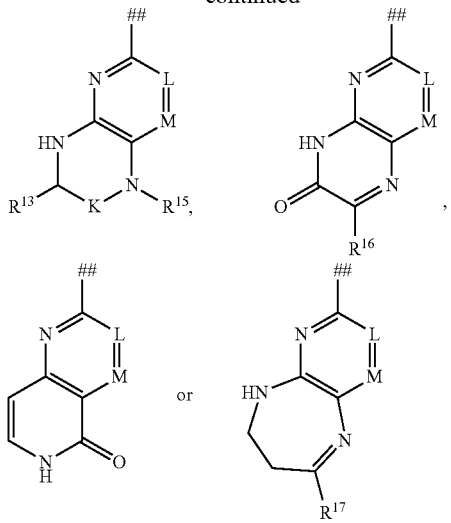

where
## is the attachment site to the ring P,
L is CH or N,
M is $CR^4$ or N,
  in which
    $R^4$ is hydrogen, chlorine, cyano, $(C_1-C_4)$-alkyl, $(C_2-C_4)$-alkynyl, amino, methylamino, ethylamino, dimethylamino, diethylamino or azetidinyl,
      in which $(C_1-C_4)$-alkyl, $(C_2-C_4)$-alkynyl, ethylamino and diethylamino may themselves be substituted by 1 or 2 substituents selected independently from the group of fluorine, hydroxyl and amino,
$A^1$ is O, S or $NR^5$,
  in which
    $R^5$ is hydrogen, trifluoromethyl or $(C_1-C_4)$-alkyl,
      in which $(C_1-C_4)$-alkyl may itself be substituted by 1 or 2 substituents each independently selected from the group of fluorine, trifluoromethyl, hydroxyl, methoxy and ethoxy,
$A^2$ is N or $CR^6$,
  in which
    $R^6$ is hydrogen, fluorine, chlorine, trifluoromethyl, 2,2,2-trifluoroethyl, $(C_2-C_4)$-alkyl, hydroxyl, $(C_1-C_4)$-alkoxy, methylamino, ethylamino, dimethylamino or diethylamino,
      in which $(C_2-C_4)$-alkyl and $(C_1-C_4)$-alkoxy may themselves be substituted by 1 or 2 substituents each independently selected from the group of fluorine, trifluoromethyl, hydroxyl, methoxy and ethoxy,
$A^3$ is N or $CR^7$,
  in which
    $R^7$ is hydrogen, fluorine, trifluoromethyl, $(C_1-C_4)$-alkyl, hydroxyl, $(C_1-C_4)$— alkoxy, amino, methylamino, ethylamino, dimethylamino or diethylamino,
      in which $(C_1-C_4)$-alkyl and $(C_1-C_4)$-alkoxy may themselves be substituted by 1 or 2 substituents each independently selected from the group of fluorine, trifluoromethyl, hydroxyl, methoxy and ethoxy,
$A^4$ and $A^6$ are each independently N or $CR^8$,
  in which
    $R^8$ is hydrogen, fluorine, chlorine, trifluoromethyl, $(C_1-C_4)$-alkyl, hydroxyl, $(C_1-C_4)$-alkoxy, methylamino, ethylamino, dimethylamino or diethylamino,
      in which $(C_1-C_4)$-alkyl and $(C_1-C_4)$-alkoxy may themselves be substituted by 1 or 2 substituents each independently selected from the group of fluorine, trifluoromethyl, hydroxyl, methoxy and ethoxy,
$A^5$ is $NR^9$,
  in which
    $R^9$ is hydrogen or $(C_1-C_4)$-alkyl,
      in which $(C_1-C_4)$-alkyl may itself be substituted by 1 or 2 substituents each independently selected from the group of fluorine, trifluoromethyl, hydroxyl, methoxy and ethoxy,
$D^1$, $D^2$, $D^3$ and $D^4$ are each independently N or $CR^{10}$,
  in which
    $R^{10}$ is hydrogen, fluorine, chlorine or trifluoromethyl,
  with the proviso that not more than two of the $D^1$, $D^2$, $D^3$ and $D^4$ groups are nitrogen,
E is C=O, C=S or $SO_2$,
G is O or $NR^{12}$,
  in which
    $R^{12}$ is hydrogen, trideuteromethyl, $(C_1-C_6)$-alkyl, $(C_2-C_6)$-alkenyl, $(C_3-C_7)$-cycloalkyl, azetidinyl, pyrrolidinyl, piperidinyl or benzyl,
      in which $(C_1-C_6)$-alkyl may itself be substituted by 1 or 2 substituents each independently selected from the group of fluorine, trifluoromethyl, cyclopropyl, cyclobutyl, hydroxyl, methoxy and ethoxy,
      in which azetidinyl, pyrrolidinyl and piperidinyl may themselves be substituted by 1 or 2 substituents each independently selected from the group of fluorine, trifluoromethyl, methyl, ethyl, cyclopropyl and cyclobutyl,
        in which methyl and ethyl may themselves be substituted by 1 or 2 substituents each independently selected from the group of fluorine, trifluoromethyl, cyclopropyl, cyclobutyl, hydroxyl, methoxy and ethoxy,
      and
      in which benzyl may itself be substituted by 1 or 2 fluorine, chlorine, trifluoromethyl, methyl, ethyl, methylsulfonyl and ethylsulfonyl substituents,
K is N or $CR^{14}$,
  in which
    $R^{14}$ is hydrogen or oxo,
$R^{11}$ is hydrogen, trideuteromethyl, $(C_1-C_6)$-alkyl or $(C_2-C_6)$-alkenyl,
  in which $(C_1-C_4)$-alkyl may be substituted by 1 or 2 substituents each independently selected from the group of fluorine, trifluoromethyl, cyclopropyl, cyclobutyl, hydroxyl, methoxy and ethoxy,
$R^{13}$ is hydrogen or oxo,
$R^{15}$ is hydrogen, $(C_1-C_3)$-alkoxycarbonyl or aminosulfonyl, in which $(C_1-C_3)$-alkoxycarbonyl may be substituted by 1 or 2 substituents each independently selected from the group of fluorine, trifluoromethyl, hydroxyl, methoxy and ethoxy,
$R^{16}$ is hydrogen, trifluoromethyl, $(C_1-C_4)$-alkyl, $(C_3-C_6)$-cycloalkyl and phenyl,
  in which phenyl may be substituted by 1 or 2 substituents each independently selected from the group of fluorine, chlorine, trifluoromethyl, $(C_1-C_4)$-alkyl, methoxy and ethoxy,
$R^{17}$ is hydrogen, trifluoromethyl, $(C_1-C_4)$-alkyl, cyclopropyl, cyclobutyl and phenyl, in which phenyl may be substituted by 1 or 2 substituents each independently selected from the group of fluorine, chlorine, trifluoromethyl, methyl, ethyl, methoxy and ethoxy, and the salts, solvates and solvates of the salts thereof.

Particular preference is given in the context of the present invention to compounds of the formula (I) in which the ring P is a group of the formula where
* is the attachment site to $R^2$,
# is the attachment site to $R^3$,
$\#_1$ is the attachment site to the nitrogen atom,
$\#_2$ is the attachment site to the carbon atom,
Y is CH,
$R^1$ is hydrogen or fluorine,
$R^2$ is 2-fluorobenzyl,
$R^3$ is a group of the formula where
## is the attachment site to the ring P,
M is $CR^4$ or N,
where
$R^4$ is hydrogen or amino,
$R^{11}$ is hydrogen,
$R^{12}$ is hydrogen, trideuteromethyl, $(C_1-C_4)$-alkyl, cyclopropyl, cyclobutyl, azetidinyl, pyrrolidinyl or piperidinyl,
in which $(C_1-C_4)$-alkyl may itself be substituted by 1 or 2 substituents each independently selected from the group of fluorine, trifluoromethyl, cyclopropyl, cyclobutyl and hydroxyl,
and
in which azetidinyl, pyrrolidinyl and piperidinyl may themselves be substituted by 1 or 2 substituents each independently selected from the group of fluorine, trifluoromethyl, methyl, ethyl, cyclopropyl and cyclobutyl, and the salts, solvates and solvates of the salts thereof.

Preference is given in the context of the present invention to compounds of the formula (I) in which the ring P is a group of the formula where
* is the attachment site to $R^2$,
# is the attachment site to $R^3$,
$\#_1$ is the attachment site to the nitrogen atom,
$\#_2$ is the attachment site to the carbon atom,
Y is CH,
$R^1$ is hydrogen or fluorine,
$R^2$ is 2-fluorobenzyl,
$R^3$ is a group of the formula where
## is the attachment site to the ring P,
L is N or CH,
M is N or $CR^4$,
in which
$R^4$ is hydrogen or amino,
with the proviso that only one of the L and M groups is N,
$A^1$ is $NR^5$,
in which
$R^5$ is hydrogen,
$A^2$ is N,
$A^3$ is N or $CR^7$,
in which
$R^7$ is hydrogen, fluorine, trifluoromethyl, $(C_1-C_4)$-alkyl, $(C_1-C_4)$-alkoxy, amino, methylamino, ethylamino, dimethylamino or diethylamino,
in which $(C_1-C_4)$-alkyl and $(C_1-C_4)$-alkoxy may themselves be substituted by 1 or 2 substituents each independently selected from the group of fluorine, trifluoromethyl, hydroxyl, methoxy and ethoxy,
E is C=O,
G is $NR^{12}$,
in which
$R^{12}$ is trideuteromethyl, $(C_1-C_6)$-alkyl, cyclopropyl, cyclobutyl, azetidin-3-yl, pyrrolidin-3-yl or piperidin-4-yl, in which $(C_1-C_6)$-alkyl may itself be substituted by 1 to 3 substituents each independently selected from the group of fluorine, trifluoromethyl, cyclopropyl, cyclobutyl, hydroxyl, oxetanyl and morpholin-1-yl, and in which azetidin-3-yl, pyrrolidin-3-yl and piperidin-4-yl are themselves substituted by 1 or 2 substituents each independently selected from the group of fluorine, trifluoromethyl, 2,2-difluoroethyl, 2,2,2-trifluoroethyl, methyl and ethyl, cyclopropyl and cyclobutyl, $R^{11}$ is hydrogen, $R^{15}$ is hydrogen or $(C_1-C_3)$-alkoxycarbonyl, in which $(C_1-C_3)$-alkoxycarbonyl may be substituted by 1 or 2 substituents each independently selected from the group of fluorine, trifluoromethyl, hydroxyl, methoxy and ethoxy, and the salts, solvates and solvates of the salts thereof.

In the context of the present invention, particular preference is also given to compounds of the formula (I) in which the ring P is a group of the formula

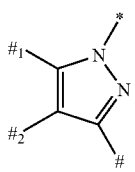

where

* is the attachment site to $R^2$,
# is the attachment site to $R^3$,
$\#_1$ is the attachment site to the nitrogen atom,
$\#_2$ is the attachment site to the carbon atom, Y is CH, $R^1$ is hydrogen or fluorine, $R^2$ is 2-fluorobenzyl, $R^3$ is a group of the formula

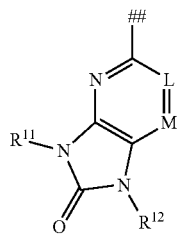

where ## is the attachment site to the ring P,

L is CH or N,

M is N or $CR^4$, where $R^4$ is hydrogen or amino, with the proviso that only one of the L and M groups is N, $R^{11}$ is hydrogen, $R^{12}$ is trideuteromethyl, $(C_1-C_6)$-alkyl, cyclopropyl, cyclobutyl, azetidin-3-yl, pyrrolidin-3-yl or piperidin-4-yl, in which $(C_1-C_6)$-alkyl may itself be substituted by 1 to 3 substituents each independently selected from the group of fluorine, trifluoromethyl, cyclopropyl, cyclobutyl, hydroxyl, oxetanyl and morpholin-1-yl, and in which azetidin-3-yl, pyrrolidin-3-yl and piperidin-4-yl are themselves substituted by 1 or 2 substituents each independently selected from the group of fluorine, trifluoromethyl, 2,2-difluoroethyl, 2,2,2-trifluoroethyl, methyl and ethyl, cyclopropyl and cyclobutyl, and the salts, solvates and solvates of the salts thereof.

Preference is also given in the context of the present invention to compounds of the formula (I) in which the ring P is a group of the formula

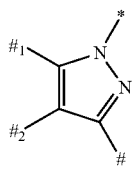

where

* is the attachment site to $R^2$,
# is the attachment site to $R^3$,
$\#_1$ is the attachment site to the nitrogen atom,
$\#_2$ is the attachment site to the carbon atom, Y is CH, $R^1$ is hydrogen or fluorine, $R^2$ is 2-fluorobenzyl, $R^3$ is a group of the formula

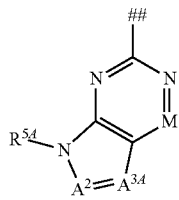 or 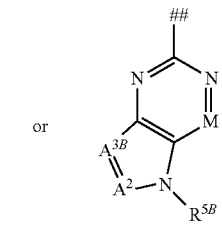

where ## is the attachment site to the ring P,

M is $CR^4$ or N, where $R^4$ is hydrogen or amino, $A^2$ is N or $CR^6$, in which $R^6$ is hydrogen, trifluoromethyl or 2,2,2-trifluoroethyl, $A^{3A}$ is N or $CR^{7A}$, in which $R^{7A}$ is hydrogen, fluorine, trifluoromethyl, 2,2,2-trifluoroethyl, $(C_2-C_4)$-alkyl, hydroxyl, $(C_1-C_4)$-alkoxy, amino, methylamino, ethylamino, dimethylamino or diethylamino, in which $(C_2-C_4)$-alkyl and $(C_1-C_4)$-alkoxy may themselves be substituted by one substituent selected from the group of hydroxyl and methoxy, $A^{3B}$ is N or CH, with the proviso that at least one of the $A^2$ and $A^{3A}$ or $A^{3B}$ groups is N, $R^{5A}$ is hydrogen, $R^{5B}$ is hydrogen, 2,2,2-trifluoroethyl or methyl, and the salts, solvates and solvates of the salts thereof.

Preference is also given in the context of the present invention to compounds of the formula (I) in which Y is CH, and to the salts, solvates and solvates of the salts thereof.

Preference is also given in the context of the present invention to compounds of the formula (I) in which $R^2$ is 2-fluorobenzyl, and to the salts, solvates and solvates of the salts thereof.

Preference is also given in the context of the present invention to compounds of the formula (I) in which
L is N
and
M is N,
and the salts, solvates and solvates of the salts thereof.

Preference is also given in the context of the present invention to compounds of the formula (I) in which
L is N
and
M is CH,
and the salts, solvates and solvates of the salts thereof.

Preference is also given in the context of the present invention to compounds of the formula (I) in which
L is N
and
M is $CR^4$,
where
$R^4$ is amino,
and the salts, solvates and solvates of the salts thereof.

Preference is also given in the context of the present invention to compounds of the formula (I) in which L is N, and to the salts, solvates and solvates of the salts thereof.

Preference is also given in the context of the present invention to compounds of the formula (I) in which M is N, and to the salts, solvates and solvates of the salts thereof.

Preference is also given in the context of the present invention to compounds of the formula (I) in which M is CH, and to the salts, solvates and solvates of the salts thereof.

Preference is also given in the context of the present invention to compounds of the formula (I) in which
M is $CR^4$,
where
$R^4$ is hydrogen or amino,
and the salts, solvates and solvates of the salts thereof.

Preference is also given in the context of the present invention to compounds of the formula (I) in which
L is CH or N,
M is N or $CR^4$,
where
$R^4$ is hydrogen or amino,
with the proviso that only one of the L and M groups is N,
and the salts, solvates and solvates of the salts thereof.

Preference is also given in the context of the present invention to compounds of the formula (I) in which
$R^3$ is a group of the formula

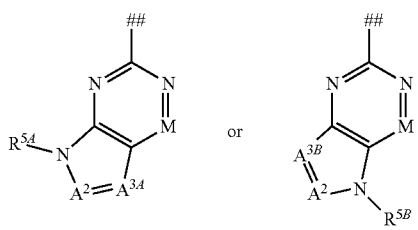

where
## is the attachment site to the ring P,
M is $CR^4$ or N,
where
$R^4$ is hydrogen or amino,
$A^2$ is N or $CR^6$,
in which
$R^6$ is hydrogen, trifluoromethyl, 2,2,2-trifluoroethyl or methyl,
$A^{3A}$ is N or $CR^{7A}$,
in which
$R^{7A}$ is hydrogen, fluorine, trifluoromethyl, 2,2,2-trifluoroethyl, $(C_2-C_4)$-alkyl, hydroxyl, $(C_1-C_4)$-alkoxy, amino, methylamino, ethylamino, dimethylamino or diethylamino,
in which $(C_2-C_4)$-alkyl and $(C_1-C_4)$-alkoxy may themselves be substituted by one substituent selected from the group of hydroxyl and methoxy,
$A^{3B}$ is N or CH,
with the proviso that at least one of the $A^2$ and $A^{3A}$ or $A^{3B}$ groups is N,
$R^{5A}$ is hydrogen,
$R^{5B}$ is hydrogen, 2,2,2-trifluoroethyl or methyl,
and the salts, solvates and solvates of the salts thereof.

Preference is also given in the context of the present invention to compounds of the formula (I) in which
$R^3$ is a group of the formula

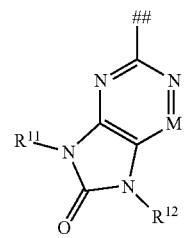

where
## is the attachment site to the ring P,
M is $CR^4$ or N,
where
$R^4$ is hydrogen or amino,
$R^{11}$ is hydrogen,
$R^{12}$ is trideuteromethyl, $(C_1-C_4)$-alkyl, cyclopropyl, cyclobutyl, azetidin-3-yl, pyrrolidin-3-yl or piperidin-4-yl,
in which $(C_1-C_4)$-alkyl may itself be substituted by 1 to 3 substituents each independently selected from the group of fluorine, trifluoromethyl, cyclopropyl, cyclobutyl, hydroxyl, oxetanyl and morpholin-1-yl,
and
in which azetidin-3-yl, pyrrolidin-3-yl and piperidin-4-yl are themselves substituted by 1 or 2 substituents each independently selected from the group of fluorine, trifluoromethyl, 2,2-difluoroethyl, 2,2,2-trifluoroethyl, methyl and ethyl, cyclopropyl and cyclobutyl,
and the salts, solvates and solvates of the salts thereof.

Preference is also given in the context of the present invention to compounds of the formula (I) in which
the ring P is a group of the formula

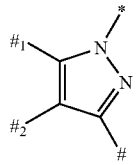

where
* is the attachment site to $R^2$,
# is the attachment site to $R^3$,
$\#_1$ is the attachment site to the nitrogen atom,
$\#_2$ is the attachment site to the carbon atom,
and the salts, solvates and solvates of the salts thereof.

Preference is also given in the context of the present invention to compounds of the formula (I) in which
the ring P is a group of the formula

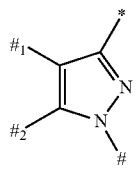

where
* is the attachment site to $R^2$,
# is the attachment site to $R^3$,
$\#_1$ is the attachment site to the nitrogen atom,
$\#_2$ is the attachment site to the carbon atom,
and the salts, solvates and solvates of the salts thereof.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention further provides a process for preparing the inventive compounds of the formula (I), characterized in that
[A] a compound of the formula (II-1) or (II-2)

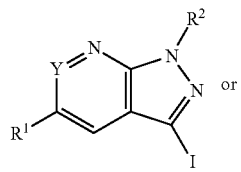

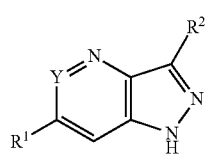

in which Y, $R^1$ and $R^2$ are each as defined above is reacted in an inert solvent in the presence of a suitable transition metal catalyst with a compound of the formula (III)

$$R^3—X^1 \qquad (III)$$

in which $R^3$ is as defined above and
$X^1$ is a suitable leaving group, for example halogen, mesylate, tosylate or triflate, to give a compound of the formula (I-A-1) or (1-A-2)

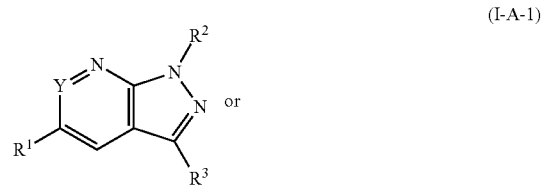

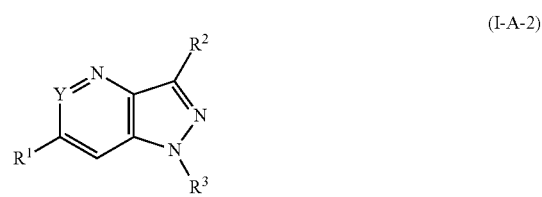

in which Y, $R^1$ and $R^2$ are each as defined above,
or
[B] a compound of the formula (IV)

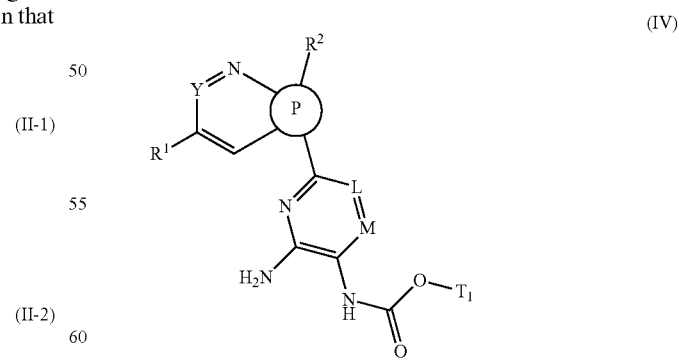

in which L, M, P, Y, $R^1$ and $R^2$ are each as defined above and
$T^1$ is $(C_1-C_4)$-alkyl
is converted in an inert solvent in the presence of a suitable base to a compound of the formula (I-B)

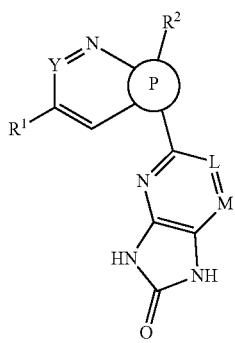

(I-B)

in which L, M, P, Y, $R^1$ and $R^2$ are each as defined above, or

[C] a compound of the formula (IV) is first reacted in an inert solvent in the presence of a suitable base with a compound of the formula (V)

$$R^{12A}-X^2 \quad (V)$$

in which $R^{12A}$ is trideuteromethyl, $(C_1\text{-}C_6)$-alkyl, $(C_2\text{-}C_6)$-alkenyl, $(C_3\text{-}C_7)$-cycloalkyl, azetidinyl, pyrrolidinyl, piperidinyl or benzyl, in which $(C_1\text{-}C_6)$-alkyl may itself be substituted by 1 to 3 substituents each independently selected from the group of fluorine, trifluoromethyl, cyclopropyl, cyclobutyl, hydroxyl, methoxy, ethoxy, methylsulfonyl, ethylsulfonyl, azetidinyl, oxetanyl, pyrrolidinyl, piperidinyl and morpholinyl, in which azetidinyl, oxetanyl, pyrrolidinyl, piperidinyl and morpholinyl in turn may themselves be substituted by 1 or 2 substituents each independently selected from the group of fluorine, trifluoromethyl, 2,2-difluoroethyl, 2,2,2-trifluoroethyl, methyl and ethyl, in which azetidinyl, pyrrolidinyl and piperidinyl may themselves be substituted by 1 or 2 substituents each independently selected from the group of fluorine, trifluoromethyl, methyl, ethyl, cyclopropyl and cyclobutyl, in which methyl and ethyl in turn may themselves be substituted by 1 or 2 substituents each independently selected from the group of fluorine, trifluoromethyl, cyclopropyl, cyclobutyl, hydroxyl, methoxy and ethoxy, and in which benzyl may itself be substituted by 1 or 2 fluorine, chlorine, trifluoromethyl, methyl, ethyl, methylsulfonyl and ethylsulfonyl substituents, and $X^2$ is a suitable leaving group, for example halogen, especially chlorine or bromine, mesylate or tosylate, to give a compound of the formula (VI)

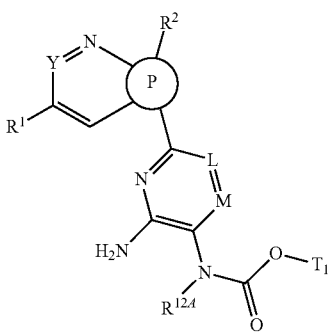

(VI)

in which L, M, P, Y, $R^1$, $R^2$, $R^{12A}$ and $T^1$ are each as defined above, and this is then cyclized in an inert solvent, in the presence of a suitable base, to give a compound of the formula (I-C)

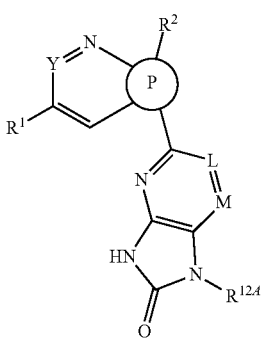

(I-C)

in which L, M, P, Y, R', $R^2$ and $R^{12A}$ are each as defined above, or

[D] a compound of the formula (VII)

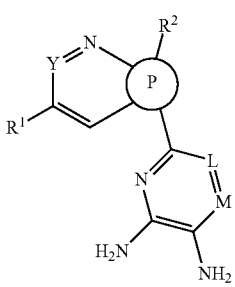

(VII)

in which L, M, P, Y, $R^1$ and $R^2$ are each as defined above is reductively aminated with a compound of the formula (VIII)

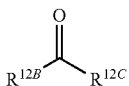

(VIII)

in which $R^{12B}$ is trifluoromethyl, $(C_1\text{-}C_5)$-alkyl, $(C_2\text{-}C_6)$-alkenyl, cyclopropyl, cyclobutyl or phenyl, in which $(C_1\text{-}C_5)$-alkyl may itself be substituted by 1 or 2 substituents each independently selected from the group of fluorine, trifluoromethyl, hydroxyl, methoxy and ethoxy, and in which phenyl may itself be substituted by 1 or 2 fluorine, chlorine, trifluoromethyl, methyl, ethyl, methylsulfonyl and ethylsulfonyl substituents, $R^{12C}$ is hydrogen or $(C_1\text{-}C_5)$-alkyl, in which $(C_1\text{-}C_5)$-alkyl may itself be substituted by 1 or 2 substituents each independently selected from the group of fluorine, trifluoromethyl, cyclopropyl, cyclobutyl, hydroxyl, methoxy and ethoxy, or where $R^{12B}$ and $R^{12C}$ together with the carbon atom to which they are bonded form a cyclobutyl, azetidinyl, pyrrolidinyl or piperidinyl ring, in which the azetidinyl, pyrrolidinyl and piperidinyl ring may itself be substituted by 1 or 2 substituents each independently selected from the group of fluorine, trifluoromethyl, methyl, ethyl, cyclopropyl and cyclobutyl, in which methyl and ethyl in turn may themselves be substituted by 1 or 2 substituents each independently selected from the group of fluorine, trifluoromethyl, cyclopropyl, cyclobutyl, hydroxyl, methoxy and ethoxy, to give a compound of the formula (IX)

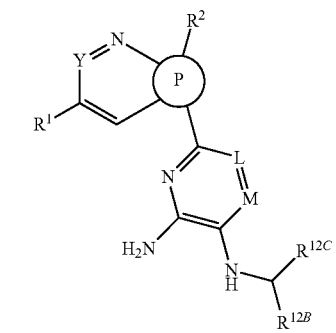

(IX)

in which L, M, P, Y, $R^1$, $R^2$, $R^{12B}$ and $R^{12C}$ are each as defined above, and this is cyclized in an inert solvent in the presence of a suitable base with phosgene, a phosgene derivative or a phosgene equivalent to give a compound of the formula (I-D)

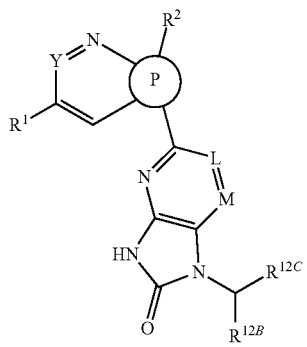

(I-D)

in which L, M, P, Y, $R^1$, $R^2$, $R^{12B}$ and $R^{12C}$ are each as defined above, or

[E] a compound of the formula (X)

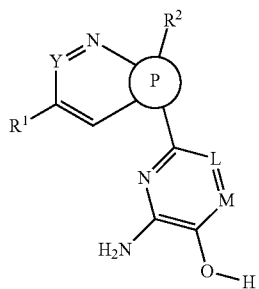

(X)

in which L, M, P, Y, $R^1$ and $R^2$ are each as defined above is cyclized in an inert solvent in the presence of a suitable base with phosgene, a phosgene derivative or a phosgene equivalent to give a compound of the formula (I-E)

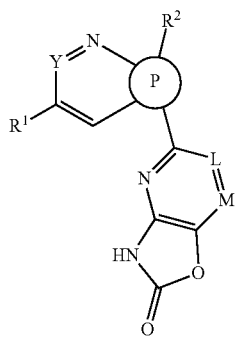

(I-E)

in which L, M, P, Y, $R^1$ and $R^2$ are each as defined above, or

[F] a compound of the formula (VII) is reacted in an inert solvent under acidic conditions with a suitable nitrite to give a compound of the formula (I-F)

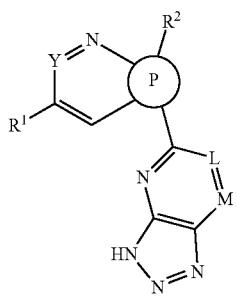
(I-F)

in which L, M, P, Y, $R^1$ and $R^2$ are each as defined above, or

[G] a compound of the formula (VII) is reacted in an inert solvent with a compound of the formula (XI)

(XI)

in which $R^{5C}$ is trifluoromethyl or $(C_1-C_4)$-alkyl, in which $(C_1-C_4)$-alkyl may itself be substituted by 1 or 2 substituents each independently selected from the group of fluorine, trifluoromethyl, hydroxyl, methoxy and ethoxy, and $X^3$ is a suitable leaving group, for example halogen, especially chlorine or bromine, mesylate or tosylate, to give a compound of the formula (XII)

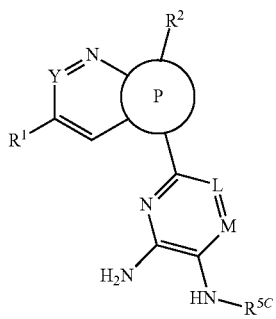
(XII)

in which L, M, P, Y, $R^1$, $R^2$ and $R^{5C}$ are each as defined above, and this is then cyclized in an inert solvent with a compound of the formula (XIII)

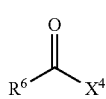
(XIII)

in which $R^6$ is as defined above and $X^4$ is chlorine, hydroxyl, $(C_1-C_4)$-alkoxycarbonyl or a group of the formula $O(C=O)R^6$ to give a compound of the formula (I-G)

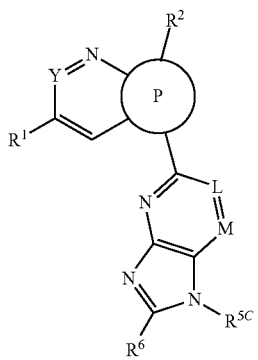
(I-G)

in which L, M, P, Y, $R^1$, $R^2$, $R^{5C}$ and $R^6$ are each as defined above, or

[H] a compound of the formula (XIV)

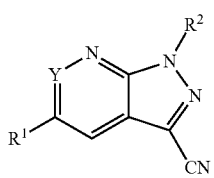
(XIV)

in which Y, $R^1$ and $R^2$ are each as defined above is reacted in an inert solvent in the presence of a suitable base with a compound of the formula (XV-1) or (XV-2)

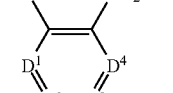
(XV-1)

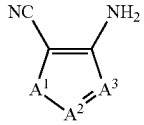
(XV-2)

in which $D^1$, $D^2$, $D^3$, $D^4$, $A^1$, $A^2$ and $A^3$ are each as defined above to give a compound of the formula (I-H-1) or (I-H-2)

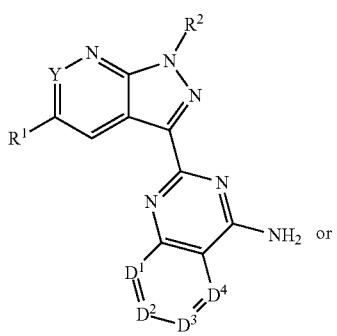
(I-H-1)

(I-H-2)

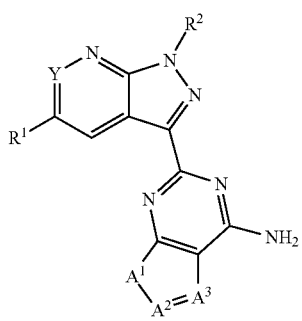

in which Y, R¹, R², D¹, D², D³, D⁴, A¹, A² and A³ are each as defined above, or

[I] a compound of the formula (I-I-1) or (I-I-2)

(I-I-1)

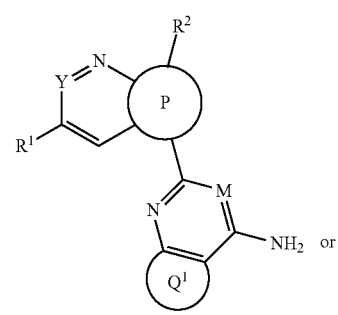

(I-I-2)

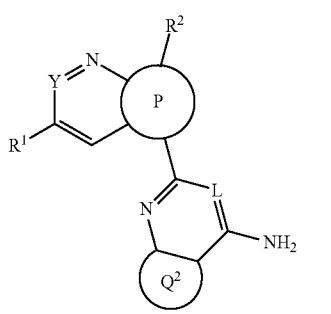

in which M, P, Y, R¹, R², Q¹ and Q² are each as defined above is reacted in an inert solvent with a suitable nitrite to give a compound of the formula (I-I-3) or (I-I-4)

(I-I-3)

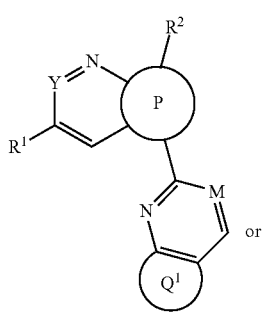

(I-I-4)

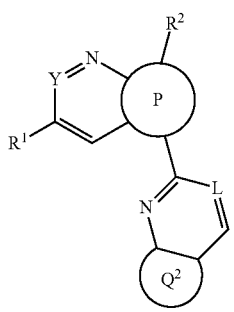

in which M, P, Y, R¹, R², Q¹ and Q² are each as defined above, or

[J] a compound of the formula (I-I-1) or (I-I-2) is reacted in an inert solvent with isopentyl (I-J-1)

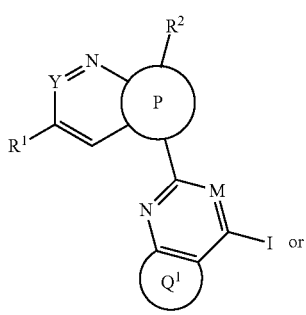

(I-J-2)

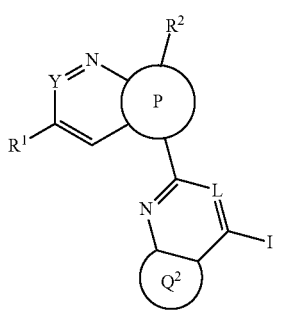

in which M, P, Y, R', R², Q¹ and Q² are each as defined above or

[K] a compound of the formula (I-J-1) or (I-J-2) is reacted in an inert solvent with a compound of the formula (XVI)

$$R^{4A}-X^5 \quad (XVI)$$

in which $R^{4A}$ is cyano, $(C_1-C_4)$-alkyl, $(C_2-C_4)$-alkynyl, hydroxyl, $(C_1-C_4)$-alkoxy, $(C_1-C_4)$-alkylcarbonyl, $(C_1-C_4)$-alkoxycarbonyl, amino, mono-$(C_1-C_4)$-alkylamino, di-$(C_1-C_4)$-alkylamino or azetidinyl, in which $(C_1-C_4)$-alkyl, $(C_2-C_4)$-alkynyl, $(C_1-C_4)$-alkoxy, mono-$(C_1-C_4)$-alkylamino and di-$(C_1-C_4)$-alkylamino may themselves be substituted by 1 or 2 substituents each independently selected from the group of fluorine, hydroxyl and amino, and $X^5$ is hydrogen, halogen, tosylate, mesylate, or a suitable cation, to give a compound of the formula (I-K-1) or (I-K-2)

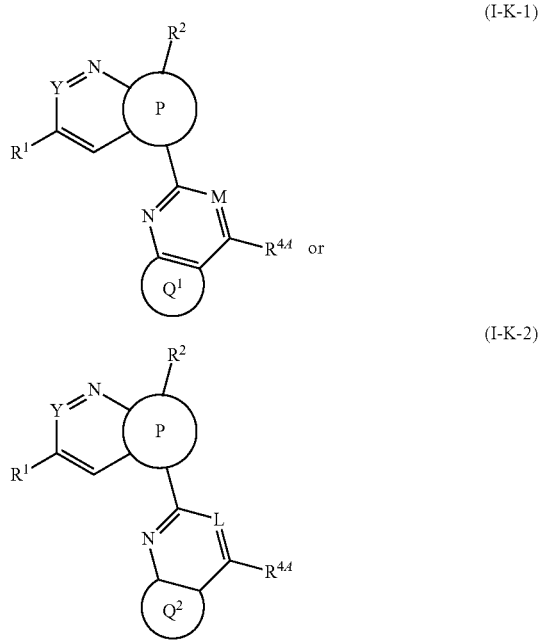

(I-K-1)

(I-K-2)

in which M, P, Y, R$^1$, R$^2$, R$^{4,4}$, Q$^1$ and Q$^2$ are each as defined above, and any protecting groups present are detached by methods known to those skilled in the art, and the resulting compounds of the formula (I) are optionally converted with the appropriate (i) solvents and/or (ii) acids or bases to the solvates, salts and/or solvates of the salts thereof.

Inert solvents for the process step (II-1) or (II-2)+(III)→(I-A-1) or (I-A-2) are, for example, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), dimethylacetamide, N-methylpyrrolidone (NMP), pyridine, acetonitrile, sulfolane or else water. It is likewise possible to use mixtures of the solvents mentioned. Preference is given to dioxane.

The conversion (II-1)+(III)→(I-A-1) is effected in the presence of hexabutyltin and a suitable palladium catalyst with intermediate formation of a tin species.

A suitable palladium catalyst for the process step (II-1)+(III)→(I-A-1) is, for example, palladium on activated carbon, palladium(II) acetate, tetrakis(triphenylphosphine)palladium (0), bis(triphenylphosphine)palladium(II) chloride, bis(acetonitrile)palladium(II) chloride and [1,1'-bis(diphenylphosphino)ferrocene]dichloropalladium(II)-dichloromethane complex, optionally in conjunction with additional phosphine ligands, for example (2-biphenyl)di-tert-butylphosphine, dicyclohexyl[2',4',6'-tris(1-methylethyl)biphenyl-2-yl] phosphine (XPHOS), bis(2-phenylphosphinophenyl) ether (DPEphos) or 4,5-bis(diphenylphosphino)-9,9-dimethylxanthene (Xantphos) [cf., for example, Hassan J. et al., Chem. Rev. 102, 1359-1469 (2002)].

The reaction (II-1)+(III) (I-A-1) is generally performed within a temperature range from +20° C. to +180° C., preferably at +50° C. to +120° C., optionally in a microwave. The conversion can be effected at standard, elevated or reduced pressure (for example from 0.5 to 5 bar). The working pressure is generally atmospheric pressure.

The conversion (II-2)+(III)→(I-A-2) is effected in the presence of a suitable base. Suitable bases for this conversion are the customary inorganic or organic bases. These preferably include alkali metal hydroxides, for example lithium, sodium or potassium hydroxide, alkali metal or alkaline earth metal carbonates such as lithium, sodium, potassium, calcium or cesium carbonate, alkali metal alkoxides such as sodium or potassium methoxide, sodium or potassium ethoxide or sodium or potassium tert-butoxide, alkali metal hydrides such as sodium or potassium hydride, amides such as sodium amide, lithium, sodium or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicycl[5.4.0]undec-7-ene (DBU) or 1,4-diazabicyclo[2.2.2] octane (DABCO®). Preference is given to using sodium hydride or cesium carbonate.

The reaction (II-2)+(III)→(I-A-2) is generally performed within a temperature range from 0° C. to +80° C., preferably at +10° C. to +40° C. The conversion can be effected at standard, elevated or reduced pressure (for example from 0.5 to 5 bar). The working pressure is generally atmospheric pressure.

Optionally, the conversion (II-2)+(III)→(I-A-2) can be effected in the presence of a suitable palladium or copper catalyst. A suitable palladium catalyst is, for example, palladium on activated carbon, palladium(II) acetate, tetrakis(triphenylphosphine)palladium(0), bis(triphenylphosphine) palladium(II) chloride, bis(acetonitrile)palladium(II) chloride and [1,1'-bis(diphenylphosphino)ferrocene]dichloropalladium(II)-dichloromethane complex, optionally in conjunction with additional phosphine ligands, for example (2-biphenyl)di-tert-butylphosphine, dicyclohexyl[2',4',6'-tris (1-methylethyl)biphenyl-2-yl]phosphine (XPHOS), bis(2-phenylphosphinophenyl)ether (DPEphos) or 4,5-bis(diphenylphosphino)-9,9-dimethylxanthene (Xantphos) [cf., for example, Hassan J. et al., Chem. Rev. 102, 1359-1469 (2002)]. Suitable copper catalysts are, for example, copper bronze, copper(I) iodide or copper(I) bromide.

The reaction (II-2)+(III)→(I-A-2) is generally performed within a temperature range from +20° C. to +180° C., preferably at +50° C. to +120° C., optionally in a microwave. The conversion can be effected at standard, elevated or reduced pressure (for example from 0.5 to 5 bar). The working pressure is generally atmospheric pressure.

Suitable inert solvents for the cyclizations (IV)→(I-B) and (VI)→(I-C) are ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), dimethylacetamide, N-methylpyrrolidone (NMP), pyridine, acetonitrile or sulfolane. It is likewise possible to use mixtures of the solvents mentioned. Preference is given to tetrahydrofuran.

Suitable bases for the cyclizations (IV)→(I-B) and (VI)→ (I-C) are the customary inorganic or organic bases. These preferably include alkali metal hydroxides, for example lithium, sodium or potassium hydroxide, alkali metal or alkaline earth metal carbonates such as lithium, sodium, potassium, calcium or cesium carbonate, alkali metal alkoxides such as sodium or potassium methoxide, sodium or potassium ethoxide or sodium or potassium tert-butoxide, alkali metal hydrides such as sodium or potassium hydride, amides such as sodium amide, lithium, sodium or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using sodium bis(trimethylsilyl)amide.

The reactions (IV)→(I-B) and (VI)→(I-C) are generally performed within a temperature range from −10° C. to +80° C., preferably at +10° C. to +30° C. The conversion can be effected at standard, elevated or reduced pressure (for example from 0.5 to 5 bar). The working pressure is generally atmospheric pressure.

Inert solvents for the conversions (IV)+(V)→(VI) and (VII)+(XI)→(XII) are ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), dimethylacetamide, N-methylpyrrolidone (NMP), pyridine, acetonitrile or sulfolane. It is likewise possible to use mixtures of the solvents mentioned. Preference is given to tetrahydrofuran.

Suitable bases for the conversions (IV)+(V)→(VI) and (VII)+(XI)→(XII) are the customary inorganic or organic bases. These preferably include alkali metal hydroxides, for example lithium, sodium or potassium hydroxide, alkali metal or alkaline earth metal carbonates such as lithium, sodium, potassium, calcium or cesium carbonate, alkali metal alkoxides such as sodium or potassium methoxide, sodium or potassium ethoxide or sodium or potassium tert-butoxide, alkali metal hydrides such as sodium or potassium hydride, amides such as sodium amide, lithium, sodium or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane) (DABCO®. Preference is given to using sodium hydride.

The reactions (IV)+(V)→(VI) and (VII)+(XI)→(XII) are generally performed within a temperature range from −10° C. to +80° C., preferably at +10° C. to +30° C. The conversion can be effected at standard, elevated or reduced pressure (for example from 0.5 to 5 bar). The working pressure is generally atmospheric pressure.

The conversions (IX)→(I-D) and (X)→(I-E) are effected with phosgene, a phosgene derivative such as di- or triphosgene, or a phosgene equivalent, for example N,N-carbonyldiimidazole or a chloroformic ester.

Inert solvents for the process steps (IX)→(I-D) and (X)→(I-E) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, dimethyl sulfoxide, N,N'-dimethylpropyleneurea (DMPU), N-methylpyrrolidone (NMP) or pyridine. It is likewise possible to use mixtures of the solvents mentioned. Preference is given to using DMF.

Suitable bases for the process steps (IX)→(I-D) and (X)→(I-E) are the customary inorganic or organic bases. These preferably include alkali metal hydroxides, for example lithium, sodium or potassium hydroxide, alkali metal or alkaline earth metal carbonates such as lithium, sodium, potassium, calcium or cesium carbonate, alkali metal alkoxides such as sodium or potassium methoxide, sodium or potassium ethoxide or sodium or potassium tert-butoxide, alkali metal hydrides such as sodium or potassium hydride, amides such as sodium amide, lithium or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane)(DABCO®). Preference is given to using triethylamine.

The process steps (IX)→(I-D) and (X)→(I-E) are generally performed within a temperature range from −10° C. to +50° C., preferably at 0° C. to +30° C. The conversion can be effected at standard, elevated or reduced pressure (for example from 0.5 to 5 bar). The working pressure is generally atmospheric pressure.

The reductive amination (VII)+(VIII)→(IX) is effected in the presence of alkali metal borohydrides, for example sodium triacetoxyborohydride, sodium cyanoborohydride or sodium borohydride, using catalytic amounts of a suitable acid, for example formic acid or acetic acid.

Inert solvents for the conversion (VII)+(VIII)→(IX) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), dimethylacetamide, N-methylpyrrolidone (NMP), pyridine, acetonitrile, sulfolane or else water. It is likewise possible to use mixtures of the solvents mentioned. Preference is given to dichloroethane or methanol.

The reductive amination (VII)+(VIII)→(IX) is generally performed at temperatures between 0° C. and +100° C., preferably at +10° C. to +40° C. The conversion can be effected at standard, elevated or reduced pressure (for example from 0.5 to 5 bar). The working pressure is generally atmospheric pressure.

Suitable nitrites for the conversions (VII)→(I-F) and (I-I-1) or (I-I-2)→(I-I-3) or (I-I-4) are, for example, sodium nitrite, isopentyl nitrite or tert-butyl nitrite.

Inert solvents for the conversions (VII)→(I-F) and (I-I-1) or (I-I-2)→(I-1-3) or (I-I-4) are, for example, ethers such as diethyl ether, dioxane, tetrahydrofuran, glycol dimethyl ether or diethylene glycol dimethyl ether, or other solvents such as dimethylformamide (DMF), dimethyl sulfoxide (DMSO), N,N'-dimethylpropyleneurea (DMPU), N-methylpyrrolidone (NMP), pyridine or acetonitrile. It is likewise possible to use mixtures of the solvents mentioned. Preference is given to tetrahydrofuran or DMF.

The reactions (VII)→(I-F) and (I-I-1) or (I-I-2)→(I-1-3) or (I-I-4) are generally performed within a temperature range from 0° C. to +120° C., preferably at +40° C. to +80° C. The conversion can be effected at standard, elevated or reduced pressure (for example from 0.5 to 5 bar). The working pressure is generally atmospheric pressure.

Suitable inert solvents for the process step (XII)+(XIII)→(I-G) in the conversion of carboxylic anhydrides are ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2- dichloroethane, trichloroethylene or chlorobenzene, or other solvents such as acetone, ethyl acetate, acetonitrile, pyridine, dimethyl sulfoxide, N,N-dimethylformamide, N,N'-dimethylpropyleneurea (DMPU) or N-methylpyrrolidone (NMP).

The conversion of carboxylic anhydrides in process step (XII)+(XIII)→(I-G) is effected in the presence of a suitable base, for example organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using triethylamine.

The process step (XII)+(XIII)→(I-G) with carboxylic anhydrides is generally performed within a temperature range from +20° C. to +120° C., preferably at +50° C. to +80° C. The conversion can be effected at standard, elevated or reduced pressure (for example from 0.5 to 5 bar). The working pressure is generally atmospheric pressure.

Inert solvents for the process step (XIV)+(XV-1)→(I-H-1) or (XIV)+(XV-2)→(I-H-2) are, for example, halohydrocarbons such as hydrocarbons such as benzene, toluene, xylene, hexane, cyclohexane or mineral oil fractions, or other solvents such as acetone, methyl ethyl ketone, ethyl acetate, acetonitrile, N,N-dimethylformamide (DMF), dimethyl sulfoxide (DMSO), N,N'-dimethylpropyleneurea (DMPU), N-methylpyrrolidone (NMP), sulfolane or pyridine. It is likewise possible to use mixtures of the solvents mentioned. Preference is given to using DMF.

Suitable bases for the process step (XIV)+(XV-1)→(I-H-1) or (XIV)+(XV-2)→(I-H-2) are the customary inorganic or organic bases. These preferably include alkali metal alkoxides such as sodium or potassium methoxide, sodium or potassium ethoxide or sodium or potassium tert-butoxide, alkali metal hydrides such as sodium or potassium hydride, or amides such as sodium amide, lithium or potassium bis(trimethylsilyl)amide or lithium diisopropylamide. Preference is given to using potassium tert-butoxide.

The process step (XIV)+(XV-1)→(I-H-1) or (XIV)+(XV-2)→(I-H-2) is generally performed within a temperature range from +100° C. to +200° C., preferably at +140° C. to +180° C., optionally in a microwave. The conversion can be effected at standard, elevated or reduced pressure (for example from 0.5 to 5 bar). The working pressure is generally elevated pressure or atmospheric pressure.

The process step (I-I-1)→(I-J-1) or (I-I-2)→(I-J-2) is effected with or without solvents. Suitable solvents are all organic solvents which are inert under the reaction conditions. A preferred solvent is dimethoxyethane.

The reaction (I-I-1)→(I-J-1) or (I-I-2)→(I-J-2) is generally effected within a temperature range from +20° C. to +100° C., preferably within the range from +50° C. to +100° C., optionally in a microwave. The conversion can be performed at standard, elevated or reduced pressure (for example from 0.5 to 5 bar). The working pressure is generally atmospheric pressure.

The process step (I-I-1)→(I-J-1) or (I-I-2)→(I-J-2) is generally effected with a molar ratio of 10 to 30 mol of isopentyl nitrite and 10 to 30 mol of the iodine equivalent based on 1 mol of the compound of the formula (IV).

Examples of suitable iodine sources in the conversion (I-I-1)→(I-J-1) are (I-I-2)→(I-J-2) include diiodomethane or a mixture of cesium iodide, iodine and copper(I) iodide.

Inert solvents for the process step (I-I-1)→(I-1-3) or (I-I-2)→(I-1-4) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is likewise possible to use mixtures of the solvents mentioned. Preference is given to DMF.

The reduction (I-I-1)→(I-I-3) or (I-I-2)→(I-I-4) is effected with hydrogen in conjunction with transition metal catalysts, for example palladium (10% on activated carbon), Raney nickel or palladium hydroxide.

The reaction (I-I-1)→(I-I-3) or (I-I-2)→(I-I-4) is generally effected within a temperature range from +20° C. to +50° C. The conversion can be performed at standard or elevated pressure (for example in the range from 0.5 to 5 bar). The working pressure is generally atmospheric pressure.

The conversion (I-J-1)+(XVI)→(I-K-1) or (I-J-2)+(XVI)→(I-K-2) is effected in a solvent which is inert under the reaction conditions, or if appropriate without solvent. Inert solvents are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, dimethyl sulfoxide, N,N'-dimethylpropyleneurea (DMPU), N-methylpyrrolidone (NMP), sulfolane or pyridine. Preference is given to NMP.

The conversion (I-J-1)+(XVI)→(I-K-1) or (I-J-2)+(XVI)→(I-K-2) is generally effected within a temperature range from +50° C. to +200° C., preferably from +100° C. to +160° C., preferably in a microwave. The conversion can be performed at standard or elevated pressure (for example in the range from 0.5 to 5 bar). The working pressure is generally elevated pressure or atmospheric pressure.

If $R^{4A}$ is $(C_1-C_4)$-alkoxy, optionally with the range of substitution specified above, the conversion (I-J-1)+(XVI)→(I-K-1) or (I-J-2)+(XVI)→(I-K-2) is effected in the presence of a suitable copper catalyst, for example copper(I) iodide, with addition of 3,4,7,8-tetramethyl-1,10-phenanthroline, and of a suitable base, for example alkaline earth metal carbonates such as lithium, sodium, potassium, calcium or cesium carbonate, preferably cesium carbonate.

If $R^{4A}$ is $(C_2-C_4)$-alkynyl, optionally with the range of substitution specified above, the conversion (I-J-1)+(XVI)→(I-K-1) or (I-J-2)+(XVI)→(I-K-2) is effected in the presence of a suitable palladium and/or copper catalyst, suitable compounds being those mentioned for the process step (II-2)+(III)→(I-A-2).

The further derivatives $R^{4A}$ are prepared by the methods known to those skilled in the art.

The preparation processes described above are illustrated by way of example by the following synthesis schemes (Schemes 1 to 9):

Scheme 1:
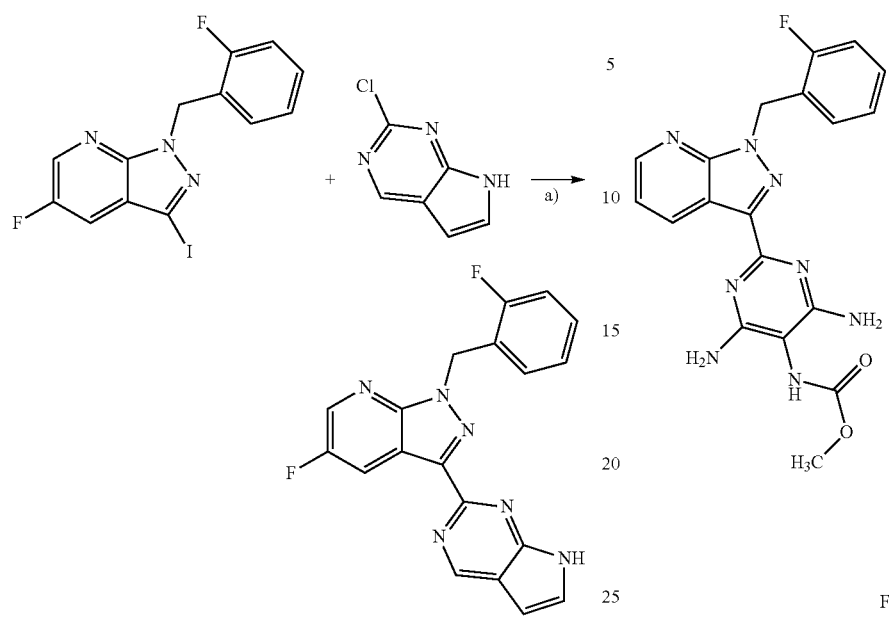
[a]: Sn$_2$Bu$_6$, Pd(PPh$_3$)$_4$, dioxane, reflux].
Scheme 2:
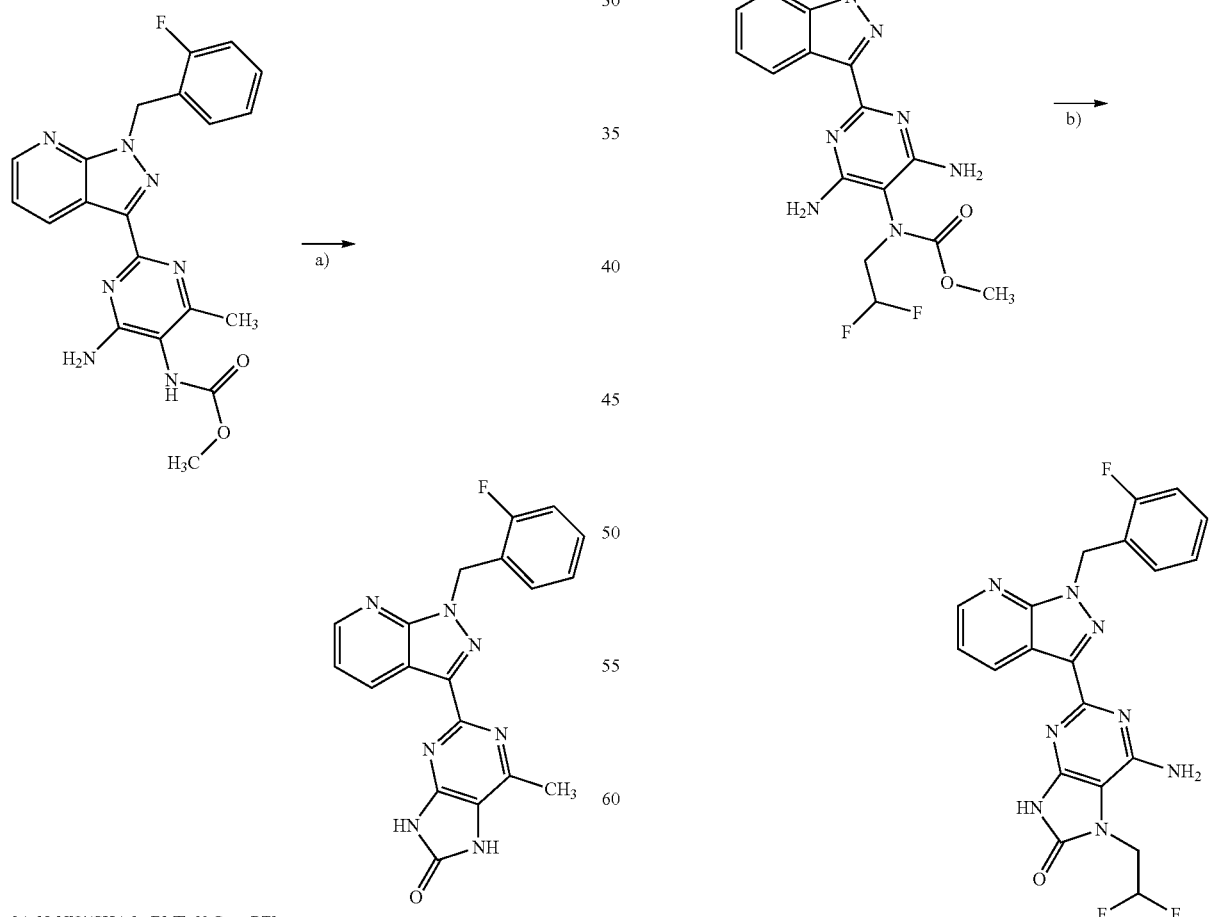
[a]: NaN[Si(CH$_3$)$_3$]$_2$, DMF, 0° C. → RT].
Scheme 3:
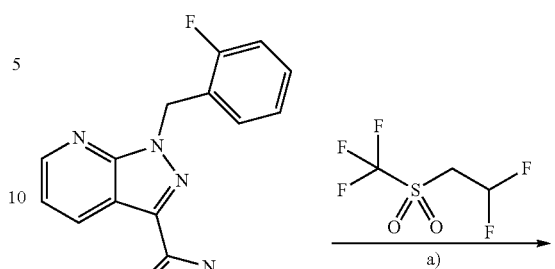
[a]: NaH, THF, 0° C. → RT; b): NaN[Si(CH$_3$)$_3$]$_2$, THF, 0° C. → RT].

Scheme 4:
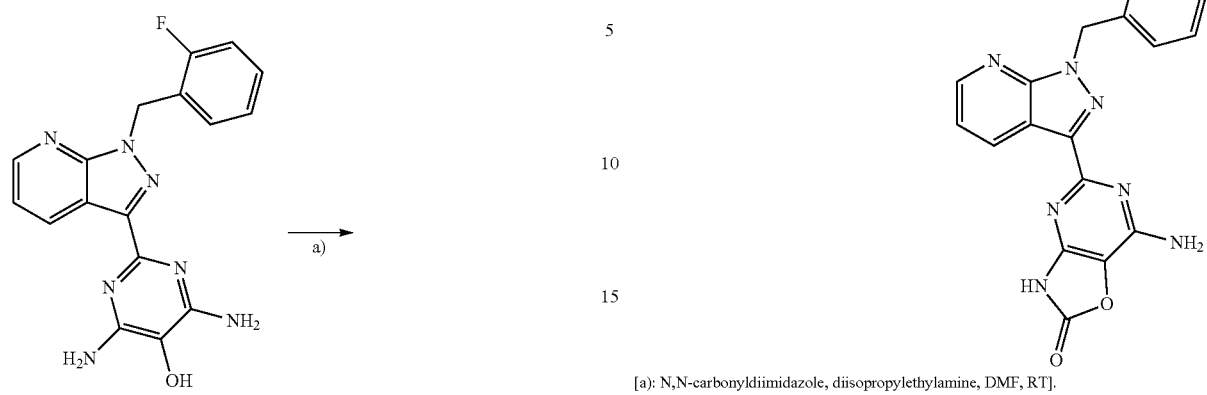
[a]: N,N-carbonyldiimidazole, diisopropylethylamine, DMF, RT].
Scheme 5:
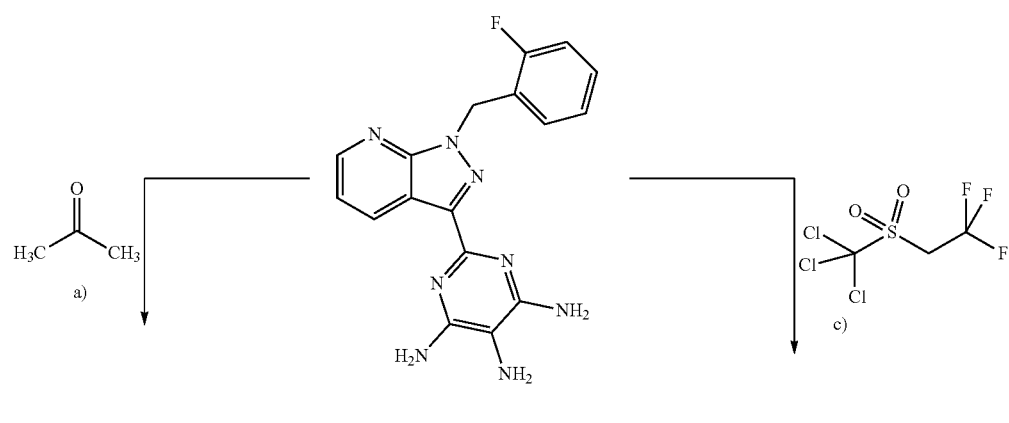
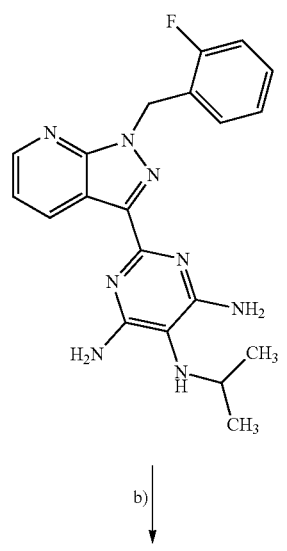
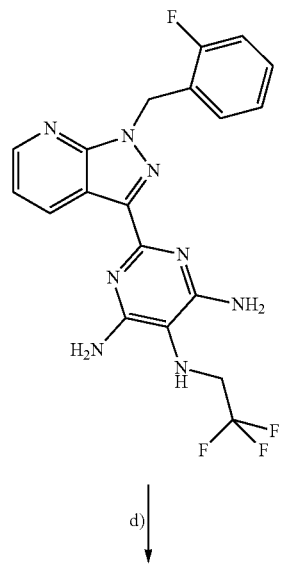

-continued
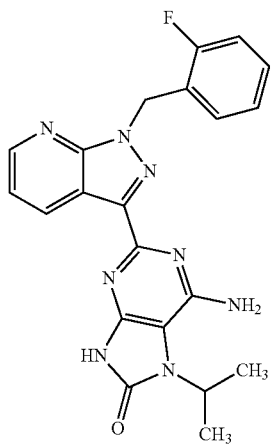
[a]: NaCNBH₃, HOAc, MeOH, RT; b): N,N-carbonyldiimidazole, NEt₃, DMF, 100° C.; c): DMF, microwave, 150° C.; d): HCO₂H, NaOAc, reflux].
Scheme 6:
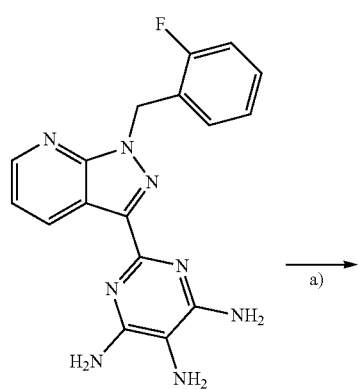
a)
-continued
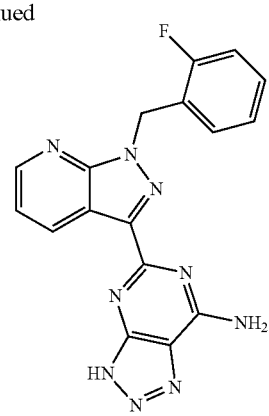
[a]: NaNO₂, glacial acetic acid/H₂O, reflux].
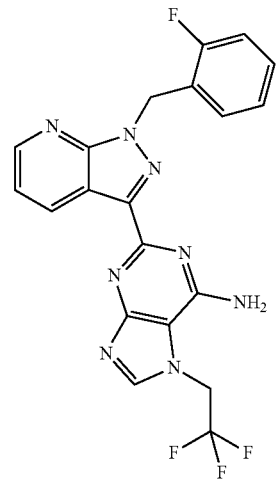
Scheme 7:
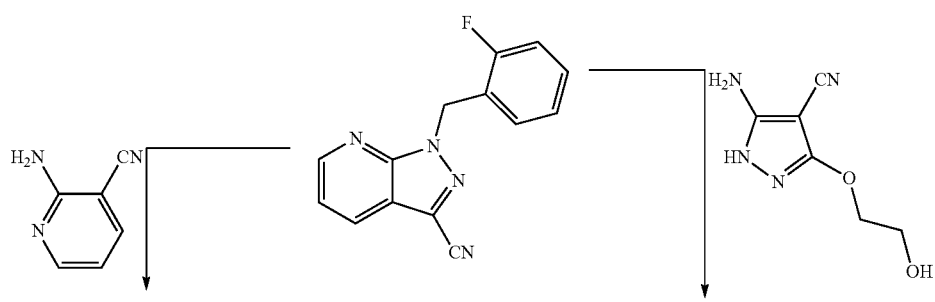

-continued
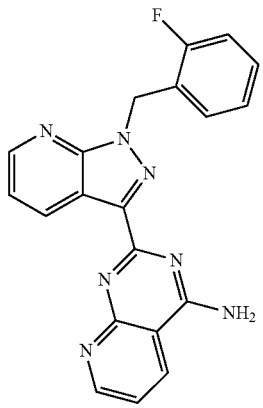
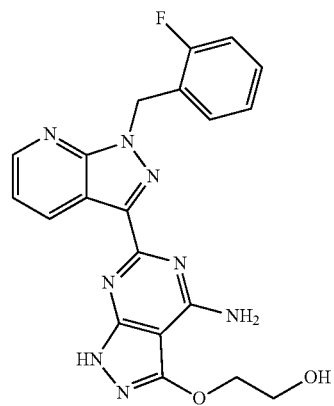
[potassium tert-butoxide, DMF, microwave, 200° C.].
Scheme 8:
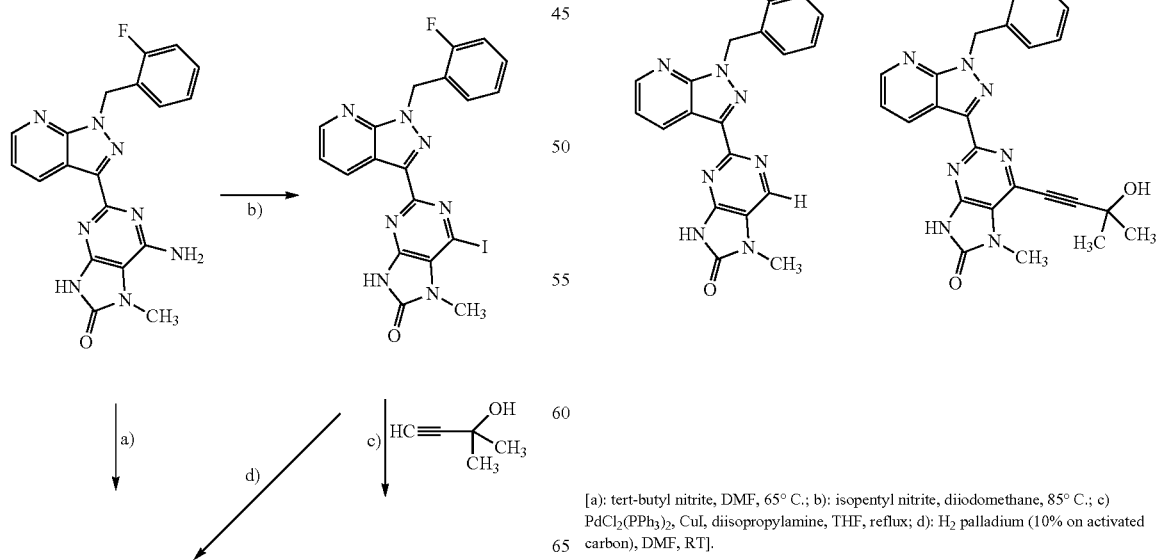
[a): tert-butyl nitrite, DMF, 65° C.; b): isopentyl nitrite, diiodomethane, 85° C.; c) PdCl$_2$(PPh$_3$)$_2$, CuI, diisopropylamine, THF, reflux; d): H$_2$ palladium (10% on activated carbon), DMF, RT].

Scheme 9:

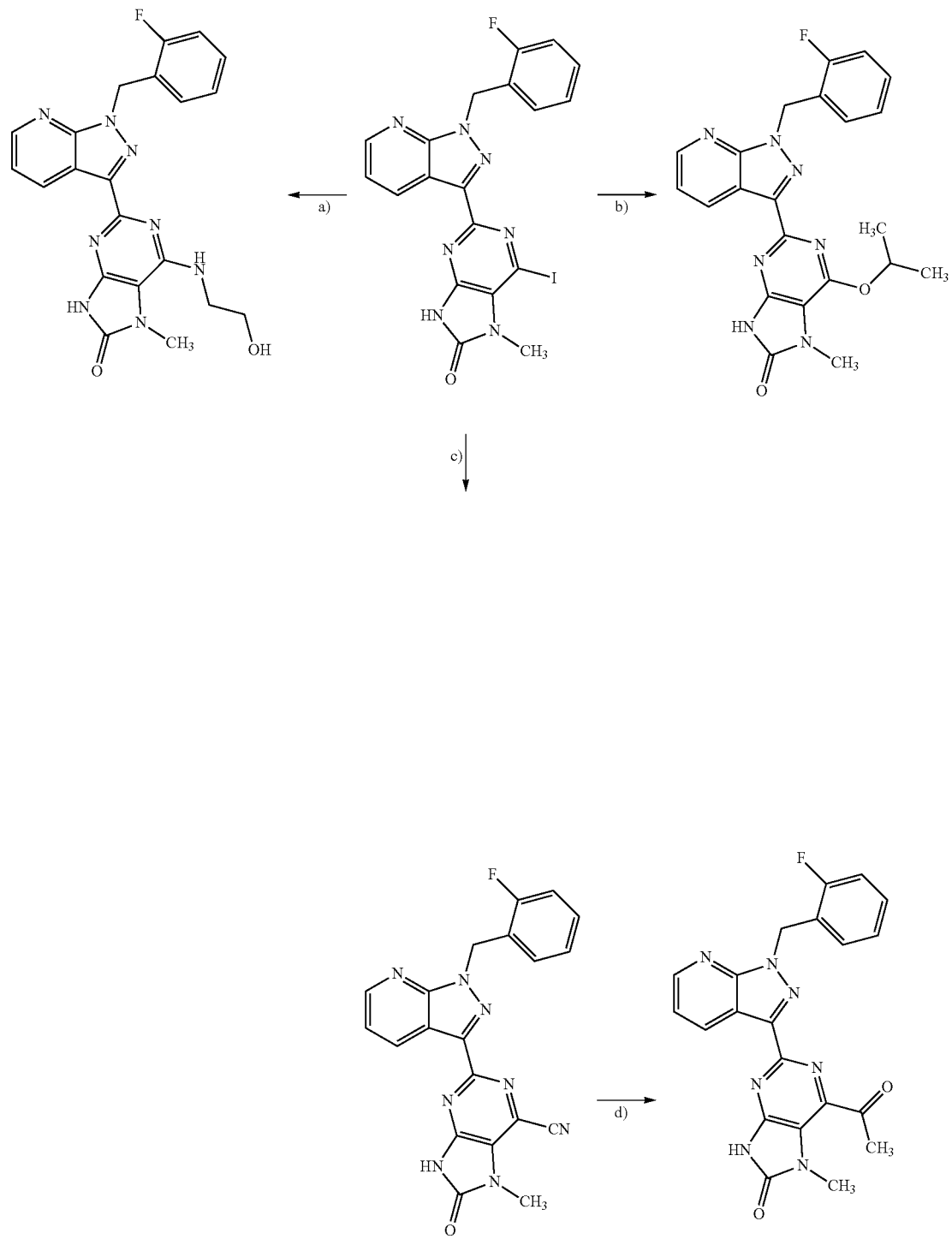

[a); 2-aminoethanol, NMP, microwave, 150° C.; b): isopropanol, CuI, $Cs_2CO_3$, 3,4,7,8-tetramethyl-1,10-phenanthroline, microwave, 140° C.; c) KCN, pyridine, reflux; d): 1. MeMgBr, THF, RT; 2. HCl, $H_2O$].

Further inventive compounds can be prepared by methods known to those skilled in the art, in analogy to processes known from the literature, as described in the present experimental section and as shown in the following synthesis schemes (schemes 10 to 13, 17 and 18):

Scheme 10:
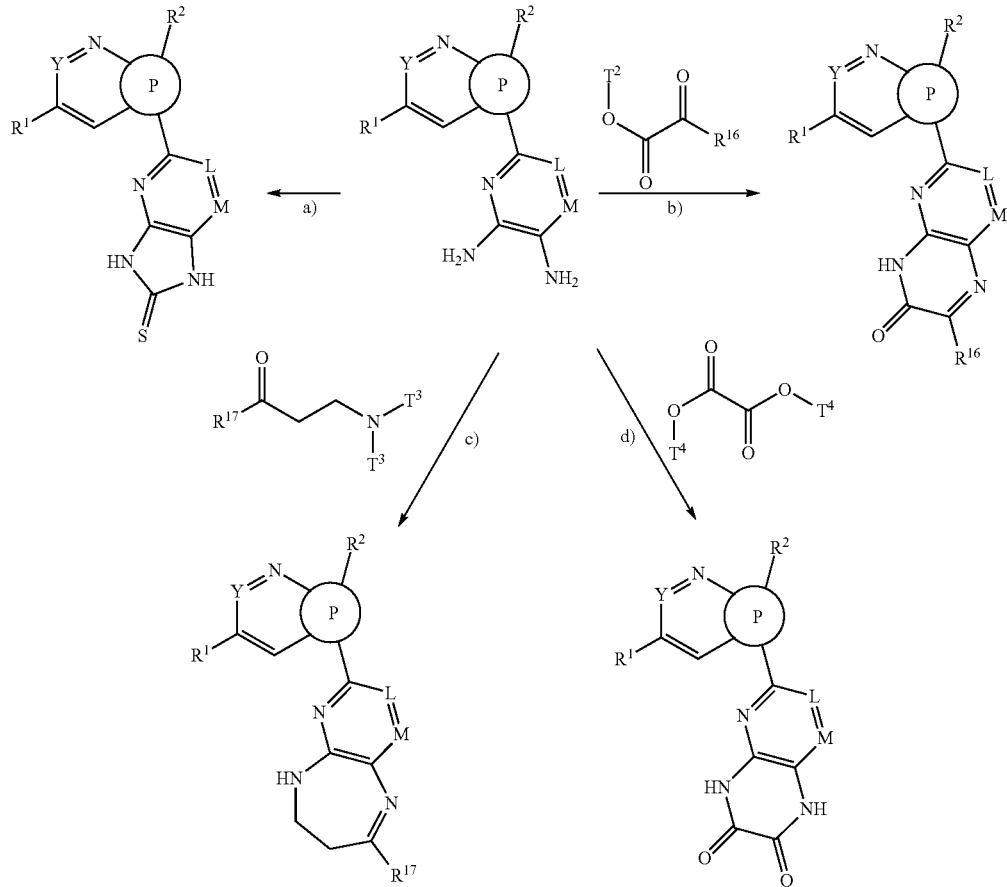
[a]: EtC(=S)SK, ethanol, microwave, 150° C.; b): EtOH, cat. H$_2$SO$_4$, reflux; c): EtOH, microwave, 150° C.; d): NaOMe, EtOH, reflux; T$^2$, T$^3$, T$^4$ = (C$_1$-C$_4$)-alkyl].
Scheme 11:
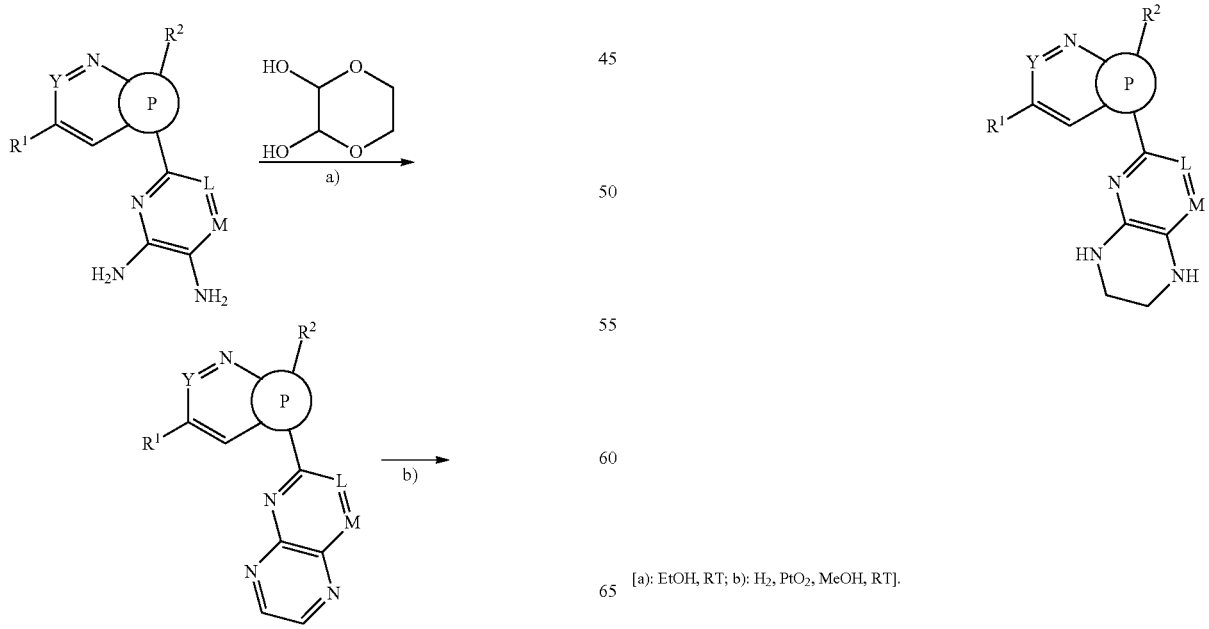
[a): EtOH, RT; b): H$_2$, PtO$_2$, MeOH, RT].

Scheme 12:
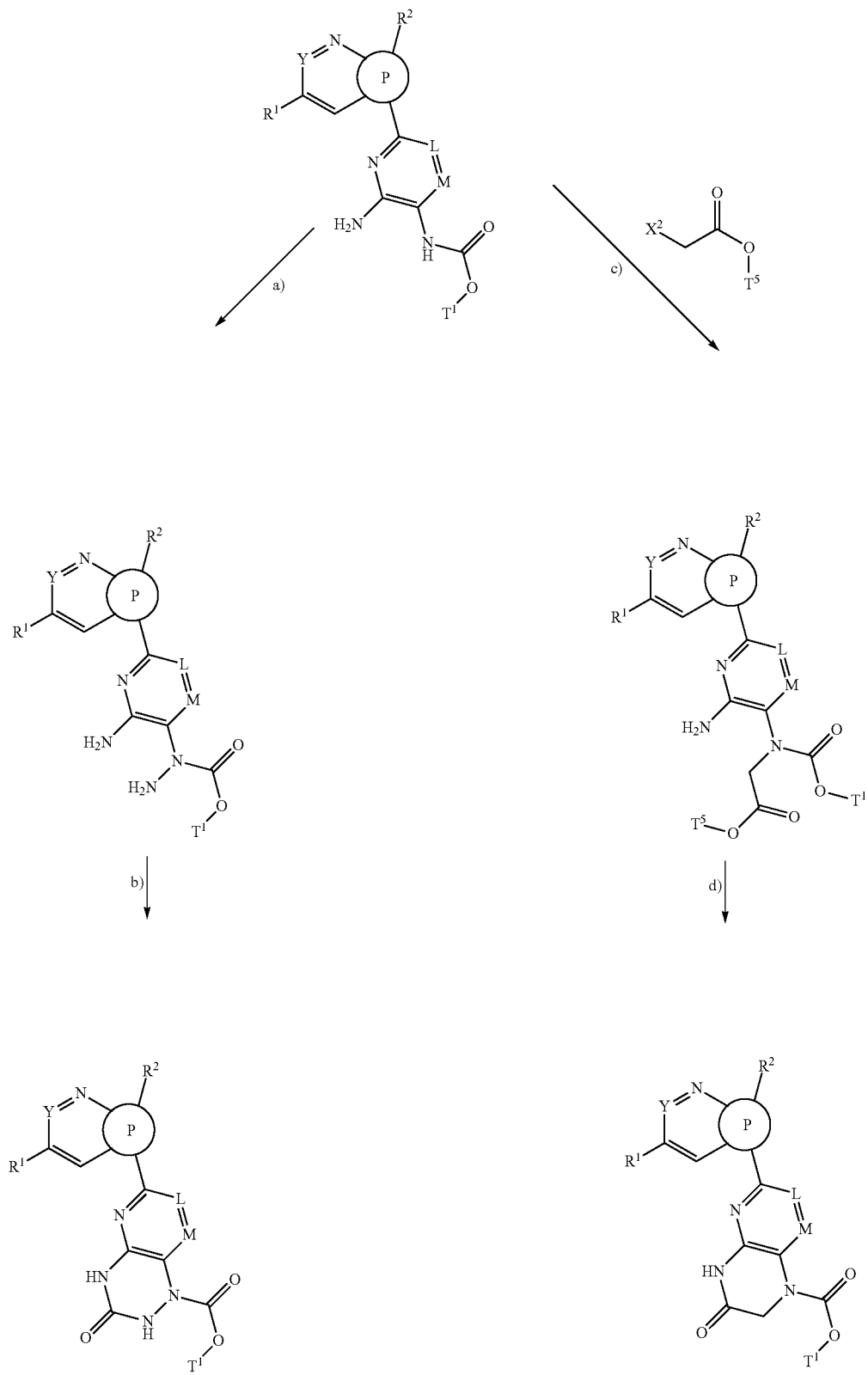
[a]: O-(4-nitrobenzoyl)hydroxylamine, NaN[Si(CH₃)₃]₂, THF, 0° C. → RT; N,N-carbonyldiimidazole, diisopropylethylamine, DMF, RT → 60° C.; c): NaN[Si(CH₃)₃]₂, THF, 0° C. → RT d): LiOH, EtOH/H₂O, RT; $T^1$, $T^5$ = ($C_1$-$C_4$)-alkyl].

Scheme 13:
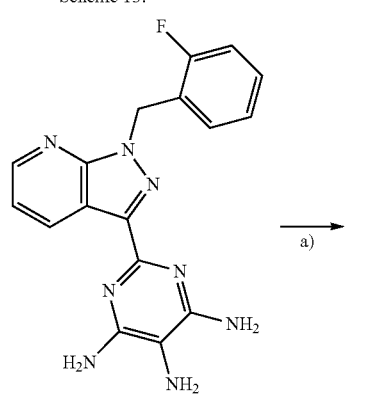
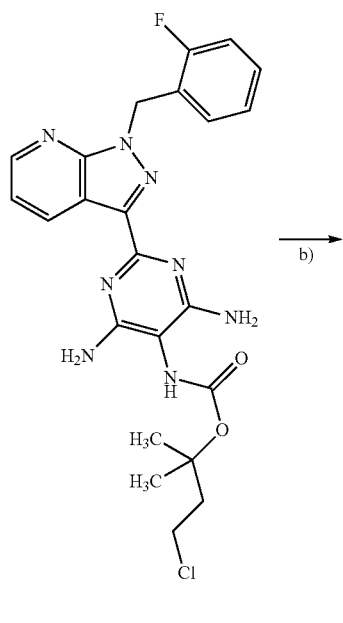
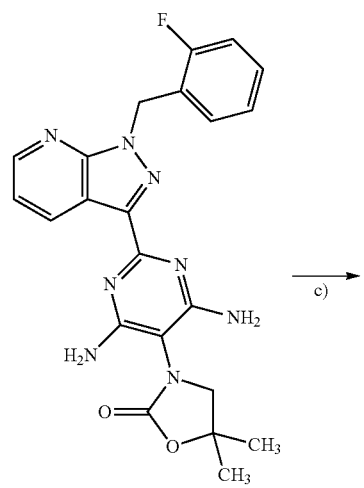
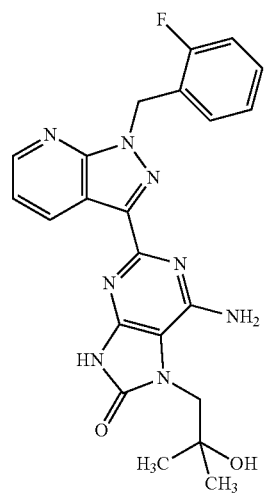
[a]: pyridine, 0° C.; b): NaN[Si(CH$_3$)$_3$]$_2$, THF, 0° C.; c): NaN[Si(CH$_3$)$_3$]$_2$, THF, 0° C.].
Scheme 17:
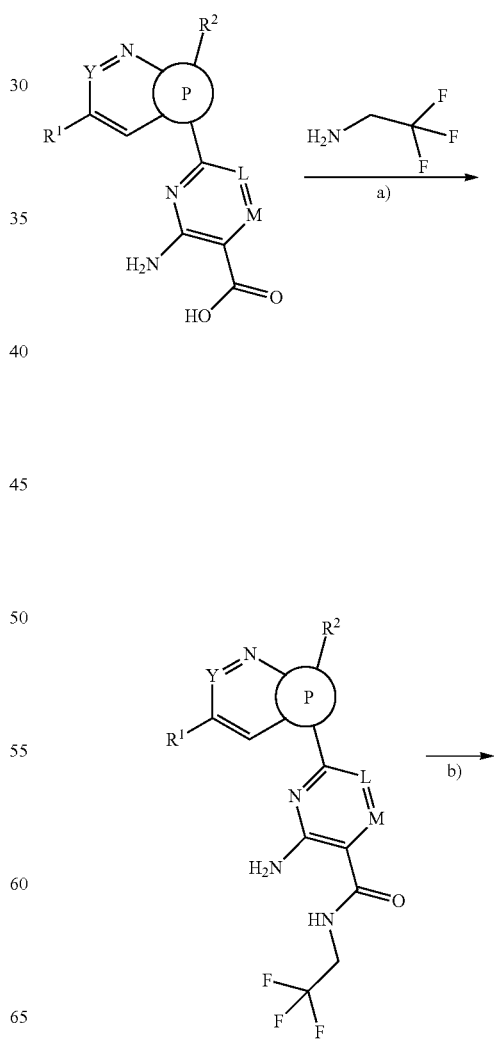

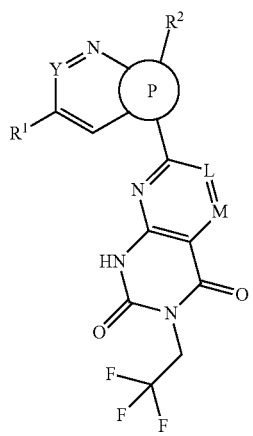

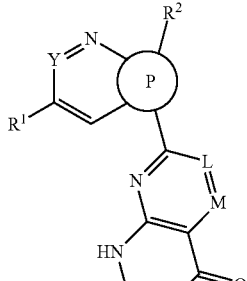

[a]: triethylamine, HOBt, EDC, DMF, 0° C. → RT; b): NaH, CDI, THF, 0° C. → reflux].

Scheme 18:

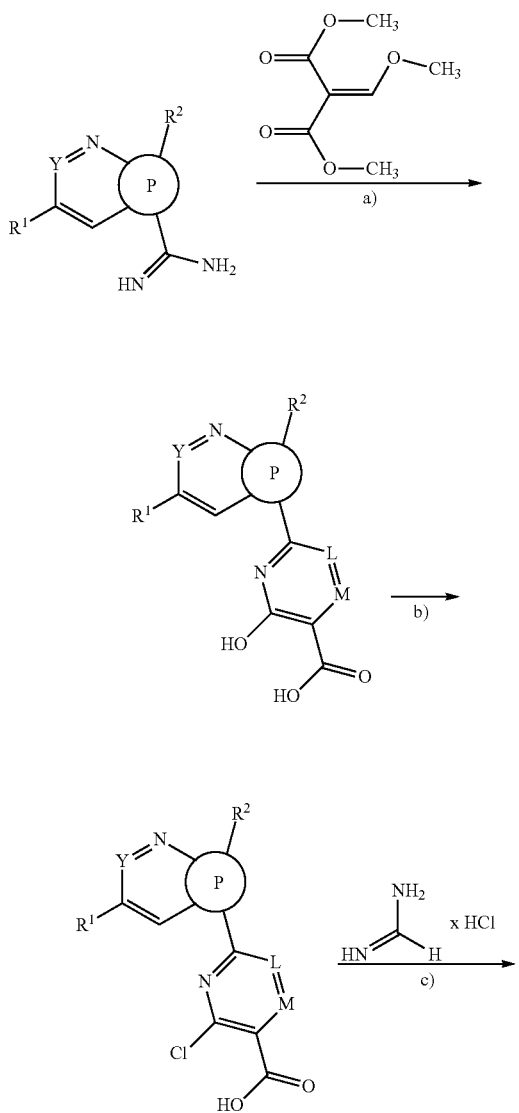

[a]: sodium methoxide, methanol, 50° C.; b): POCl₃, diethylaniline, 90° C.; c): triethylamine, DMF, 80° C.].

The compounds of the formulae (III), (V), (VIII), (X), (XI), (XIII), (XV-1), (XV-2) and (XVI) are commercially available or known from the literature, or can be prepared in analogy to processes known from the literature.

The compounds (II-1), (II-2), (IV), (VII) and (XIV) are prepared as described in WO 03/095451 or WO 2008/031513, or as shown by way of example in the following synthesis schemes (scheme 14 and 15):

Scheme 14:

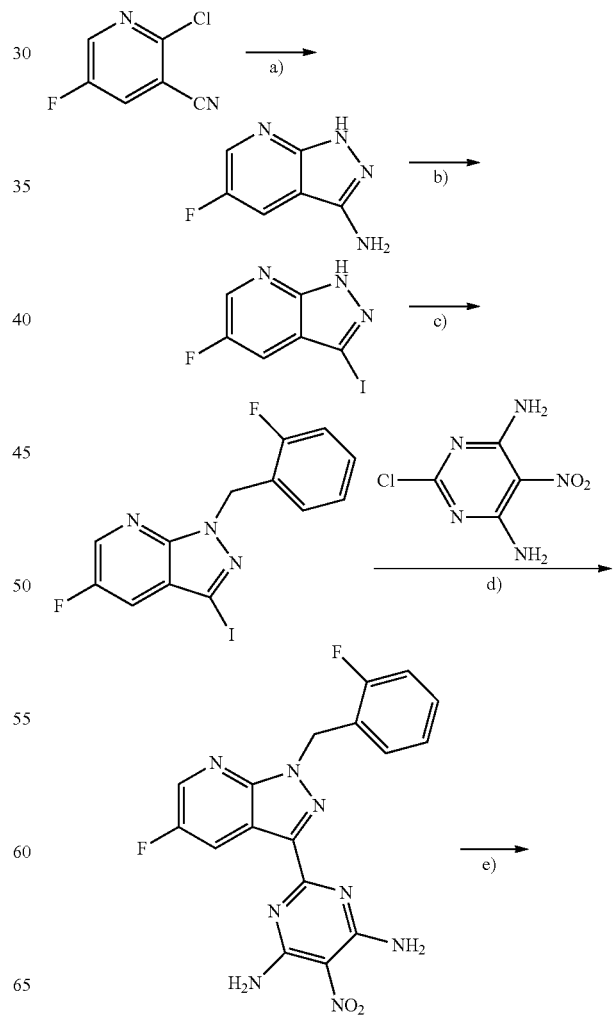

55
-continued
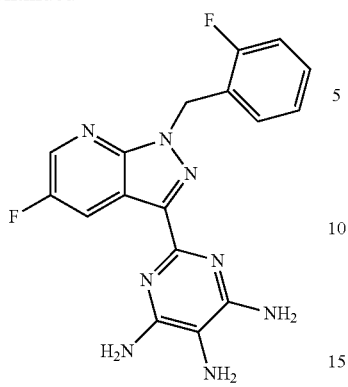
[a]: hydrazine hydrate, 1,2-ethanediol; b): isopentyl nitrite, NaI, THF; c): 2-fluorobenzyl bromide, Cs₂CO₃, DMF; d): Pd(PPh₃)₄, hexabutylditin; e) H₂, Pd—C].
56
-continued
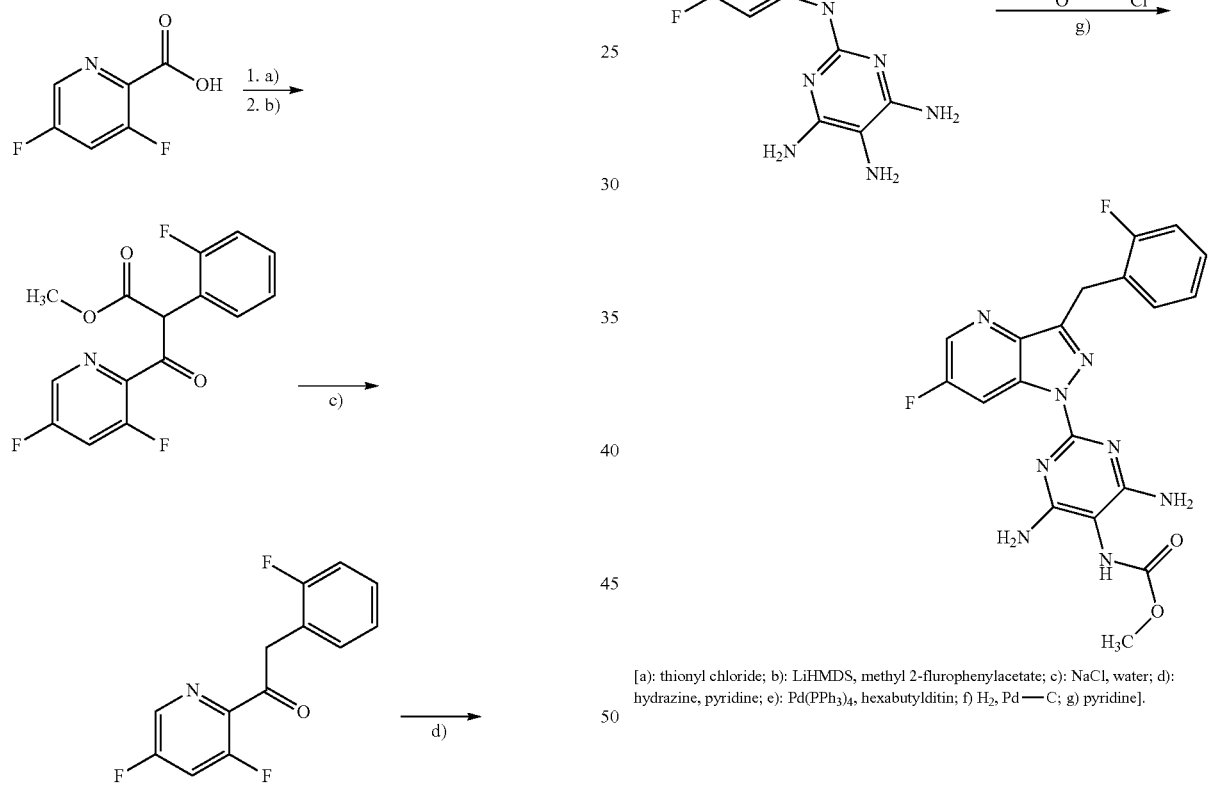
[a]: thionyl chloride; b): LiHMDS, methyl 2-flurophenylacetate; c): NaCl, water; d): hydrazine, pyridine; e): Pd(PPh₃)₄, hexabutylditin; f) H₂, Pd—C; g) pyridine].
Scheme 15:
Scheme 16:

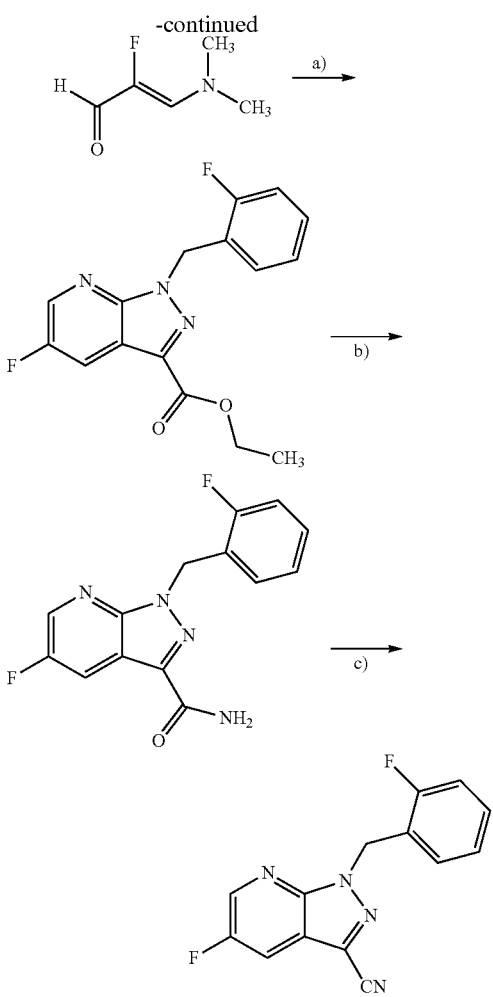

[a]: TFA, dioxane; b) NH₃; c) trifluoroacetic anhydride].

Further reactants can be prepared as described in the present experimental section, including examples 4A, 37A, 39A, 42A, 45A, 50A, 51A, 61A and 65A.

Further inventive compounds can optionally also be prepared by conversions of functional groups of individual substituents, especially those listed for $R^3$, proceeding from compounds of the formula (I) obtained by above processes. These conversions are performed as described in the present experimental section, by customary methods known to those skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carbonamides, and introduction and removal of temporary protecting groups, The inventive compounds act as very potent stimulators of soluble guanylate cyclase, have valuable pharmacological properties and are therefore suitable for treatment and/or prophylaxis of disorders in humans and animals.

The inventive compounds cause vasorelaxation and inhibition of platelet aggregation, and lead to a decrease in blood pressure and to a rise in coronary blood flow. These effects are mediated by direct stimulation of soluble guanylate cyclase and an intracellular rise in cGMP. In addition, the inventive compounds enhance the action of substances which increase the cGMP level, for example EDRF (endothelium-derived relaxing factor), NO donors, protoporphyrin IX, arachidonic acid or phenylhydrazine derivatives.

The inventive compounds are suitable for treatment and/or prophylaxis of cardiovascular, pulmonary, thromboembolic and fibrotic disorders.

The inventive compounds can therefore be used in medicaments for treatment and/or prophylaxis of cardiovascular disorders, for example hypertension, acute and chronic heart failure, coronary heart disease, stable and unstable angina pectoris, peripheral and cardiovascular disorders, arrhythmias, atrial and ventricular arrhythmias and impaired conduction, for example atrioventricular grade I-III blocks (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, Sick-Sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation, for example pulmonary edema, cerebral edema, renal edema or edema caused by heart failure, impaired peripheral perfusion, reperfusion damage, arterial and venous thromboses, microalbuminuria, myocardial insufficiency, endothelial dysfunction, for prevention of restenoses, such as after thrombolysis treatments, percutaneous transluminal angioplasties (PTA), percutaneous transluminal coronary angioplasties (PTCA), heart transplants and bypass operations, and micro- and macrovascular damage (vasculitis), elevated levels of fibrinogen and of low-density LDL, and elevated concentrations of plasminogen activator inhibitor 1 (PAI-1), and for treatment and/or prophylaxis of erectile dysfunction and female sexual dysfunction.

In the context of the present invention, the term heart failure also includes more specific or related types of disease, such as acute decompensated heart failure, right heart failure, left heart failure, global failure, ischemic cardiomyopathy, dilated cardiomyopathy, hypertrophic cardiomyopathy, idiopathic cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

In addition, the compounds according to the invention can also be used for the treatment and/or prophylaxis of arteriosclerosis, impaired lipid metabolism, hypolipoproteinemias, dyslipidemias, hypertriglyceridemias, hyperlipidemias, hypercholesterolemias, abetalipoproteinemias, sitosterolemia, xanthomatosis, Tangier disease, adiposity, obesity and of combined hyperlipidemias and metabolic syndrome.

Moreover, the inventive compounds can be used for treatment and/or prophylaxis of primary and secondary Raynaud's phenomenon, of microcirculation disorders, claudication, peripheral and autonomic neuropathies, diabetic microangiopathies, diabetic retinopathy, diabetic ulcers at the extremities, gangrene, CREST syndrome, erythematosis, onychomycosis, rheumatic disorders, and for promotion of wound healing.

Furthermore, the inventive compounds are suitable for treatment urological disorders, for example benign prostate syndrome (BPS), benign prostate hyperplasia (BPH), benign prostate enlargement (BPE), bladder outlet obstruction (BOO), lower urinary tract syndrome (LUTS, including feline urological syndrome (FUS)), disorders of the urogenital system including neurogenic overactive bladder (OAB) and (IC), incontinence (UI), for example mixed, urge, stress or overflow incontinence (MUI, UUI, SUI, OUI), pelvic pain, benign and malignant disorders of the organs in the male and female urogenital systems.

Furthermore, the inventive compounds are suitable for treatment and/or prophylaxis of renal disorders, especially of acute and chronic renal insufficiency, and of acute and chronic kidney failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the inventive compounds for treatment and/or prophylaxis of sequelae of renal insufficiency, for example pulmonary edema, heart failure, uremia, anemia, electrolyte disturbances (for example hypercalemia, hyponatremia) and disturbances in bone and carbohydrate metabolism.

Furthermore, the inventive compounds are also suitable for treatment and/or prophylaxis of asthmatic disorders, pulmonary arterial hypertension (PAH) and other forms of pulmonary hypertension (PH) including pulmonary hypertension associated with left heart disease, HIV, sickle cell anemia, thromboembolisms (CTEPH), sarcoidosis, COPD or pulmonary fibrosis, or chronic-obstructive pulmonary disease (COPD), acute respiratory distress syndrome (ARDS), acute lung injury (ALI), alpha-1 antitrypsin deficiency (AATD), pulmonary fibrosis, pulmonary emphysema (for example pulmonary emphysema induced by cigarette smoke) and cystic fibrosis (CF).

The compounds described in the present invention are also active ingredients for control of central nervous system disorders characterized by disturbances of the NO/cGMP system. More particularly, they are suitable for improving perception, concentration, learning or memory after cognitive impairments such as those occurring particularly in the event of situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children having learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunction and disrupted sleep, and for control of pathological disturbances of the intake of food, stimulants and addictive substances.

Furthermore, the inventive compounds are also suitable for regulating cerebral blood flow and are thus effective agents for control of migraine. They are also suitable for prophylaxis and control of sequelae of cerebral infarct (cerebral apoplexy) such as stroke, cerebral ischemia and skull-brain trauma. The inventive compounds can likewise be used to control states of pain and tinnitus.

Moreover, the inventive compounds have antiinflammatory action and can therefore be used as antiinflammatories for treatment and/or prophylaxis of sepsis (SIRS), multiple organ failure (MODS, MOF), inflammatory disorders of the kidney, chronic bowel inflammation (IBD, Crohn's Disease, UC), pancreatitis, peritonitis, rheumatoid disorders, inflammatory skin disorders and inflammatory eye disorders.

In addition, the inventive compounds can likewise be used for treatment and/or prophylaxis of autoimmune disorders.

Furthermore, the inventive compounds are suitable for treatment and/or prophylaxis of fibrotic disorders of the internal organs, for example of the lung, of the heart, of the kidneys, of the bone marrow and especially of the liver, and also of dermatological fibroses and fibrotic disorders of the eye. In the context of the present inventions, the term "fibrotic disorders" encompasses especially the following terms: hepatic fibrosis, hepatic cirrhosis, pulmonary fibrosis, endomyocardial fibrosis, nephropathy, glomerulonephritis, interstitial renal fibrosis, fibrotic damage resulting from diabetes, myelofibrosis and similar fibrotic disorders, scleroderma, morphea, keloids, hypertrophic scarring (including after surgical interventions), naevi, diabetic retinopathy, proliferative vitreoretinopathy and disorders of the connective tissue (for example sarcoidosis).

Furthermore, the inventive compounds are suitable for control of postoperative scarring, for example resulting from glaucoma operations.

The inventive compounds can likewise be used cosmetically, in the case of ageing and keratinized skin.

Moreover, the inventive compounds are suitable for treatment and/or prophylaxis of hepatitis, neoplasms, osteoporosis, glaucoma and gastroparesis.

The present invention further provides for the use of the inventive compounds for treatment and/or prophylaxis of disorders, especially of the aforementioned disorders.

The present invention further provides for the use of the inventive compounds for treatment and/or prophylaxis of heart failure, angina pectoris, hypertension, pulmonary hypertension, ischemia, vascular disorders, renal insufficiency, thromboembolic disorders, fibrotic disorders and arteriosclerosis.

The present invention further provides the inventive compounds for use in a method for treatment and/or prophylaxis of heart failure, angina pectoris, hypertension, pulmonary hypertension, ischemia, vascular disorders, kidney failure, thromboembolic disorders, fibrotic disorders and arteriosclerosis.

The present invention further provides for the use of the inventive compounds for production of a medicament for treatment and/or prophylaxis of disorders, especially of the aforementioned disorders.

The present invention further provides for the use of the inventive compounds for production of a medicament for treatment and/or prophylaxis of heart failure, angina pectoris, hypertension, pulmonary hypertension, ischemia, vascular disorders, kidney failure, thromboembolic disorders, fibrotic disorders and arteriosclerosis.

The present invention further provides a method for treatment and/or prophylaxis of disorders, especially of the aforementioned disorders, using an effective amount of at least one of the inventive compounds.

The present invention further provides a method for treatment and/or prophylaxis of heart failure, angina pectoris, hypertension, pulmonary hypertension, ischemia, vascular disorders, kidney failure, thromboembolic disorders, fibrotic disorders and arteriosclerosis using an effective amount of at least one of the inventive compounds.

The inventive compounds can be used alone or, if required, in combination with other active ingredients. The present invention further provides medicaments comprising at least one of the inventive compounds and one or more further active ingredients, especially for treatment and/or prophylaxis of the aforementioned disorders. Preferred examples of suitable combination active ingredients include:

- organic nitrates and NO donors, for example sodium nitroprusside, nitroglycerine, isosorbide mononitrate, isosorbide dinitrate, molsidomine or SIN-1, and inhaled NO;
- compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;
- antithrombotic agents, by way of example and with preference from the group of the platelet aggregation inhibitors, the anticoagulants or the profibrinolytic substances;
- hypotensive active ingredients, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or
- active ingredients which modify lipid metabolism, by way of example and with preference from the group of the thyroid receptor agonists, cholesterol synthesis inhibitors, by way of example and with preference HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Antithrombotic agents are preferably understood to mean compounds from the group of the platelet aggregation inhibitors, the anticoagulants or the profibrinolytic substances.

In a preferred embodiment of the invention, the inventive compounds are administered in combination with a platelet aggregation inhibitor, by way of example and with preference aspirin, clopidogrel, ticlopidin or dipyridamole.

In a preferred embodiment of the invention, the inventive compounds are administered in combination with a thrombin inhibitor, by way of example and with preference ximelagatran, melagatran, bivalirudin or clexane.

In a preferred embodiment of the invention, the inventive compounds are administered in combination with a GPIIb/IIIa antagonist, by way of example and with preference tirofiban or abciximab.

In a preferred embodiment of the invention, the inventive compounds are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the inventive compounds are administered in combination with heparin or with a low molecular weight (LMW) heparin derivative.

In a preferred embodiment of the invention, the inventive compounds are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists and the diuretics.

In a preferred embodiment of the invention, the inventive compounds are administered in combination with a calcium antagonist, by way of example and with preference nifedipine, amlodipine, verapamil or diltiazem.

In a preferred embodiment of the invention, the inventive compounds are administered in combination with an alpha-1-receptor blocker, by way of example and with preference prazosin.

In a preferred embodiment of the invention, the inventive compounds are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, by way of example and with preference losartan, candesartan, valsartan, telmisartan or embursatan.

In a preferred embodiment of the invention, the inventive compounds are administered in combination with an ACE inhibitor, by way of example and with preference enalapril, captopril, lisinopril, ramipril, delapril, fosinopril, quinopril, perindopril or trandopril.

In a preferred embodiment of the invention, the inventive compounds are administered in combination with an endothelin antagonist, by way of example and with preference bosentan, darusentan, ambrisentan or sitaxsentan.

In a preferred embodiment of the invention, the inventive compounds are administered in combination with a renin inhibitor, by way of example and with preference aliskiren, SPP-600 or SPP-800.

In a preferred embodiment of the invention, the inventive compounds are administered in combination with a mineralocorticoid receptor antagonist, by way of example and with preference spironolactone or eplerenone.

In a preferred embodiment of the invention, the inventive compounds are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein (a) antagonists.

In a preferred embodiment of the invention, the inventive compounds are administered in combination with a CETP inhibitor, by way of example and with preference dalcetrapib, BAY 60-5521, anacetrapib or CETP vaccine (CETi-1).

In a preferred embodiment of the invention, the inventive compounds are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the inventive compounds are administered in combination with an HMG-CoA reductase inhibitor from the class of statins, by way of example and with preference lovastatin, simvastatin, pravastatin, fluvastatin, atorvastatin, rosuvastatin, cerivastatin or pitavastatin.

In a preferred embodiment of the invention, the inventive compounds are administered in combination with a squalene synthesis inhibitor, by way of example and with preference BMS-188494 or TAK-475.

In a preferred embodiment of the invention, the inventive compounds are administered in combination with an ACAT inhibitor, by way of example and with preference avasimibe, melinamide, pactimibe, eflucimibe or SMP-797.

In a preferred embodiment of the invention, the inventive compounds are administered in combination with an MTP inhibitor, by way of example and with preference implitapide, BMS-201038, R-103757 or JTT-130.

In a preferred embodiment of the invention, the inventive compounds are administered in combination with a PPAR-gamma agonist, by way of example and with preference pioglitazone or rosiglitazone.

In a preferred embodiment of the invention, the inventive compounds are administered in combination with a PPAR-delta agonist, by way of example and with preference GW 501516 or BAY 68-5042.

In a preferred embodiment of the invention, the inventive compounds are administered in combination with a cholesterol absorption inhibitor, by way of example and with preference ezetimibe, tiqueside or pamaqueside.

In a preferred embodiment of the invention, the inventive compounds are administered in combination with a lipase inhibitor, by way of example and with preference orlistat.

In a preferred embodiment of the invention, the inventive compounds are administered in combination with a polymeric bile acid adsorbent, by way of example and with preference cholestyramine, colestipol, colesolvam, CholestaGel or colestimide.

In a preferred embodiment of the invention, the inventive compounds are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the inventive compounds are administered in combination with a lipoprotein (a) antagonist, by way of example and with preference gemcabene calcium (CI-1027) or nicotinic acid.

The present invention further provides medicaments which comprise at least one inventive compound, typically together with one or more inert nontoxic pharmaceutically suitable excipients, and for the use thereof for the aforementioned purposes.

The inventive compounds can act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

For these administration routes, the inventive compounds can be administered in suitable administration forms.

Suitable administration forms for oral administration are those which work according to the prior art, which release the inventive compounds rapidly and/or in a modified manner and which contain the inventive compounds in crystalline and/or amorphized and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The inventive compounds can be converted to the administration forms listed. This can be accomplished in a manner known per se by mixing with inert nontoxic pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavor and/or odor correctors.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dosage is about 0.01 to 100 mg/kg, preferably about 0.01 to 20 mg/kg and most preferably 0.1 to 10 mg/kg of body weight.

It may nevertheless be necessary where appropriate to deviate from the stated amounts, specifically as a function of the body weight, route of administration, individual response to the active ingredient, nature of the preparation and time or interval over which administration takes place. For instance, in some cases, less than the aforementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not limited to the examples.

Unless stated otherwise, the percentages in the tests and examples which follow are percentages by weight; parts are parts by weight. Solvent ratios, dilution ratios and concentration figures for liquid/liquid solutions are each based on volume.

A. EXAMPLES

Abbreviations and Acronyms aq. aqueous solution
BEMP 2-(tert-butylimino)-N,N-diethyl-1,3-dimethyl-1,3,2lambda$^5$-diazaphosphinan-2-amine
calc. calculated
DCI direct chemical ionization (in MS)
DMF dimethylformamide
DMSO dimethyl sulfoxide
eq. equivalent(s)
ESI electrospray ionization (in MS)
Et ethyl
h hour(s)
HPLC high-pressure high-performance liquid chromatography
HRMS high-resolution mass spectrometry
conc. concentrated
LC/MS liquid chromatography-coupled mass spectrometry
LiHMDS lithium hexamethyldisilazide
Me methyl
min minute(s)
MS mass spectrometry
NMR nuclear magnetic resonance spectrometry
Pd/C palladium on activated carbon (10%)
Pd$_2$dba$_3$ tris(dibenzylideneacetone)dipalladium
Ph phenyl
RT room temperature
R$_t$ retention time (in HPLC)
THF tetrahydrofuran
UV ultraviolet spectrometry
v/v volume to volume ratio (of a solution)
XPHOS dicyclohexyl(2',4',6'-triisopropylbiphenyl-2-yl)phosphine LC/MS Methods:
Method 1 (LC-MS):
Instrument: Micromass Quattro LCZ with HPLC Agilent Series 1100; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 2 (LC-MS):
Instrument: Waters ACQUITY SQD UPLC System; column: Waters Acquity UPLC HSS T3 1.8µ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 210-400 nm.

Method 3 (LC-MS):
Instrument: Micromass QuattroPremier with Waters UPLC Acquity; column: Thermo Hypersil GOLD 1.9µ 50 mm×1 mm; eluent A: 1 l water+0.5 ml 50% formic acid, eluent B: 1 l acetonitrile+0.5 ml 50% formic acid; gradient: 0.0 min 90% A→0.1 min 90% A→1.5 min 10% A→2.2 min 10% A; flow rate: 0.33 ml/min; oven: 50° C.; UV detection: 210 nm.

Method 4 (LC-MS):
Instrument: Micromass Quattro Micro MS with HPLC Agilent Series 1100; column: Thermo Hypersil GOLD 3µ 20 mm×4 mm; eluent A: 1 l water+0.5 ml 50% formic acid, eluent B: 1 l acetonitrile+0.5 ml 50% formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 5 (LC-MS): MCW-SQ3-HSST3-2-30 mm
Instrument: Waters ACQUITY SQD UPLC System; column: Waters Acquity UPLC HSS T3 1.8µ 30×2 mm; eluent A: 1 l water+0.25 ml 99% formic acid, eluent B: 1 l acetonitrile+0.25 ml 99% formic acid; gradient: 0.0 min 90% A→>1.2 min 5% A→>2.0 min 5% A; oven: 50° C.; flow rate: 0.60 ml/min; UV detection: 208-400 nm.

General Methods:

General Method 1:

In a microwave vessel with stirrer magnet, 1.0 eq of example 3A was dissolved together with 1.0 eq of the appropriate amino nitrile and 1.0 eq of potassium tert-butoxide in dimethylformamide (1.5 ml), and the vessel was closed and heated at 160° C. under microwave irradiation for 1 h. This was followed by reaction analysis. In the case of incomplete conversion, a further 0.5 eq of potassium tert-butoxide was added and the mixture was heated again at 160° C. under microwave irradiation until complete conversion. The reaction mixture was purified by means of preparative HPLC (eluent: acetonitrile/water with 0.05% formic acid, gradient).

Starting Compounds and Intermediates

Example 1A

2-[1-(2-Fluorobenzyl)-1H-pyrazolo[3,4-b]pyridin-3-yl]pyrimidine-4,5,6-triamine

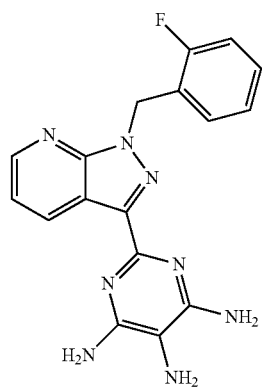 [SMILES: Nc1nc(-c2nn(Cc3ccccc3F)c3ncccc23)nc(N)c1N]

The synthesis of this compound is described in WO 03/095451, example 8A.

Example 2A

2-[3-(2-Fluorobenzyl)-1H-pyrazolo[4,3-b]pyridin-1-yl]pyrimidine-4,5,6-triamine

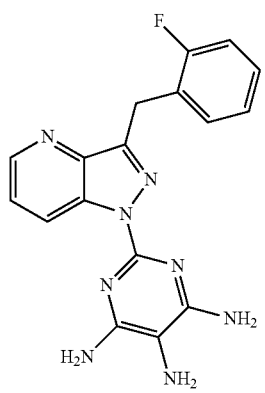 [SMILES: Nc1nc(-n2nc(Cc3ccccc3F)c3ncccc32)nc(N)c1N]

The synthesis of this compound is described in WO 2008/031513, example 8.

Example 3A 1-(2-Fluorobenzyl)-1H-pyrazolo[3,4-b]pyridine-3-carbonitrile

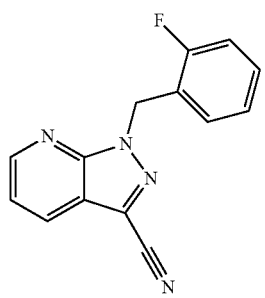 [SMILES: N#Cc1nn(Cc2ccccc2F)c2ncccc12]

The synthesis of this compound is described in WO 03/095451, example 4A.

Example 4A

4-Amino-2-[1-(2-fluorobenzyl)-1H-pyrazolo[3,4-b]pyridin-3-yl]pyrimidin-5-ol

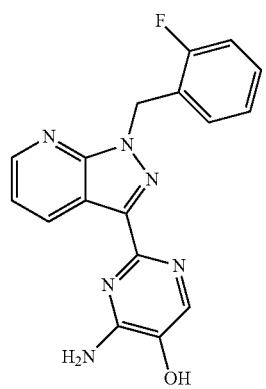 [SMILES: Nc1nc(-c2nn(Cc3ccccc3F)c3ncccc23)ncc1O]

The synthesis of this compound is described in ChemMedChem, 4(5), 853-865; 2009.

Example 5A 1-(2-Fluorobenzyl)-1H-pyrazolo[3,4-b]pyridine-3-carboximidamide hydrochloride

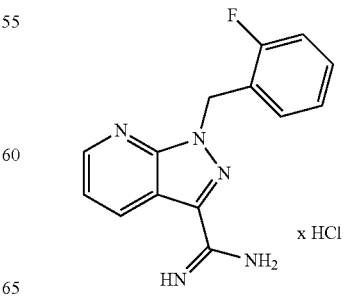

The synthesis of this compound is described in WO 03/095451, example 6A.

Example 6A

2-Chloroethyl {4,6-diamino-2-[1-(2-fluorobenzyl)-1H-pyrazolo[3,4-b]pyridin-3-yl]pyrimidin-5-yl}carbamate

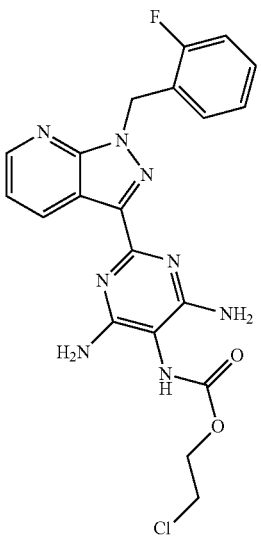 [SMILES: Nc1nc(-c2nn(Cc3ccccc3F)c3ncccc23)nc(N)c1NC(=O)OCCCl]

1.50 g (4.281 mmol) of the compound from example 1A were dissolved in 15 ml of dichloromethane and 15 ml of pyridine. Thereafter, 612 mg (4.281 mmol) of 2-chloroethyl chloroformate were added while stirring. The mixture was then warmed to RT and stirred at this temperature for 12 h. The mixture was then poured onto ice-water and extracted twice with dichloromethane. The combined organic phases were dried with sodium sulfate and concentrated under reduced pressure. This gave 1.031 g (52% of theory) of the title compound, which were converted further without further purification.

LC-MS (method 2): $R_t$=0.78 min; MS (EIpos): m/z=457 (M+H)$^+$.

Example 7A

1-Chloro-2-methylpropan-2-yl {4,6-diamino-2-[1-(2-fluorobenzyl)-1H-pyrazolo[3,4-b]pyridin-3-yl]pyrimidin-5-yl}carbamate

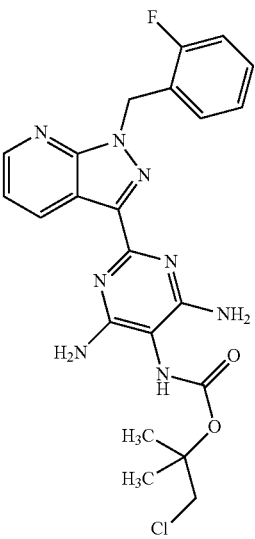 [SMILES: CC(C)(CCl)OC(=O)Nc1c(N)nc(-c2nn(Cc3ccccc3F)c3ncccc23)nc1N]

175 µl (1.713 mmol) of 1-chloro-2-methyl-2-propanol were initially charged in 6 ml of dichloromethane, 169 mg (0.571 mmol) of bis(trichloromethyl) carbonate were added and the mixture was cooled to 0° C. Thereafter, 110 µl (1.37 mmol) of pyridine were added dropwise and the mixture was stirred at 0° C. for 30 min. Subsequently, 400 mg (1.142 mmol) of the compound from example 1A were added, and then 2.93 ml (36.26 mmol) of pyridine. The mixture was stirred at 0° C. for a further 30 min. Then a separate flask was initially charged with 87 µl (0.856 mmol) of 1-chloro-2-methyl-2-propanol in 3 ml of dichloromethane, and 85 mg (0.285 mmol) of bis(trichloromethyl) carbonate were added. After adding 55 µl (0.685 mmol) of pyridine, the mixture was stirred at 0° C. for 30 min and the solution thus prepared was added to the mixture described above. After stirring at 0° C. for a further 30 min, the reaction was stopped by addition of 10 ml of saturated aqueous sodium hydrogencarbonate solution and extracted three times with dichloromethane. The combined organic phases were dried with sodium sulfate and concentrated under reduced pressure. This gave 500 mg (84% of theory) of the title compound, which were used without further purification in the subsequent experiments.

LC-MS (method 2): $R_t$=0.86 min; MS (EIpos): m/z=485 (M+H)$^+$.

Example 8A

3-{4,6-Diamino-2-[1-(2-fluorobenzyl)-1H-pyrazolo[3,4-b]pyridin-3-yl]pyrimidin-5-yl}-5,5-dimethyl-1,3-oxazolidin-2-one

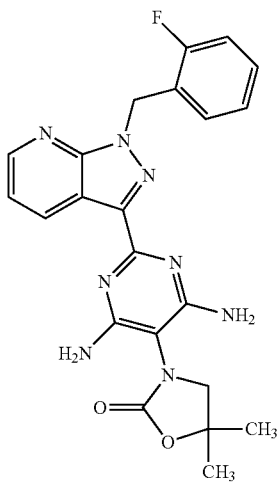 [SMILES: CC1(C)CN(c2c(N)nc(-c3nn(Cc4ccccc4F)c4ncccc34)nc2N)C(=O)O1]

500 mg (1.033 mmol) of the compound prepared in example 7A were dissolved in tetrahydrofuran (10 ml), and 1.033 ml of a 1M solution of bis(trimethylsilyl)sodium amide solution in tetrahydrofuran were added at 0° C. After stirring at 0° C. for 5 min, the reaction was stopped by addition of saturated aqueous sodium hydrogencarbonate solution and extracted twice with ethyl acetate. The combined organic phases were dried with sodium sulfate and concentrated under reduced pressure. The residue was purified by means of preparative HPLC (acetonitrile:water (+0.05% formic acid) gradient). 329 mg of the title compound were obtained (71% of theory).

LC-MS (method 2): $R_t$=0.83 min; MS (EIpos): m/z=449 (M+H)$^+$.

$^1$H NMR (400 MHz, DMSO-d$_6$): δ [ppm]=1.55 (s, 6H), 3.43 (s, 2H), 5.81 (s, 2H), 6.44 (s br, 4H) 7.10-7.14 (m, 2H), 7.20-7.25 (m, 1H), 7.32-7.37 (m, 2H), 8.61 (dd, 1H), 9.08 (dd, 1H).

Example 9A

3-Bromo-1,1,1-trifluoropropan-2-yl {4,6-diamino-2-[1-(2-fluorobenzyl)-1H-pyrazolo[3,4-b]pyridin-3-yl]pyrimidin-5-yl}carbamate

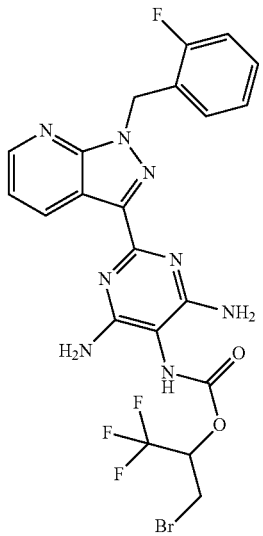 [SMILES: Nc1nc(-c2nn(Cc3ccccc3F)c3ncccc23)nc(N)c1NC(=O)OC(CBr)C(F)(F)F]

0.888 ml (8.563 mmol) of 3-bromo-1,1,1-trifluoro-2-propanol were initially charged in 22 ml of dichloromethane, 952 mg (3.211 mmol) of bis(trichloromethyl) carbonate were added and the mixture was cooled to 0° C. Thereafter, 0.519 ml (6.422 mmol) of pyridine were added dropwise and the mixture was stirred at 0° C. for 1 h. Then 1.5 g (4.281 mmol) of the compound from example 1A dissolved in pyridine (11 ml) were added and the mixture was stirred at 0° C. for a further 30 min. After a further 12 h at RT, the reaction was stopped by addition of 30 ml of saturated aqueous sodium hydrogencarbonate solution and extracted three times with dichloromethane. The combined organic phases were dried with sodium sulfate and concentrated under reduced pressure. The residue was purified by chromatography on silica gel (dichloromethane/methanol gradient). This gave 532 mg (21% of theory) of the title compound.

LC-MS (method 2): $R_t$=0.92 min; MS (EIpos): m/z=569/571 [M+H, Br pattern]⁺.

Example 10A

3-{4,6-Diamino-2-[1-(2-fluorobenzyl)-1H-pyrazolo[3,4-b]pyridin-3-yl]pyrimidin-5-yl}-5-(trifluoromethyl)-1,3-oxazolidin-2-one

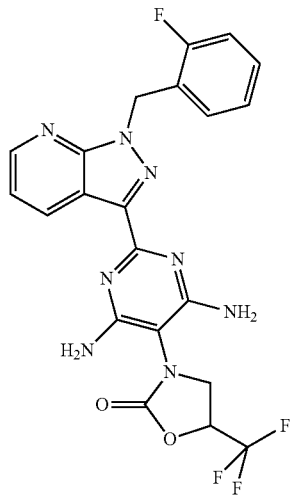 [SMILES: Nc1nc(-c2nn(Cc3ccccc3F)c3ncccc23)nc(N)c1N1CC(C(F)(F)F)OC1=O]

Example 10A was prepared from example 9A in analogy to the preparation of example 8A.

LC-MS (method 2): $R_t$=0.89 min; MS (EIpos): m/z=489 (M+H)⁺.

Example 11A

Methyl {4,6-diamino-2-[1-(2-fluorobenzyl)-1H-pyrazolo[3,4-b]pyridin-3-yl]pyrimidin-5-yl}carbamate

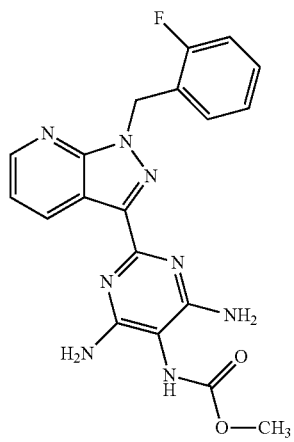 [SMILES: COC(=O)Nc1c(N)nc(-c2nn(Cc3ccccc3F)c3ncccc23)nc1N]

The synthesis of this compound is described in WO 03/095451, example 5.

Example 12A

Methyl {4,6-diamino-2-[1-(2-fluorobenzyl)-1H-pyrazolo[3,4-b]pyridin-3-yl]pyrimidin-5-yl}(2,2-difluoroethyl)carbamate

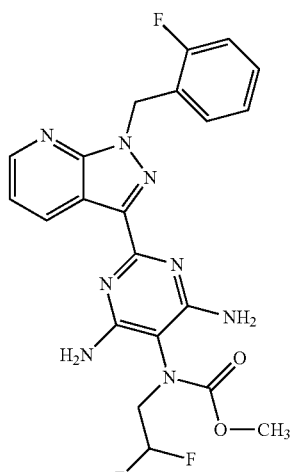

400 mg (0.979 mmol) of the compound from example 11A were initially charged in 10 ml of tetrahydrofuran and cooled to 0° C. Thereafter, 43 mg (1.077 mmol) of sodium hydride (60% in mineral oil) were added and the mixture was stirred at 0° C. while stirring for 30 min Subsequently, 230 mg (1.077 mmol) of 2,2-difluoroethyl trifluoromethanesulfonate were added and the mixture was stirred at RT for 1 h. Thereafter, the same amount of sodium hydride and 2,2-difluoroethyl trifluoromethanesulfonate again was added and the mixture was stirred at RT overnight. Thereafter, the reaction was stopped with 0.5 ml of water. The reaction mixture was purified by means of preparative HPLC (acetonitrile/water (+0.05% formic acid) gradient). 198 mg of the title compound were obtained (42% of theory).

LC-MS (method 2): $R_t$=0.86 min; MS (EIpos): m/z=473 (M+H)⁺.

$^1$H NMR (400 MHz, DMSO-d$_6$): δ [ppm]=3.61 (s, 3H), 3.69-3.75 (m, 2H), 5.81 (s, 2H), 6.15-6.47 (m, 1H), 6.55 (s br, 4H) 7.07-7.14 (m, 2H), 7.20-7.26 (m, 1H), 7.31-7.40 (m, 2H), 8.61 (dd, 1H), 9.04 (dd, 1H).

Example 13A

Methyl {4,6-diamino-2-[1-(2-fluorobenzyl)-1H-pyrazolo[3,4-b]pyridin-3-yl]pyrimidin-5-yl}methylcarbamate

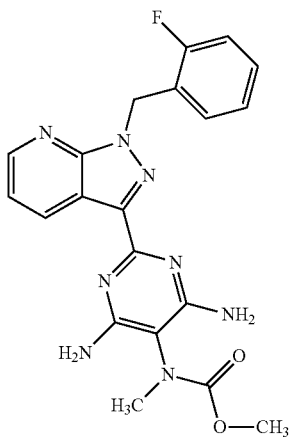 [SMILES: COC(=O)N(C)c1c(N)nc(-c2nn(Cc3ccccc3F)c3ncccc23)nc1N]

The synthesis of this compound is described in WO 03/095451, example 1.

Example 14A

Methyl {4,6-diamino-2-[1-(2-fluorobenzyl)-1H-pyrazolo[3,4-b]pyridin-3-yl]pyrimidin-5-yl}ethylcarbamate

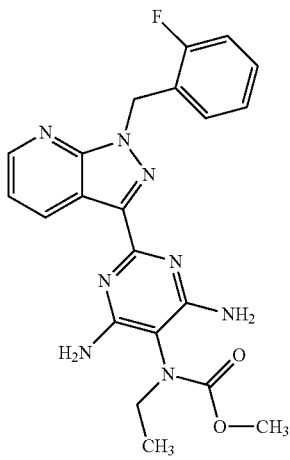 [SMILES: CCN(C(=O)OC)c1c(N)nc(-c2nn(Cc3ccccc3F)c3ncccc23)nc1N]

200 mg (0.490 mmol) of the compound from example 11A were dissolved in 2 ml of tetrahydrofuran, 22 mg (0.539 mmol) of sodium hydride (60% in mineral oil) were added at 0° C. and the mixture was stirred at 0° C. for 90 min. 84 mg (0.539 mmol) of ethyl iodide were added and the mixture was stirred at RT for 48 h. Water was added and the reaction mixture was concentrated under reduced pressure and the residue was purified by means of preparative HPLC (eluent: methanol/water, gradient 30:70→90:10). 59 mg of the title compound were obtained (28% of theory).

LC-MS (method 2): R$_t$=0.82 min; MS (EIpos): m/z=437 (M+H)$^+$.

$^1$H NMR (400 MHz, DMSO-d$_6$): δ [ppm]=1.06 (t, 3H), 3.50 (q, 2H), 3.54 (s, 3H) 5.80 (s, 2H), 6.31 (s br, 4H) 7.07-7.14 (m, 2H), 7.20-7.25 (m, 1H), 7.32-7.37 (m, 2H), 8.60 (dd, 1H), 9.07 (dd, 1H).

Example 15A

Methyl {4,6-diamino-2-[1-(2-fluorobenzyl)-1H-pyrazolo[3,4-b]pyridin-3-yl]pyrimidin-5-yl}(2,2,2-trifluoroethyl)carbamate

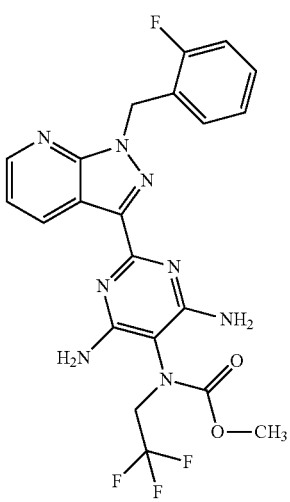 [SMILES: COC(=O)N(CC(F)(F)F)c1c(N)nc(-c2nn(Cc3ccccc3F)c3ncccc23)nc1N]

5.000 g (12.243 mmol) of the compound from example 11A were suspended in 50 ml of tetrahydrofuran, 539 mg (13.467 mmol) of sodium hydride (60% in mineral oil) were added at 0° C. and the mixture was stirred at 0° C. for 90 min, forming a solution. 3.791 g (13.467 mmol) of 2,2,2-trifluoroethyl trichloromethanesulfonate were added and the mixture was stirred at RT for 48 h. Water and 1N hydrochloric acid were added, and the mixture was extracted with ethyl acetate. The combined organic phases were dried over sodium sulfate and concentrated on a rotary evaporator. The residue was purified by means of preparative HPLC (eluent: methanol/water, gradient 20:80→90:10). 2.900 g of the title compound were obtained (48% of theory).

LC-MS (method 2): R$_t$=0.89 min; MS (EIpos): m/z=491 (M+H)$^+$.

<sup>1</sup>H NMR (400 MHz, DMSO-d<sub>6</sub>): δ [ppm]=3.63 (s, 3H), 4.06-4.15 (m, 2H), 5.80 (s, 2H), 6.40 (s br, 4H) 7.08-7.14 (m, 2H), 7.20-7.25 (m, 1H), 7.32-7.38 (m, 2H), 8.61 (dd, 1H), 9.07 (dd, 1H).

$^1$H NMR (400 MHz, DMSO-$d_6$): δ [ppm]=3.63 (s, 3H), 4.06-4.15 (m, 2H), 5.80 (s, 2H), 6.40 (s br, 4H) 7.08-7.14 (m, 2H), 7.20-7.25 (m, 1H), 7.32-7.38 (m, 2H), 8.61 (dd, 1H), 9.07 (dd, 1H).

$^1$H NMR (400 MHz, DMSO-$d_6$): δ [ppm]=3.52 (s, 1.9H), 3.65 (s, 1.1H), 5.80 (s, 2H), 6.34-6.38 (m, 4H) 7.06-7.14 (m, 2H), 7.20-7.25 (m, 1H), 7.31-7.37 (m, 2H), 8.59 (dd, 1H), 9.06 (dd, 1H).

Example 16A

Methyl {4,6-diamino-2-[1-(2-fluorobenzyl)-1H-pyrazolo[3,4-b]pyridin-3-yl]pyrimidin-5-yl}($^2$H$_3$)methylcarbamate

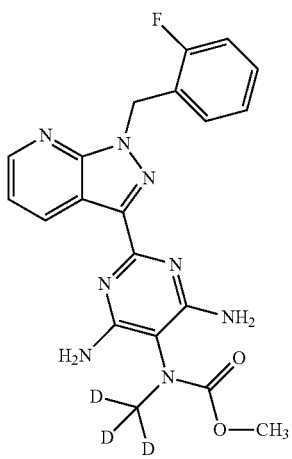 [SMILES: [2H]C([2H])([2H])N(C(=O)OC)c1c(N)nc(-c2nn(Cc3ccccc3F)c3ncccc23)nc1N]

Example 17A

2-[1-(2-Fluorobenzyl)-1H-pyrazolo[3,4-b]pyridin-3-yl]-N-5-(2,2,2-trifluoroethyl)pyrimidine-4,5,6-triamine

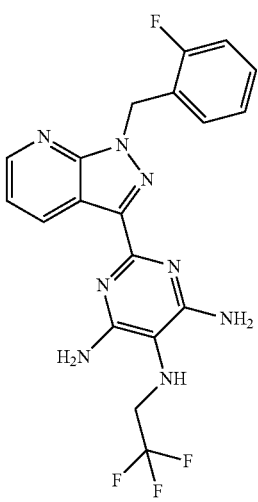 [SMILES: Nc1nc(-c2nn(Cc3ccccc3F)c3ncccc23)nc(N)c1NCC(F)(F)F]

200 mg (0.490 mmol) of the compound from example 11A were dissolved in 2 ml of tetrahydrofuran, 43 mg (1.077 mmol) of sodium hydride (60% in mineral oil) were added at 0° C. and the mixture was stirred at 0° C. for 90 min. 78 mg (0.539 mmol) of iodomethane-d$_3$ were added and the mixture was stirred at RT for 48 h. Water was added and the reaction mixture was concentrated under reduced pressure and the residue was purified by means of preparative HPLC (eluent: methanol/water, gradient 30:70→90:10). 49 mg of the title compound were obtained (24% of theory).

LC-MS (method 2): R$_t$=0.78 min; MS (EIpos): m/z=426 (M+H)$^+$.

500 mg (1.427 mmol) of the compound from example 1A were admixed with 3.5 ml of dimethylformamide and 1205 mg (4.281 mmol) of 2,2,2-trifluoroethyl trichloromethanesulfonate, and the mixture was heated at 150° C. in a microwave for 1 h. The reaction mixture was concentrated under reduced pressure, and the residue was purified by means of preparative HPLC (eluent: acetonitrile/water with 0.1% formic acid, gradient 50:50→70:30). 236 mg of the title compound were obtained (29% of theory).

LC-MS (method 2): R$_t$=0.87 min; MS (EIpos): m/z=433 (M+H)$^+$.

<sup>1</sup>H NMR (400 MHz, DMSO-d$_6$): δ [ppm]=3.43-3.53 (m, 2H), 4.05 (t, 1H), 5.78 (s, 2H), 6.13 (s br, 4H) 7.10-7.15 (m, 2H), 7.20-7.25 (m, 1H), 7.32-7.38 (m, 2H), 8.60 (dd, 1H), 9.04 (dd, 1H).

Example 18A

3-{4,6-Diamino-2-[1-(2-fluorobenzyl)-1H-pyrazolo[3,4-b]pyridin-3-yl]pyrimidin-5-yl}-1,3-oxazolidin-2-one

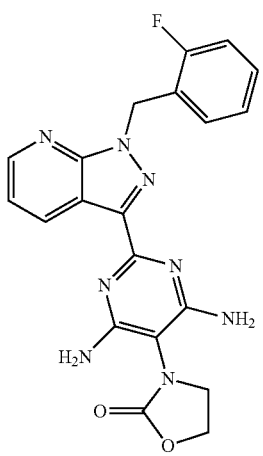 [SMILES: Nc1nc(-c2nn(Cc3ccccc3F)c3ncccc23)nc(N)c1N1CCOC1=O]

The compound was prepared proceeding from 1.109 mg (2.427 mmol) of example 6A in analogy to example 8A. 362 mg of the title compound were obtained (35% of theory).

LC-MS (method 2): R$_t$=0.73 min; MS (EIpos): m/z=421 (M+H)$^+$.

<sup>1</sup>H NMR (400 MHz, DMSO-d$_6$): δ [ppm]=3.63-3.67 (m, 2H), 4.40-4.44 (m, 2H), 5.80 (s, 2H), 6.60 (s br, 4H) 7.12-7.14 (m, 2H), 7.21-7.25 (m, 1H), 7.32-7.37 (m, 2H), 8.61 (dd, 1H), 9.04 (dd, 1H).

Example 19A 2,6-Dichloro-5-fluoronicotinamide

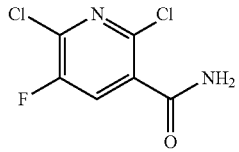 [SMILES: NC(=O)c1cc(F)c(Cl)nc1Cl]

A suspension of 25 g (130.90 mmol) of 2,6-dichloro-5-fluoro-3-cyanopyridine in conc. sulfuric acid (125 ml) was stirred at 60-65° C. for 1 h. After cooling to RT, the contents of the flask were poured onto ice-water and extracted three times with ethyl acetate (100 ml each time). The combined organic phases were washed with water (100 ml) and then with saturated aqueous sodium hydrogencarbonate solution (100 ml), dried and concentrated on a rotary evaporator. The material obtained was dried under high vacuum.

Yield: 24.5 g (90% of theory)

<sup>1</sup>H NMR (400 MHz, DMSO-d$_6$): δ=7.95 (br s, 1H), 8.11 (br s, 1H), 8.24 (d, 1H).

Example 20A

2-Chloro-5-fluoronicotinamide

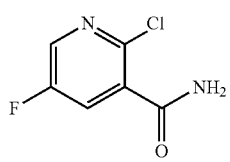

A suspension of 21.9 g (335.35 mmol) of zinc in methanol (207 ml) was admixed at RT with 44 g (210.58 mmol) of 2,6-dichloro-5-fluoronicotinamide. Acetic acid (18.5 ml) was then added, and the mixture was heated to reflux while stirring for 24 h. The contents of the flask were then decanted off from the zinc, and ethyl acetate (414 ml) and saturated aqueous sodium hydrogencarbonate solution (414 ml) were added, followed by extraction by vigorous stirring. Subsequently, the reaction mixture was filtered with suction through kieselguhr and washed through three times with ethyl acetate (517 ml each time). The organic phase was removed and the aqueous phase was washed with ethyl acetate (258 ml). The combined organic phases were washed once with saturated aqueous sodium hydrogencarbonate solution (414 ml), dried and concentrated under reduced pressure. Dichloromethane (388 ml) was added to the crystals thus obtained, and extraction was effected by stirring for 20 min. The mixture was once more filtered with suction, washed through with diethyl ether and sucked dry.

Yield: 20.2 g (53% of theory)

<sup>1</sup>H NMR (400 MHz, DMSO-d$_6$): δ=7.87 (br s, 1H), 7.99 (dd, 1H), 8.10 (br s, 1H), 8.52 (d, 1H).

Example 21A

2-Chloro-5-fluoronicotinonitrile

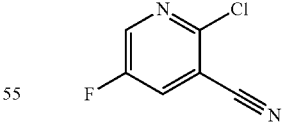

81.2 ml (582.25 mmol) of triethylamine were added to a suspension of 46.2 g (264.66 mmol) of 2-chloro-5-fluoronicotinamide in dichloromethane (783 ml), and the mixture was cooled to 0° C. Then, while stirring, 41.12 ml (291.13 mmol) of trifluoroacetic anhydride were slowly added dropwise and the mixture was stirred at 0° C. for 1.5 h. The reaction solution was subsequently washed twice with saturated aqueous sodium hydrogencarbonate solution (391 ml each time), dried and concentrated under reduced pressure.

Yield: 42.1 g (90% of theory)

$^1$H NMR (400 MHz, DMSO-d$_6$): δ=8.66 (dd, 1H), 8.82 (d, 1H).

Example 22A

5-Fluoro-1H-pyrazolo[3,4-b]pyridine-3-amine

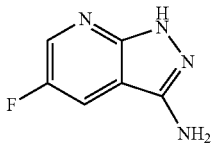 [SMILES: Nc1n[nH]c2ncc(F)cc12]

A suspension of 38.5 g (245.93 mmol) of 2-chloro-5-fluoronicotinonitrile was initially charged in 1,2-ethanediol (380 ml), and hydrazine hydrate (119.6 ml, 2.459 mol) was then added. The mixture was heated under reflux while stirring for 4 h. The product precipitated out in the course of cooling. Water (380 ml) was added to the yellow crystals, and extraction was effected by stirring at RT for 10 min. The suspension was then filtered with suction through a frit and washed through with water (200 ml) and with THF at −10° C. (200 ml). The residue was dried under high vacuum over phosphorus pentoxide.

Yield: 22.8 g (61% of theory)

$^1$H NMR (400 MHz, DMSO-d$_6$): δ=5.54 (s, 2H), 7.96 (dd, 1H), 8.38 (m, 1H), 12.07 (m, 1H).

Example 23A

5-Fluoro-3-iodo-1H-pyrazolo[3,4-b]pyridine

10 g (65.75 mmol) of 5-fluoro-1H-pyrazolo[3,4-b]pyridine-3-amine were initially charged in THF (329 ml), and the mixture was cooled to 0° C. 16.65 ml (131.46 mmol) of boron trifluoride diethyl ether complex were then added gradually. The reaction mixture was cooled further to −10° C. A solution of 10.01 g (85.45 mmol) of isopentyl nitrite in THF (24.39 ml) was then added gradually, and the mixture was stirred for a further 30 min. The mixture was diluted with cold diethyl ether (329 ml) and the resulting solid was filtered off. The diazonium salt thus prepared was added in portions to a solution at 0° C. of 12.81 g (85.45 mmol) of sodium iodide in acetone (329 ml), and the mixture was stirred at RT for 30 min. The reaction mixture was poured onto ice-water (1.8 l) and extracted twice with ethyl acetate (487 ml each time). The collected organic phases were washed with saturated aqueous sodium chloride solution (244 ml), dried, filtered and concentrated. This gave 12.1 g (86% purity, 60% of theory) of the title compound in the form of a brown solid. The crude product was converted without further purification.

LC-MS (method 1): R$_t$=1.68 min; MS (ESIpos): m/z=264 (M+H)$^+$

Example 24A

5-Fluoro-1-(2-fluorobenzyl)-3-iodo-1H-pyrazolo[3,4-b]pyridine

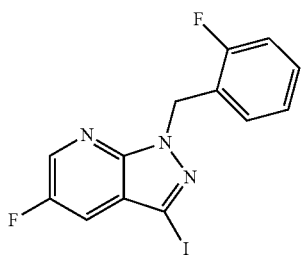 [SMILES: Fc1cnc2c(c1)c(I)nn2Cc1ccccc1F]

141 g (462.11 mmol) of the compound from Example 23A were initially charged in DMF (2538 ml), and 96.09 g (508.32 mmol) of 2-fluorobenzyl bromide and 165.62 g (508.32 mmol) of cesium carbonate were then added. The mixture was stirred at RT for two hours. The reaction mixture was then poured into saturated aqueous sodium chloride solution (13 670 ml) and extracted twice with ethyl acetate (5858 ml). The collected organic phases were washed with saturated aqueous sodium chloride solution (3905 ml), dried, filtered and concentrated. The residue was chromatographed on silica gel (eluent: 97:3 petroleum ether/ethyl acetate) and the product fractions were concentrated. The resulting solid was dissolved in dichloromethane and washed once with saturated aqueous sodium thiosulfate solution (500 ml) and then with saturated aqueous sodium chloride solution (500 ml). The product was concentrated to dryness and the residue was suspended in diethyl ether, isolated by filtration with suction and dried under high vacuum. This gave 106.6 g (62% of theory) of the title compound.

LC-MS (method 1): R$_t$=2.57 min

MS (ESIpos): m/z=372 (M+H)$^+$ $^1$H NMR (400 MHz, DMSO-d$_6$): δ=5.73 (s, 2H), 7.13-7.26 (m, 3H), 7.33-7.41 (m, 1H), 7.94 (dd, 1H), 8.69-8.73 (m, 1H).

Example 25A

Ethyl 5-fluoro-1-(2-fluorobenzyl)-1H-pyrazolo[3,4-b]pyridine-3-carboxylate

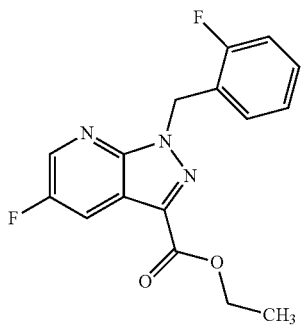 [SMILES: CCOC(=O)c1nn(Cc2ccccc2F)c2ncc(F)cc12]

13.487 g (51.228 mmol) of ethyl 5-amino-1-(2-fluorobenzyl)-1H-pyrazole-3-carboxylate (preparation described for example 20A in WO 00/06569) were initially charged in 300 ml of dioxane, and 6 g (51.228 mmol) of 3-(dimethylamino)-2-fluoroacrylaldehyde (preparation described in *Justus Liebigs Annalen der Chemie* 1970; 99-107) were added at RT. Subsequently, 4.736 ml (61.473 mmol) of trifluoroacetic acid were added and the mixture was heated to reflux while stirring for 3 days. After cooling, the mixture was concentrated under reduced pressure, and water and ethyl acetate were added to the residue. The phases were separated and the organic phase was washed twice with water. The combined aqueous phases were subsequently extracted twice with ethyl acetate. The combined organic phases were dried over sodium sulfate, filtered and concentrated under reduced pressure. The residue (22 g) was subsequently purified by chromatography on silica gel (eluent: dichloromethane). This gave 5.67 g (35% of theory) of the title compound.

LC-MS (method 2): $R_t$=1.17 min

MS (ESIpos): m/z=318 (M+H)$^+$ $^1$H NMR (400 MHz, DMSO-d$_6$): δ=1.37 (t, 3H), 4.40 (q, 2H), 5.86 (s, 2H), 7.15-7.27 (m, 3H), 7.36-7.41 (m, 1H), 8.25 (d, 1H), 8.78 (s br., 1H).

Example 26A

5-Fluoro-1-(2-fluorobenzyl)-1H-pyrazolo[3,4-b]pyridine-3-carboxamide

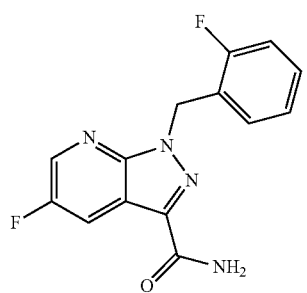 [SMILES: NC(=O)c1nn(Cc2ccccc2F)c2ncc(F)cc12]

1.00 g (3.152 mmol) of the compound obtained in example 25A was stirred in 10 ml of a 7N solution of ammonia in methanol at RT for three days. This was followed by concentration under reduced pressure. This gave 908 mg (99% of theory) of the title compound.

LC-MS (method 2): $R_t$=0.85 min

MS (ESIpos): m/z=289 (M+H)$^+$ $^1$H NMR (400 MHz, DMSO-d$_6$): δ=5.87 (s, 2H), 7.12-7.26 (m, 3H), 7.34-7.40 (m, 1H), 7.60 (s br., 1H), 7.87 (s br., 1H), 8.28 (dd, 1H), 8.72 (dd, 1H).

Example 27A

5-Fluoro-1-(2-fluorobenzyl)-1H-pyrazolo[3,4-b]pyridine-3-carbonitrile

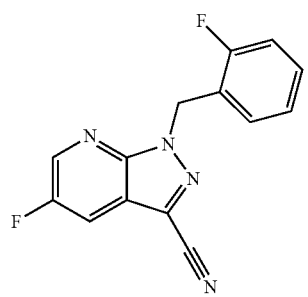 [SMILES: N#Cc1nn(Cc2ccccc2F)c2ncc(F)cc12]

Variant A:

A suspension of 16.03 g (43.19 mmol) of 5-fluoro-1-(2-fluorobenzyl)-3-iodo-1H-pyrazolo[3,4-b]pyridine (Example 24A) and 4.25 g (47.51 mmol) of copper cyanide was initially charged in DMSO (120 ml) and stirred at 150° C. for 2 h. After cooling, the contents of the flask were cooled to about 40° C. and poured onto a solution of conc. aqueous ammonia (90 ml) and water (500 ml), ethyl acetate (200 ml) was added and extraction was effected briefly by stirring. The aqueous phase was removed and extracted twice more with ethyl acetate (200 ml each time). The combined organic phases were washed twice with 10% aqueous sodium chloride solution (100 ml each time), dried and concentrated under reduced pressure. The crude product was converted without further purification.

Yield: 11.1 g (91% of theory)

Variant B:

900 mg (3.122 mmol) of the compound obtained in example 26A were dissolved in THF (14 ml), and 0.646 ml (7.993 mmol) of pyridine was added. Thereafter, 1.129 ml (7.993 mmol) of trifluoroacetic anhydride were slowly added dropwise while stirring and then the mixture was stirred at RT overnight. Thereafter, the reaction mixture was poured onto water and extracted three times with ethyl acetate. The combined organic phases were extracted with saturated aqueous sodium hydrogencarbonate solution and 1N hydrochloric acid, and then washed with saturated aqueous sodium chloride solution. The organic phase was dried over sodium sulfate, filtered and concentrated. This gave 850 mg (99% of theory) of the title compound.

LC-MS (method 2): $R_t$=1.06 min

MS (ESIpos): m/z=271 (M+H)$^+$

¹H NMR (400 MHz, DMSO-$d_6$): δ=5.87 (s, 2H), 7.17-7.42 (m, 4H), 8.52 (dd, 1H), 8.87 (dd, 1H).

Example 28A

5-Fluoro-1-(2-fluorobenzyl)-1H-pyrazolo[3,4-b]pyridine-3-carboximidamide acetate

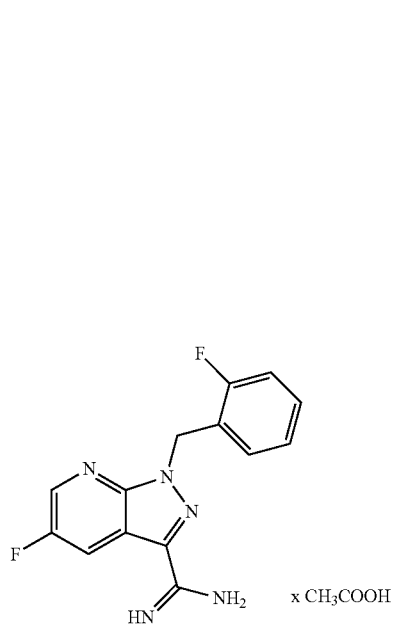 [SMILES: N=C(N)c1nn(Cc2ccccc2F)c2ncc(F)cc12]

11.1 g (41.07 mmol) of 5-fluoro-1-(2-fluorobenzyl)-1H-pyrazolo[3,4-b]pyridine-3-carbonitrile (Example 27A) were added to 2.22 g (41.07 mmol) of sodium methoxide in methanol (270 ml), and the mixture was stirred at RT for 2 h. 2.64 g (49.29 mmol) of ammonium chloride and acetic acid (9.17 ml) were then added, and the mixture was heated to reflux overnight. It was then concentrated to dryness and the residue was taken up in water (100 ml) and ethyl acetate (100 ml) and adjusted to a pH of 10 using 2N aqueous sodium hydroxide solution. The mixture was stirred vigorously at RT for about 1 h. The resulting suspension was filtered with suction and washed through with ethyl acetate (100 ml), with water (100 ml) and once more with ethyl acetate (100 ml). The residue was dried under high vacuum over phosphorus pentoxide.

Yield: 9.6 g (78% of theory)

MS (ESIpos): m/z=288 (M+H)⁺

¹H NMR (400 MHz, DMSO-$d_6$): δ=1.85 (s, 3H), 5.80 (s, 2H), 7.14-7.25 (m, 3H), 7.36 (m, 1H), 8.42 (dd, 1H), 8.72 (dd, 1H).

Example 29A

2-[5-Fluoro-1-(2-fluorobenzyl)-1H-pyrazolo[3,4-b]pyridin-3-yl]-5-[(E)-phenyldiazenyl]pyrimidine-4,6-diamine

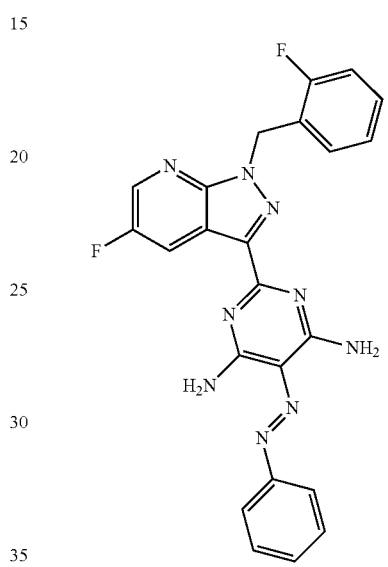

With stirring, 3.85 g (41.34 mmol) of aniline were added to water (40 ml) and conc. hydrochloric acid (7.07 ml), and this mixture was cooled to 0° C. A solution of 2.85 g (41.34 mmol) of sodium nitrite in water (21 ml) was then added dropwise at between 0° C. and 5° C., followed by stirring at 0° C. for 15 min. Thereafter, at 0° C., a solution of 4.28 g (52.25 mmol) of sodium acetate in water (19 ml) was rapidly added dropwise, and then, with good stirring, a solution of 2.73 g (41.34 mmol) of malononitrile in ethanol (10 ml) was added dropwise. After 2 h at 0° C., the resulting precipitate was filtered off with suction and washed three times with water (50 ml each time) and with petroleum ether (50 ml). The still-moist residue was dissolved in DMF (46 ml) and added dropwise at exactly 85° C. to a solution of 9.5 g (33.07 mmol) of 5-fluoro-1-(2-fluorobenzyl)-1H-pyrazolo[3,4-b]pyridine-3-carboximidamide acetate (example 28A) in DMF (46 ml) and triethylamine (5.76 ml). The mixture was then stirred at 100° C. for 4 h and left to cool to RT overnight. The mixture was poured onto water (480 ml) and extraction was effected by stirring at RT for 1 h. After the precipitate had been filtered off with suction, it was washed twice with water (100 ml each time) and twice with methanol (50 ml each time) and then dried under high vacuum.

Yield: 9.6 g (59% of theory)

LC-MS (method 2): $R_t$=1.21 min

MS (ESIpos): m/z=458 (M+H)⁺

Example 30A

2-[5-Fluoro-1-(2-fluorobenzyl)-1H-pyrazolo[3,4-b]pyridin-3-yl]pyrimidine-4,5,6-triamine

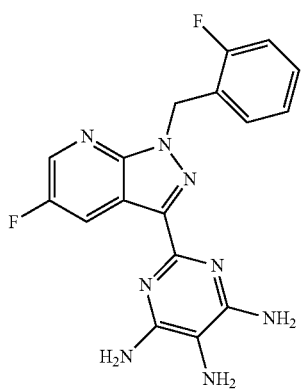 [SMILES: Nc1nc(-c2nn(Cc3ccccc3F)c3ncc(F)cc23)nc(N)c1N]

39.23 g (85.75 mmol) of the compound from example 29A were initially charged in DMF (800 ml) and then 4 g of palladium (10% on charcoal) were added. Hydrogenation was effected at standard hydrogen pressure while stirring overnight. The mixture was filtered through kieselguhr, washed through with a little DMF and a little methanol and concentrated to dryness. The residue was admixed with ethyl acetate and stirred vigorously, and the precipitate was filtered off with suction, washed with ethyl acetate and diisopropyl ether and dried under a high vacuum over Sicapent.

Yield: 31.7 g (100% of theory)
LC-MS (method 2): $R_t$=0.81 min
MS (ESIpos): m/z=369 (M+H)$^+$

Example 31A

Methyl {4,6-diamino-2-[5-fluoro-1-(2-fluorobenzyl)-1H-pyrazolo[3,4-b]pyridin-3-yl]pyrimidin-5-yl}carbamate

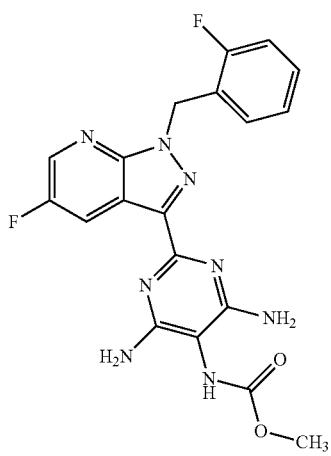 [SMILES: COC(=O)Nc1c(N)nc(-c2nn(Cc3ccccc3F)c3ncc(F)cc23)nc1N]

31.75 g (86.20 mmol) of the compound from example 30A were initially charged in pyridine (600 ml) under argon and cooled to 0° C. Then a solution of 6.66 ml (86.20 mmol) of methyl chloroformate in dichloromethane (10 ml) was added dropwise and the mixture was stirred at 0° C. for 1 h. Thereafter, the reaction mixture was brought to RT, concentrated under reduced pressure and co-distilled repeatedly with toluene. The residue was stirred with water/ethanol and then filtered off with suction using a frit, and subsequently washed with ethanol and ethyl acetate. Subsequently, the residue was stirred again with diethyl ether, filtered off with suction and then dried under high vacuum.

Yield: 24.24 g (65% of theory)
LC-MS (method 2): $R_t$=0.79 min
MS (ESIpos): m/z=427 (M+H)$^+$
$^1$H NMR (400 MHz, DMSO-d$_6$): δ=3.62 (br. s, 3H), 5.79 (s, 2H), 6.22 (br. s, 4H), 7.10-7.19 (m, 2H), 7.19-7.26 (m, 1H), 7.32-7.40 (m, 1H), 7.67 (br. s, 0.2H), 7.99 (br. s, 0.8H), 8.66 (m, 1H), 8.89 (d, 1H).

Example 32A

Methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate

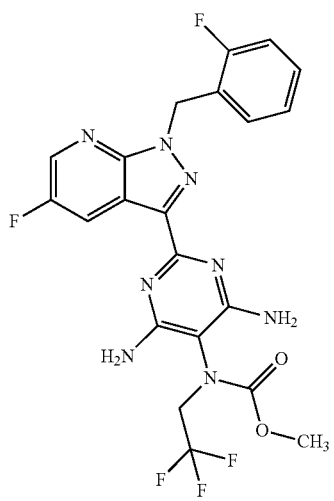 [SMILES: COC(=O)N(CC(F)(F)F)c1c(N)nc(-c2nn(Cc3ccccc3F)c3ncc(F)cc23)nc1N]

3.470 g (8.138 mmol) of the compound from example 31A were suspended in 35 ml of THF, 358 mg (8.952 mmol) of sodium hydride (60% suspension in mineral oil) were added at 0° C. and the mixture was stirred at 0° C. for 90 min, forming a solution. 2.519 g (8.952 mmol) of 2,2,2-trifluoroethyl trichloromethanesulfonate were added and the mixture was stirred at RT for 48 h. The mixture was then stirred with water and concentrated on a rotary evaporator. The residue was taken up in ethyl acetate, and the organic phase was washed twice with water and dried over sodium sulfate. This gave 5.005 g of the target compound (79% of theory, purity by HPLC 65%). 250 mg of residue were purified by means of preparative HPLC (eluent: methanol/water, gradient 30:70→90:10).

LC-MS (method 2): $R_t$=0.97 min; MS (EIpos): m/z=509 (M+H)$^+$.

¹H NMR (400 MHz, DMSO-d₆): δ [ppm]=3.63 (s, 3H), 4.06-4.15 (m, 2H), 5.80 (s, 2H), 6.46 (s br, 4H) 7.11-7.15 (m, 2H), 7.20-7.25 (m, 1H), 7.33-7.38 (m, 1H), 8.66 (dd, 1H), 8.91 (dd, 1H).

Example 33A 1-(2-Fluorobenzyl)-3-iodo-1H-pyrazolo[3,4-b]pyridine

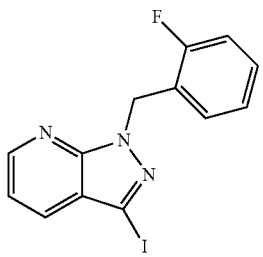 [SMILES: Fc1ccccc1Cn1nc(I)c2cccnc21]

In analogy to example 24A, 25.00 g (102.031 mmol) of 3-iodo-1H-pyrazolo[3,4-b]pyridine (synthesis described in WO 2006/130673, scheme D) were reacted with 21.21 g (112.234 mmol) of 2-fluorobenzyl bromide. 34.49 g of the title compound were obtained (95% of theory).

LC-MS (method 2): $R_t$=1.16 min; MS (ESIpos): m/z=354 (M+H)⁺

¹H NMR (400 MHz, DMSO-d₆): δ=5.74 (s, 2H), 7.13-7.24 (m, 3H), 7.32-7.37 (m, 2H), 7.97 (dd, 1H), 8.65 (dd, 1H).

Example 34A

N⁵-(1-Cyclopropylpiperidin-4-yl)-2-[1-(2-fluorobenzyl)-1H-pyrazolo[3,4-b]pyridin-3-yl]pyrimidine-4,5-diamine

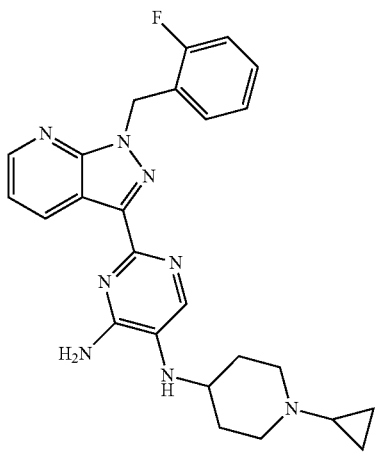 [SMILES: Nc1nc(-c2nn(Cc3ccccc3F)c3ncccc23)ncc1NC1CCN(C2CC2)CC1]

200 mg (0.596 mmol) of 2-[1-(2-fluorobenzyl)-1H-pyrazolo[3,4-b]pyridin-3-yl]pyrimidine-4,5-diamine (synthesis described in US2004/67937; Example V) were initially charged in methanol (16 ml) and admixed with 75 μl (1.312 mmol) of acetic acid, and then 182 mg (1.312 mmol) of 1-cyclopropyl-4-piperidinone were added. After stirring at RT for 15 min, 104 mg (1.67 mmol) of sodium cyanoborohydride were added and the mixture was stirred at RT for 2.5 h. Subsequently, within 2 days, the above-stated amounts of reagents (1-cyclopropyl-4-piperidinone, acetic acid, sodium cyanoborohydride) were added three times, in order to achieve substantially full conversion. Thereafter, saturated aqueous sodium hydrogencarbonate solution (5 ml) was added and the mixture was stirred vigorously for 10 min. Subsequently, the mixture was extracted with water and ethyl acetate. The phases were separated and the aqueous phase was extracted twice with ethyl acetate. The combined organic phases were washed with saturated aqueous sodium chloride solution, dried over sodium sulfate, filtered, concentrated and then purified by means of preparative HPLC (acetonitrile:water (+0.05% formic acid) gradient). 165 mg of the title compound were obtained (60% of theory).

LC-MS (method 2): $R_t$=0.60 min; MS (EIpos): m/z=459 [M+H]⁺.

Example 35A 3,5-Difluoropyridine-2-carbonyl chloride

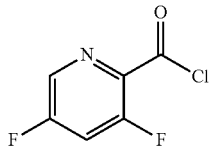 [SMILES: O=C(Cl)c1ncc(F)cc1F]

A suspension of 5.00 g (31.4 mmol) of 3,5-difluoropyridine-2-carboxylic acid in thionyl chloride (21 ml) was heated to reflux for 5 h. The solution was concentrated, and the residue was twice taken up in a little toluene and concentrated again. This gave 3.80 g of a solid, which was converted further directly without further purification.

Example 36A

Methyl 3-(3,5-difluoropyridin-2-yl)-2-(2-fluorophenyl)-3-oxopropanoate

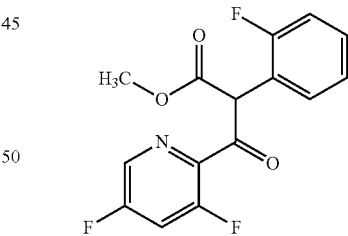

21.4 ml (21.4 mmol) of lithium hexamethyldisilazide (1.0 M in THF) were initially charged in THF (30 ml) under argon and a solution of 3.00 g (17.8 mmol) of methyl 2-fluorophenylacetate in THF (15 ml) was added dropwise at −78° C. The reaction mixture was stirred at −78° C. for 1 h, and then a solution of 3.80 g (21.4 mmol) of the compound from Example 1A in THF (15 ml) was added dropwise. The solution was stirred at −78° C. for 1 h, then brought to RT, and saturated aqueous ammonium chloride solution was added in portions. The mixture was diluted with water and extracted twice with ethyl acetate. The combined organic phases were dried over sodium sulfate, filtered and concentrated. The residue was stirred with tert-butyl methyl ether, the solids were filtered off and the filtrate was concentrated. Silica gel chromatography (eluent: 30:1, 20:1-cyclohexane-ethyl acetate) of the residue gave 3.66 g (87% purity, 57% of theory) of the title compound. The crude product was converted without further purification.

LC-MS (method 2): $R_t$=1.05 min; MS (ESIpos): m/z=310 (M+H)$^+$ $^1$H NMR (400 MHz, DMSO-d$_6$): δ=3.66 (s, 3H), 6.25 (s, 1H), 7.20-7.28 (m, 4H), 7.31-7.38 (m, 1H), 8.15-8.23 (m, 1H), 8.68-8.71 (m, 1H).

Example 37A 1-(3,5-Difluoropyridin-2-yl)-2-(2-fluorophenyl)ethanone

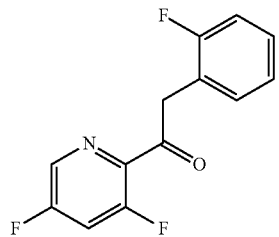 [SMILES: O=C(Cc1ccccc1F)c1ncc(F)cc1F]

11.65 g (37.67 mmol) of the compound from example 36A were initially charged in DMSO (37 ml). Subsequently, 2.42 g (41.44 mmol) of sodium chloride and water (7 ml) were added, and the mixture was stirred in a microwave at 150° C. for 30 min. The reaction mixture was diluted with ethyl acetate, and the organic phase was washed three times with water and once with saturated aqueous sodium chloride solution, dried over sodium sulfate, filtered and concentrated. This gave 9.07 g (89% purity, 85% of theory) of the title compound in solid form, which was converted without further purification.

LC-MS (method 2): $R_t$=1.05 min; MS (ESIpos): m/z=252 (M+H)$^+$ $^1$H NMR (400 MHz, DMSO-d$_6$): δ=4.53 (s, 2H), 7.15-7.22 (m, 2H), 7.30-7.37 (m, 2H), 8.11-8.18 (m, 1H), 8.70-8.72 (m, 1H).

Example 38A

6-Fluoro-3-(2-fluorobenzyl)-1H-pyrazolo[4,3-b]pyridine

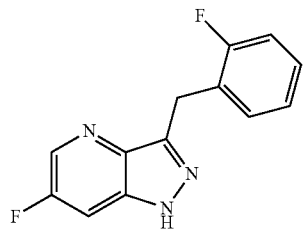 [SMILES: Fc1cnc2c(Cc3ccccc3F)n[nH]c2c1]

9.07 g (32.4 mmol) of the compound from example 37A were initially charged in pyridine (84 ml). Subsequently, 8.10 g (162 mmol) of hydrazine hydrate and 19.8 mg (0.162 mmol) of 4-dimethylaminopyridine were added, and the mixture was heated to reflux for 30 min. The reaction mixture was diluted with ethyl acetate at RT and washed four times with 10% aqueous citric acid solution. The organic phase was subsequently washed with saturated aqueous sodium chloride solution, dried over sodium sulfate, filtered and concentrated. The residue was admixed with tert-butyl methyl ether and the solids were filtered off. The latter were dried under high vacuum and gave 1.79 g (79% purity, 18% of theory) of the title compound. The filtrate was concentrated and gave a further 4.86 g (61% purity, 37% of theory) of the title compound. The two fractions were combined and converted without further purification.

LC-MS (method 4): $R_t$=1.87 min

MS (ESIpos): m/z=246 (M+H)$^+$ $^1$H NMR (400 MHz, DMSO-d$_6$): δ=4.33 (s, 2H), 7.06-7.12 (m, 1H), 7.12-7.19 (m, 1H), 7.22-7.29 (m, 1H), 7.29-7.35 (m, 1H), 7.87 (dd, 1H), 7.84-7.89 (m, 1H), 8.48-8.51 (br. s, 1H).

Example 39A

6-[6-Fluoro-3-(2-fluorobenzyl)-1H-pyrazolo[4,3-b]pyridin-1-yl]-3-nitropyridin-2-amine

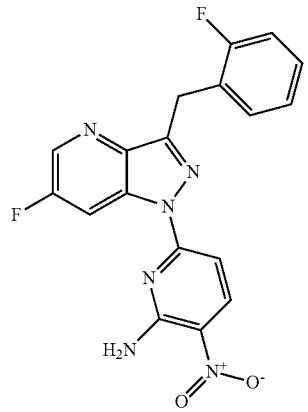 [SMILES: Nc1nc(-n2nc(Cc3ccccc3F)c3ncc(F)cc32)ccc1[N+](=O)[O-]]

192 mg (approx. 0.517 mmol) of the compound from example 38A were dissolved in dimethylformamide (4 ml), then 34.5 mg (0.862 mmol) of sodium hydride (60% in mineral oil) were added and the mixture was stirred at RT for 30 min. Then 129 mg (0.744 mmol) of 6-chloro-3-nitropyridin-2-amine were added and the reaction mixture was stirred at RT for 1 h. The mixture was added to water, and the solids were filtered off, washed repeatedly with water and dried under high vacuum overnight. This gave 348 mg (85% purity, 84% of theory) of the title compound in solid form.

LC-MS (method 2): $R_t$=1.29 min

MS (ESIpos): m/z=383 (M+H)$^+$ $^1$H NMR (400 MHz, DMSO-d$_6$): δ=4.46 (s, 2H), 7.11-7.17 (m, 1H), 7.19-7.24 (m, 2H), 7.27-7.34 (m, 1H), 7.39-7.45 (m, 1H), 8.22-8.30 (m, 1H), 8.55 (d, 1H), 8.74-8.76 (m, 2H), 9.30-9.35 (m, 1H).

Example 40A

6-[6-Fluoro-3-(2-fluorobenzyl)-1H-pyrazolo[4,3-b]pyridin-1-yl]pyridine-2,3-diamine

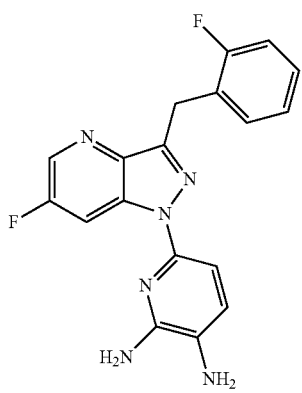 [SMILES: Nc1ccc(-n2nc(Cc3ccccc3F)c3ncc(F)cc32)nc1N]

300 mg (0.785 mmol) of the compound from example 39A were initially charged in pyridine (35 ml), then 119 mg of palladium (10% on charcoal) were added and the mixture was hydrogenated at standard hydrogen pressure overnight. The reaction mixture was filtered through kieselguhr and washed through with ethanol, and the filtrate was concentrated. This gave 219 mg (92% purity, 73% of theory) of the title compound in solid form.

LC-MS (method 2): R$_t$=1.05 min
MS (ESIpos): m/z=353 (M+H)$^+$
$^1$H NMR (400 MHz, DMSO-d$_6$): δ=4.40 (s, 2H), 4.72 (s, 2H), 5.98 (s, 2H), 6.88 (m, 2H), 7.08-7.14 (m, 1H), 7.15-7.22 (m, 1H), 7.24-7.31 (m, 1H), 7.33-7.41 (m, 1H), 8.56-8.60 (m, 1H), 8.97 (dd, 1H).

Example 41A tert-Butyl ({4-amino-2-[1-(2-fluorobenzyl)-1H-pyrazolo[3,4-b]pyridin-3-yl]-7,8-dihydropteridin-5(6H)-yl}sulfonyl)carbamate

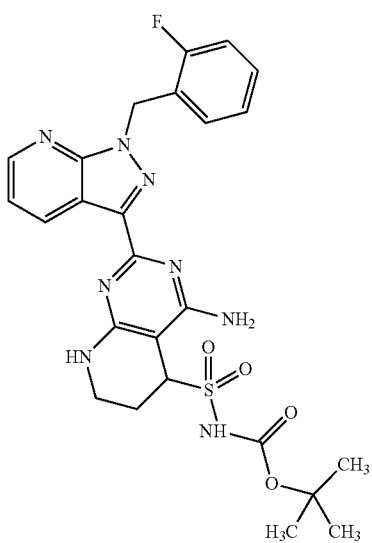 [SMILES: CC(C)(C)OC(=O)NS(=O)(=O)C1CCNc2nc(-c3nn(Cc4ccccc4F)c4ncccc34)nc(N)c21]

300 mg (0.727 mmol) of the compound from example 81 were initially charged in dimethylformamide (5 ml), then 0.25 ml (1.45 mmol) N,N-diisopropylethylamine were added dropwise and then 188 mg (0.872 mmol) of tert-butyl (chlorosulfonyl)carbamate (prepared according to U.S. Pat. No. 6,313,312, Preparation 83) were added. The reaction solution was stirred at RT overnight and separated directly by means of preparative HPLC (eluent: acetonitrile/water with 0.1% formic acid gradient), and the product fractions were concentrated. This gave 97 mg (92%, 22% of theory) of the title compound in solid form.

LC-MS (method 2): R$_t$=0.93 min
MS (ESIpos): m/z=556 (M+H)$^+$
$^1$H NMR (400 MHz, DMSO-d$_6$): δ=1.38 (s, 9H), 3.17-3.28 (m, 2H), 3.47-3.56 (m, 2H), 5.80 (s, 2H), 6.79-6.92 (m, 2H), 7.08-7.15 (m, 2H), 7.19-7.26 (m, 1H), 7.30-7.39 (m, 2H), 8.58-8.62 (m, 1H), 8.99-9.04 (m, 1H).

Example 42A

6-[1-(2-Fluorobenzyl)-1H-pyrazolo[3,4-b]pyridin-3-yl]-3-nitropyridin-2-amine

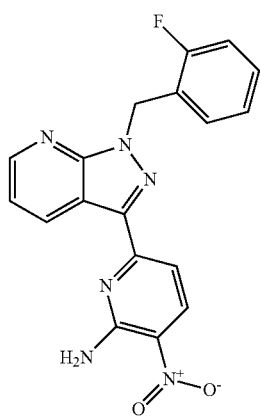 [SMILES: Nc1nc(-c2nn(Cc3ccccc3F)c3ncccc23)ccc1[N+](=O)[O-]]

200 mg (0.57 mmol) of the compound from example 33A were initially charged in dimethylformamide (5.3 ml) under argon, then 0.43 ml (0.85 mmol) of hexabutylditin and 160 mg (0.92 mmol) of 6-chloro-3-nitropyridin-2-amine were added, and the reaction mixture was purged with argon for 10 min. Subsequently, 231 mg (0.28 mmol) of [1,1'-bis(diphenylphosphino)ferrocene]dichloropalladium(II)-dichloromethane complex (1:1) were added and the reaction mixture was stirred at 110° C. overnight. The mixture was then cooled to RT, saturated aqueous sodium hydrogencarbonate solution was added and the mixture was extracted three times with ethyl acetate. The combined organic phases were dried over magnesium sulfate, filtered and concentrated. The residue was extracted by stirring in dichloromethane/methanol (1:1), and the solids were filtered off and dried under high vacuum. This gave 95 mg (54% purity, 15% of theory) of the title compound. The filtrate was chromatographed on silica gel (eluent: 20:1 cyclohexane/ethyl acetate) and the product fractions were concentrated. The residue was suspended in methanol, the solids were filtered off and drying under high vacuum afforded a further 30 mg (15% of theory) of the title compound in solid form. The fractions were combined and converted without further purification (purity approx. 60%).

LC-MS (method 2): R$_t$=1.21 min
MS (ESIpos): m/z=365 (M+H)$^+$ $^1$H NMR (400 MHz, DMSO-d$_6$): δ=4.46 (s, 2H), 7.11-7.17 (m, 1H), 7.19-7.24 (m, 2H), 7.27-7.34 (m, 1H), 7.39-7.45 (m, 2H), 8.22-8.30 (m, 2H), 8.55 (d, 1H), 8.74-8.76 (m, 1H), 9.30-9.35 (m, 1H).

Example 43A

6-[1-(2-Fluorobenzyl)-1H-pyrazolo[3,4-b]pyridin-3-yl]pyridine-2,3-diamine

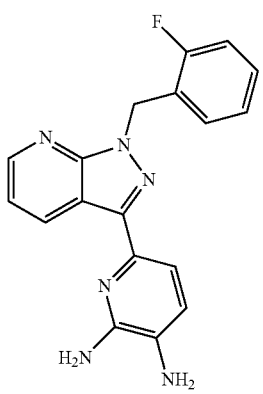 [SMILES: Nc1ccc(-c2nn(Cc3ccccc3F)c3ncccc23)nc1N]

1.22 g (approx. 3.34 mmol, purity approx. 60%) of the compound from example 42A were initially charged in pyridine (149 ml) and then 505 mg (0.47 mmol) of palladium (10% on charcoal) were added. The mixture was hydrogenated under standard hydrogen pressure at RT overnight. The reaction mixture was then filtered through kieselguhr and the filtercake was washed with methanol. The filtrate was concentrated, methanol was added and the solids were filtered off. The filtrate was concentrated by rotary evaporation, the residue was chromatographed on silica gel (eluent: 5:1, 3:1 cyclohexane/ethyl acetate) and the product fractions were concentrated. This gave 491 mg (44% of theory) of the title compound.

LC-MS (method 2): R$_t$=0.74 min

MS (ESIpos): m/z=335 (M+H)$^+$ $^1$H NMR (400 MHz, DMSO-d$_6$): δ=4.95 (m, 2H), 5.64 (m, 2H), 5.73 (s, 2H), 6.78 (d, 1H), 7.09-7.14 (m, 2H), 7.16-7.28 (m, 3H), 7.30-7.37 (m, 1H), 8.55 (dd, 1H), 9.06 (dd, 1H).

Example 44A

Methyl 2-[1-(2-fluorobenzyl)-1H-pyrazolo[3,4-b]pyridin-3-yl]-4-methylpyrimidine-5-carboxylate

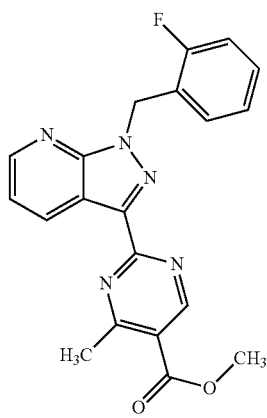 [SMILES: COC(=O)c1cnc(-c2nn(Cc3ccccc3F)c3ncccc23)nc1C]

2.00 g (6.54 mmol) of the compound from example 5A were initially charged in methanol (10 ml) and a solution of 6.5 ml of 1M sodium hydroxide solution in methanol (10 ml) was added. Subsequently, 1.03 g (6.54 mmol) of methyl (2E)-2-(methoxymethylene)-3-oxobutanoate (Russ. J. Org. Chem. 2003, 39, 273) were added dropwise and the reaction mixture was stirred at RT overnight. Subsequently, a further 6.5 ml of 1M sodium hydroxide solution in methanol and 2.06 g (13.08 mmol) of methyl (2E)-2-(methoxymethylene)-3-oxobutanoate were added and the mixture was again stirred at RT overnight. Thereafter, the reaction solution was concentrated to half of its volume and tert-butyl methyl ether was added, and a solid precipitated out. This was filtered off, washed with water and tert-butyl methyl ether, and dried under high vacuum. This gave 1.68 g (68% of theory) of the title compound in solid form.

LC-MS (method 2): R$_t$=1.17 min

MS (ESIpos): m/z=378 (M+H)$^+$

¹H NMR (400 MHz, DMSO-d$_6$): δ=2.86 (s, 3H), 3.92 (s, 3H), 5.91 (s, 2H), 7.13-7.19 (m, 1H), 7.24 (m, 2H), 7.34-7.41 (m, 1H), 7.46-7.51 (m, 1H), 8.69-8.74 (m, 1H), 8.93-8.99 (m, 1H), 9.22 (s, 1H).

Example 45A

2-[1-(2-Fluorobenzyl)-1H-pyrazolo[3,4-b]pyridin-3-yl]-4-methylpyrimidine-5-carboxylic acid

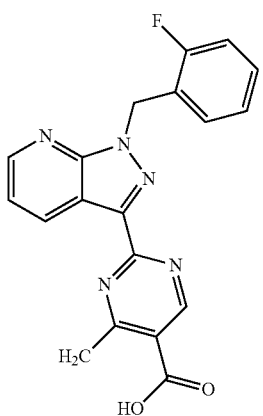

830 mg (2.20 mmol) of the compound from example 44A were initially charged in tetrahydrofuran (10 ml), 4.40 ml (4.40 mmol) of aqueous lithium hydroxide solution (1.0 M) were added and the suspension was stirred at RT for 90 min Subsequently, the now clear solution was concentrated and the residue was partitioned between ethyl acetate and water. The aqueous phase was adjusted to pH<7 with 1M hydrochloric acid, and a solid precipitated out. This was filtered off, washed with water and tert-butyl methyl ether, and dried under high vacuum. This gave 710 mg (89% of theory) of the title compound in solid form.

LC-MS (method 2): R$_t$=0.99 min

MS (ESIpos): m/z=364 (M+H)$^+$

¹H NMR (400 MHz, DMSO-d$_6$): δ=2.85 (s, 3H), 5.90 (s, 2H), 7.13-7.19 (m, 1H), 7.20-7.27 (m, 2H), 7.33-7.41 (m, 1H), 7.45-7.50 (m, 1H), 8.68-8.72 (m, 1H), 8.93-8.98 (m, 1H), 9.17 (s, 1H).

Example 46A

2-[1-(2-Fluorobenzyl)-1H-pyrazolo[3,4-b]pyridin-3-yl]-4-methylpyrimidine-5-carboxamide

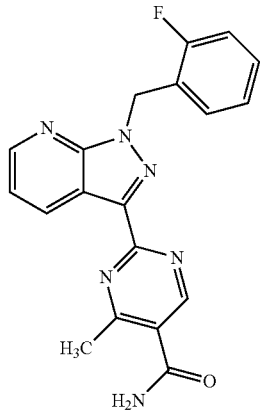 [SMILES: Cc1nc(-c2nn(Cc3ccccc3F)c3ncccc23)ncc1C(N)=O]

Under argon, 250 mg (0.688 mmol) of the compound from example 45A were initially charged in dimethylformamide (3.8 ml). Subsequently, 145 mg (0.757 mmol) of EDC and 116 mg (0.757 mmol) of HOBt were added, and finally 77 μl (1.03 mmol) of aqueous ammonia solution (25%) were added. The reaction mixture was stirred at RT overnight and then diluted with ethyl acetate. The organic phase was washed once each with water and saturated aqueous sodium chloride solution, dried over magnesium sulfate, filtered and concentrated by rotary evaporation. The residue was admixed with tert-butyl methyl ether, and the solids were filtered off and dried under high vacuum. This gave 171 mg (66% of theory) of the title compound in solid form.

LC-MS (method 2): R$_t$=0.88 min

MS (ESIpos): m/z=363 (M+H)$^+$

¹H NMR (400 MHz, DMSO-d$_6$): δ=2.70 (s, 3H), 5.89 (s, 2H), 7.13-7.18 (m, 1H), 7.19-7.27 (m, 2H), 7.34-7.41 (m,

1H), 7.46 (dd, 2H), 7.78 (br. s, 1H), 8.13 (br. s, 1H), 8.67-8.71 (m, 1H), 8.89 (s, 1H), 8.91-8.95 (m, 1H).

Example 47A

N-(5-Cyanopyrimidin-4-yl)-1-(2-fluorobenzyl)-1H-pyrazolo[3,4-b]pyridine-3-carboxamide

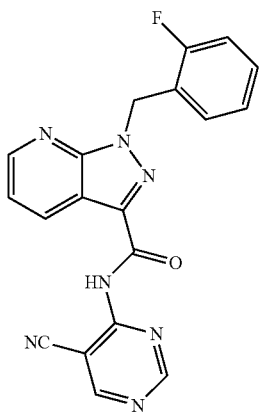 [SMILES: N#Cc1cncnc1NC(=O)c1nn(Cc2ccccc2F)c2ncccc12]

At RT, 39.4 g (145 mmol) of 1-(2-fluorobenzyl)-1H-pyrazolo[3,4-b]pyridine-3-carboxylic acid (preparation described in US2010/004235, page 27) were initially charged, and then thionyl chloride (370 ml) was added. The suspension was heated to reflux for 2 h and the now clear solution was concentrated under reduced pressure. 100 mg (0.345 mmol) of the acid chloride thus prepared were initially charged in pyridine (1.0 ml) and then 41.5 mg (0.345 mmol) of 4-amino-5-cyanopyrimidine were added in portions. The mixture was stirred at RT for 7 h and then left to stand overnight. Subsequently, volatile constituents were removed under high vacuum, the residue was separated by means of preparative HPLC (eluent: acetonitrile/water with 0.1% formic acid gradient) and the product fractions were concentrated. This gave 30 mg (23% of theory) of the title compound in solid form.

LC-MS (method 1): $R_t$=2.06 min

MS (ESIpos): m/z=374 (M+H)$^+$ $^1$H NMR (400 MHz, DMSO-d$_6$): δ=5.91 (s, 2H), 7.14-7.20 (m, 1H), 7.22-7.33 (m, 2H), 7.35-7.42 (m, 1H), 7.49-7.54 (m, 1H), 8.57-8.62 (m, 1H), 8.73-8.77 (m, 1H), 9.28 (d, 2H), 11.64 (s, 1H).

Example 48A

N-(5-Carbamoylpyrimidin-4-yl)-1-(2-fluorobenzyl)-1H-pyrazolo[3,4-b]pyridine-3-carboxamide

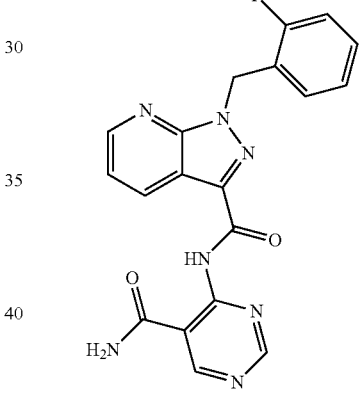

581 mg (1.56 mmol) of the compound from example 47A were introduced in portions at 0° C. into conc. sulfuric acid (2.0 ml) and the mixture was stirred for a further 30 min. Subsequently, the solution was added to ice and extracted twice with ethyl acetate. The combined organic phases were dried over sodium sulfate, filtered and concentrated. The residue was stirred with ethyl acetate, and the solids were filtered off and dried under high vacuum. This gave 246 mg (40% of theory) of the title compound in solid form.

LC-MS (method 3): $R_t$=0.92 min

MS (ESIpos): m/z=392 (M+H)$^+$.

Example 49A

Prop-1-en-2-yl {4,6-diamino-2-[3-(2-fluorobenzyl)-1H-pyrazolo[4,3-b]pyridin-1-yl]pyrimidin-5-yl}carbamate

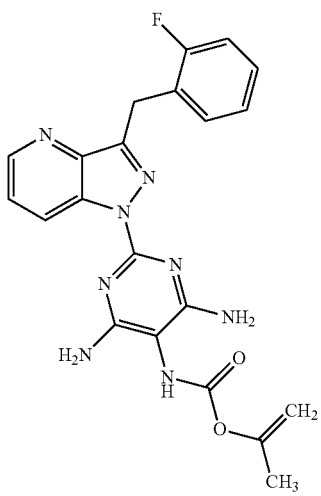 [SMILES: C=C(C)OC(=O)Nc1c(N)nc(-n2nc(Cc3ccccc3F)c3ncccc32)nc1N]

540 mg (1.54 mmol) of 2-[3-(2-fluorobenzyl)-1H-pyrazolo[4,3-b]pyridin-1-yl]pyrimidine-4,5,6-triamine (example 2A) were initially charged in pyridine (5.4 ml) and the mixture was cooled to 0° C. Subsequently, 223 mg (1.85 mmol) of propenyl chloroformate were added dropwise and the mixture was stirred at 0° C. for a further 5 min and at RT for 1 h. The reaction mixture was then diluted with water and extracted three times with ethyl acetate. The collected organic phases were dried over magnesium sulfate, filtered and concentrated by rotary evaporation. The residue was extracted by stirring with tert-butyl methyl ether, filtered and dried under high vacuum at 40° C. for 2 h. This gave 335 mg (79% purity, 39% of theory) of the title compound in solid form. The crude product was converted without further purification.

LC-MS (method 2): $R_t$=0.87 min

MS (ESIpos): m/z=435 (M+H)$^+$.

Example 50A

Methyl {4,6-diamino-2-[3-(2-fluorobenzyl)-1H-pyrazolo[4,3-b]pyridin-1-yl]pyrimidin-5-yl}(4-fluorobenzyl)carbamate

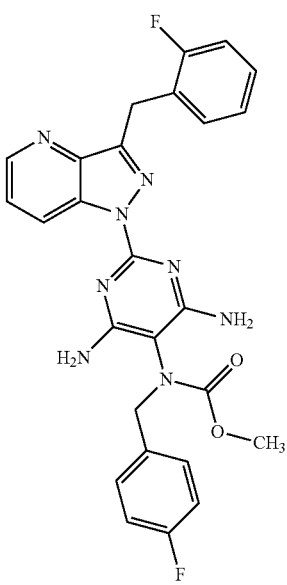 [SMILES: COC(=O)N(Cc1ccc(F)cc1)c1c(N)nc(-n2nc(Cc3ccccc3F)c3ncccc32)nc1N]

Under argon, 100 mg (0.245 mmol) of methyl {4,6-diamino-2-[3-(2-fluorobenzyl)-1H-pyrazolo[4,3-b]pyridin-1-yl]pyrimidin-5-yl}carbamate (preparation described in WO 2008/031513, example 9) were initially charged in tetrahydrofuran (10.0 ml) and the suspension was cooled to 0° C. Subsequently, 9.8 mg (0.245 mmol) of sodium hydride (60% in mineral oil) were added and the mixture was stirred at 0° C. for a further 30 min. Thereafter, 30.5 µl (0.245 mmol) of 4-fluorobenzyl bromide were added dropwise and the reaction mixture was stirred at RT overnight. Subsequently, the reaction mixture was diluted with ethyl acetate, and the organic phase was washed twice with saturated aqueous sodium hydrogencarbonate solution, dried over magnesium sulfate, filtered and concentrated by rotary evaporation. The residue was separated by means of preparative HPLC (eluent: acetonitrile/water with 0.1% formic acid gradient) and the product fractions were concentrated. This gave 91.8 mg (72% of theory) of the title compound in solid form.

LC-MS (method 2): $R_t$=1.03 min

MS (ESIpos): m/z=517 (M+H)$^+$

1H NMR (400 MHz, DMSO-d$_6$): δ=3.60 (s, 2H), 3.75 (s, 1H), 4.39 (s, 2H), 4.59 (m, 2H), 6.34 (br. s, 4H), 7.01-7.13 (m,

3H), 7.13-7.21 (m, 1H), 7.22-7.35 (m, 2H), 7.36-7.44 (m, 2H), 7.44-7.50 (m, 1H), 8.56-8.61 (m, 1H), 9.11 (d, 1H).

Example 51A

2-Chloroethyl {4,6-diamino-2-[3-(2-fluorobenzyl)-1H-pyrazolo[4,3-b]pyridin-1-yl]pyrimidin-5-yl}carbamate

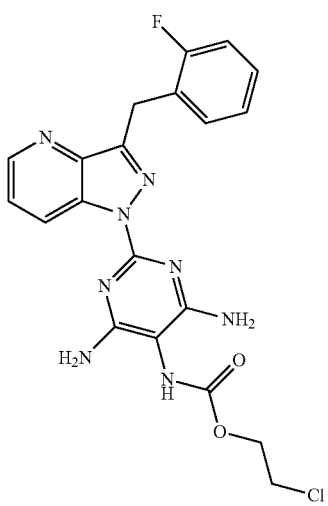 [SMILES: Nc1nc(-n2nc(Cc3ccccc3F)c3ncccc32)nc(N)c1NC(=O)OCCCl]

The compound was prepared from 100 mg (0.285 mmol) of 2-[3-(2-fluorobenzyl)-1H-pyrazolo[4,3-b]pyridin-1-yl]pyrimidine-4,5,6-triamine (example 2A) and 38 μl (0.371 mmol) of 2-chloroethanol according to the method for example 6A. This gave 140 mg (91% purity, 98% of theory) of the title compound in solid form.
LC-MS (method 4): $R_t$=1.75 min
MS (ESIpos): m/z=457 (M+H)$^+$.

Example 52A

5-[1-(2-Fluorobenzyl)-1H-pyrazolo[3,4-b]pyridin-3-yl]pyrazine-2,3-diamine

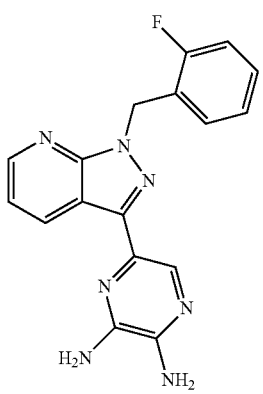

Under argon, 425 mg (1.20 mmol) of the compound from Example 33A were initially charged in 1,4-dioxane (11 ml), and the reaction mixture was purged with argon for 10 min. Thereafter, 0.91 ml (1.80 mmol) of hexabutylditin and 250 mg (1.32 mmol) of 2,3-diamino-5-bromopyrazine were added. Subsequently, 422 mg (0.60 mmol) of bis(triphenylphosphine)palladium(II) chloride were added and the reaction mixture was heated to reflux overnight. Thereafter, the mixture was cooled to RT and filtered through Celite, and the filtrate was concentrated. The residue was admixed with methanol, and the solids were filtered off and discarded. The filtrate was taken up in methanol-dichloromethane, absorbed onto diatomaceous earth and purified on silica gel (eluent: cyclohexane-ethyl acetate 2:1, 1:1). This gave 151 mg (31% purity, 11% of theory) of the title compound. The crude product was converted further without further purification.
LC-MS (method 3): $R_t$=0.91 min
MS (ESIpos): m/z=336 (M+H)$^+$ Example 53A 2-[1-(2-Fluorobenzyl)-1H-pyrazolo[3,4-b]pyridin-3-yl]-6-methyl-5-nitropyrimidin-4-amine

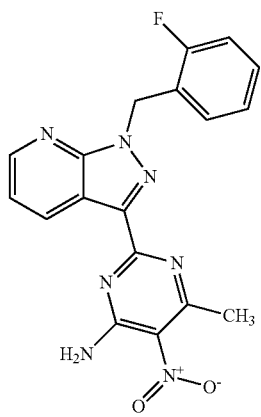 [SMILES: Cc1nc(-c2nn(Cc3ccccc3F)c3ncccc23)nc(N)c1[N+](=O)[O-]]

Under argon, 1.50 g (4.25 mmol) of the compound from Example 33A were initially charged in 1,4-dioxane (37.5 ml), and the reaction mixture was purged with argon for 10 min. Thereafter, 3.22 ml (6.37 mmol) of hexabutylditin and 881 mg (4.67 mmol) of 2-chloro-6-methyl-5-nitropyrimidin-4-amine were added. Subsequently, 1.49 g (2.12 mmol) of bis(triphenylphosphine)palladium(II) chloride were added and the reaction mixture was heated to reflux overnight. Thereafter, the mixture was cooled to RT and filtered through Celite, and the filtrate was washed through with methanol. The solids formed were filtered off and discarded. The remaining filtrate was concentrated, ethyl acetate was added, and the solids formed were filtered off and dried under high vacuum. This gave 640 mg (69% purity, 27% of theory) of the title compound. The crude product was converted further without further purification.
LC-MS (method 2): $R_t$=1.09 min
MS (ESIpos): m/z=380 (M+H)$^+$

Example 54A

2-[1-(2-Fluorobenzyl)-1H-pyrazolo[3,4-b]pyridin-3-yl]-6-methylpyrimidine-4,5-diamine

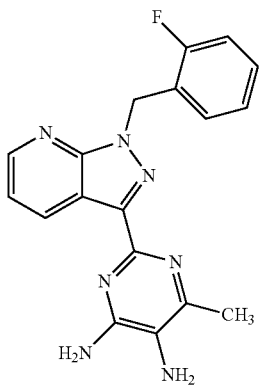 [SMILES: Cc1nc(-c2nn(Cc3ccccc3F)c3ncccc23)nc(N)c1N]

592 mg (1.56 mmol) of the compound from example 53A were initially charged in pyridine (25 ml) and then 133 mg (0.125 mmol) of palladium (10% on charcoal) were added. The mixture was stirred at standard hydrogen pressure overnight. The suspension was then filtered through Celite and the filtercake was washed with methanol. The filtrate was concentrated, methanol was added and the mixture was filtered and concentrated again. The residue was dried under high vacuum. This gave 396 mg of the title compound (80% purity, 45% of theory), which were converted without further purification.

LC-MS (method 3): $R_t$=0.86 min
MS (ESIpos): m/z=350 (M+H)$^+$

Example 55A

Methyl N-{4,6-diamino-2-[1-(2-fluorobenzyl)-1H-pyrazolo[3,4-b]pyridin-3-yl]pyrimidin-5-yl}-N-(methoxycarbonyl)glycinate

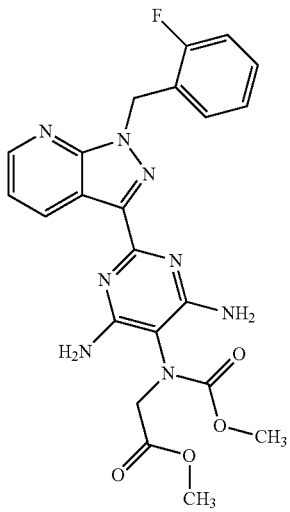 [SMILES: COC(=O)CN(C(=O)OC)c1c(N)nc(-c2nn(Cc3ccccc3F)c3ncccc23)nc1N]

3.00 g (7.346 mmol) of the compound from example 11A in tetrahydrofuran (50 ml) were cooled to 0° C., and 7.346 ml (7.346 mmol) of bis(trimethylsilyl)sodium amide solution (1.0 M in tetrahydrofuran) were added. Subsequently, 0.695 ml (7.346 mmol) of methyl bromoacetate were added dropwise while stirring and the mixture was left at 0° C. for a further 20 min The mixture was then stirred at RT overnight. Then the reaction was stopped with saturated aqueous ammonium chloride solution (20 ml) and the phases were separated. The organic phase was washed twice more with saturated aqueous ammonium chloride solution, dried with sodium sulfate, filtered and concentrated to dryness. This gave 3.68 g (100% of theory) of the title compound. The crude product was converted further without further purification.

LC-MS (method 2): $R_t$=0.83 min
MS (ESIpos): m/z=481 (M+H)$^+$

Example 56A

Methyl 1-{4,6-diamino-2-[1-(2-fluorobenzyl)-1H-pyrazolo[3,4-b]pyridin-3-yl]pyrimidin-5-yl}hydrazinecarboxylate

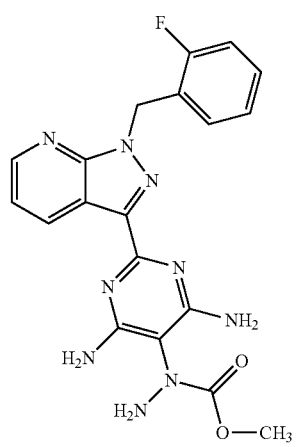

500 mg (1.224 mmol) of the compound obtained in example 11A were initially charged in 12.5 ml of tetrahydrofuran at 0° C. Then 1.224 ml of a 1M solution of bis(trimethylsilyl)sodium amide in tetrahydrofuran were added dropwise and the mixture was stirred at 0° C. for a further 20 min. Then 334 mg (1.836 mmol) of O-(4-nitrobenzoyl)hydroxylamine were added and the mixture was stirred at RT for 2 h. Subsequently, the reaction mixture was concentrated to dryness. The residue was purified by means of preparative HPLC (acetonitrile/water (+0.05% formic acid) gradient). The combined concentrated product-containing fractions were purified once again by means of chromatography on silica gel (dichloromethane-methanol 100:1). Finally, the combined concentrated product-containing fractions from the purification on silica gel were purified once again by means of preparative HPLC (acetonitrile:water (+0.05% formic acid) gradient). 79 mg of the title compound were obtained (14% of theory).

LC-MS (method 2): $R_t$=0.71 min; MS (ESIpos): m/z=424 (M+H)$^+$ $^1$H NMR (400 MHz, DMSO-d$_6$): δ [ppm]=3.55 (s, 2.3H), 3.68 (s, 0.7H), 5.02 (s br, 2H), 5.80 (s, 2H), 6.37 (s br, 4H) 7.09-7.15 (m, 2H), 7.20-7.25 (m, 2H), 7.32-7.38 (m, 2H), 8.60 (dd, 1H), 9.04 (dd, 1H).

Example 57A

5-{[tert-Butyl(dimethyl)silyl]oxy}-2-[1-(2-fluorobenzyl)-1H-pyrazolo[3,4-b]pyridin-3-yl]pyrimidine-4,6-diamine

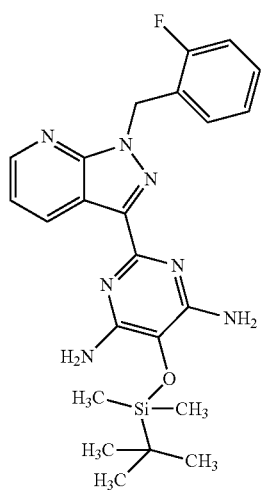 [SMILES: CC(C)(C)[Si](C)(C)Oc1c(N)nc(-c2nn(Cc3ccccc3F)c3ncccc23)nc1N]

1.245 g (4.075 mmol) of the compound obtained in example 5A were initially charged in 10 ml of tert-butanol, and 548 mg (4.890 mmol) of potassium tert-butoxide were added. Then 800 mg (4.075 mmol) of [tert-butyl(dimethyl) silyl]oxy}malononitrile (Journal of Organic Chemistry; 55, 1990; 4515-4516) in 6 ml tert-butanol were added and the mixture was heated to reflux overnight. After cooling, the reaction mixture was admixed with ethyl acetate and water, and the phases were separated. The aqueous phase was extracted twice with ethyl acetate and the combined organic phases were washed once with water and once with saturated aqueous sodium chloride solution, dried with sodium sulfate, filtered and concentrated to dryness. The residue was purified by means of chromatography on silica gel (cyclohexane-ethyl acetate). 450 mg of the title compound were obtained (73% purity; 23% of theory).

LC-MS (method 2): $R_t$=1.11 min; MS (ESIpos): m/z=466 (M+H)$^+$

Example 58A 4,6-Diamino-2-[1-(2-fluorobenzyl)-1H-pyrazolo[3,4-b]pyridin-3-yl]pyrimidin-5-ol

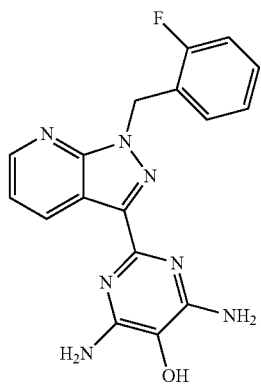 [SMILES: Nc1nc(-c2nn(Cc3ccccc3F)c3ncccc23)nc(N)c1O]

447 mg (0.96 mmol) of the compound obtained in example 57A were initially charged in 10 ml of tetrahydrofuran, and 6 ml of 3M hydrochloric acid were added. The next day, the mixture was concentrated to dryness and the residue was stirred with acetonitrile, water and dimethylformamide The precipitate was filtered off and washed with acetonitrile. 159 mg of the title compound were obtained (92% purity; 43% of theory).

LC-MS (method 2): $R_t$=0.71 min; MS (ESIpos): m/z=352 (M+H)$^+$

Example 59A

6-Amino-7-(2-{[tert-butyl(dimethyl)silyl]oxy}ethyl)-2-[1-(2-fluorobenzyl)-1H-pyrazolo[3,4-b]pyridin-3-yl]-7,9-dihydro-8H-purin-8-one

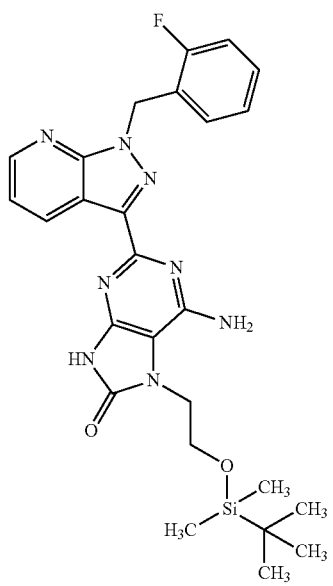 [SMILES: CC(C)(C)[Si](C)(C)OCCn1c(=O)[nH]c2nc(-c3nn(Cc4ccccc4F)c4ncccc34)nc(N)c21]

186 mg (0.442 mmol) of the compound obtained in example 1 in 3 ml of dimethylformamide were admixed with 47 mg (0.686 mmol) of imidazole and 100 mg (0.664 mmol) of tert-butyldimethylsilyl chloride. Then the mixture was stirred at RT for 2 h. Subsequently, the mixture was admixed with ethyl acetate and extracted with 0.1 M hydrochloric acid. The phases were separated and the aqueous phase was extracted with ethyl acetate. The combined organic phases were washed with water, saturated aqueous sodium hydrogencarbonate solution and then with saturated aqueous sodium chloride solution, dried over sodium sulfate, filtered and concentrated to dryness. 243 mg of the title compound were obtained (94% purity, 96% of theory), which were used in the next stage without further purification.

LC-MS (method 2): $R_t$=1.20 min; MS (ESIpos): m/z=535 (M+H)$^+$ $^1$H NMR (400 MHz, DMSO-d$_6$): δ [ppm]=0.00 (s, 6H), 0.86 (s, 9H), 3.91 (t, 2H), 4.19 (t, 2H), 5.92 (s, 2H), 6.76 (s, 2H), 7.25-7.37 (m, 3H), 7.46-7.51 (m, 2H), 8.75 (dd, 1H), 9.15 (dd, 1H), 11.76 (s br, 1H).

Example 60A 7-(2-{[tert-Butyl(dimethyl)silyl]oxy}ethyl)-2-[1-(2-fluorobenzyl)-1H-pyrazolo[3,4-b]pyridin-3-yl]-6-iodo-7,9-dihydro-8H-purin-8-one

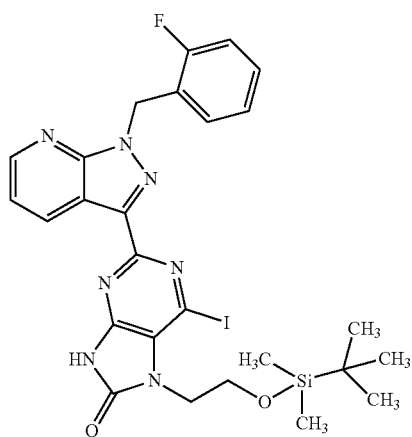 [SMILES: CC(C)(C)[Si](C)(C)OCCn1c(=O)[nH]c2nc(-c3nn(Cc4ccccc4F)c4ncccc34)nc(I)c21]

241 mg (0.423 mmol) of the compound obtained in example 59A were converted in analogy to the method described in example 101. The reaction mixture was purified by chromatography on silica gel (dichloromethane/methanol). 232 mg of the title compound were obtained (46% purity, 80% of theory), which have been used in the next stage without further purification.

LC-MS (method 2): $R_t$=1.45 min; MS (ESIpos): m/z=646 (M+H)$^+$

Example 61A

2-[1-(2-Fluorobenzyl)-1H-pyrazolo[3,4-b]pyridin-3-yl]-N$^5$-isopropylpyrimidine-4,5,6-triamine

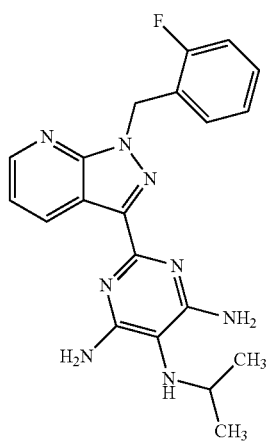 [SMILES: CC(C)Nc1c(N)nc(-c2nn(Cc3ccccc3F)c3ncccc23)nc1N]

500 mg (1.427 mmol) of the compound from example 1A were added to a solution of methanol (20.0 ml) and 180 μl of acetic acid, then 231 μl of acetone were added and the mixture was stirred for 15 min. Then 251 mg (4.00 mmol) of sodium cyanoborohydride were added and the reaction mixture was stirred further at RT overnight. Subsequently, saturated aqueous sodium hydrogencarbonate solution were added and the mixture was stirred for a further 30 min. Thereafter, the mixture was concentrated and the residue was taken up in ethyl acetate. The organic phase was washed twice with water and once with saturated aqueous sodium chloride solution, dried over sodium sulfate, filtered and concentrated. This gave 517 mg (92% of theory) of the title compound in solid form.

LC-MS (method 2): $R_t$=0.84 min

MS (EIpos): m/z=393 (M+H)$^+$.

$^1$H NMR (400 MHz, DMSO-d$_6$): δ [ppm]=1.05 (d, 6H), 3.11-3.19 (m, 2H), 5.77 (s, 2H), 5.99 (s, 4H), 7.09-7.16 (m, 2H), 7.19-7.26 (m, 1H), 7.29-7.38 (m, 2H), 8.57-8.60 (m, 1H), 9.03-9.08 (m, 1H).

Example 62A

Ethyl 6-amino-2-[1-(2-fluorobenzyl)-1H-pyrazolo[3,4-b]pyridin-3-yl]-5-nitropyrimidine-4-carboxylate

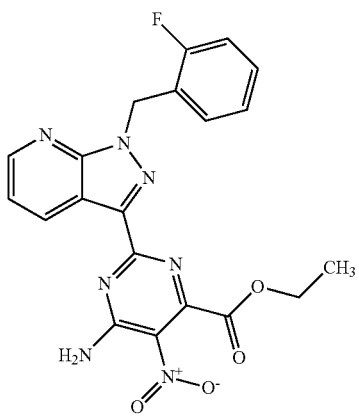 [SMILES: CCOC(=O)c1nc(-c2nn(Cc3ccccc3F)c3ncccc23)nc(N)c1[N+](=O)[O-]]

Under argon, 3.85 g (10.91 mmol) of the compound from example 24A were initially charged in dioxane (100 ml) and the reaction mixture was purged with argon. Subsequently, 8.27 ml (16.36 mmol) of hexabutylditin and 2.96 g (12.00 mmol) of ethyl 6-amino-2-chloro-5-nitropyrimidine-4-carboxylate (prepared according to J. Chem. Res. 1989, 2086-2097) were added. Thereafter, 3.83 g (5.45 mmol) of bis(triphenylphosphine)palladium(II) chloride were added and the reaction mixture was stirred at 100° C. overnight. Thereafter, the mixture was cooled to RT and filtered through Celite, and the residue was washed with methanol. The filtrate was concentrated, and the residue was extracted by stirring with ethyl acetate and filtered off. The filtrate was concentrated and the residue was purified by means of prep. HPLC (eluent: acetonitrile/water with 0.1% formic acid gradient). This gave 1.36 g (71% purity, 14% of theory) of crude product, which was converted without further purification.

LC-MS (method 2): R$_t$=1.13 min; MS (ESIpos): m/z=438 [M+H]$^+$.

Example 63A

Ethyl 5,6-diamino-2-[1-(2-fluorobenzyl)-1H-pyrazolo[3,4-b]pyridin-3-yl]pyrimidine-4-carboxylate

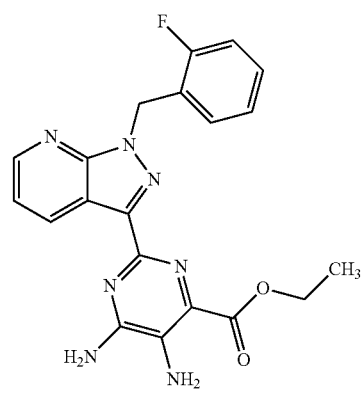 [SMILES: CCOC(=O)c1nc(-c2nn(Cc3ccccc3F)c3ncccc23)nc(N)c1N]

130 mg (0.30 mmol) of the compound from example 62A were initially charged in pyridine (9 ml) and then 25 mg of palladium (10% on charcoal) were added. The mixture was hydrogenated under standard hydrogen pressure at RT overnight. The reaction mixture was then filtered through Celite and the filtercake was washed with methanol. The filtrate was concentrated, methanol was added to the residue, and the solids were filtered off. The filtrate was concentrated by rotary evaporation and the residue was dried under high vacuum. This gave 51 mg (83% purity, 36% of theory) of the title compound, which were converted without further purification.

LC-MS (method 2): R$_t$=0.98 min

MS (ESIpos): m/z=408 (M+H)$^+$

¹H NMR (400 MHz, DMSO-d₆): δ [ppm]=1.40 (t, 3H), 4.36 (q, 2H), 5.79 (s, 2H), 6.61-6.66 (m, 2H), 7.08-7.16 (m, 2H), 7.20-7.28 (m, 3H), 7.31-7.39 (m, 2H), 8.58-8.62 (m, 1H), 9.02-9.06 (m, 1H).

Example 64A

N⁵-(2,2-Dimethylpropyl)-2-[1-(2-fluorobenzyl)-1H-pyrazolo[3,4-b]pyridin-3-yl]pyrimidine-4,5,6-triamine

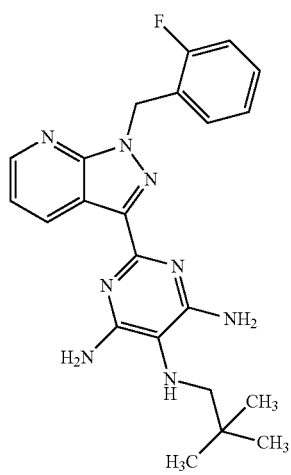 [SMILES: CC(C)(C)CNc1c(N)nc(-c2nn(Cc3ccccc3F)c3ncccc23)nc1N]

500 mg (1.43 mmol) of the compound from example 1A were added to a solution of methanol (20.0 ml) and 180 μl of acetic acid, then 349 μl (3.14 mmol) of pivalaldehyde were added and the mixture was stirred at RT for 15 min. Then 251 mg (4.00 mmol) of sodium cyanoborohydride were added and the reaction mixture was stirred further at RT overnight. Then a further 349 μl of pivalaldehyde, 180 μl of acetic acid and 251 mg of sodium cyanoborohydride were added to the reaction mixture and stirring of the mixture at RT continued overnight. Thereafter, another 349 of pivalaldehyde, 180 μl of acetic acid and 251 mg of sodium cyanoborohydride were added and the mixture was stirred further at RT overnight. Subsequently, saturated aqueous sodium hydrogencarbonate solution were added and the mixture was stirred for a further 30 min. Thereafter, the mixture was concentrated and the residue was taken up in ethyl acetate. The organic phase was washed twice with water and once with saturated aqueous sodium chloride solution, dried over sodium sulfate, filtered and concentrated. The residue was stirred with tert-butyl methyl ether, filtered, washed with tert-butyl methyl ether and then dried under high vacuum. This gave 447 mg (88% purity, 66% of theory) of the title compound, which were converted without further purification.

LC-MS (method 2): $R_t$=0.96 min

MS (EIpos): m/z=421 (M+H)⁺.

¹H NMR (400 MHz, DMSO-d₆): δ [ppm]=0.96 (s, 9H), 3.30 (s, 2H), 5.78 (s, 2H), 5.97 (s, 4H), 7.10-7.15 (m, 2H), 7.19-7.26 (m, 1H), 7.30-7.39 (m, 2H), 8.57-8.61 (m, 1H), 9.02-9.07 (m, 1H).

Example 65A

N⁵-Cyclobutyl-2-[1-(2-fluorobenzyl)-1H-pyrazolo[3,4-b]pyridin-3-yl]pyrimidine-4,5,6-triamine

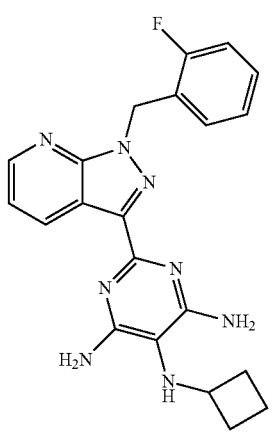 [SMILES: Nc1nc(-c2nn(Cc3ccccc3F)c3ncccc23)nc(N)c1NC1CCC1]

500 mg (1.43 mmol) of the compound from example 1A were added to a solution of methanol (20.0 ml) and 180 ml of acetic acid, then 237 μl (3.14 mmol) of cyclobutanone were added and the mixture was stirred at RT for 15 min. Subsequently, 251 mg (4.00 mmol) of sodium cyanoborohydride were added and the reaction mixture was stirred at RT overnight. Thereafter, saturated aqueous sodium hydrogencarbonate solution was added and the mixture was stirred for a further 30 min. Subsequently, the mixture was concentrated and the residue was taken up in ethyl acetate. The organic phase was washed twice with water and once with saturated aqueous sodium chloride solution, dried over sodium sulfate, filtered and concentrated. The residue was stirred with cyclohexane/ethyl acetate, and the solids were filtered off, washed with ethyl acetate and then dried under high vacuum. This gave 134 mg (22% of theory) of the title compound as a yellow solid. Concentration of the mother liquor gave a further 285 mg (76% purity, 38% of theory) of the title compound.

LC-MS (method 2): $R_t$=0.88 min

MS (EIpos): m/z=405 (M+H)⁺.

¹H NMR (400 MHz, DMSO-d₆): δ [ppm]=1.38-1.62 (m, 2H), 1.84-1.96 (m, 2H), 2.01-2.11 (m, 2H), 3.45-3.56 (m, 1H), 3.68 (d, 1H), 5.77 (s, 2H), 6.00 (s, 4H), 7.09-7.15 (m, 2H), 7.20-7.26 (m, 1H), 7.29-7.38 (m, 2H), 8.57-8.61 (m, 1H), 9.02-9.07 (m, 1H).

Example 66A

N⁵-(2-Fluorobenzyl)-2-[1-(2-fluorobenzyl)-1H-pyrazolo[3,4-b]pyridin-3-yl]pyrimidine-4,5,6-triamine

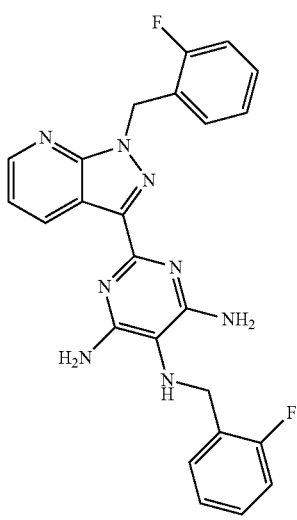 [SMILES: Nc1nc(-c2nn(Cc3ccccc3F)c3ncccc23)nc(N)c1NCc1ccccc1F]

500 mg (1.43 mmol) of the compound from example 1A were added to a solution of methanol (20.0 ml) and 180 μl of acetic acid, then 333 μl (3.14 mmol) of 2-fluorobenzaldehyde were added and the mixture was stirred at RT for 15 min. Subsequently, 251 mg (4.00 mmol) of sodium cyanoborohydride were added and the reaction mixture was stirred at RT overnight. Thereafter, saturated aqueous sodium hydrogencarbonate solution was added and the mixture was stirred for a further 30 min. Subsequently, the mixture was concentrated and the residue was taken up in ethyl acetate. The organic phase was washed twice with water and once with saturated aqueous sodium chloride solution, dried over sodium sulfate, filtered and concentrated. The residue was stirred with cyclohexane/ethyl acetate, and the solids were filtered off, washed with ethyl acetate and then dried under high vacuum. This gave 267 mg (82% purity, 34% of theory) of the title compound in solid form. Concentration of the mother liquor gave a further 490 mg (53% purity, 40% of theory) of the title compound. The crude product (82% purity) was converted without further purification.

LC-MS (method 2): $R_t$=0.90 min

MS (EIpos): m/z=459 (M+H)⁺.

Example 67A

1-[1-(2-Fluorobenzyl)-1H-pyrazolo[3,4-b]pyridin-3-yl]ethanone

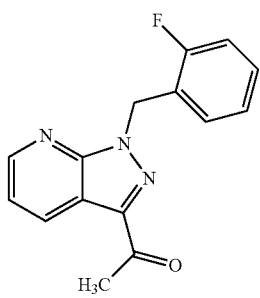 [SMILES: CC(=O)c1nn(Cc2ccccc2F)c2ncccc12]

Under an argon atmosphere, 20 g (79.285 mmol) of the compound from example 3A were dissolved in 250 ml of ether, and 40 ml (120.000 mmol) of a 3 N solution of methylmagnesium iodide in diethyl ether were added while stirring vigorously. The mixture was stirred at RT for 1 h and another 20 ml (60.000 mmol) of a 3 N solution of methylmagnesium iodide in diethyl ether were added. The reaction mixture was boiled under reflux for 20 h and then added to a mixture of 400 ml of tert-butyl methyl ether, 400 ml of ice-water and 400 ml of 1 N hydrochloric acid. The organic phase was removed and the aqueous phase was extracted once with tert-butyl methyl ether. The combined organic phases were dried over sodium sulfate and concentrated on a rotary evaporator. This gave 20.95 g (purity 94%, 92% of theory) of the title compound. The crude product was converted further without further purification.

LC-MS (method 2): $R_t$=1.08 min; MS (EIpos): m/z=270 (M+H)⁺.

Example 68A

1-[1-(2-Fluorobenzyl)-1H-pyrazolo[3,4-b]pyridin-3-yl]-2,2-dihydroxyethanone

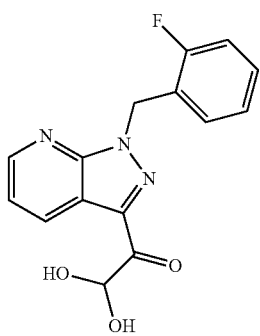 [SMILES: O=C(c1nn(Cc2ccccc2F)c2ncccc12)C(O)O]

9.7 g (36.022 mmol) of example 67A were dissolved in 68 ml of DMSO, 12.15 ml (108.066 mmol) of a 48% aqueous hydrogen bromide solution were added and the mixture was stirred at 55° C. for 5 h. The reaction mixture was concentrated and the residue was stirred with methanol. This gave 9.94 g (75% purity, 68% of theory) of the title compound. The crude product was converted further without further purification.

Example 69A

Methyl {4-amino-2-[1-(2-fluorobenzyl)-1H-pyrazolo[3,4-b]pyridin-3-yl]-6-methylpyrimidin-5-yl}carbamate formate

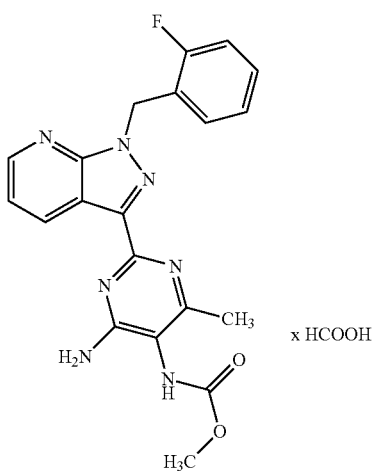 [SMILES: COC(=O)Nc1c(C)nc(-c2nn(Cc3ccccc3F)c3ncccc23)nc1N]

150 mg (0.343 mmol) of the compound from example 54A were initially charged in pyridine (3 ml) under argon and cooled to 0° C. Subsequently, a solution of 27 μl (0.34 mmol) of methyl chloroformate in dichloromethane (1 ml) was added dropwise, and the mixture was brought to RT and stirred overnight. Then the mixture was cooled again to 0° C., then 5 μl of methyl chloroformate (dissolved in 0.5 ml of dichloromethane) were added and the mixture was stirred at RT for a further 30 min. Subsequently, another 5 μl of methyl chloroformate (dissolved in 0.5 ml of dichloromethane) were added at 0° C. and the mixture was stirred at RT overnight. The reaction mixture was brought to RT and concentrated by rotary evaporation. The residue was separated by means of preparative HPLC (eluent: acetonitrile-water with 0.1% formic acid gradient) and the product fractions were concentrated. This gave 113 mg (71% of theory) of the title compound in solid form.

LC-MS (method 3): $R_t$=0.86 min

MS (ESIpos): m/z=408 (M+H)$^+$ $^1$H NMR (400 MHz, DMSO-d$_6$): δ=2.26 (s, 3H), 3.65 (m, 3H), 5.83 (s, 2H), 6.88 (br. s, 2H), 7.10-7.16 (m, 2H), 7.20-7.27 (m, 1H), 7.32-7.41 (m, 2H), 8.15 (s, 1H), 8.56 (br. s, 1H), 8.61-8.65 (m, 1H), 8.97-9.01 (m, 1H).

Example 70A

2-[5-Fluoro-1-(2-fluorobenzyl)-1H-pyrazolo[3,4-b]pyridin-3-yl]-5-nitropyrimidin-4-ol

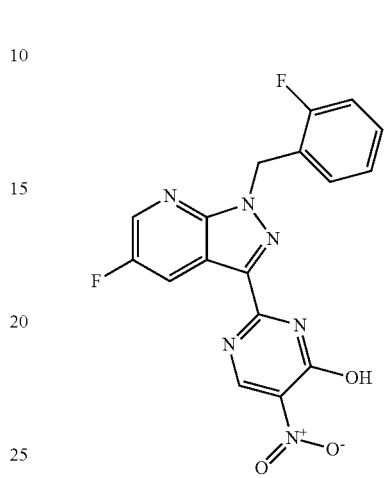

25 g (71.978 mmol) of example 28A in p-xylene (250 ml) were admixed with 20.318 g (107.967 mmol) of ethyl 3-(dimethylamino)-2-nitroacrylate (synthesis described in Chemische Berichte 101; 8; 1968; 2925-2930) and heated to reflux for 5 h. After cooling, the precipitate formed was filtered off with suction, washed with diethyl ether and then dried. This gave 24.7 g (89% of theory) of the title compound.

LC-MS (method 2): $R_t$=0.97 min; MS (ESIpos): m/z=385 (M+H)±

$^1$H NMR (400 MHz, DMSO-d$_6$): δ [ppm]=5.82 (s, 2H), 7.16 (t, 1H), 7.21-7.25 (m, 2H), 7.34-7.40 (m, 1H), 8.40 (s br, 1H), 8.57 (dd, 1H), 8.69 (dd, 1H), 8.76 (s, 1H).

Example 71A 3-(4-Chloro-5-nitropyrimidin-2-yl)-5-fluoro-1-(2-fluorobenzyl)-1H-pyrazolo[3,4-b]pyridine

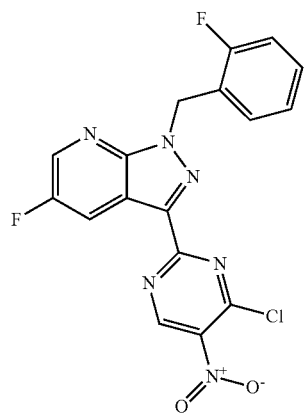 [SMILES: O=[N+]([O-])c1cnc(-c2nn(Cc3ccccc3F)c3ncc(F)cc23)nc1Cl]

24.5 g (63.752 mmol) of example 70A were initially charged in sulfolane (125 ml), then 11.885 ml (127.503 mmol) of phosphoryl chloride were added and the mixture was heated to 120° C. for 1 h. After cooling, the mixture was added cautiously to water (700 ml) and stirred for 15 min. The precipitate formed was washed first with water, then with isopropanol and finally with diethyl ether, and subsequently dried. This gave 21.5 g (80% of theory) of the title compound.

LC-MS (method 3): $R_t$=1.51 min; MS (ESIpos): m/z=403 (M+H)$^+$ $^1$H NMR (400 MHz, DMSO-d$_6$): δ [ppm]=5.94 (s, 2H), 7.16-7.26 (m, 2H), 7.33-7.42 (m, 2H), 8.52 (dd, 1H), 8.83 (dd, 1H), 9.61 (s, 1H).

Example 72A

2-[5-Fluoro-1-(2-fluorobenzyl)-1H-pyrazolo[3,4-b]pyridin-3-yl]-5-nitropyrimidin-4-amine

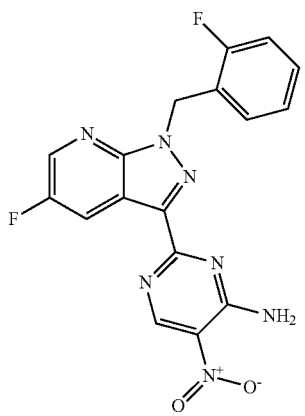 [SMILES: Nc1nc(-c2nn(Cc3ccccc3F)c3ncc(F)cc23)ncc1[N+](=O)[O-]]

11.00 g (27.312 mmol) of example 71A were initially charged in isopropanol (185 ml) and dimethylformamide (123 ml), then 54.62 ml of a 2M solution of ammonia in isopropanol were added and the mixture was heated to 60° C. for 1.5 h. After cooling, the mixture was added to water (350 ml) and stirred for 10 min. The precipitate formed was washed first with water, then with isopropanol and finally with diethyl ether, and subsequently dried. This gave 10.3 g (92% of theory) of the title compound.

LC-MS (method 2): $R_t$=1.05 min; MS (ESIpos): m/z=384 (M+H)$^+$

1H NMR (400 MHz, DMSO-d$_6$): δ [ppm]=5.87 (s, 2H), 7.15-7.30 (m, 3H), 7.35-7.41 (m, 1H), 8.46 (s br, 1H), 8.75 (m, 1H), 8.93 (dd, 1H), 9.11 (s br, 1H), 9.22 (s, 1H).

Example 73A

2-[5-Fluoro-1-(2-fluorobenzyl)-1H-pyrazolo[3,4-b]pyridin-3-yl]pyrimidine-4,5-diamine

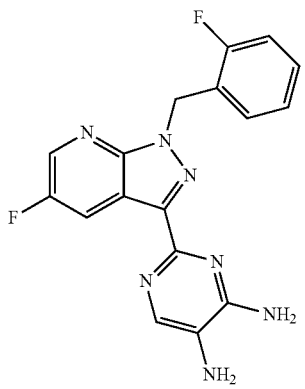 [SMILES: Nc1cnc(-c2nn(Cc3ccccc3F)c3ncc(F)cc23)nc1N]

10.00 g (26.088 mmol) of example 72A in ethanol (600 ml) were admixed with 2 g of palladium on charcoal (10%) and hydrogenated at RT and under standard hydrogen pressure overnight. Then dichloromethane (500 ml) was added and the mixture was stirred for 30 min Subsequently, the mixture was filtered through kieselguhr and the filtrate was concentrated a little. Then diethyl ether was added and the precipitate formed was filtered off with suction, washed with diethyl ether and then dried. This gave 6.7 g (71% of theory) of the title compound.

LC-MS (method 2): $R_t$=0.76 min; MS (ESIpos): m/z=354 (M+H)$^+$ $^1$H NMR (400 MHz, DMSO-d$_6$): δ [ppm]=4.97-5.01 (m, 2H), 5.76 (s, 2H), 6.60 (s br, 2H), 7.12-7.25 (m, 3H), 7.33-7.39 (m, 1H), 7.71 (s, 1H), 8.65 (m, 1H), 8.70 (dd, 1H).

Example 74A

Methyl {4-amino-2-[5-fluoro-1-(2-fluorobenzyl)-1H-pyrazolo[3,4-b]pyridin-3-yl]pyrimidin-5-yl}carbamate

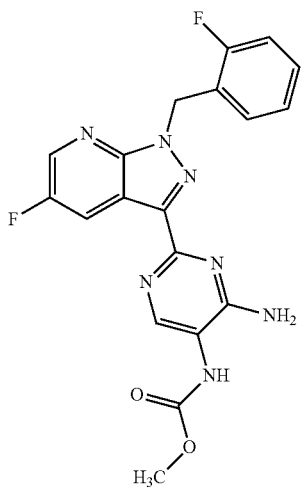 [SMILES: COC(=O)Nc1cnc(-c2nn(Cc3ccccc3F)c3ncc(F)cc23)nc1N]

The compound was prepared in analogy to example 31A. This gave 140 mg (12% of theory) of the title compound proceeding from 1.00 g (2.830 mmol) of example 73A.

LC-MS (method 2): $R_t$=0.86 min; MS (ESIpos): m/z=412 (M+H)$^+$ $^1$H NMR (400 MHz, DMSO-d$_6$): δ [ppm]=3.68 (s, 3H), 5.81 (s, 2H), 6.95-7.25 (m, 5H), 7.34-7.40 (m, 1H), 8.40 (s br, 1H), 8.69 (dd, 1H), 8.75 (dd, 1H), 8.88 (s br, 1H).

Example 75A

Methyl {4-amino-2-[5-fluoro-1-(2-fluorobenzyl)-1H-pyrazolo[3,4-b]pyridin-3-yl]pyrimidin-5-yl}methylcarbamate

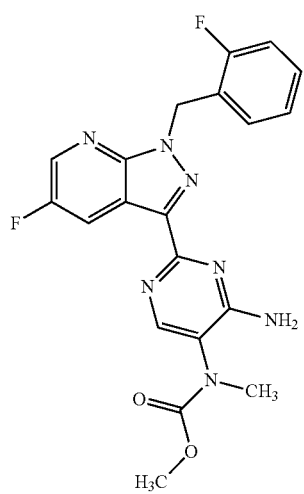 [SMILES: COC(=O)N(C)c1cnc(-c2nn(Cc3ccccc3F)c3ncc(F)cc23)nc1N]

700 mg (1.702 mmol) of the compound obtained in example 74A were initially charged in tetrahydrofuran (15 ml) and 2.552 ml (2.552 mmol) of lithium hexamethyldisilazide (1.0 M in tetrahydrofuran) were added at 0° C. After 20 min at 0° C., 158 μl (2.552 mmol) of iodomethane were added and then the mixture was stirred at RT overnight. Then water was added (1 ml), and the mixture was stirred for 10 min and then concentrated to dryness. 300 mg of the crude material (approx. 1 g) were taken and purified by means of preparative HPLC (acetonitrile:water (+0.05% formic acid) gradient). 31 mg of the title compound were obtained (4% of theory).

The remaining amount was dried under high vacuum overnight. This gave 417 mg of the title compound in approx. 70% purity, which had been used without further purification in example 95.

LC-MS (method 2): $R_t$=0.89 min; MS (ESIpos): m/z=426 (M+H)$^+$ $^1$H NMR (400 MHz, DMSO-d$_6$): δ [ppm]=3.09 (s, 3H), 3.55 and 3.69 (s br, together 3H), 5.82 (s, 2H), 7.13-7.26 (m, 3H), 7.33-7.40 (m, 1H), 8.18 (s, 1H), 8.70 (dd, 1H), 8.74 (dd, 1H).

Example 76A

3-Bromo-1,1,1-trifluoropropan-2-yl {4-amino-2-[1-(2-fluorobenzyl)-1H-pyrazolo[3,4-b]pyridin-3-yl]pyrimidin-5-yl}carbamate

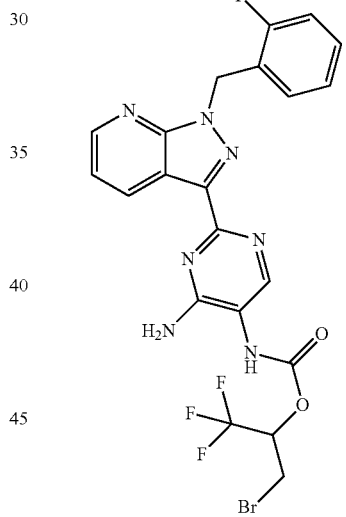

The title compound was prepared in analogy to example 9A proceeding from 1.30 g (3.877 mmol) of 2-[1-(2-fluorobenzyl)-1H-pyrazolo[3,4-b]pyridin-3-yl]pyrimidine-4,5-diamine (synthesis described in WO 02/042302, starting compound V). This gave 281 mg (13% of theory) of the title compound.

LC-MS (method 2): $R_t$=1.01 min; MS (EIpos): m/z=554/556 [M+H, Br pattern]$^+$.

Example 77A

3-{4-Amino-2-[1-(2-fluorobenzyl)-1H-pyrazolo[3,4-b]pyridin-3-yl]pyrimidin-5-yl}-5-(trifluoromethyl)-1,3-oxazolidin-2-one

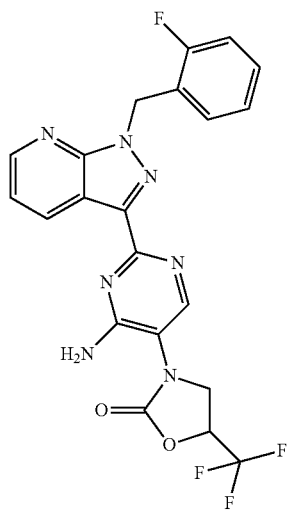 [SMILES: Nc1nc(-c2nn(Cc3ccccc3F)c3ncccc23)ncc1N1CC(C(F)(F)F)OC1=O]

Proceeding from 768 mg (1.386 mmol) of example 76A, in analogy to example 8A, 658 mg (100% of theory) of the title compound were obtained.

LC-MS (method 2): $R_t$=0.98 min; MS (EIpos): m/z=474 (M+H)$^+$.

Example 78A

2-[1-(2-Fluorobenzyl)-1H-pyrazolo[3,4-b]pyridin-3-yl]-5-nitropyrimidin-4-ol

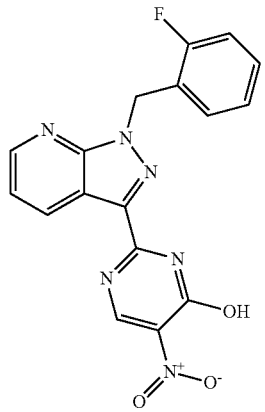 [SMILES: O=[N+]([O-])c1cnc(-c2nn(Cc3ccccc3F)c3ncccc23)nc1O]

100.00 g (327.07 mmol) of the compound from example 5A were suspended in p-xylene (1), 92.32 g (490.60 mmol) of ethyl 3-(dimethylamino)-2-nitroacrylate (synthesis described in Chemische Berichte 101; 8; 1968; 2925-2930) were added and the mixture was heated to reflux for 6 h. After cooling, the precipitate formed was filtered off with suction, washed with diethyl ether and then dried. This gave 109.00 g (76% of theory) of the title compound.

LC-MS (method 2): $R_t$=0.91 min; MS (ESIpos): m/z=367 (M+H)$^+$ $^1$H NMR (400 MHz, DMSO-d$_6$): δ [ppm]=5.92 (s, 2H), 7.17 (t, 1H), 7.22-7.27 (m, 1H), 7.34-7.41 (m, 1H), 7.52-7.55 (m, 1H), 8.67 (s br, 1H), 8.75-8.77 (m, 2H), 9.01 (s br, 1H), 13.91 (s br, 1H).

Example 79A 3-(4-Chloro-5-nitropyrimidin-2-yl)-1-(2-fluorobenzyl)-1H-pyrazolo[3,4-b]pyridine

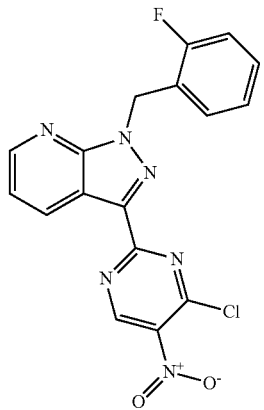 [SMILES: O=[N+]([O-])c1cnc(-c2nn(Cc3ccccc3F)c3ncccc23)nc1Cl]

109.00 g (249.95 mmol) of the compound from example 78A were initially charged in sulfolane (490 ml), then 55.92 ml (599.88 mmol) of phosphoryl chloride were added and the mixture was heated to 120° C. for 1 h. After cooling, the mixture was added cautiously to water (3 l) and stirred for 15 min. Sodium hydrogencarbonate was added in portions until the pH was 6. The precipitate formed was filtered off with suction and washed with water. The residue was stirred with 200 ml of dichloromethane/methanol (v/v=4:1) for 30 min, filtered off with suction, washed with dichloromethane, acetone and petroleum ether and dried under high vacuum. This gave 63.00 g (62% of theory) of the title compound.

LC-MS (method 2): $R_t$=1.18 min; MS (ESIpos): m/z=385 (M+H)$^+$

Example 80A

N-(2,4-Dimethoxybenzyl)-2-[1-(2-fluorobenzyl)-1H-pyrazolo[3,4-b]pyridin-3-yl]-5-nitropyrimidin-4-amine

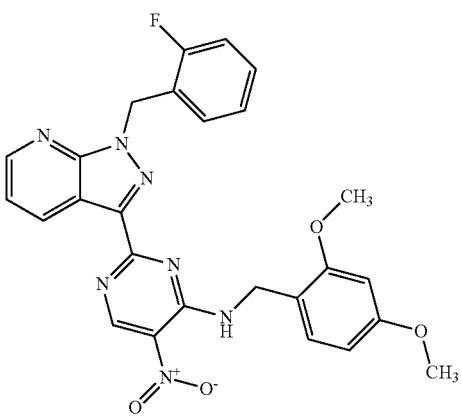 [SMILES: COc1ccc(CNc2nc(-c3nn(Cc4ccccc4F)c4ncccc34)ncc2[N+](=O)[O-])c(OC)c1]

15.00 g (38.99 mmol) of the compound from example 79A were dissolved in 200 ml of dioxane, 6.98 g (40.94 mmol) of 2,4-dimethoxybenzylamine and 5.54 g (42.88 mmol) of N,N-diisopropylamine were added and the mixture was stirred at 85° C. for 1 h. After cooling, the mixture was filtered and the filtrate was concentrated on a rotary evaporator and the residue was dried under high vacuum. The residue was crushed with a mortar and pestle, stirred with 250 ml of water, filtered off with suction and dried under high vacuum. 19.96 g (89% of theory) of the title compound were obtained.

LC-MS (method 2): $R_t$=1.29 min; MS (ESIpos): m/z=516 (M+H)$^+$ $^1$H NMR (400 MHz, DMSO-d$_6$): δ [ppm]=3.71 (s, 3H), 3.91 (s, 3H), 4.83 (d, 2H), 5.87 (s, 2H), 6.39 (dd, 1H), 6.66 (d, 1H), 7.13-7.25 (m, 4H), 7.29-7.40 (m, 2H), 8.35 (dd, 1H), 8.65 (dd, 1H), 9.25 (s, 1H), 9.29 (t, 1H).

Example 81A

N$^4$-(2,4-Dimethoxybenzyl)-2-[1-(2-fluorobenzyl)-1H-pyrazolo[3,4-b]pyridin-3-yl]pyrimidine-4,5-diamine

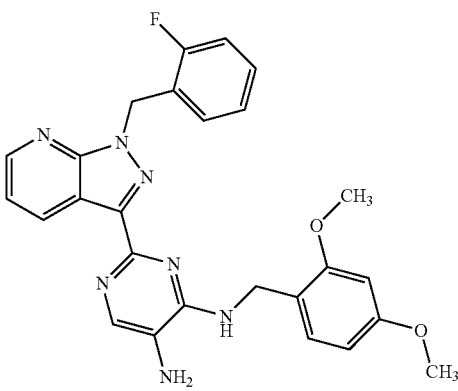 [SMILES: COc1ccc(CNc2nc(-c3nn(Cc4ccccc4F)c4ncccc34)ncc2N)c(OC)c1]

19.64 g (38.10 mmol) of the compound from example 80A were dissolved in 300 ml of pyridine, 2.00 g of palladium on charcoal (10%) were added and the mixture was hydrogenated at RT and standard hydrogen pressure for 2 h. The mixture was filtered through Celite and washed through with a little pyridine, and the filtrate was concentrated by rotary evaporation on a rotary evaporator. 19.02 g (78% of theory) of the title compound were obtained.

LC-MS (method 2): $R_t$=0.89 min; MS (ESIpos): m/z=486 (M+H)±

Example 82A 9-(2,4-Dimethoxybenzyl)-2-[1-(2-fluorobenzyl)-1H-pyrazolo[3,4-b]pyridin-3-yl]-7,9-dihydro-8H-purin-8-one

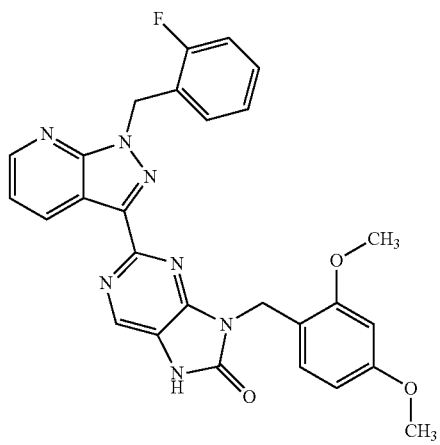 [SMILES: COc1ccc(Cn2c(=O)[nH]c3cnc(-c4nn(Cc5ccccc5F)c5ncccc45)nc32)c(OC)c1]

14.00 g (21.91 mmol) of the compound from example 81A were dissolved in 800 ml of acetonitrile, 4.62 g (28.49 mmol) of N,N'-carbonyldiimidazole were added and the mixture was boiled under reflux for 4 h. After cooling, the precipitate was filtered off and dried under high vacuum. 10.16 g (79% of theory) of the title compound were obtained.

LC-MS (method 2): $R_t$=1.08 min; MS (ESIpos): m/z=512 (M+H)$^+$ $^1$H NMR (400 MHz, DMSO-d$_6$): δ [ppm]=3.71 (s, 3H), 3.81 (s, 3H), 5.03 (s, 2H), 5.83 (s, 2H), 6.44 (dd, 1H), 6.60 (d, 1H), 7.02 (d, 1H), 7.10-7.17 (m, 2H), 7.20-7.25 (m, 1H), 7.32-7.36 (m, 1H), 7.39 (dd, 1H), 8.39 (s, 1H), 8.64 (dd, 1H), 8.77 (dd, 1H), 11.59 (s, 1H).

Example 83A 9-(2,4-Dimethoxybenzyl)-2-[1-(2-fluorobenzyl)-1H-pyrazolo[3,4-b]pyridin-3-yl]-7-(2-methoxyethyl)-7,9-dihydro-8H-purin-8-one

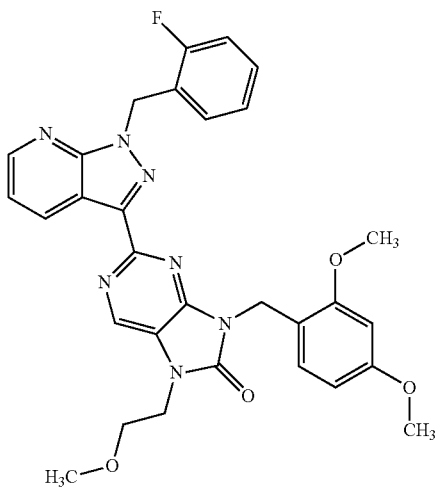 [SMILES: COCCn1c(=O)n(Cc2ccc(OC)cc2OC)c2nc(-c3nn(Cc4ccccc4F)c4ncccc34)ncc21]

500 mg (0.977 mmol) of the compound from example 82A were dissolved in 10 ml of DMF, 414 mg (1.271 mmol) of cesium carbonate and 149 mg (1.075 mmol) of 2-bromoethyl methyl ether were added and the mixture was stirred at RT for 18 h. Water was added and the mixture was extracted with ethyl acetate. The combined organic phases were dried over sodium sulfate and concentrated on a rotary evaporator. The residue was dried under high vacuum. 453 mg (74% of theory) of the title compound were obtained.

LC-MS (method 2): $R_t$=1.19 min; MS (ESIpos): m/z=570 (M+H)$^+$ $^1$H NMR (400 MHz, DMSO-d$_6$): δ [ppm]=3.26 (s, 3H), 3.67 (t, 2H), 3.71 (s, 3H), 3.80 (s, 3H), 4.13 (t, 2H), 5.08 (s, 2H), 5.84 (s, 2H), 6.45 (dd, 1H), 6.59 (d, 1H), 7.04 (d, 1H), 7.10-7.18 (m, 2H), 7.21-7.25 (m, 1H), 7.32-7.38 (m, 1H), 7.40 (dd, 1H), 8.61 (s, 1H), 8.65 (dd, 1H), 8.78 (dd, 1H).

Example 84A 7-(Cyclopropylmethyl)-9-(2,4-dimethoxybenzyl)-2-[1-(2-fluorobenzyl)-1H-pyrazolo[3,4-b]pyridin-3-yl]-7,9-dihydro-8H-purin-8-one

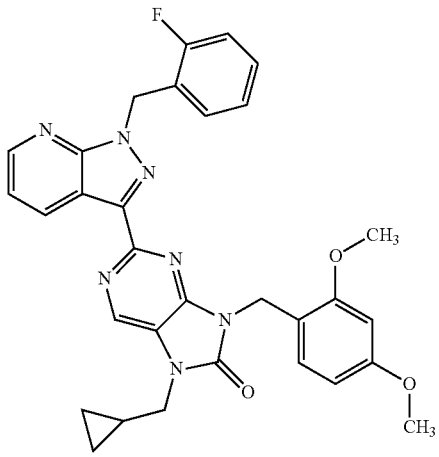 [SMILES: COc1ccc(Cn2c(=O)n(CC3CC3)c3cnc(-c4nn(Cc5ccccc5F)c5ncccc45)nc32)c(OC)c1]

500 mg (0.980 mmol) of the compound from example 82A were dissolved in 10 ml of DMF, 414 mg (1.270 mmol) of cesium carbonate and 150 mg (1.08 mmol) of 2-bromomethylcyclopropane were added and the mixture was stirred at RT for 18 h. Water was added and the mixture was extracted with ethyl acetate. The combined organic phases were dried over sodium sulfate and concentrated on a rotary evaporator. The residue was dried under high vacuum. 482 mg (72% of theory, purity 82%) of the title compound were obtained.

LC-MS (method 2): $R_t$=1.25 min; MS (ESIpos): m/z=566 (M+H)$^+$

Example 85A 9-(2,4-Dimethoxybenzyl)-2-[1-(2-fluorobenzyl)-1H-pyrazolo[3,4-b]pyridin-3-yl]-7-(2,2,3,3,3-pentafluoropropyl)-7,9-dihydro-8H-purin-8-one

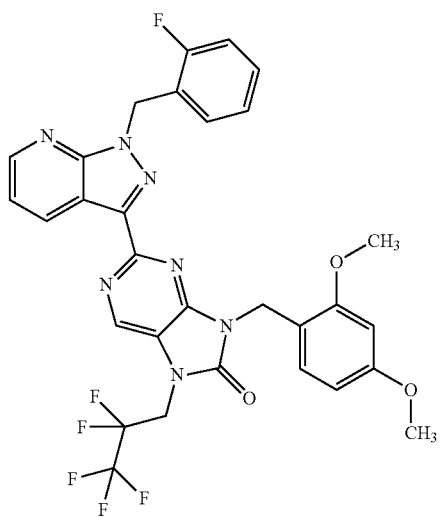 [SMILES: COc1ccc(Cn2c(=O)n(CC(F)(F)C(F)(F)F)c3cnc(-c4nn(Cc5ccccc5F)c5ncccc45)nc32)c(OC)c1]

500 mg (0.980 mmol) of the compound from example 82A were dissolved in 10 ml of DMF, 414 mg (1.270 mmol) of cesium carbonate and 313 mg (1.08 mmol) of 2,3,3,3,3-pentafluoropropyl trifluoromethanesulfonate were added and the mixture was stirred at RT for 18 h. Water was added and the mixture was extracted with ethyl acetate. The combined organic phases were dried over sodium sulfate and concentrated on a rotary evaporator. The residue was dried under high vacuum. 471 mg (61% of theory, purity 82%) of the title compound were obtained.

LC-MS (method 2): $R_t$=1.31 min; MS (ESIpos): m/z=644 (M+H)$^+$

Example 86A 9-(2,4-Dimethoxybenzyl)-2-[1-(2-fluorobenzyl)-1H-pyrazolo[3,4-b]pyridin-3-yl]-7-(oxetan-2-ylmethyl)-7,9-dihydro-8H-purin-8-one

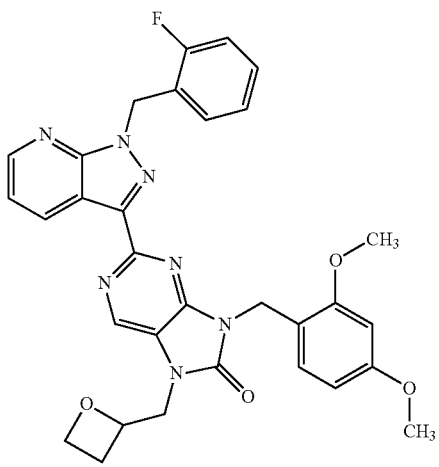 [SMILES: COc1ccc(Cn2c(=O)n(CC3CCO3)c3cnc(-c4nn(Cc5ccccc5F)c5ncccc45)nc32)c(OC)c1]

500 mg (0.980 mmol) of the compound from example 82A were dissolved in 10 ml of DMF, 414 mg (1.270 mmol) of cesium carbonate and 150 mg (1.08 mmol) of 2-(bromomethyl)oxetane were added and the mixture was stirred at RT for 18 h, at 40° C. for 18 h and at 100° C. for 4 h. After cooling, water was added and the mixture was extracted with ethyl acetate. The combined organic phases were dried over sodium sulfate and concentrated on a rotary evaporator. The residue was dried under high vacuum. 581 mg (53% of theory, purity 63%) of the title compound were obtained.

LC-MS (method 2): $R_t$=1.19 min; MS (ESIpos): m/z=582 (M+H)$^+$

Example 87A 9-(2,4-Dimethoxybenzyl)-2-[1-(2-fluorobenzyl)-1H-pyrazolo[3,4-b]pyridin-3-yl]-7-[2-(morpholin-4-yl)ethyl]-7,9-dihydro-8H-purin-8-one

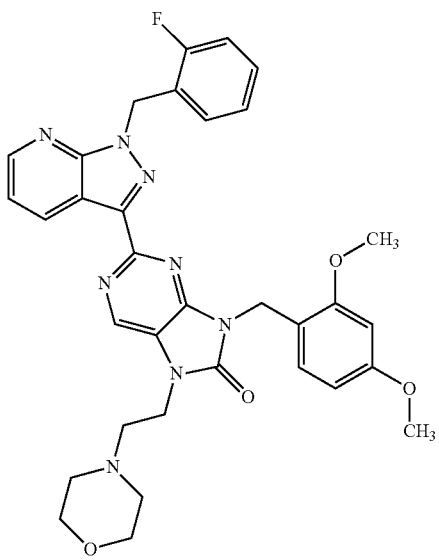 [SMILES: COc1ccc(Cn2c(=O)n(CCN3CCOCC3)c3cnc(-c4nn(Cc5ccccc5F)c5ncccc45)nc32)c(OC)c1]

500 mg (0.980 mmol) of the compound from example 82A were dissolved in 10 ml of DMF, 414 mg (1.270 mmol) of cesium carbonate and 259 mg (1.08 mmol) of 4-(2-iodoethyl)morpholine were added and the mixture was stirred at RT for 18 h, at 40° C. for 18 h and at 100° C. for 8 h. After cooling, water was added and the mixture was extracted with ethyl acetate. The combined organic phases were dried over sodium sulfate and concentrated on a rotary evaporator. The purification was effected by means of preparative HPLC (eluent: methanol/water, gradient 30:70→90:10). 102 mg (17% of theory) of the title compound were obtained.

LC-MS (method 2): $R_t$=0.86 min; MS (ESIpos): m/z=625 (M+H)$^+$

Example 88A

2-[1-(2-Fluorobenzyl)-1H-pyrazolo[3,4-b]pyridin-3-yl]-N$^5$-[1-(2,2,2-trifluoroethyl)piperidin-4-yl]pyrimidine-4,5-diamine

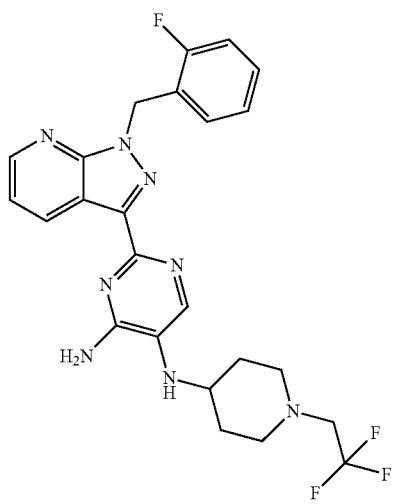 [SMILES: Nc1nc(-c2nn(Cc3ccccc3F)c3ncccc23)ncc1NC1CCN(CC(F)(F)F)CC1]

200 mg (0.596 mmol) of 2-[1-(2-fluorobenzyl)-1H-pyrazolo[3,4-b]pyridin-3-yl]pyrimidine-4,5-diamine (synthesis described in US2004/67937; Example V) were initially charged in methanol (16 ml) and admixed with 75 µl (1.312 mmol) of acetic acid, and then 237 mg (1.312 mmol) of 1-(2,2,2-trifluoroethyl)piperidin-4-one were added. After stirring at RT for 15 min, 104 mg (1.67 mmol) of sodium cyanoborohydride were added and the mixture was stirred at RT for 2.5 h. Subsequently, within 2 days, the above-stated amounts of reagents (1-(2,2,2-trifluoroethyl)piperidin-4-one, acetic acid, sodium cyanoborohydride) were added three times, in order to achieve substantially full conversion. Thereafter, saturated aqueous sodium hydrogencarbonate solution (5 ml) was added to the reaction mixture, which was stirred vigorously for 10 min. Subsequently, the reaction mixture was extracted with water and ethyl acetate. The phases were separated and the aqueous phase was extracted twice with ethyl acetate. The combined organic phases were washed with saturated aqueous sodium chloride solution, dried over sodium sulfate, filtered, concentrated and then purified by means of preparative HPLC (acetonitrile:water (+0.05% formic acid) gradient). 269 mg of the title compound were obtained (90% of theory).

LC-MS (method 5): $R_t$=0.80 min; MS (EIpos): m/z=501 (M+H)$^+$.

Example 89A

2-[1-(2-Fluorobenzyl)-1H-pyrazolo[3,4-b]pyridin-3-yl]-N$^5$-[1-(2,2,2-trifluoroethyl)pyrrolidin-3-yl]pyrimidine-4,5-diamine

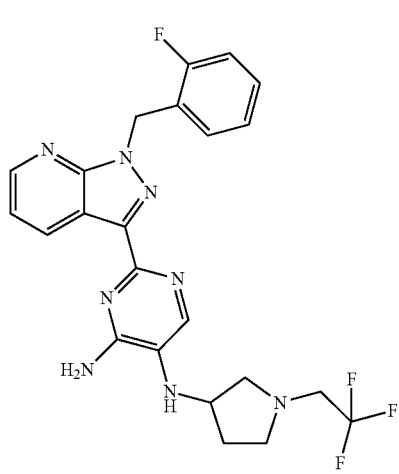 [SMILES: Nc1nc(-c2nn(Cc3ccccc3F)c3ncccc23)ncc1NC1CCN(CC(F)(F)F)C1]

LC-MS (method 2): $R_t$=0.86 min; MS (EIpos): m/z=487 (M+H)$^+$.

Example 90A

N$^5$-[1-(2,2-Difluoroethyl)piperidin-4-yl]-2-[1-(2-fluorobenzyl)-1H-pyrazolo[3,4-b]pyridin-3-yl]pyrimidine-4,5-diamine

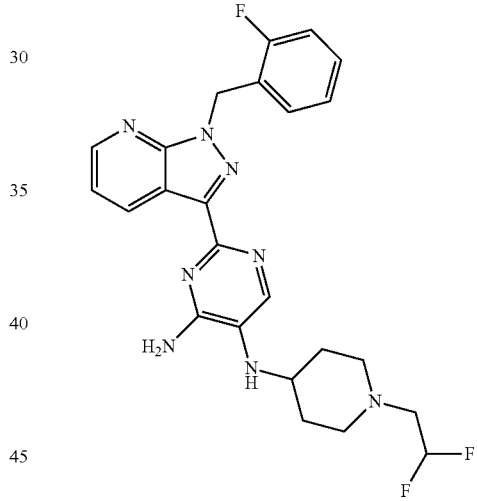

400 mg (1.193 mmol) of 2-[1-(2-fluorobenzyl)-1H-pyrazolo[3,4-b]pyridin-3-yl]pyrimidine-4,5-diamine (synthesis described in US2004/67937; Example V) were reacted in analogy to the method in example 88A with 1-(2,2,2-trifluoroethyl)pyrrolidinone. After purification by means of preparative HPLC (acetonitrile:water (+0.05% formic acid) gradient), this gave 482 mg of the title compound (83% of theory).

200 mg (0.596 mmol) of 2-[1-(2-fluorobenzyl)-1H-pyrazolo[3,4-b]pyridin-3-yl]pyrimidine-4,5-diamine (synthesis described in US2004/67937; Example V) were reacted in analogy to the method in example 88A with 1-(2,2-difluoroethyl)piperidin-4-one. After purification by means of preparative HPLC (acetonitrile:water (+0.05% formic acid) gradient), this gave 219 mg of the title compound (76% of theory).

LC-MS (method 2): $R_t$=0.60 min; MS (EIpos): m/z=483 (M+H)$^+$.

Example 91A

N-(2,4-Dimethoxybenzyl)-2-[5-fluoro-1-(2-fluorobenzyl)-1H-pyrazolo[3,4-b]pyridin-3-yl]-5-nitropyrimidin-4-amine

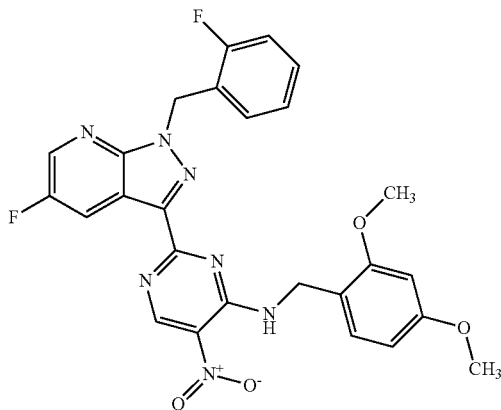 [SMILES: COc1ccc(CNc2nc(-c3nn(Cc4ccccc4F)c4ncc(F)cc34)ncc2[N+](=O)[O-])c(OC)c1]

10.070 g (25.003 mmol) of the compound from example 71A were converted in analogy to the method in example 80A. 13.31 g (99% of theory) of the title compound were obtained.

LC-MS (method 2): $R_t$=1.38 min; MS (ESIpos): m/z=534 (M+H)$^+$

Example 92A

N4-(2,4-Dimethoxybenzyl)-2-[5-fluoro-1-(2-fluorobenzyl)-1H-pyrazolo[3,4-b]pyridin-3-yl]pyrimidine-4,5-diamine

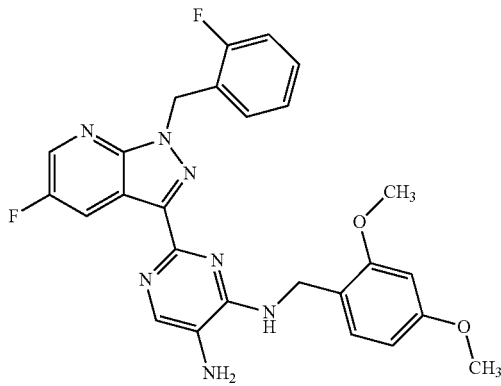 [SMILES: COc1ccc(CNc2nc(-c3nn(Cc4ccccc4F)c4ncc(F)cc34)ncc2N)c(OC)c1]

13.310 g (24.949 mmol) of the compound from example 91A were converted in analogy to the method in example 81A. 14.93 g (approx. 100% of theory, 84% purity) of the title compound were obtained.

LC-MS (method 2): $R_t$=1.02 min; MS (ESIpos): m/z=504 (M+H)$^+$

Example 93A 9-(2,4-Dimethoxybenzyl)-2-[5-fluoro-1-(2-fluorobenzyl)-1H-pyrazolo[3,4-b]pyridin-3-yl]-7,9-dihydro-8H-purin-8-one

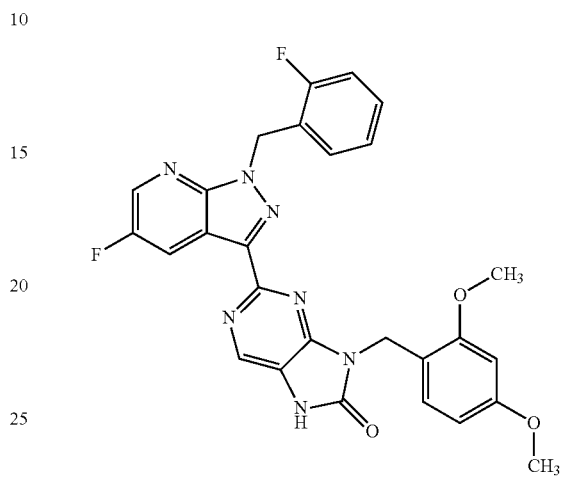

6.281 g (10.479 mmol, 84% purity) of the compound from example 92A were converted in analogy to the method in example 82A. 5.61 g (approx. 100% of theory) of the title compound were obtained.

LC-MS (method 2): $R_t$=1.11 min; MS (ESIpos): m/z=530 (M+H)±

Example 94A 9-(2,4-Dimethoxybenzyl)-2-[5-fluoro-1-(2-fluorobenzyl)-1H-pyrazolo[3,4-b]pyridin-3-yl]-7-[2-(methylsulfonyl)ethyl]-7,9-dihydro-8H-purin-8-one

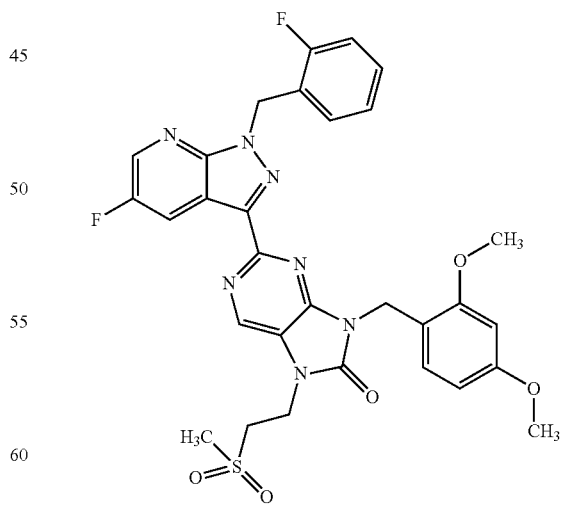

300 mg (0.567 mmol) of the compound from example 93A were reacted in analogy to the method in example 83A with 2-bromoethyl methyl sulfone. 490 mg (100% of theory, 73% purity) of the title compound were obtained.

LC-MS (method 2): R$_t$=1.16 min; MS (ESIpos): m/z=636 (M+H)$^+$

Example 95A tert-Butyl 3-({4,6-diamino-2-[1-(2-fluorobenzyl)-1H-pyrazolo[3,4-b]pyridin-3-yl]pyrimidin-5-yl}amino)azetidine-1-carboxylate

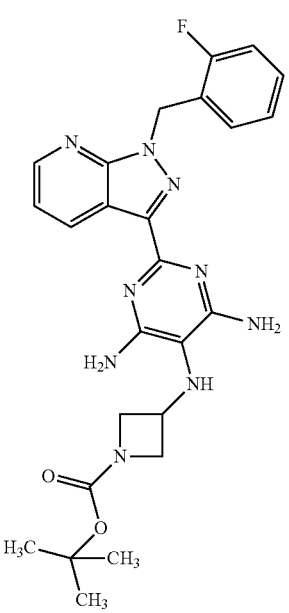 [SMILES: CC(C)(C)OC(=O)N1CC(Nc2c(N)nc(-c3nn(Cc4ccccc4F)c4ncccc34)nc2N)C1]

7.70 g (21.977 mmol) of the compound from example 1A were reacted in analogy to the method in example 34A with tert-butyl 3-oxoazetidine-1-carboxylate. 5.26 g (47% of theory) of the title compound were obtained.

LC-MS (method 5): R$_t$=0.81 min; MS (ESIpos): m/z=506 (M+H)$^+$

Example 96A tert-Butyl 3-{6-amino-2-[1-(2-fluorobenzyl)-1H-pyrazolo[3,4-b]pyridin-3-yl]-8-oxo-8,9-dihydro-7H-purin-7-yl}azetidine-1-carboxylate

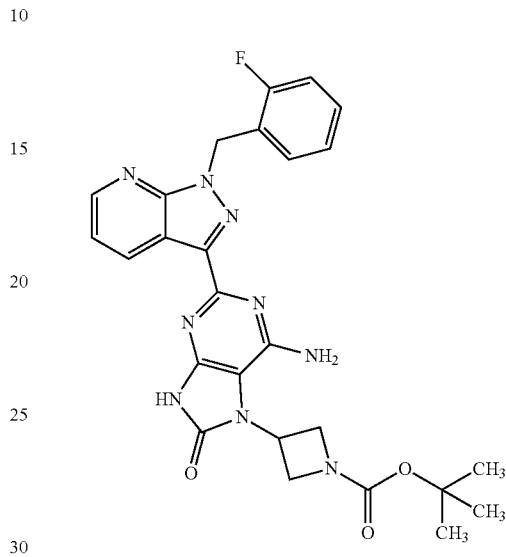

2.61 g (5.163 mmol) of the compound from example 95A were converted in analogy to the method in example 82A. 2.24 g (81% of theory) of the title compound were obtained.

LC-MS (method 2): R$_t$=1.02 min; MS (ESIpos): m/z=532 (M+H)$^+$

Example 97A tert-Butyl 3-{2-[1-(2-fluorobenzyl)-1H-pyrazolo[3,4-b]pyridin-3-yl]-6-iodo-8-oxo-8,9-dihydro-7H-purin-7-yl}azetidine-1-carboxylate

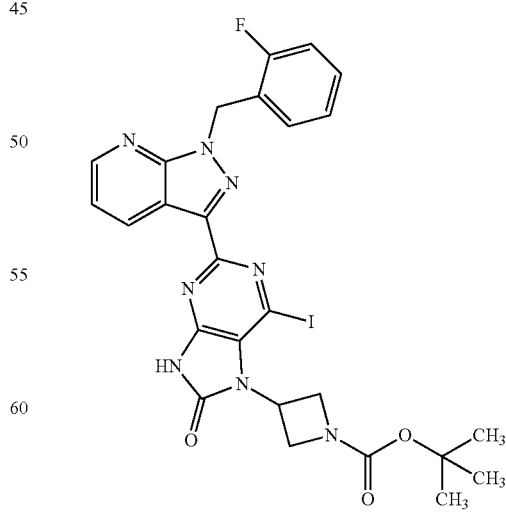

1.788 g (3.364 mmol) of the compound from example 96A were initially charged in 20 ml of 1,2-dimethoxyethane and then admixed at RT with 873 mg (3.364 mmol) of cesium iodide, 426 mg (1.682 mmol) of iodine and 192 mg (1.009 mmol) of copper(I) iodide. After addition of 2.961 ml of isopentyl nitrite, the mixture was heated to 60° C. overnight. After cooling, a precipitate was filtered off and washed with ethyl acetate. Subsequently, water was added to the precipitate, the mixture was stirred and then the precipitate was again filtered off with suction and washed with a little water and acetonitrile. 0.373 g (17% of theory) of the title compound were obtained after drying under high vacuum.

LC-MS (method 2): $R_t$=1.23 min; MS (ESIpos): m/z=643 (M+H)$^+$

Example 98A tert-Butyl 3-{2-[1-(2-fluorobenzyl)-1H-pyrazolo[3,4-b]pyridin-3-yl]-8-oxo-8,9-dihydro-7H-purin-7-yl}azetidine-1-carboxylate

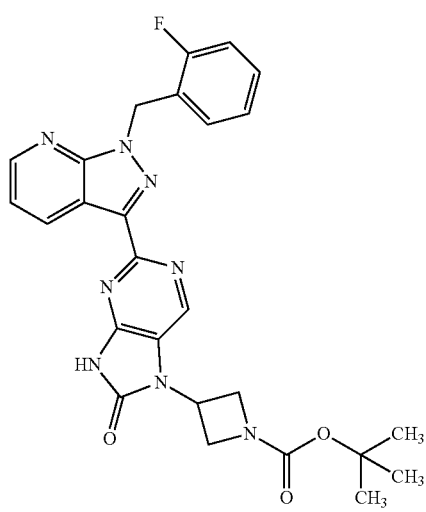 [SMILES: CC(C)(C)OC(=O)N1CC(n2c(=O)[nH]c3nc(-c4nn(Cc5ccccc5F)c5ncccc45)ncc32)C1]

570 mg (0.887 mmol) of the compound from example 97A were hydrogenated analogy to the method in example 102. 0.669 g (90% of theory, purity 79%) of the title compound were obtained after drying under high vacuum.

LC-MS (method 5): $R_t$=1.08 min; MS (ESIpos): m/z=517 (M+H)$^+$

Example 99A 3-(2,4-Dimethoxybenzyl)-5-[5-fluoro-1-(2-fluorobenzyl)-1H-pyrazolo[3,4-b]pyridin-3-yl]-1,3-dihydro[1,2,5]thiadiazolo[3,4-d]pyrimidine 2,2-dioxide

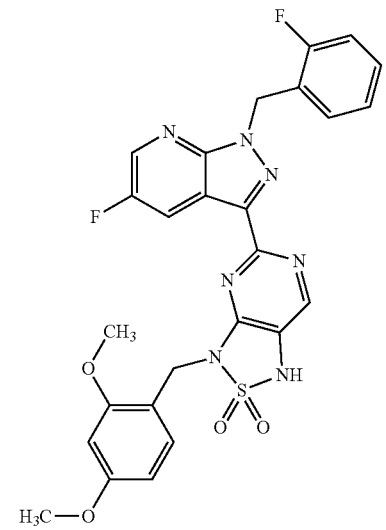 [SMILES: COc1ccc(CN2c3nc(-c4nn(Cc5ccccc5F)c5ncc(F)cc45)ncc3NS2(=O)=O)c(OC)c1]

550 mg (1.093 mmol) of the compound from example 92A were divided between 11 microwave vessels. 50 mg of the substance in each were admixed with 48 mg (0.496 mmol) of sulfamide and 2.5 ml of pyridine and then heated at 160° C. under microwave radiation for 30 min. Subsequently, all batches were combined and freed of the solvent under reduced pressure. The residue was taken up in dichloromethane and extracted three times with water. The phases were separated and the organic phase was dried with sodium sulfate, filtered and concentrated under reduced pressure. The residue was then purified by means of preparative HPLC (acetonitrile:water (+0.05% formic acid) gradient). This gave 0.130 g (12% of theory, purity 50%) of the title compound.

LC-MS (method 5): $R_t$=1.12 min; MS (ESIpos): m/z=566 (M+H)$^+$

Example 100A 3-(2,4-Dimethoxybenzyl)-5-[5-fluoro-1-(2-fluorobenzyl)-1H-pyrazolo[3,4-b]pyridin-3-yl]-1-methyl-1,3-dihydro[1,2,5]thiadiazolo[3,4-d]pyrimidine 2,2-dioxide

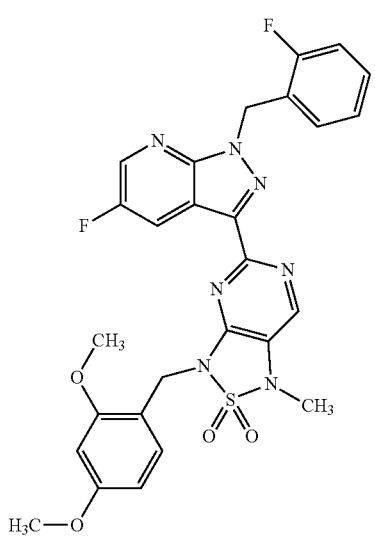 [SMILES: COc1ccc(CN2c3nc(-c4nn(Cc5ccccc5F)c5ncc(F)cc45)ncc3N(C)S2(=O)=O)c(OC)c1]

130 mg (approx. 0.115 mmol, 50% purity) of the compound from example 99A were initially charged in 5 ml of DMF, 44 mg (0.138 mmol) of cesium carbonate and 8.5 µl (0.138 mmol) of iodomethane were added and the mixture was stirred at RT overnight. Subsequently, another 14.3 µl (0.230 mmol) of iodomethane were added and the mixture was heated to 50° C. overnight. After cooling, the mixture was purified by means of preparative HPLC (acetonitrile:water (+0.05% formic acid) gradient). This gave 30.9 mg (46% of theory) of the title compound.

LC-MS (method 2): $R_t$=1.30 min; MS (ESIpos): m/z=580 (M+H)$^+$

Example 101A

Ethyl 4-amino-2-[1-(2-fluorobenzyl)-1H-pyrazolo[3,4-b]pyridin-3-yl]pyrimidine-5-carboxylate

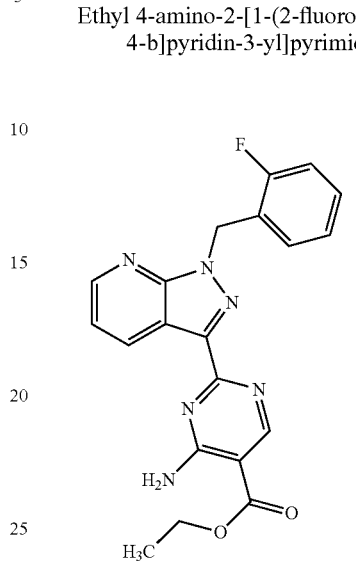

The synthesis of this compound is described in A. Straub et al., *Bioorg. Med. Chem.*, 10, 1711-1717; 2002.

Example 102A

4-Amino-2-[1-(2-fluorobenzyl)-1H-pyrazolo[3,4-b]pyridin-3-yl]pyrimidine-5-carboxylic acid

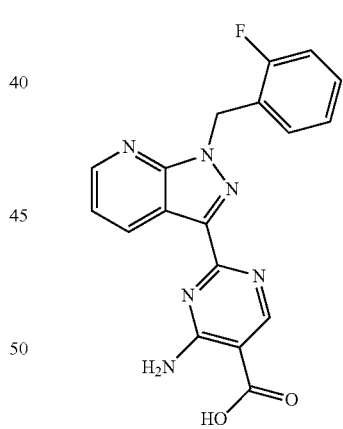

1000 mg (2.55 mmol) of ethyl 4-amino-2-[1-(2-fluorobenzyl)-1H-pyrazolo[3,4-b]pyridin-3-yl]pyrimidine-5-carboxylate (example 101A) were suspended in 80 ml of dioxane and admixed cautiously with 50.1 ml (948 mmol) of aqueous sodium hydroxide solution (50% by weight). The mixture was then stirred at 60° C. for 4 h and then poured onto 200 ml of ice-water. Concentrated hydrochloric acid was used to cautiously adjust the mixture to pH 2, and the precipitate observed was removed by means of filtration. The precipitate was washed with a little water and finally dried under high vacuum. Thus, 993 mg (approx. 105% of theory, the batch probably still contained small amounts of inorganic salts) of the target compound were obtained.

LC-MS (method 2): R$_t$=0.77 min; MS (ESIpos): m/z=360 (M+H)$^+$ $^1$H NMR (400 MHz, DMSO-d$_6$): δ [ppm]=5.91 (s, 2H), 7.16 (t, 1H), 7.20-7.30 (m, 2H), 7.38 (dd, 1H), 7.51 (dd, 1H), 8.48 (s br, 1H), 8.72 (s, 1H), 8.74 (d, 1H), 9.07 (d, 1H), 9.14 (s br, 1H), COOH not assigned.

Example 103A

4-Amino-2-[1-(2-fluorobenzyl)-1H-pyrazolo[3,4-b]pyridin-3-yl]-N-(2,2,2-trifluoroethyl)pyrimidine-5-carboxamide

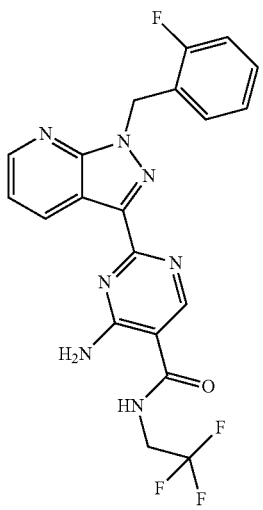 [SMILES: Nc1nc(-c2nn(Cc3ccccc3F)c3ncccc23)ncc1C(=O)NCC(F)(F)F]

300 mg (0.82 mmol) of 4-amino-2-[1-(2-fluorobenzyl)-1H-pyrazolo[3,4-b]pyridin-3-yl]pyrimidine-5-carboxylic acid (example 102A), 0.230 ml (1.65 mmol) of triethylamine and 139 mg (0.91 mmol) of 1-hydroxyl-1H-benzotriazole were dissolved in 2.2 ml of DMF, and 174 mg (0.91 mmol) of 1-(3-dimethylaminopropyl)-3-ethylcarbodiimide hydrochloride were added. While cooling with ice, 70 μl (90 mg, 0.91 mmol) of 2,2,2-trifluoroethylamine were added, and the mixture was reacted at room temperature overnight. The mixture was brought into solution with 4 ml of acetonitrile/water and purified by means of preparative HPLC [column: Reprosil C18, 10 μm, 250*40 mm; eluent: acetonitrile/0.05% formic acid; gradient: 15% acetonitrile→95% acetonitrile]. Thus, 110 mg (28% of theory) of the target compound were obtained.

LC-MS (method 5): R$_t$=0.99 min; MS (ESIpos): m/z=446 (M+H)$^+$ $^1$H NMR (400 MHz, DMSO-d$_6$): δ [ppm]=4.11 (m, 2H), 5.86 (s, 2H), 7.12-7.28 (m, 3H), 7.37 (m, 1H), 7.43 (dd, 1H), 8.07 (s br, 2H), 8.67 (d, 1H), 8.86 (s, 1H), 9.02 (d, 1H), 9.23 (t, 1H).

Example 104A

4-Amino-2-[1-(2-fluorobenzyl)-1H-pyrazolo[3,4-b]pyridin-3-yl]pyrimidine-5-carboxamide

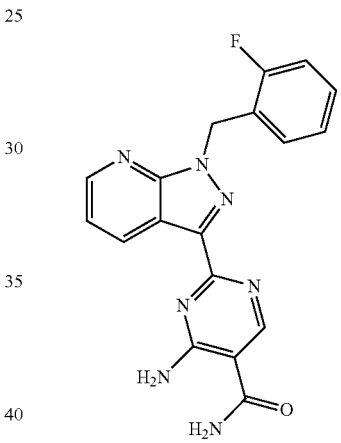

300 mg (0.82 mmol) of 4-amino-2-[1-(2-fluorobenzyl)-1H-pyrazolo[3,4-b]pyridin-3-yl]pyrimidine-5-carboxylic acid (example 102A) and 139 mg (0.91 mmol) of 1-hydroxyl-1H-benzotriazole were dissolved in 2.2 ml of DMF, and 174 mg (0.91 mmol) of 1-(3-dimethylaminopropyl)-3-ethylcarbodiimide hydrochloride were added. While cooling with ice, 140 ml (0.99 mmol) of ammonium hydroxide (28%) were added, and the mixture was reacted at room temperature overnight. 4 ml of acetonitrile/water (1/1) were added and the precipitate formed was filtered off. After drying under high vacuum, 145 mg (48% of theory) of the target compound were obtained.

LC-MS (method 2): R$_t$=0.78 min; MS (ESIpos): m/z=364 (M+H)$^+$

¹H NMR (400 MHz, DMSO-d₆): δ [ppm]=5.85 (s, 2H), 7.10-7.29 (m, 3H), 7.36 (t, 1H), 7.42 (dd, 1H), 7.52 (s br, 1H), 7.95 (s, 1H), 8.15 (s br, 1H), 8.66 (d, 1H), 8.83 (s, 1H), 9.00 (d, 1H), 1×NH not assigned.

Example 105A

Methyl 2-[1-(2-fluorobenzyl)-1H-pyrazolo[3,4-b]pyridin-3-yl]-4-hydroxypyrimidine-5-carboxylate

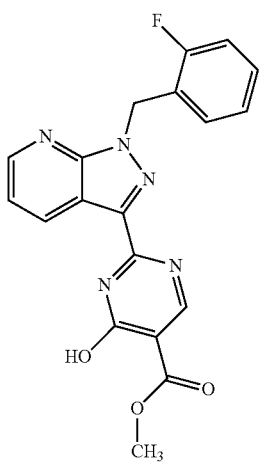 [SMILES: COC(=O)c1cnc(-c2nn(Cc3ccccc3F)c3ncccc23)nc1O]

10.0 g (32.7 mmol) of 1-(2-fluorobenzyl)-1H-pyrazolo[3,4-b]pyridine-3-carboximidamide hydrochloride (example 5A) and 8.54 g (49.1 mmol) of dimethyl (methoxymethylene)malonate were initially charged in 400 ml of methanol, and 1.77 g (32.7 mmol) of sodium methoxide were added cautiously. The mixture was reacted at 50° C. overnight. The precipitate formed was filtered off, washed with a little methanol and dried under high vacuum. Thus, 6.54 g (52% of theory) of the target compound were obtained.

LC-MS (method 2): $R_t$=0.88 min; MS (ESIpos): m/z=380 (M+H)⁺

¹H NMR (400 MHz, DMSO-d₆): δ [ppm]=3.73 (s, 3H), 5.84 (s, 2H), 7.15 (t, 1H), 7.20-7.30 (m, 2H), 7.36 (m, 1H), 7.42 (dd, 1H), 8.55 (s, 1H), 8.67 (d, 1H), 8.84 (dd, 1H), OH not assigned.

Example 106A

Methyl 4-chloro-2-[1-(2-fluorobenzyl)-1H-pyrazolo[3,4-b]pyridin-3-yl]pyrimidine-5-carboxylate

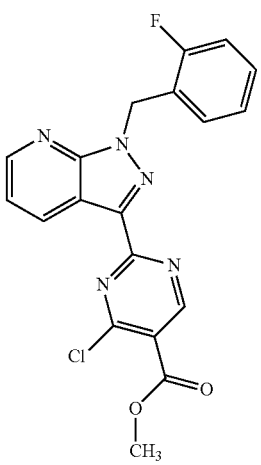 [SMILES: COC(=O)c1cnc(-c2nn(Cc3ccccc3F)c3ncccc23)nc1Cl]

6.54 g (17.2 mmol) of methyl 2-[1-(2-fluorobenzyl)-1H-pyrazolo[3,4-b]pyridin-3-yl]-4-hydroxypyrimidine-5-carboxylate (example 105A) were taken up in 26.5 ml (284 mmol) of phosphoryl chloride. Then 5.95 g (34.5 mmol) of diethylaniline were added and the mixture was reacted at 90° C. for 60 min. After cooling, the precipitate formed was filtered off and washed with water. Then it was dried under high vacuum. Thus, 6.11 g (78% of theory) of the target compound were obtained.

LC-MS (method 5): $R_t$=1.22 min; MS (ESIpos): m/z=398 (M+H)⁺

$^1$H NMR (400 MHz, DMSO-d$_6$): δ [ppm]=3.94 (s, 3H), 5.92 (s, 2H), 7.17 (dt, 1H), 7.21-7.31 (m, 2H), 7.38 (m, 1H), 7.53 (dd, 1H), 8.74 (dd, 1H), 8.85 (dd, 1H), 9.32 (s, 1H).

WORKING EXAMPLES

Example 1

6-Amino-2-[1-(2-fluorobenzyl)-1H-pyrazolo[3,4-b]pyridin-3-yl]-7-(2-hydroxyethyl)-7,9-dihydro-8H-purin-8-one

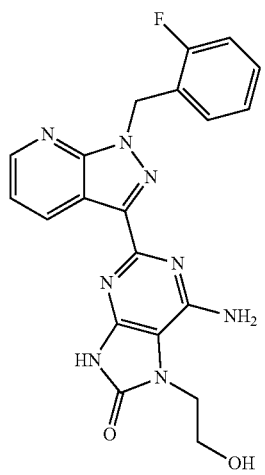 [SMILES: Nc1nc(-c2nn(Cc3ccccc3F)c3ncccc23)nc2[nH]c(=O)n(CCO)c12]

350 mg (0.833 mmol) of the compound obtained in example 6A were initially charged in 12 ml of tetrahydrofuran at 0° C. Then 1.665 ml of a 1M solution of bis(trimethylsilyl)sodium amide in tetrahydrofuran were added dropwise and the mixture was stirred at 0° C. for a further 10 min. The mixture was then stirred at RT overnight. Subsequently, 2 ml of water were added to the mixture, which was concentrated to dryness. The residue was purified by means of preparative HPLC (acetonitrile/water (+0.05% formic acid) gradient). 188 mg of the title compound were obtained (53% of theory).

LC-MS (method 2): R$_t$=0.80 min; MS (ESIpos): m/z=421 (M+H)$^+$ $^1$H NMR (400 MHz, DMSO-d$_6$): δ [ppm]=3.63 (q, 2H), 3.97 (t, 2H), 5.35 (t, 1H), 5.80 (s, 2H), 6.74 (s, 2H) 7.13-7.25 (m, 3H), 7.33-7.39 (m, 2H), 8.63 (dd, 1H), 9.03 (dd, 1H), 11.64 (s, 1H).

Example 2

6-Amino-2-[1-(2-fluorobenzyl)-1H-pyrazolo[3,4-b]pyridin-3-yl]-7-(2-hydroxy-2-methylpropyl)-7,9-dihydro-8H-purin-8-one

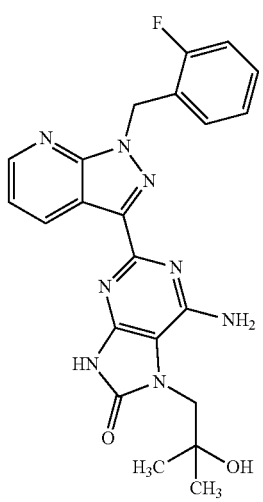 [SMILES: CC(C)(O)Cn1c(=O)[nH]c2nc(-c3nn(Cc4ccccc4F)c4ncccc34)nc(N)c21]

In analogy to the method in example 1, proceeding from 150 mg (0.334 mmol) of example 8A and 0.368 ml of a 1M solution of bis(trimethylsilyl)sodium amide in tetrahydrofuran, 87.8 mg (58.5% of theory) of the title compound were obtained.

LC-MS (method 2): R$_t$=0.89 min; MS (EIpos): m/z=449 (M+H)$^+$.

$^1$H NMR (400 MHz, DMSO-d$_6$): δ [ppm]=1.20 (s, 6H), 3.78 (s, 2H), 5.62 (s, 1H), 5.80 (s, 2H), 6.95 (s br, 2H) 7.14 (m, 1H), 7.20 (m, 1H), 7.23 (m, 1H), 7.33-7.39 (m, 2H), 8.62 (dd, 1H), 9.02 (dd, 1H), 11.64 (s, 1H).

Example 3

6-Amino-2-[1-(2-fluorobenzyl)-1H-pyrazolo[3,4-b]pyridin-3-yl]-7-(3,3,3-trifluoro-2-hydroxypropyl)-7,9-dihydro-8H-purin-8-one

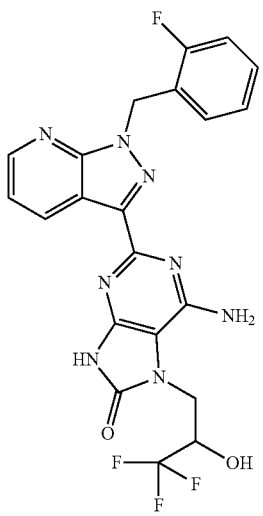 [SMILES: Nc1nc(-c2nn(Cc3ccccc3F)c3ncccc23)nc2[nH]c(=O)n(CC(O)C(F)(F)F)c12]

In analogy to the method in example 1, proceeding from 28.5 mg (0.058 mmol) of example 10A and 0.117 ml of a 1M solution of bis(trimethylsilyl)sodium amide in tetrahydrofuran, 10.4 mg (36.5% of theory) of the title compound were obtained.

LC-MS (method 2): $R_t$=0.89 min; MS (EIpos): m/z=489 (M+H)$^+$.

$^1$H NMR (400 MHz, DMSO-d$_6$): δ [ppm]=4.01-4.07 (m, 1H), 4.21-4.26 (m, 2H), 5.81 (s, 2H), 6.66 (br s, 2H), 7.10-7.24 (m, 4H), 7.33-7.40 (m, 2H), 8.63 (dd, 1H), 9.02 (dd, 1H), 11.78 (s, 1H).

Example 4

6-Amino-7-(2,2-difluoroethyl)-2-[1-(2-fluorobenzyl)-1H-pyrazolo[3,4-b]pyridin-3-yl]-7,9-dihydro-8H-purin-8-one

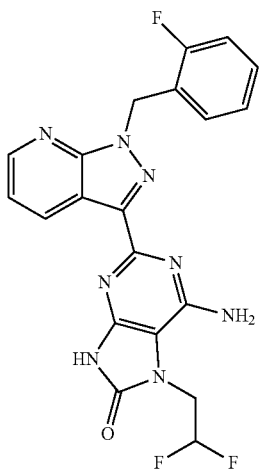 [SMILES: Nc1nc(-c2nn(Cc3ccccc3F)c3ncccc23)nc2[nH]c(=O)n(CC(F)F)c12]

132 mg (0.279 mmol) of the compound prepared in example 12A were dissolved in tetrahydrofuran (8 ml), and 0.307 ml of a 1M solution of bis(trimethylsilyl)sodium amide in tetrahydrofuran were added at 0° C. Stirring of the mixture at RT was continued overnight. This was followed by concentration and purification of the residue by means of preparative HPLC (eluent: acetonitrile/water with 0.05% formic acid, gradient). 81 mg of the title compound were obtained (62% of theory).

LC-MS (method 2): $R_t$=0.90 min; MS (EIpos): m/z=441 (M+H)$^+$.

$^1$H NMR (400 MHz, DMSO-d$_6$): δ [ppm]=4.48 (m, 2H), 5.81 (s, 2H), 6.06-6.36 (m, 1H), 6.81 (br s, 2H), 7.12-7.39 (m, 5H), 7.33-7.40 (m, 2H), 8.63 (dd, 1H), 9.03 (dd, 1H), 11.82 (s, 1H).

Example 5

2-[1-(2-Fluorobenzyl)-1H-pyrazolo[3,4-b]pyridin-3-yl]quinazolin-4-amine

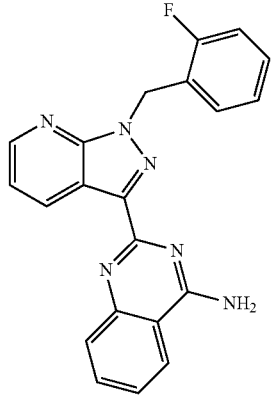 [SMILES: Nc1nc(-c2nn(Cc3ccccc3F)c3ncccc23)nc2ccccc12]

According to general method 1, 95 mg (0.377 mmol) of example 3A were reacted together with 1.0 eq of 2-aminobenzonitrile and 0.1 eq of potassium tert-butoxide. After checking the reaction, a further 0.5 eq of potassium tert-butoxide was added and the mixture was heated again at 160° C. under microwave irradiation until complete conversion. The reaction mixture was purified by means of preparative HPLC (eluent: acetonitrile/water with 0.05% formic acid, gradient).

Yield: 27 mg (19% of theory)

LC-MS (method 2): $R_t$=0.82 min; MS (EIpos): m/z=371 (M+H)$^+$.

¹H NMR (400 MHz, DMSO-d₆): δ [ppm]=5.86 (s, 2H), 7.12-7.37 (m, 3H), 7.32-7.43 (m, 2H), 7.50 (m, 1H), 7.78-7.84 (m, 2H), 8.02 (br s, 2H), 8.25 (d, 1H), 8.65 (dd, 1H), 9.19 (dd, 1H).

Example 6

6-Chloro-2-[1-(2-fluorobenzyl)-1H-pyrazolo[3,4-b]pyridin-3-yl]quinazolin-4-amine

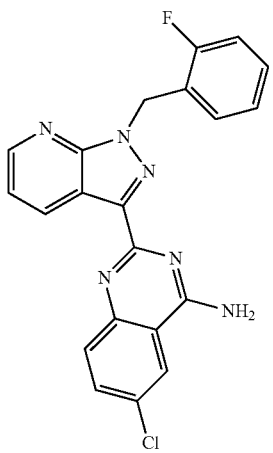 [SMILES: Nc1nc(-c2nn(Cc3ccccc3F)c3ncccc23)nc2ccc(Cl)cc12]

The substance was prepared according to general method 1. 200 mg (0.793 mmol) of example 3A and 121 mg (0.793 mmol) of 2-amino-5-chlorobenzonitrile, and also 1.0 eq of potassium tert-butoxide (89 mg, 0.793 mmol) from the start, were used. Purification was effected by precipitating the substance from an acetonitrile-water mixture.

Yield: 218 mg (65% of theory)

LC-MS (method 2): $R_t$=0.97 min; MS (EIpos): m/z=405 (M+H)⁺.

¹H NMR (400 MHz, DMSO-d₆): δ [ppm]=5.86 (s, 2H), 7.11-7.27 (m, 3H), 7.33-7.44 (m, 2H), 7.81-7.87 (m, 2H), 8.11 (br s, 2H), 8.41 (d, 1H), 8.66 (dd, 1H), 9.15 (dd, 1H).

Example 7

5-Chloro-2-[1-(2-fluorobenzyl)-1H-pyrazolo[3,4-b]pyridin-3-yl]quinazolin-4-amine

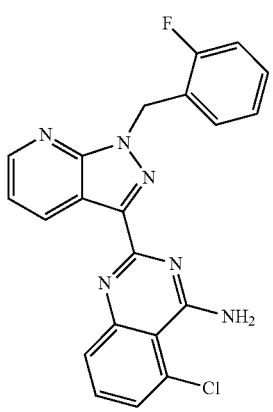 [SMILES: Nc1nc(-c2nn(Cc3ccccc3F)c3ncccc23)nc2cccc(Cl)c12]

The substance was prepared according to general method 1. 200 mg (0.793 mmol) of example 3A and 121 mg (0.793 mmol) of 2-amino-6-chlorobenzonitrile, and also 1.0 eq of potassium tert-butoxide (89 mg, 0.793 mmol) from the start, were used. Purification was effected by precipitating the substance from an acetonitrile-water mixture.

Yield: 160 mg (47% of theory)

LC-MS (method 2): $R_t$=1.01 min; MS (EIpos): m/z=405 (M+H)⁺.

¹H NMR (400 MHz, DMSO-d₆): δ [ppm]=5.87 (s, 2H), 7.14-7.16 (m, 2H), 7.24 (t, 1H), 7.33-7.44 (m, 2H), 7.55 (d, 1H), 7.74 (t, 1H), 7.81 (d, 1H), 8.66 (d, 1H), 9.21 (dd, 1H).

Example 8

7-Chloro-2-[1-(2-fluorobenzyl)-1H-pyrazolo[3,4-b]pyridin-3-yl]quinazolin-4-amine

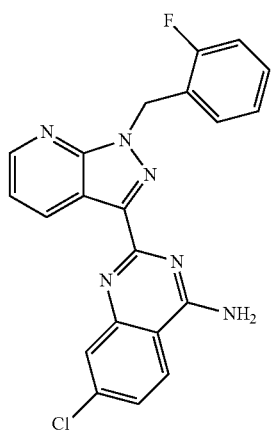 [SMILES: Nc1nc(-c2nn(Cc3ccccc3F)c3ncccc23)nc2cc(Cl)ccc12]

The substance was prepared according to general method 1. 200 mg (0.793 mmol) of example 3A and 121 mg (0.793 mmol) of 2-amino-4-chlorobenzonitrile, and also 1.0 eq of potassium tert-butoxide (89 mg, 0.793 mmol) from the start, were used.

Yield: 40 mg (12% of theory)

LC-MS (method 2): $R_t$=1.00 min; MS (EIpos): m/z=405 (M+H)⁺.

¹H NMR (400 MHz, DMSO-d₆): δ [ppm]=5.86 (s, 2H), 7.12-7.27 (m, 3H), 7.33-7.43 (m, 2H), 7.54 (dd, 1H), 7.90 (d, 1H), 8.15 (br s, 2H), 8.28 (d, 1H), 8.65 (dd, 1H), 9.18 (dd, 1H).

Example 9

2-[1-(2-Fluorobenzyl)-1H-pyrazolo[3,4-b]pyridin-3-yl]-6-(trifluoromethyl)quinazolin-4-amine

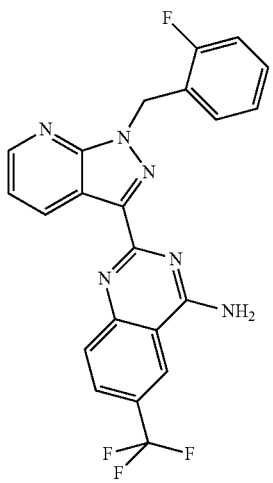 [SMILES: Nc1nc(-c2nn(Cc3ccccc3F)c3ncccc23)nc2ccc(C(F)(F)F)cc12]

The substance was prepared according to general method 1. 200 mg (0.793 mmol) of example 3A and 147 mg (0.793 mmol) of 2-amino-5-(trifluoromethyl)benzonitrile, and also 1.0 eq of potassium tert-butoxide (89 mg, 0.793 mmol) from the start, were used. Purification was effected by precipitating the substance from an acetonitrile-water mixture.

Yield: 144 mg (39% of theory)

LC-MS (method 2): $R_t$=1.06 min; MS (EIpos): m/z=439 (M+H)⁺.

¹H NMR (400 MHz, DMSO-d₆): δ [ppm]=5.88 (s, 2H), 7.13-7.27 (m, 3H), 7.36 (m, 1H), 7.44 (dd, 1H), 7.99 (d, 1H), 8.05 (dd, 1H), 8.36 (br s, 2H), 8.67 (dd, 1H), 8.77 (m, 1H), 9.18 (dd, 1H).

Example 10

6-Fluoro-2-[1-(2-fluorobenzyl)-1H-pyrazolo[3,4-b]pyridin-3-yl]quinazolin-4-amine

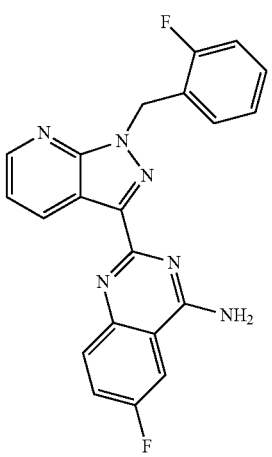 [SMILES: Nc1nc(-c2nn(Cc3ccccc3F)c3ncccc23)nc2ccc(F)cc12]

The substance was prepared according to general method 1. 200 mg (0.793 mmol) of example 3A and 108 mg (0.793 mmol) of 2-amino-5-fluorobenzonitrile, and also 1.0 eq of potassium tert-butoxide (89 mg, 0.793 mmol) from the start, were used. Purification was effected by precipitating the substance from an acetonitrile-water mixture.

Yield: 145 mg (45% of theory)

LC-MS (method 2): $R_t$=0.89 min; MS (EIpos): m/z=389 (M+H)⁺.

¹H NMR (400 MHz, DMSO-d₆): δ [ppm]=5.86 (s, 2H), 7.12-7.20 (m, 2H), 7.22-7.27 (m, 1H), 7.33-7.37 (m, 1H), 7.41 (dd, 1H), 7.72 (dt, 1H), 7.91 (dd, 1H), 8.02 (br s, 2H), 8.10 (dd, 1H), 8.65 (dd, 1H), 9.16 (dd, 1H).

Example 11

6,8-Dichloro-2-[1-(2-fluorobenzyl)-1H-pyrazolo[3,4-b]pyridin-3-yl]quinazolin-4-amine

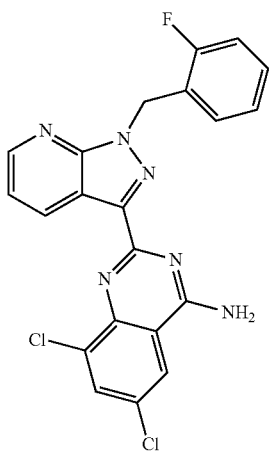 [SMILES: Nc1nc(-c2nn(Cc3ccccc3F)c3ncccc23)nc2c(Cl)cc(Cl)cc12]

The substance was prepared according to general method 1. 200 mg (0.793 mmol) of example 3A and 148 mg (0.793 mmol) of 2-amino-3,5-dichlorobenzonitrile, and also 1.0 eq of potassium tert-butoxide (89 mg, 0.793 mmol) from the start, were used.

Yield: 11 mg (3% of theory)

LC-MS (method 2): $R_t$=1.30 min; MS (EIpos): m/z=440 (M+H)$^+$.

$^1$H NMR (400 MHz, DMSO-d$_6$): δ [ppm]=5.87 (s, 2H), 7.12-7.20 (m, 2H), 7.22-7.27 (m, 1H), 7.32-7.40 (m, 1H), 7.47 (dd, 1H), 8.14 (d, 1H), 8.40 (d, 1H), 8.67 (dd, 1H), 9.22 (dd, 1H).

Example 12

2-[1-(2-Fluorobenzyl)-1H-pyrazolo[3,4-b]pyridin-3-yl]thieno[2,3-d]pyrimidin-4-amine

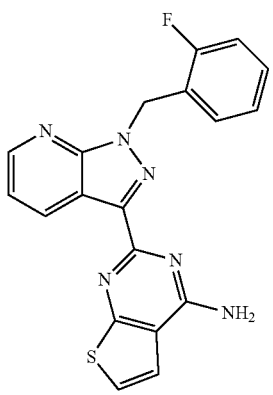 [SMILES: Nc1nc(-c2nn(Cc3ccccc3F)c3ncccc23)nc2sccc12]

The substance was prepared according to general method 1. 200 mg (0.793 mmol) of example 3A and 98 mg (0.793 mmol) of 2-aminothiophene-3-carbonitrile, and also 1.0 eq of potassium tert-butoxide (89 mg, 0.793 mmol) from the start, were used.

Yield: 111 mg (36% of theory)

LC-MS (method 2): $R_t$=1.03 min; MS (EIpos): m/z=377 (M+H)$^+$.

$^1$H NMR (400 MHz, DMSO-d$_6$): δ [ppm]=5.84 (s, 2H), 7.13-7.26 (m, 3H), 7.33-7.42 (m, 2H), 7.57-7.61 (m, 2H), 7.72 (br s, 2H), 8.64 (dd, 1H), 9.05 (dd, 1H).

Example 13

6-[1-(2-Fluorobenzyl)-1H-pyrazolo[3,4-b]pyridin-3-yl]-3-methyl[1,2]thiazolo[5,4-d]pyrimidin-4-amine

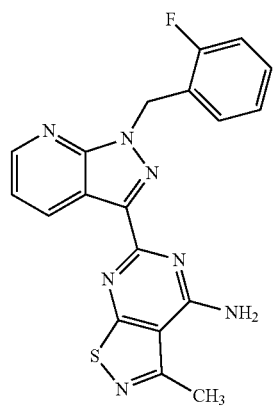 [SMILES: Cc1noc2nc(-c3nn(Cc4ccccc4F)c4ncccc34)nc(N)c12]

The substance was prepared according to general method 1. 200 mg (0.793 mmol) of example 3A and 110 mg (0.793 mmol) of 5-amino-3-methylisothiazole-4-carbonitrile, and also 1.0 eq of potassium tert-butoxide (89 mg, 0.793 mmol) from the start, were used. Purification was effected by precipitating the substance from an acetonitrile-water mixture.

Yield: 234 mg (75% of theory)

LC-MS (method 2): $R_t$=1.05 min; MS (EIpos): m/z=392 (M+H)$^+$.

¹H NMR (400 MHz, DMSO-d₆): δ [ppm]=2.80 (s, 3H), 5.87 (s, 2H), 7.13-7.26 (m, 3H), 7.34-7.39 (m, 1H), 7.42-7.45 (m, 1H), 8.67 (dd, 1H), 9.12 (dd, 1H).

Example 14

6-[1-(2-Fluorobenzyl)-1H-pyrazolo[3,4-b]pyridin-3-yl]-3-methyl[1,2]oxazolo[5,4-d]pyrimidin-4-amine

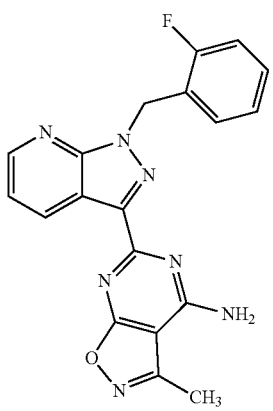

The substance was prepared according to general method 1. 300 mg (1.189 mmol) of example 3A and 146 mg (1.189 mmol) of 5-amino-3-methyl-4-isoxazole-4-carbonitrile, and also 1.0 eq of potassium tert-butoxide (133 mg, 1.189 mmol) from the start, were used.

Yield: 43 mg (10% of theory)

LC-MS (method 2): R$_t$=0.99 min; MS (EIpos): m/z=376 (M+H)⁺.

¹H NMR (400 MHz, DMSO-d₆): δ [ppm]=2.60 (s, 3H), 5.87 (s, 2H), 7.13-7.27 (m, 3H), 7.34-7.39 (m, 1H), 7.43-7.46 (m, 1H), 8.67 (dd, 1H), 9.06 (dd, 1H).

Example 15

6-[1-(2-Fluorobenzyl)-1H-pyrazolo[3,4-b]pyridin-3-yl]-3-(trifluoromethyl)[1,2]oxazolo[5,4-d]pyrimidin-4-amine

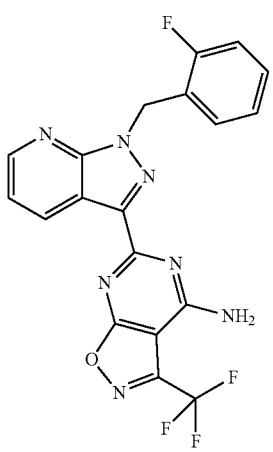 [SMILES: Nc1nc(-c2nn(Cc3ccccc3F)c3ncccc23)nc2onc(C(F)(F)F)c12]

The substance was prepared according to general method 1. 200 mg (0.793 mmol) of example 3A and 140 mg (0.793 mmol) of 5-amino-3-(trifluoromethyl)isoxazole-4-carbonitrile, and also 1.0 eq of potassium tert-butoxide (89 mg, 0.793 mmol) from the start, were used. The reaction mixture was irradiated in a microwave three times for 2 h each time.

Yield: 19 mg (5% of theory)

LC-MS (method 3): R$_t$=1.30 min; MS (EIpos): m/z=430 (M+H)⁺.

¹H NMR (400 MHz, DMSO-d₆): δ [ppm]=5.89 (s, 2H), 7.14-7.18 (m, 1H), 7.21-7.27 (m, 2H), 7.35-7.40 (m, 1H), 7.46-7.49 (m, 1H), 8.70 (dd, 1H), 9.15 (dd, 1H).

Example 16

6-[1-(2-Fluorobenzyl)-1H-pyrazolo[3,4-b]pyridin-3-yl]-1H-pyrazolo[3,4-d]pyrimidin-4-amine

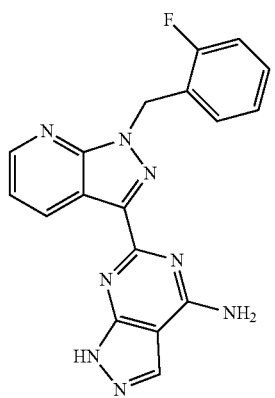 [SMILES: Nc1nc(-c2nn(Cc3ccccc3F)c3ncccc23)nc2[nH]ncc12]

The substance was prepared according to general method 1. 200 mg (0.793 mmol) of example 3A and 140 mg (0.793 mmol) of 3-amino-1H-pyrazole-4-carbonitrile, and also 0.1 eq of potassium tert-butoxide (8.9 mg, 0.079 mmol), were used. After 1 h at 160° C. in a microwave, another 0.5 eq of potassium tert-butoxide (44 mg, 0.396 mmol) was added and the mixture was left at 160° C. in the microwave for a further 2 h. Thereafter, another 0.25 eq of potassium tert-butoxide (22 mg, 0.198 mmol) was added and the mixture was left at 160° C. in the microwave for a further 2 h, and then another 0.25 eq of potassium tert-butoxide (22 mg, 0.198 mmol) was added and the mixture was allowed to react at 160° C. in the microwave for a further 2 h. Purification was effected by HPLC.

Yield: 115 mg (37% of theory)

LC-MS (method 2): R$_t$=0.79 min; MS (EIpos): m/z=361 (M+H)⁺.

¹H NMR (400 MHz, DMSO-d₆): δ [ppm]=5.89 (s, 2H), 7.13-7.26 (m, 3H), 7.33-7.42 (m, 2H), 7.81 (s br, 2H), 8.11 (s, 1H), 8.64 (dd, 1H), 9.06 (dd, 1H), 13.41 (s br, 1H).

Example 17

6-[1-(2-Fluorobenzyl)-1H-pyrazolo[3,4-b]pyridin-3-yl]-1-methyl-1H-pyrazolo[3,4-d]pyrimidin-4-amine

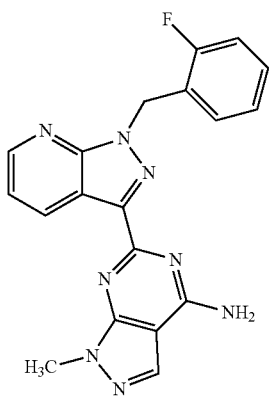 [SMILES: Cn1ncc2c(N)nc(-c3nn(Cc4ccccc4F)c4ncccc34)nc21]

The substance was prepared according to general method 1. 200 mg (0.793 mmol) of example 3A and 96 mg (0.793 mmol) of 5-amino-1-methyl-1H-pyrazole-4-carbonitrile, and also 1.0 eq of potassium tert-butoxide (89 mg, 0.793 mmol) from the start, were used. Purification was effected by precipitating the substance from an acetonitrile-water mixture.

Yield: 155 mg (52% of theory)

LC-MS (method 2): $R_t$=0.89 min; MS (EIpos): m/z=375 (M+H)±.

$^1$H NMR (400 MHz, DMSO-$d_6$): δ [ppm]=4.00 (s, 3H), 5.86 (s, 2H), 7.13-7.15 (m, 2H), 7.22-7.27 (m, 1H), 7.33-7.37 (m, 1H), 7.40-7.43 (m, 1H), 7.90 (s br, 2H), 8.10 (s, 1H), 8.65 (dd, 1H), 9.13 (dd, 1H).

Example 18

6-[1-(2-Fluorobenzyl)-1H-pyrazolo[3,4-b]pyridin-3-yl]-3-methoxy-1H-pyrazolo[3,4-d]pyrimidin-4-amine

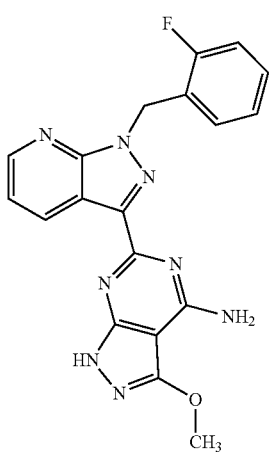 [SMILES: COc1n[nH]c2nc(-c3nn(Cc4ccccc4F)c4ncccc34)nc(N)c12]

The substance was prepared according to general method 1. 1000 mg (3.964 mmol) of example 3A and 547 mg (3.964 mmol) of 5-amino-3-methoxy-1H-pyrazole-4-carbonitrile, and also 1.0 eq of potassium tert-butoxide (444 mg, 3.964 mmol) from the start, were used. Purification was effected by precipitating the substance from an acetonitrile-water mixture, followed by preparative HPLC purification (eluent: acetonitrile/water with 0.05% formic acid, gradient).

Yield: 39 mg (3% of theory)

LC-MS (method 2): $R_t$=0.87 min; MS (EIpos): m/z=391 (M+H)$^+$.

$^1$H NMR (400 MHz, DMSO-$d_6$): δ [ppm]=3.98 (s, 3H), 5.83 (s, 2H), 7.13-7.26 (m, 3H), 7.33-7.41 (m, 2H), 8.64 (dd, 1H), 9.08 (dd, 1H), 12.43 (s, 1H).

Example 19

6-[1-(2-Fluorobenzyl)-1H-pyrazolo[3,4-b]pyridin-3-yl]-3-methyl-1H-pyrazolo[3,4-d]pyrimidin-4-amine

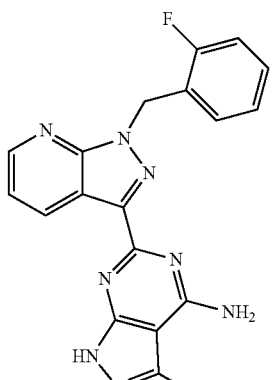

The substance was prepared according to general method 1. 200 mg (0.793 mmol) of example 3A and 96 mg (0.793 mmol) of 3-amino-4-cyano-5-methylpyrazole, and also 1.0 eq of potassium tert-butoxide (89 mg, 0.793 mmol) from the start, were used. Purification was effected by precipitating the substance from an acetonitrile-water mixture.

Yield: 115 mg (38% of theory)

LC-MS (method 2): $R_t$=0.81 min; MS (EIpos): m/z=375 (M+H)$^+$.

¹H NMR (400 MHz, DMSO-d₆): δ [ppm]=2.56 (s, 3H), 5.83 (s, 2H), 7.13-7.17 (m, 1H), 7.19-7.26 (m, 2H), 7.34-7.41 (m, 2H), 8.64 (dd, 1H), 9.10 (dd, 1H), 12.92 (s br, 1H).

Example 20

3-({4-Amino-6-[1-(2-fluorobenzyl)-1H-pyrazolo[3,4-b]pyridin-3-yl]-1H-pyrazolo[3,4-d]pyrimidin-3-yl}oxy)propan-1-ol

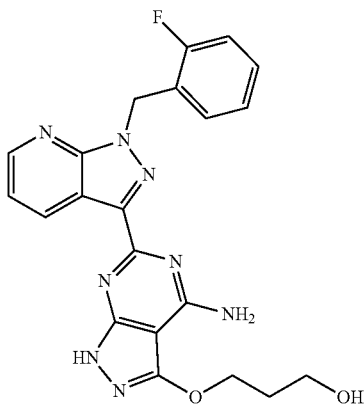 [SMILES: Nc1nc(-c2nn(Cc3ccccc3F)c3ncccc23)nc2[nH]nc(OCCCO)c12]

The substance was prepared according to general method 1. 300 mg (1.189 mmol) of example 3A and 216 mg (1.189 mmol) of 5-amino-3-(3-hydroxypropoxy)-1H-pyrazole-4-carbonitrile, and also 1.0 eq of potassium tert-butoxide (133 mg, 1.189 mmol) from the start, were used.

Yield: 128 mg (22% of theory)

LC-MS (method 2): R$_t$=0.83 min; MS (EIpos): m/z=435 (M+H)⁺.

¹H NMR (400 MHz, DMSO-d₆): δ [ppm]=1.92-1.99 (m, 2H), 3.61 (q, 2H), 4.36 (t, 2H), 4.55 (t, 1H), 5.83 (s, 2H), 7.13-7.26 (m, 3H), 7.34-7.41 (m, 2H), 8.64 (dd, 1H), 9.08 (dd, 1H), 12.39 (s, 1H).

Example 21

2-({4-Amino-6-[1-(2-fluorobenzyl)-1H-pyrazolo[3,4-b]pyridin-3-yl]-1H-pyrazolo[3,4-d]pyrimidin-3-yl}oxy)ethanol

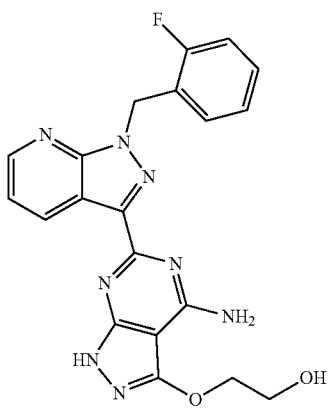 [SMILES: Nc1nc(-c2nn(Cc3ccccc3F)c3ncccc23)nc2[nH]nc(OCCO)c12]

The substance was prepared according to general method 1. 300 mg (1.189 mmol) of example 3A and 199 mg (1.189 mmol) of 5-amino-3-(2-hydroxyethoxy)-1H-pyrazole-4-carbonitrile, and also 1.0 eq of potassium tert-butoxide (133 mg, 1.189 mmol) from the start, were used.

Yield: 223 mg (42% of theory)

LC-MS (method 2): R$_t$=0.80 min; MS (EIpos): m/z=421 (M+H)⁺.

¹H NMR (400 MHz, DMSO-d₆): δ [ppm]=3.76 (q, 2H), 4.25 (t, 2H), 5.07 (t, 1H), 5.83 (s, 2H), 7.13-7.26 (m, 3H), 7.34-7.42 (m, 2H), 8.64 (dd, 1H), 9.07 (dd, 1H), 12.40 (s, 1H).

Example 22

N³,N³-Diethyl-6-[1-(2-fluorobenzyl)-1H-pyrazolo[3,4-b]pyridin-3-yl]-1H-pyrazolo[3,4-d]pyrimidine-3,4-diamine

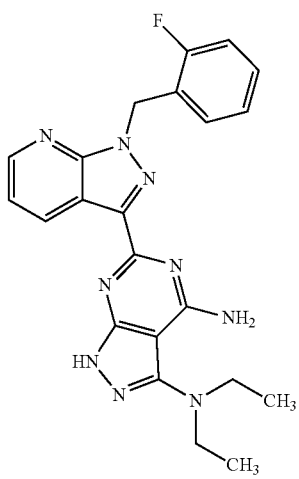 [SMILES: CCN(CC)c1n[nH]c2nc(-c3nn(Cc4ccccc4F)c4ncccc34)nc(N)c12]

The substance was prepared according to general method 1. 250 mg (0.991 mmol) of example 3A and 177 mg (0.991 mmol) of 5-amino-3-(3-hydroxypropoxy)-1H-pyrazole-4-carbonitrile, and also 1.0 eq of potassium tert-butoxide (111 mg, 0.991 mmol) from the start, were used.

Yield: 131 mg (30% of theory)

LC-MS (method 2): R$_t$=0.98 min; MS (EIpos): m/z=432 (M+H)⁺.

$^1$H NMR (400 MHz, DMSO-d$_6$): δ [ppm]=1.04 (t, 6H), 3.21 (q, 4H), 5.83 (s, 2H), 7.13-7.26 (m, 3H), 7.33-7.41 (m, 2H), 8.64 (dd, 1H), 9.09 (dd, 1H), 12.61 (s, 1H).

Example 23

2-[1-(2-Fluorobenzyl)-1H-pyrazolo[3,4-b]pyridin-3-yl]-6-methyl-8,9-dihydro-7H-pyrimido[4,5-b][1,4]diazepin-4-amine

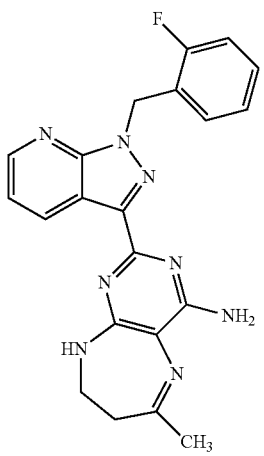 [SMILES: CC1=Nc2c(N)nc(-c3nn(Cc4ccccc4F)c4ncccc34)nc2NCC1]

300 mg (0.856 mmol) of the compound from example 1A were dissolved in 3 ml of ethanol, and 129 mg (0.856 mmol) of 4-(dimethylamino)butan-2-one hydrochloride were added. The mixture was stirred in a microwave at 150° C. for 1 h. After cooling, the mixture was concentrated on a rotary evaporator, and the residue was taken up in dichloromethane and filtered through silica gel. The filtercake was washed with dichloromethane and the filtrate was concentrated on a rotary evaporator. The residue was purified by means of preparative HPLC (eluent: acetonitrile/water with 0.1% trifluoroacetic acid, gradient 10:90→90:10). The residue was partitioned between ethyl acetate and saturated aqueous sodium hydrogencarbonate solution, and the organic phase was concentrated. 18 mg (5% of theory) of the title compound were obtained.

LC-MS (method 2): R$_t$=0.82 min; MS (EIpos): m/z=403 (M+H)$^+$.

$^1$H NMR (400 MHz, DMSO-d$_6$): δ [ppm]=2.17 (s, 3H), 2.64-2.71 (m, 2H), 3.35-3.38 (m, 2H), 5.79 (s, 2H), 6.56 (s br, 2H), 7.11-7.16 (m, 2H), 7.20-7.25 (m, 1H), 7.32-7.38 (m, 3H), 8.61 (dd, 1H), 9.08 (dd, 1H).

Example 24

6-(4-Chlorophenyl)-2-[1-(2-fluorobenzyl)-1H-pyrazolo[3,4-b]pyridin-3-yl]-8,9-dihydro-7H-pyrimido[4,5-b][1,4]diazepin-4-amine

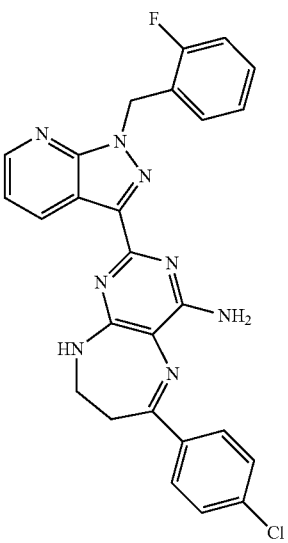 [SMILES: Nc1nc(-c2nn(Cc3ccccc3F)c3ncccc23)nc2c1N=C(c1ccc(Cl)cc1)CCN2]

The preparation was effected analogously to example 23, from 300 mg (0.856 mmol) of the compound from example 1A and 212 mg (0.856 mmol) of 1-(4-chlorophenyl)-3-(dimethylamino)propan-1-one hydrochloride. 104 mg (23% of theory) of the title compound were obtained.

LC-MS (method 2): R$_t$=1.42 min; MS (EIpos): m/z=499 (M+H)$^+$.

$^1$H NMR (400 MHz, DMSO-d$_6$): δ [ppm]=3.14-3.18 (m, 2H), 3.46-3.51 (m, 2H), 5.81 (s, 2H), 6.78 (s br, 2H), 7.11-

7.18 (m, 2H), 7.21-7.26 (m, 1H), 7.33-7.39 (m, 2H), 7.46 (d, 2H), 7.63 (t, 1H) 8.04 (d, 2H), 8.62 (dd, 1H), 9.13 (dd, 1H).

br, 1H), 7.12-7.19 (m, 2H), 7.20-7.26 (m, 1H), 7.33-7.43 (m, 4H), 7.47-7.52 (m, 1H), 7.56-7.59 (m, 1H), 7.74 (t, 1H), 8.62 (dd, 1H), 9.12 (dd, 1H).

Example 25

6-(2-Chlorophenyl)-2-[1-(2-fluorobenzyl)-1H-pyrazolo[3,4-b]pyridin-3-yl]-8,9-dihydro-7H-pyrimido[4,5-b][1,4]diazepin-4-amine Example 26

6-(3-Chlorophenyl)-2-[1-(2-fluorobenzyl)-1H-pyrazolo[3,4-b]pyridin-3-yl]-8,9-dihydro-7H-pyrimido[4,5-b][1,4]diazepin-4-amine

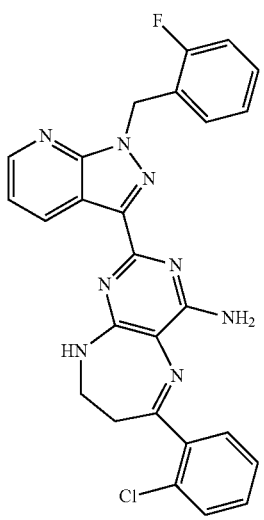 [SMILES: Nc1nc(-c2nn(Cc3ccccc3F)c3ncccc23)nc2c1N=C(c1ccccc1Cl)CCN2]

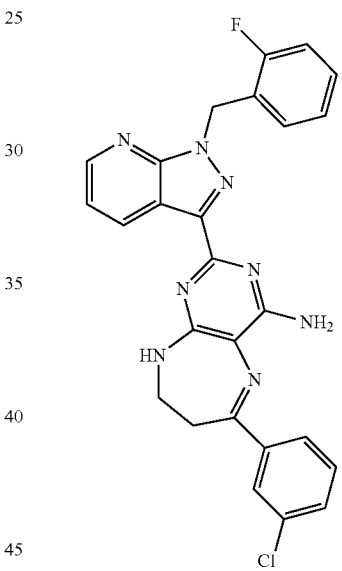

The preparation was effected analogously to example 23, from 300 mg (0.856 mmol) of the compound from example 1A and 212 mg (0.856 mmol) of 1-(2-chlorophenyl)-3-(dimethylamino)propan-1-one hydrochloride. 77 mg (17% of theory) of the title compound were obtained.

LC-MS (method 2): $R_t$=1.02 min; MS (EIpos): m/z=499 (M+H)$^+$.

$^1$H NMR (400 MHz, DMSO-d$_6$): δ [ppm]=3.05-3.08 (m, 2H), 3.52-3.56 (m, 2H), 5.81 (s, 2H), 6.40 (s br, 1H), 6.83 (s The preparation was effected analogously to example 23, from 300 mg (0.856 mmol) of the compound from example 1A and 212 mg (0.856 mmol) of 1-(3-chlorophenyl)-3-(dimethylamino)propan-1-one hydrochloride. 104 mg (23% of theory) of the title compound were obtained.

LC-MS (method 2): $R_t$=1.04 min; MS (EIpos): m/z=499 (M+H)$^+$.

$^1$H NMR (400 MHz, DMSO-d$_6$): δ [ppm]=3.15-3.17 (m, 2H), 3.47-3.51 (m, 2H), 5.81 (s, 2H), 6.80 (s br, 2H), 7.12-

7.18 (m, 2H), 7.21-7.26 (m, 1H), 7.33-7.39 (m, 2H), 7.43-7.49 (m, 2H), 7.64 (t, 1H), 7.92-7.98 (m, 1H), 8.04 (s, 1H), 8.62 (dd, 1H), 9.13 (dd, 1H).

Example 27

2-[1-(2-Fluorobenzyl)-1H-pyrazolo[3,4-b]pyridin-3-yl]-6-phenyl-8,9-dihydro-7H-pyrimido[4,5-b][1,4]diazepin-4-amine

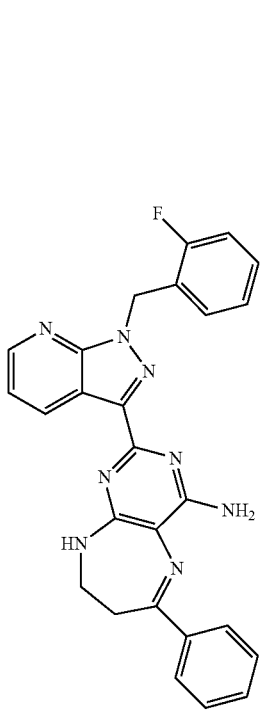 [SMILES: Nc1nc(-c2nn(Cc3ccccc3F)c3ncccc23)nc2c1N=C(c1ccccc1)CCN2]

The preparation was effected analogously to example 23, from 300 mg (0.856 mmol) of the compound from example 1A and 183 mg (0.856 mmol) of 1-phenyl-3-(dimethylamino)propan-1-one hydrochloride. 35 mg (9% of theory) of the title compound were obtained.

LC-MS (method 2): $R_t$=0.97 min; MS (EIpos): m/z=465 (M+H)$^+$.

$^1$H NMR (400 MHz, DMSO-d$_6$): δ [ppm]=3.16-3.19 (m, 2H), 3.48-3.52 (m, 2H), 5.81 (s, 2H), 6.74 (s br, 2H), 7.12-7.18 (m, 2H), 7.21-7.26 (m, 1H), 7.33-7.39 (m, 2H), 7.41-7.46 (m, 3H), 7.60 (t, 1H), 7.99-8.02 (m, 2H), 8.62 (dd, 1H), 9.13 (dd, 1H).

Example 28

6-Amino-2-[1-(2-fluorobenzyl)-1H-pyrazolo[3,4-b]pyridin-3-yl]-7,9-dihydro-8H-purine-8-thione

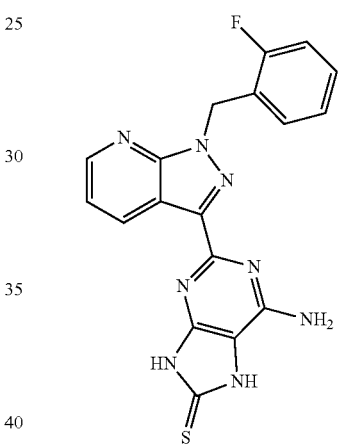

500 mg (1.427 mmol) of the compound from example 1A were admixed with 3 ml of ethanol and 423 mg (2.640 mmol) of potassium ethylxanthogenate, and the mixture was stirred at 150° C. in a microwave for 1 h. The reaction mixture was boiled with 100 ml of water. The mixture was filtered and the aqueous phase was acidified with acetic acid, forming a precipitate which was filtered off. The residue was stirred with saturated aqueous sodium hydrogencarbonate solution, filtered off and dried under high vacuum. 269 mg of the title compound (48% of theory) were obtained, which were converted without further purification.

LC-MS (method 2): $R_t$=0.85 min; MS (EIpos): m/z=493 (M+H)$^+$.

¹H NMR (400 MHz, DMSO-d₆): δ [ppm]=5.82 (s, 2H), 6.97 (s br, 2H), 7.12-7.26 (m, 3H), 7.33-7.41 (m, 2H), 8.64 (dd, 1H), 9.00 (dd, 1H), 12.16 (s br, 1H), 13.12 (s br, 1H).

Example 29

2-[1-(2-Fluorobenzyl)-1H-pyrazolo[3,4-b]pyridin-3-yl]-8-(methylsulfanyl)-7H-purin-6-amine

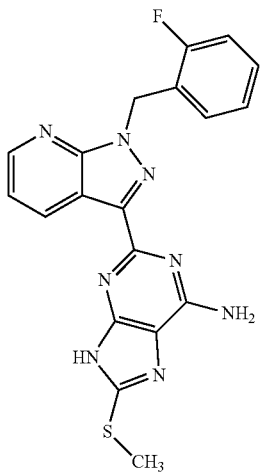 [SMILES: CSc1nc2c(N)nc(-c3nn(Cc4ccccc4F)c4ncccc34)nc2[nH]1]

100 mg (0.255 mmol) of the compound from example 28 were dissolved in 5 ml of dimethylformamide, and 49 mg (0.357 mmol) of potassium carbonate were added. The mixture was heated to 70° C. for 10 min and, after cooling, 18 μl (0.291 mmol) of iodomethane were added and the mixture was stirred at RT for 48 h. The mixture was concentrated and the residue was taken up in water and acidified with acetic acid. A solid precipitates out, which was filtered off and washed with water. The purification was effected by means of preparative HPLC (eluent: methanol/water, gradient 30:70→90:10). 18 mg of the title compound were obtained (17% of theory).

LC-MS (method 2): $R_t$=0.88 min; MS (EIpos): m/z=407 (M+H)⁺.

¹H NMR (400 MHz, DMSO-d₆): δ [ppm]=2.70 (s, 2H), 2.75 (s, 1H), 5.81 (s, 2H), 7.07-7.26 (m, 5H), 7.33-7.39 (m, 2H), 8.63 (dd, 1H), 9.06-9.09 (m, 1H), 13.06 (s, 1H).

Example 30

2-[1-(2-Fluorobenzyl)-1H-pyrazolo[3,4-b]pyridin-3-yl]-9-methyl-8-(methylsulfanyl)-9H-purin-6-amine

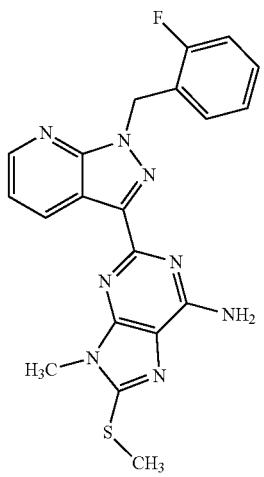 [SMILES: CSc1nc2c(N)nc(-c3nn(Cc4ccccc4F)c4ncccc34)nc2n1C]

100 mg (0.255 mmol) of the compound from example 29 were dissolved in 5 ml of dimethylformamide, and 49 mg (0.357 mmol) of potassium carbonate were added. The mixture was heated to 70° C. for 10 min and, after cooling, 18 μl (0.291 mmol) of iodomethane were added and the mixture was stirred at RT for 48 h. The mixture was concentrated and the residue was taken up in water and acidified with acetic acid. A solid precipitates out, which was filtered off and washed with water. The purification was effected by means of preparative HPLC (eluent: methanol/water, gradient 30:70→90:10). 26 mg of the title compound were obtained (24% of theory).

LC-MS (method 2): $R_t$=1.01 min; MS (EIpos): m/z=421 (M+H)⁺.

$^1$H NMR (400 MHz, DMSO-$d_6$): δ [ppm]=2.75 (s, 3H), 3.69 (s, 3H), 5.84 (s, 2H), 7.10-7.16 (m, 2H), 7.22-7.30 (m, 3H), 7.33-7.41 (m, 2H), 8.63 (d, 1H), 9.14 (dd, 1H).

Example 31

8-(Ethylsulfanyl)-2-[1-(2-fluorobenzyl)-1H-pyrazolo[3,4-b]pyridin-3-yl]-7H-purin-6-amine

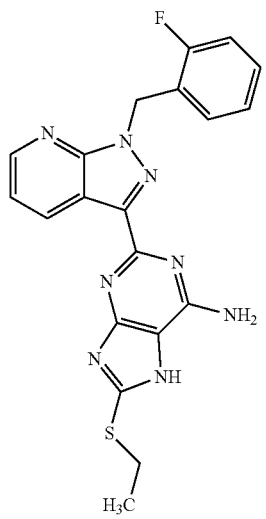 [SMILES: CCSc1nc2nc(-c3nn(Cc4ccccc4F)c4ncccc34)nc(N)c2[nH]1]

150 mg (0.382 mmol) of the compound from example 28 were dissolved in 2 ml of dimethylformamide, and 58 mg (0.420 mmol) of potassium carbonate were added. The mixture was heated to 70° C. for 10 min and, after cooling, 31 μl (0.382 mmol) of iodoethane were added and the mixture was stirred at RT for 16 h. The mixture was concentrated, and the residue was adsorbed on silica gel and purified by means of chromatography on silica gel (eluent: dichloromethane/methanol=20:1). 91 mg of the title compound were obtained (51% of theory).

LC-MS (method 3): $R_t$=1.02 min; MS (EIpos): m/z=421 (M+H)$^+$.

$^1$H NMR (400 MHz, DMSO-$d_6$): δ [ppm]=1.36 (t, 3H), 3.27 (q, 2H), 5.81 (s, 2H), 7.12-7.26 (m, 4H), 7.33-7.39 (m, 2H), 8.63 (dd, 1H), 9.07 (d, 1H), 13.06 (s, 1H).

Example 32

2-[1-(2-Fluorobenzyl)-1H-pyrazolo[3,4-b]pyridin-3-yl]-8-[(2,2,2-trifluoroethyl)sulfanyl]-7H-purin-6-amine

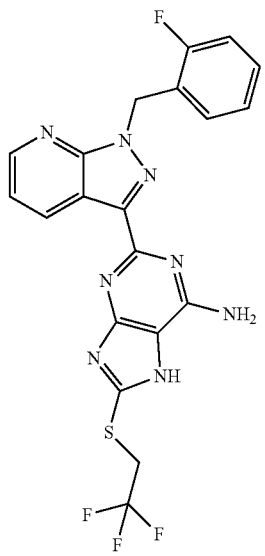 [SMILES: Nc1nc(-c2nn(Cc3ccccc3F)c3ncccc23)nc2nc(SCC(F)(F)F)[nH]c12]

150 mg (0.382 mmol) of the compound from example 28 were dissolved in 2 ml of dimethylformamide, and 58 mg (0.420 mmol) of potassium carbonate were added. The mixture was heated to 70° C. for 10 min and, after cooling, 38 μl (0.382 mmol) of trifluoroethyl iodide were added and the mixture was stirred at RT for 16 h. The mixture was concentrated, and the residue was adsorbed on silica gel and purified by means of chromatography on silica gel (eluent: dichloromethane/methanol=20:1). 49 mg of the title compound were obtained (25% of theory).

LC-MS (method 3): $R_t$=1.11 min; MS (EIpos): m/z=475 (M+H)$^+$.

¹H NMR (400 MHz, DMSO-d₆): δ [ppm]=4.35 (q, 2H), 5.82 (s, 2H), 7.12-7.26 (m, 3H), 7.33-7.41 (m, 4H), 8.63 (d, 1H), 9.06 (d, 1H), 13.35 (s, 1H).

¹H NMR (400 MHz, DMSO-d₆): δ [ppm]=5.81 (s, 2H), 6.63 (s br, 2H) 7.12-7.25 (m, 3H), 7.33-7.38 (m, 2H), 8.63 (dd, 1H), 8.96 (dd, 1H), 10.08 (s, 1H), 11.45 (s, 1H).

Example 33

6-Amino-2-[1-(2-fluorobenzyl)-1H-pyrazolo[3,4-b]pyridin-3-yl]-7,9-dihydro-8H-purin-8-one

Example 34

6-Amino-2-[1-(2-fluorobenzyl)-1H-pyrazolo[3,4-b]pyridin-3-yl]-9-(²H₃)methyl-7,9-dihydro-8H-purin-8-one

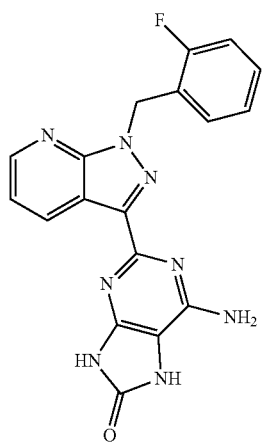

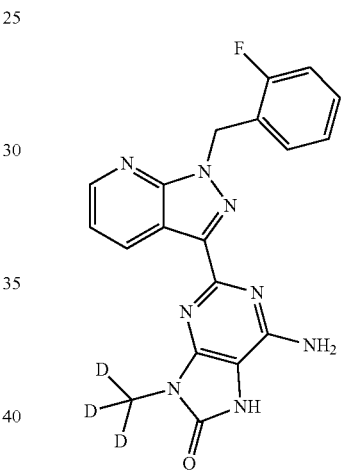

5.000 g (14.271 mmol) of the compound from example 1A were dissolved in 50 ml of dimethylformamide, and 11.570 g (71.355 mmol) of carbonyldiimidazole and 18.051 g (178.387 mmol) of triethylamine were added. The mixture was stirred at 100° C. for 16 h. The reaction mixture was partitioned between water and ethyl acetate, and the aqueous phase was extracted with ethyl acetate. The combined organic phases were concentrated under reduced pressure, and the residue was stirred with tert-butyl methyl ether. The solid formed was filtered off and purified by means of preparative HPLC (eluent: methanol/water, gradient 20:80→90:10). 2.120 g of the title compound were obtained (38% of theory).

LC-MS (method 2): R$_t$=0.80 min; MS (EIpos): m/z=377 (M+H)⁺.

200 mg (0.531 mmol) of the compound from example 33 and 146 mg (0.531 mmol) of BEMP were initially charged in 10 ml of dimethylformamide, and a solution of 77 mg (0.531 mmol) of iodomethane-d₃ in 2 ml of dimethylformamide was added dropwise at 0° C. within 10 min. The mixture was stirred at 0° C. for 1 h. Subsequently, the reaction solution was concentrated under reduced pressure, and acetonitrile/water was added. The precipitate formed was filtered off and purified by means of preparative HPLC (eluent: methanol/water with 0.2% trifluoroacetic acid=60:40). 88 mg of the title compound were obtained (42% of theory).

LC-MS (method 2): R$_t$=0.86 min; MS (EIpos): m/z=494 (M+H)⁺.

¹H NMR (400 MHz, DMSO-d₆): δ [ppm]=5.83 (s, 2H), 6.63 (s br, 2H) 7.09-7.15 (m, 2H), 7.21-7.26 (m, 1H), 7.32-7.40 (m, 2H), 8.63 (dd, 1H), 9.04 (dd, 1H), 10.27 (s, 1H).

Example 35

6-Amino-9-ethyl-2-[1-(2-fluorobenzyl)-1H-pyrazolo[3,4-b]pyridin-3-yl]-7,9-dihydro-8H-purin-8-one

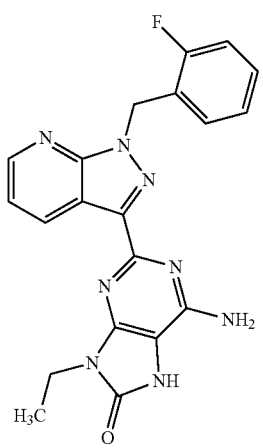 [SMILES: CCn1c(=O)[nH]c2c(N)nc(-c3nn(Cc4ccccc4F)c4ncccc34)nc21]

200 mg (0.531 mmol) of the compound from example 33 and 146 mg (0.531 mmol) of BEMP were initially charged in 10 ml of dimethylformamide, and a solution of 82 mg (0.531 mmol) of ethyl iodide in 2 ml of dimethylformamide was added dropwise at 0° C. within 10 min The mixture was stirred at 0° C. for 20 min. Subsequently, the reaction solution was concentrated under reduced pressure and the residue was purified by means of preparative HPLC (eluent: acetonitrile/water, gradient 10:90→90:10). 67 mg of the title compound were obtained (31% of theory).

LC-MS (method 4): R$_t$=0.86 min; MS (EIpos): m/z=405 (M+H)⁺.

¹H NMR (400 MHz, DMSO-d₆): δ [ppm]=1.31 (t, 3H), 3.90 (q, 2H), 5.84 (s, 2H), 6.62 (s br, 2H) 7.09-7.15 (m, 2H), 7.22-7.26 (m, 1H), 7.33-7.42 (m, 2H), 8.63 (dd, 1H), 9.00 (dd, 1H), 10.27 (s, 1H).

Example 36

6-Amino-2-[1-(2-fluorobenzyl)-1H-pyrazolo[3,4-b]pyridin-3-yl]-9-(2,2,2-trifluoroethyl)-7,9-dihydro-8H-purin-8-one

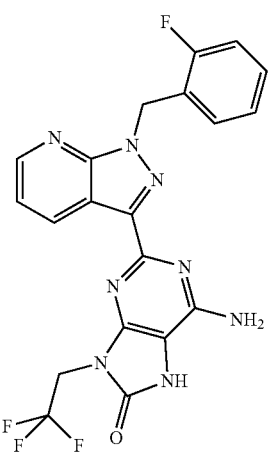 [SMILES: Nc1nc(-c2nn(Cc3ccccc3F)c3ncccc23)nc2c1[nH]c(=O)n2CC(F)(F)F]

100 mg (0.266 mmol) of the compound from example 33 and 73 mg (0.266 mmol) of BEMP were initially charged in 9 ml of dimethylformamide, and a solution of 75 mg (0.266 mmol) of 2,2,2-trifluoroethyl trichloromethanesulfonate in 1 ml of dimethylformamide was added dropwise at 0° C. within 10 min. The mixture was stirred at 0° C. for 20 min. Subsequently, the reaction solution was concentrated under reduced pressure and the residue was purified by means of preparative HPLC (eluent: methanol/water, gradient 30:70→90:10). 60 mg of the title compound were obtained (47% of theory).

LC-MS (method 2): R$_t$=1.00 min; MS (EIpos): m/z=459 (M+H)⁺.

$^1$H NMR (400 MHz, DMSO-d$_6$): δ [ppm]=4.71 (q, 2H), 5.83 (s, 2H), 6.87 (s br, 2H) 7.08-7.15 (m, 2H), 7.21-7.26 (m, 1H), 7.32-7.42 (m, 2H), 8.62 (dd, 1H), 9.01 (dd, 1H).

Example 37

6-Amino-9-(cyclopropylmethyl)-2-[1-(2-fluorobenzyl)-1H-pyrazolo[3,4-b]pyridin-3-yl]-7,9-dihydro-8H-purin-8-one

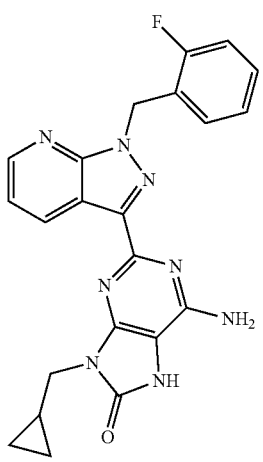 [SMILES: Nc1nc(-c2nn(Cc3ccccc3F)c3ncccc23)nc2c1[nH]c(=O)n2CC1CC1]

200 mg (0.531 mmol) of the compound from example 33 and 145 mg (0.531 mmol) of BEMP were initially charged in 10 ml of dimethylformamide, and a solution of 71 mg (0.531 mmol) of (bromomethyl)cyclopropane in 2 ml of dimethylformamide was added dropwise at 0° C. within 10 min The mixture was stirred at 0° C. for 20 min. Subsequently, the reaction solution was concentrated under reduced pressure and the residue was purified by means of preparative HPLC (eluent: acetonitrile/water, gradient 10:90→90:10). 27 mg of the title compound were obtained (11% of theory).

LC-MS (method 3): R$_t$=1.11 min; MS (EIpos): m/z=431 (M+H)$^+$.

Example 38

6-Amino-2-[1-(2-fluorobenzyl)-1H-pyrazolo[3,4-b]pyridin-3-yl]-9-(2-methylprop-2-en-1-yl)-7,9-dihydro-8H-purin-8-one

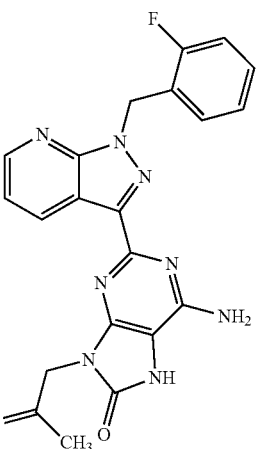

200 mg (0.531 mmol) of the compound from example 33 and 145 mg (0.531 mmol) of BEMP were initially charged in 10 ml of dimethylformamide, and a solution of 72 mg (0.531 mmol) of 3-bromo-2-methylprop-1-ene 2 ml of dimethylformamide was added dropwise at 0° C. within 10 min. The mixture was stirred at 0° C. for 1 h. Subsequently, the reaction solution was concentrated under reduced pressure and the residue was purified by means of preparative HPLC (eluent: acetonitrile/water, gradient 10:90→90:10). 88 mg of the title compound were obtained (37% of theory).

LC-MS (method 2): R$_t$=1.00 min; MS (EIpos): m/z=431 (M+H)$^+$.

$^1$H NMR (400 MHz, DMSO-d$_6$): δ [ppm]=1.76 (s, 3H), 4.40 (s, 2H), 4.71 (s, 1H), 4.87 (s, 1H), 5.82 (s, 2H), 6.66 (s br, 2H) 7.08-7.14 (m, 2H), 7.20-7.25 (m, 1H), 7.32-7.39 (m, 2H), 8.62 (dd, 1H), 8.96 (dd, 1H), 10.33 (s, 1H).

Example 39

6-Amino-2-[1-(2-fluorobenzyl)-1H-pyrazolo[3,4-b]pyridin-3-yl]-9-isopropyl-7,9-dihydro-8H-purin-8-one

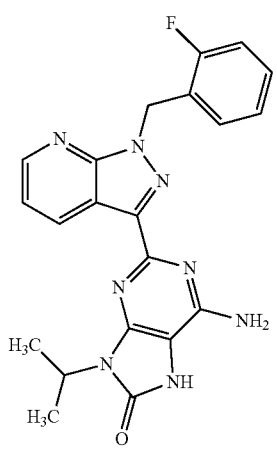 [SMILES: CC(C)n1c(=O)[nH]c2c(N)nc(-c3nn(Cc4ccccc4F)c4ncccc34)nc21]

200 mg (0.531 mmol) of the compound from example 33 and 145 mg (0.531 mmol) of BEMP were initially charged in 10 ml of dimethylformamide, and a solution of 90 mg (0.531 mmol) of 2-iodopropane ml of dimethylformamide was added dropwise at 0° C. within 10 min The mixture was stirred at 0° C. for 20 min. Subsequently, the reaction solution was concentrated under reduced pressure and the residue was purified by means of preparative HPLC (eluent: methanol/water, gradient 30:70→90:10). 117 mg of the title compound were obtained (50% of theory).

LC-MS (method 4): $R_t$=2.02 min; MS (EIpos): m/z=419 (M+H)$^+$.

$^1$H NMR (400 MHz, DMSO-d$_6$): δ [ppm]=1.56 (d, 6H), 4.67 (hept, 1H), 5.83 (s, 2H), 6.65 (s br, 2H) 7.10-7.15 (m, 2H), 7.21-7.26 (m, 1H), 7.33-7.43 (m, 2H), 8.63 (dd, 1H), 8.96 (dd, 1H), 10.43 (s br, 1H).

Example 40

6-Amino-2-[1-(2-fluorobenzyl)-1H-pyrazolo[3,4-b]pyridin-3-yl]-7-methyl-9-(2,2,2-trifluoroethyl)-7,9-dihydro-8H-purin-8-one

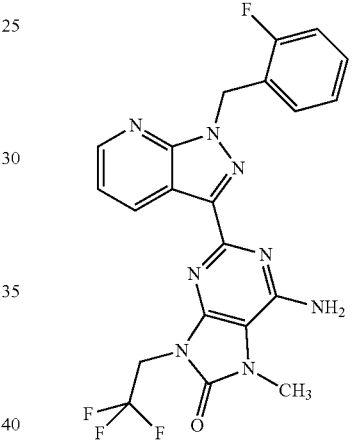

80 mg (0.175 mmol) of the compound from example 36 and 48 mg (0.175 mmol) of BEMP were initially charged in 10 ml of dimethylformamide, and a solution of 25 mg (0.175 mmol) of iodomethane in 2 ml of dimethylformamide was added dropwise at 0° C. within 10 min. The mixture was stirred at 0° C. for 20 min. Subsequently, the reaction solution was concentrated under reduced pressure and the residue was purified by means of preparative HPLC (eluent: methanol/water, gradient 30:70→90:10). 30 mg of the title compound were obtained (35% of theory).

LC-MS (method 2): $R_t$=1.02 min; MS (EIpos): m/z=473 (M+H)$^+$.

179

¹H NMR (400 MHz, DMSO-d₆): δ [ppm]=3.56 (s, 3H), 4.74 (q, 2H), 5.84 (s, 2H), 6.98 (s br, 2H) 7.08-7.15 (m, 2H), 7.21-7.26 (m, 1H), 7.32-7.42 (m, 2H), 8.63 (dd, 1H), 9.03 (dd, 1H).

Example 41

6-Amino-2-[1-(2-fluorobenzyl)-1H-pyrazolo[3,4-b]pyridin-3-yl]-7-methyl-7,9-dihydro-8H-purin-8-one

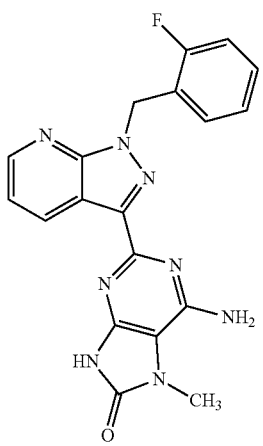 [SMILES: Cn1c(=O)[nH]c2nc(-c3nn(Cc4ccccc4F)c4ncccc34)nc(N)c21]

119 mg (0.282 mmol) of the compound from example 13A were dissolved in 5 ml of tetrahydrofuran and cooled to 0° C., and 310 µl (0.3100 mmol) of a 1N solution of bis(trimethylsilyl)sodium amide in tetrahydrofuran were added dropwise. The mixture was stirred at 0° C. for 3 h and then at RT for 16 h. Water was added, and the precipitate formed was filtered off, washed with tetrahydrofuran and dried under high vacuum. 44 mg of the title compound were obtained (39% of theory).

LC-MS (method 2): R$_t$=0.83 min; MS (EIpos): m/z=391 (M+H)⁺.

180

¹H NMR (400 MHz, DMSO-d₆): δ [ppm]=3.39 (s, 3H), 5.54 (s br, 2H), 5.77 (s, 2H) 7.09-7.14 (m, 2H), 7.20-7.25 (m, 1H), 7.28-7.37 (m, 2H), 8.55 (dd, 1H), 9.06 (dd, 1H).

Example 42

6-Amino-7-ethyl-2-[1-(2-fluorobenzyl)-1H-pyrazolo[3,4-b]pyridin-3-yl]-7,9-dihydro-8H-purin-8-one

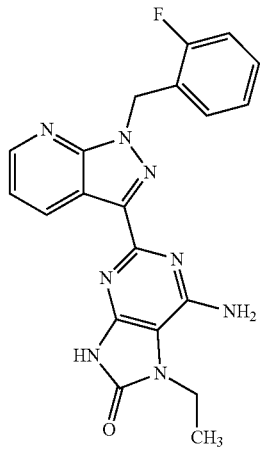 [SMILES: CCn1c(=O)[nH]c2nc(-c3nn(Cc4ccccc4F)c4ncccc34)nc(N)c21]

59 mg (0.135 mmol) of the compound from example 14A were dissolved in 7.5 ml of tetrahydrofuran and cooled to 0° C., and 150 µl (0.150 mmol) of a 1N solution of bis(trimethylsilyl)sodium amide in tetrahydrofuran were added dropwise. The mixture was stirred at 0° C. for 3 h and then at RT for 16 h. Another 150 µl (0.150 mmol) of a 1N solution of bis(trimethylsilyl)sodium amide in tetrahydrofuran were added dropwise and the mixture was stirred at RT for 2 days. Water was added and the reaction mixture was concentrated under reduced pressure and the residue was purified by means of preparative HPLC (eluent: methanol/water, gradient 30:70→90:10). 29 mg of the title compound were obtained (53% of theory).

LC-MS (method 2): R$_t$=0.86 min; MS (EIpos): m/z=405 (M+H)⁺.

¹H NMR (400 MHz, DMSO-d₆): δ [ppm]=1.18 (t, 3H), 3.99 (q, 2H), 5.80 (s, 2H), 6.75 (s br, 2H), 7.12-7.25 (m, 3H), 7.33-7.39 (m, 2H), 8.63 (dd, 1H), 9.05 (dd, 1H), 11.62 (s, 1H).

Example 43

6-Amino-2-[1-(2-fluorobenzyl)-1H-pyrazolo[3,4-b]pyridin-3-yl]-7-isopropyl-7,9-dihydro-8H-purin-8-one

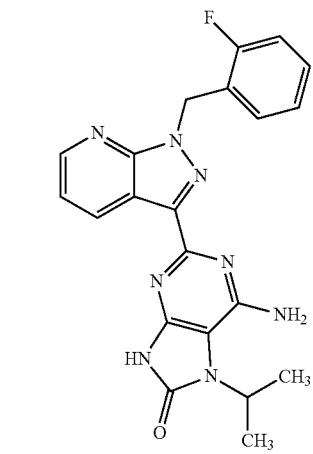 [SMILES: CC(C)n1c(=O)[nH]c2nc(-c3nn(Cc4ccccc4F)c4ncccc34)nc(N)c21]

2000 mg (4.897 mmol) of the compound from example 11A were dissolved in 20 ml of tetrahydrofuran and cooled to 0° C., and 294 mg (5.387 mmol) of sodium hydride were added. The mixture was stirred at 0° C. for 1.5 h and 916 mg (5.387 mmol) of 2-iodopropane were added. The mixture was stirred at RT for 48 h and then water was added. The reaction mixture was concentrated under reduced pressure and the residue was purified twice by means of preparative HPLC (eluent: methanol/water, gradient 30:70→90:10). 19 mg of the title compound were obtained (1% of theory).

LC-MS (method 1): $R_t$=1.91 min; MS (EIpos): m/z=419 (M+H)⁺.

¹H NMR (400 MHz, DMSO-d₆): δ [ppm]=1.47 (d, 6H), 4.60 (hept, 1H), 5.80 (s, 2H), 6.50 (s br, 2H), 7.12-7.25 (m, 3H), 7.33-7.38 (m, 2H), 8.62 (dd, 1H), 9.07 (dd, 1H).

Example 44

6-Amino-2-[1-(2-fluorobenzyl)-1H-pyrazolo[3,4-b]pyridin-3-yl]-7-(2,2,2-trifluoroethyl)-7,9-dihydro-8H-purin-8-one

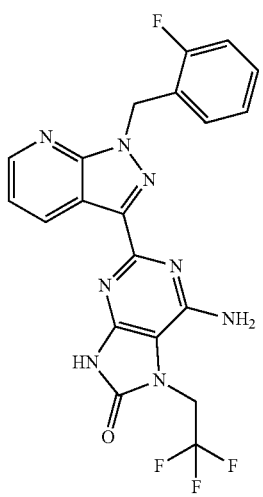 [SMILES: Nc1nc(-c2nn(Cc3ccccc3F)c3ncccc23)nc2[nH]c(=O)n(CC(F)(F)F)c12]

Under an argon atmosphere, 2.100 g (4.282 mmol) of the compound from example 15A were dissolved in 235 ml of tetrahydrofuran and cooled to 0° C., and 10.705 ml (10.705 mmol) of a 1N solution of bis(trimethylsilyl)sodium amide in tetrahydrofuran were added dropwise. The mixture was stirred at 0° C. for 2 h and then at RT for 16 h. The tetrahydrofuran was partly concentrated in an argon stream and the precipitate was filtered off. 1.290 g of the title compound were obtained (66% of theory).

LC-MS (method 3): $R_t$=1.03 min; MS (EIpos): m/z=459 (M+H)⁺.

¹H NMR (400 MHz, DMSO-d₆): δ [ppm]=4.91 (q, 2H), 5.81 (s, 2H), 6.95 (s br, 2H), 7.12-7.26 (m, 3H), 7.33-7.40 (m, 2H), 8.64 (dd, 1H), 9.04 (dd, 1H), 11.97 (s, 1H).

Example 45

2-[1-(2-Fluorobenzyl)-1H-pyrazolo[3,4-b]pyridin-3-yl]-7-(2,2,2-trifluoroethyl)-7,9-dihydro-8H-purin-8-one

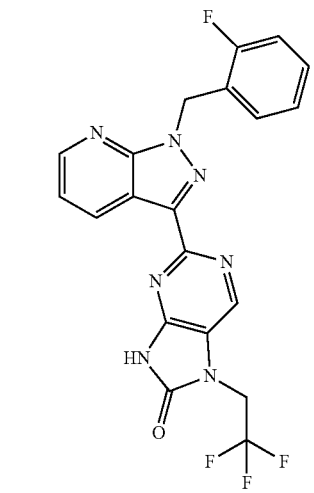 [SMILES: O=c1[nH]c2nc(-c3nn(Cc4ccccc4F)c4ncccc34)ncc2n1CC(F)(F)F]

447 mg (4.337 mmol) of tert-butyl nitrite were dissolved in 20 ml of dry dimethylformamide, and 994 mg (2.169 mmol) of the compound from example 44 dissolved in 15 ml of dimethylformamide were added at 65° C. by means of a syringe pump within 1 h. After stirring at 65° C. for a further hour, 40 ml of water were added, forming a precipitate. The precipitate was filtered off and purified by means of preparative HPLC (eluent: water/acetonitrile/water with 1% trifluoroacetic acid, gradient 68:15:17→0:100:0). 99 mg of the title compound were obtained (10% of theory).

LC-MS (method 2): R$_t$=1.03 min; MS (EIpos): m/z=444 (M+H)⁺.

¹H NMR (400 MHz, DMSO-d₆): δ [ppm]=4.87 (q, 2H), 5.85 (s, 2H), 7.14-7.17 (m, 1H), 7.21-7.27 (m, 2H), 7.34-7.40 (m, 1H), 7.43 (dd, 1H), 8.64 (s, 1H), 8.67 (dd, 1H), 8.88 (dd, 1H), 12.53 (s, 1H).

Example 46

6-Amino-2-[1-(2-fluorobenzyl)-1H-pyrazolo[3,4-b]pyridin-3-yl]-7,9-dimethyl-7,9-dihydro-8H-purin-8-one

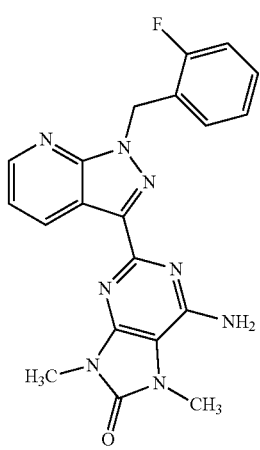 [SMILES: Cn1c(=O)n(C)c2c(N)nc(-c3nn(Cc4ccccc4F)c4ncccc34)nc21]

300 mg (0.768 mmol) of the compound from example 41 and 211 mg (0.768 mmol) of BEMP were initially charged in 10 ml of dimethylformamide, and a solution of 109 mg (0.768 mmol) of iodomethane in 2 ml of dimethylformamide was added dropwise at 0° C. within 10 min. The mixture was stirred at 0° C. for 3 h. Water was added, which formed a precipitate. The precipitate was filtered off and purified by means of preparative HPLC (eluent: methanol/water, gradient 30:70→90:10). 203 mg of the title compound were obtained (65% of theory).

LC-MS (method 4): R$_t$=1.83 min; MS (EIpos): m/z=405 (M+H)⁺.

¹H NMR (400 MHz, DMSO-d₆): δ [ppm]=3.37 (s, 3H), 3.53 (s, 3H), 5.84 (s, 2H), 6.80 (s br, 2H) 7.09-7.15 (m, 2H), 7.21-7.26 (m, 1H), 7.32-7.40 (m, 2H), 8.63 (d, 1H), 9.09 (d, 1H).

Example 47

6-Amino-2-[1-(2-fluorobenzyl)-1H-pyrazolo[3,4-b]pyridin-3-yl]-7-(²H₃)methyl-7,9-dihydro-8H-purin-8-one

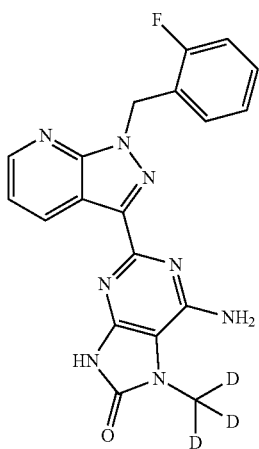 [SMILES: [2H]C([2H])([2H])n1c(=O)[nH]c2nc(-c3nn(Cc4ccccc4F)c4ncccc34)nc(N)c21]

47 mg (0.110 mmol) of the compound from example 16A were dissolved in 6 ml of tetrahydrofuran and cooled to 0° C., and 122 μl (0.112 mmol) of a 1N solution of bis(trimethylsilyl)sodium amide in tetrahydrofuran were added dropwise. The mixture was stirred at 0° C. for 3 h and then at RT for 16 h. Another 122 μl (0.112 mmol) of a 1N solution of bis(trimethylsilyl)sodium amide in tetrahydrofuran were added dropwise and the mixture was stirred at RT for 2 days. Water was added and the reaction mixture was concentrated under reduced pressure and the residue was purified twice by means of preparative HPLC (eluent: methanol/water, gradient 30:70→90:10 and acetonitrile/water with 0.1% trifluoroacetic acid=45:55). 3 mg of the title compound were obtained (7% of theory).

LC-MS (method 2): R$_t$=0.82 min; MS (EIpos): m/z=394 (M+H)⁺.

Example 48

4-Amino-2-[1-(2-fluorobenzyl)-1H-pyrazolo[3,4-b]pyridin-3-yl]pteridin-7(8H)-one

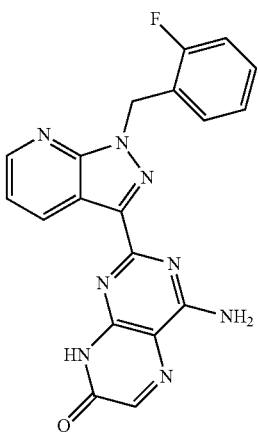 [SMILES: Nc1nc(-c2nn(Cc3ccccc3F)c3ncccc23)nc2[nH]c(=O)cnc12]

300 mg (0.856 mmol) of the compound from example 1A were dissolved in 20 ml of ethanol, and 187 μl (0.942 mmol) of a 50% solution of ethyl glyoxalate in toluene were added. The mixture was heated to reflux for 1 h, 2 drops of concentrated sulfuric acid were added and the mixture was heated to reflux for a further 16 h. The precipitate was filtered off and dried under high vacuum. 83 mg of the title compound were obtained (23% of theory).

LC-MS (method 3): R$_t$=0.93 min; MS (EIpos): m/z=389 (M+H)⁺.

¹H NMR (400 MHz, DMSO-d₆): δ [ppm]=5.85 (s, 2H), 7.13-7.26 (m, 3H), 7.34-7.39 (m, 1H), 7.43 (dd, 1H), 7.74-8.01 (m, 3H), 8.66 (dd, 1H), 9.17 (dd, 1H), 12.86 (s, 1H).

Example 49

4-Amino-2-[1-(2-fluorobenzyl)-1H-pyrazolo[3,4-b]pyridin-3-yl]-6-methylpteridin-7(8H)-one

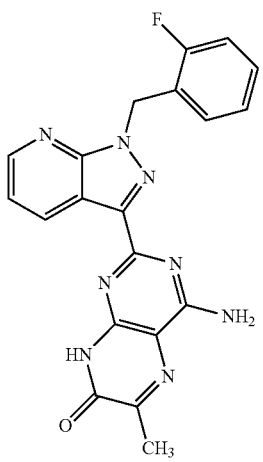 [SMILES: Cc1nc2c(N)nc(-c3nn(Cc4ccccc4F)c4ncccc34)nc2[nH]c1=O]

300 mg (0.856 mmol) of the compound from example 1A were dissolved in 20 ml of ethanol, and 105 μl (0.942 mmol) of ethyl 2-oxopropanoate were added. The mixture was heated to reflux for 16 h. The precipitate was filtered off from the hot mixture, taken up in trifluoroacetic acid and precipitated with water. The precipitate was filtered off and dried under high vacuum. 74 mg of the title compound were obtained (19% of theory).

LC-MS (method 3): $R_t$=0.98 min; MS (EIpos): m/z=403 (M+H)⁺.

¹H NMR (400 MHz, trifluoroacetic acid-d₁): δ [ppm]=2.88 (s, 3H), 6.24 (s, 2H), 7.25 (t, 1H), 7.44 (t, 1H), 7.59-7.69 (m, 2H), 8.24 (dd, 1H), 9.25 (d, 1H), 9.29 (d, 1H).

Example 50

4-Amino-2-[1-(2-fluorobenzyl)-1H-pyrazolo[3,4-b]pyridin-3-yl]-6-(trifluoromethyl)pteridin-7(8H)-one

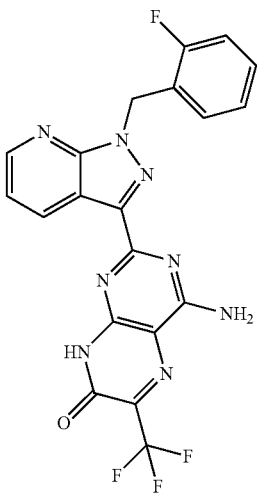 [SMILES: Nc1nc(-c2nn(Cc3ccccc3F)c3ncccc23)nc2[nH]c(=O)c(C(F)(F)F)nc12]

300 mg (0.856 mmol) of the compound from example 1A were dissolved in 25 ml of ethanol, and 118 μl (0.942 mmol) of ethyl 3,3,3-trifluoro-2-oxopropanoate were added. The mixture was heated to reflux for 16 h. The precipitate was filtered off and stirred with acetonitrile. The precipitate was filtered off and dried under high vacuum. 99 mg of the title compound were obtained (24% of theory).

LC-MS (method 2): $R_t$=1.01 min; MS (EIpos): m/z=457 (M+H)⁺.

¹H NMR (400 MHz, DMSO-d₆): δ [ppm]=5.87 (s, 2H), 7.12-7.26 (m, 3H), 7.35-7.39 (m, 1H), 7.45 (dd, 1H), 7.90 (s br, 1H), 8.36 (s br, 1H), 8.68 (dd, 1H), 9.18 (dd, 1H), 13.41 (s br, 1H).

Example 51

4-Amino-2-[1-(2-fluorobenzyl)-1H-pyrazolo[3,4-b]pyridin-3-yl]-5,8-dihydropteridine-6,7-dione

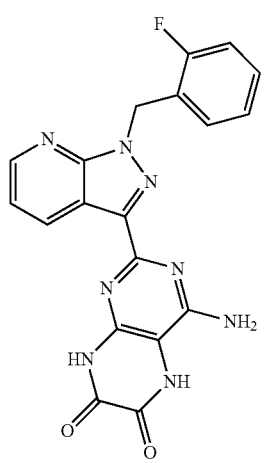 [SMILES: Nc1nc(-c2nn(Cc3ccccc3F)c3ncccc23)nc2[nH]c(=O)c(=O)[nH]c12]

300 mg (0.856 mmol) of the compound from example 1A were dissolved in 3 ml of ethanol, and 116 µl (0.856 mmol) of diethyl oxalate and 79 mg (1.156 mmol) of sodium methoxide were added. The mixture was heated to reflux for 10 h. The reaction mixture was stirred with 10 ml of ethanol. The precipitate was filtered off and stirred with 10 ml of water and then with 10 ml of acetonitrile. The precipitate was filtered off and dried under high vacuum. 112 mg of the title compound were obtained (30% of theory).

LC-MS (method 2): R$_t$=0.80 min; MS (EIpos): m/z=405 (M+H)⁺.

¹H NMR (400 MHz, DMSO-d₆): δ [ppm]=5.82 (s, 2H), 7.12-7.25 (m, 4H), 7.33-7.40 (m, 2H), 8.64 (dd, 1H), 9.14 (dd, 1H), 12.44 (s, 1H).

Example 52

2-[1-(2-Fluorobenzyl)-1H-pyrazolo[3,4-b]pyridin-3-yl]pteridin-4-amine

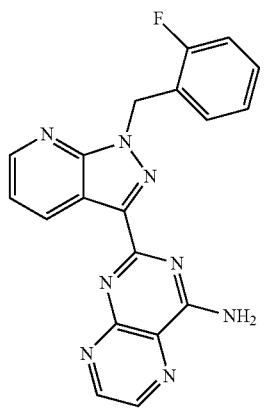 [SMILES: Nc1nc(-c2nn(Cc3ccccc3F)c3ncccc23)nc2nccnc12]

400 mg (1.142 mmol) of the compound from example 1A were dissolved in 20 ml of ethanol, and 274 mg (2.283 mmol) of 2,3-dihydroxy-1,4-dioxane were added. The mixture was stirred at RT for 16 h. The precipitate was filtered off and washed with a little ethanol. The residue was purified by means of preparative HPLC (eluent: acetonitrile/water with 0.05% trifluoroacetic acid, gradient 20:80→50:50). 96 mg of the title compound were obtained (23% of theory).

LC-MS (method 2): R$_t$=0.87 min; MS (EIpos): m/z=373 (M+H)⁺.

¹H NMR (400 MHz, DMSO-d₆): δ [ppm]=5.89 (s, 2H), 7.16 (t, 1H), 7.21-7.27 (m, 2H), 7.35-7.40 (m, 1H), 7.47 (dd, 1H), 8.50 (s br, 1H), 8.64 (s br, 1H), 8.69 (dd, 1H), 8.82 (d, 1H), 9.11 (d, 1H), 9.14 (dd, 1H).

Example 53

5-[1-(2-Fluorobenzyl)-1H-pyrazolo[3,4-b]pyridin-3-yl]-3H-[1,2,3]triazolo[4,5-d]pyrimidin-7-amine

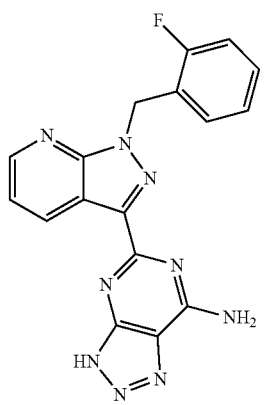 [SMILES: Nc1nc(-c2nn(Cc3ccccc3F)c3ncccc23)nc2[nH]nnc12]

1500 mg (4.281 mmol) of the compound from example 1A were dissolved in 7.3 ml of glacial acetic acid, and 54 ml of water were added, forming a suspension. While stirring, 295 mg (4.281 mmol) of sodium nitrite dissolved in 4 ml of water were added dropwise. The mixture was heated to reflux for 20 min. The precipitate was filtered off, washed with water and dried under high vacuum. 1345 mg of the title compound were obtained (87% of theory).

LC-MS (method 4): $R_t$=1.75 min; MS (EIpos): m/z=362 (M+H)$^+$.

$^1$H NMR (400 MHz, DMSO-d$_6$): δ [ppm]=5.84 (s, 2H), 7.13-7.26 (m, 3H), 7.33-7.39 (m, 1H), 7.42 (dd, 1H), 8.20 (s br, 2H), 8.66 (dd, 1H), 9.07 (dd, 1H), 16.00 (s br, 1H).

Example 54

5-[1-(2-Fluorobenzyl)-1H-pyrazolo[3,4-b]pyridin-3-yl]-3-methyl-3H-[1,2,3]triazolo[4,5-d]pyrimidin-7-amine

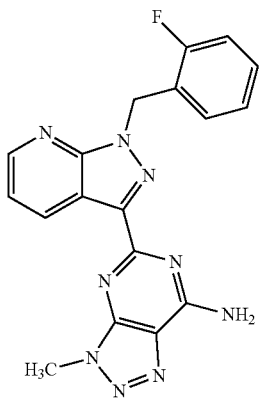 [SMILES: Cn1nnc2c(N)nc(-c3nn(Cc4ccccc4F)c4ncccc34)nc21]

250 mg (0.692 mmol) of the compound from example 53 and 190 mg (0.692 mmol) of BEMP were initially charged in 12 ml of dimethylformamide, and a solution of 98 mg (0.692 mmol) of iodomethane in 3 ml of dimethylformamide was added dropwise at 0° C. within 10 min. The mixture was stirred at 0° C. for 20 min. Subsequently, the reaction solution was concentrated under reduced pressure and the residue was purified by means of preparative HPLC (eluent: methanol/aqueous 0.1% ammonia solution=65:35). The residue was stirred with acetonitrile and filtered with suction, and the solids were dried under high vacuum. 78 mg of the title compound (30% of theory) and 50 mg of example 55 were obtained (19% of theory).

LC-MS (method 2): $R_t$=0.93 min; MS (EIpos): m/z=376 (M+H)$^+$.

$^1$H NMR (400 MHz, DMSO-d$_6$): δ [ppm]=4.23 (s, 3H) 5.88 (s, 2H), 7.12-7.17 (m, 2H), 7.22-7.27 (m, 1H), 7.33-7.39 (m, 1H), 7.44 (dd, 1H), 8.36 (s br, 1H), 8.48 (s br, 1H), 8.67 (dd, 1H), 9.16 (dd, 1H).

Example 55

5-[1-(2-Fluorobenzyl)-1H-pyrazolo[3,4-b]pyridin-3-yl]-2-methyl-2H-[1,2,3]triazolo[4,5-d]pyrimidin-7-amine

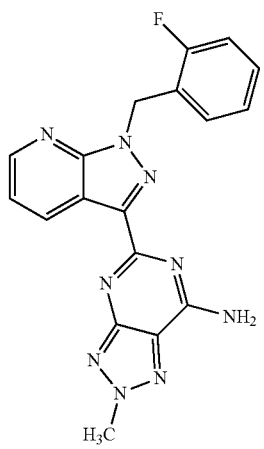 [SMILES: Cn1nc2nc(-c3nn(Cc4ccccc4F)c4ncccc34)nc(N)c2n1]

250 mg (0.692 mmol) of the compound from example 53 and 190 mg (0.692 mmol) of BEMP were initially charged in 12 ml of dimethylformamide, and a solution of 98 mg (0.692 mmol) of iodomethane in 3 ml of dimethylformamide was added dropwise at 0° C. within 10 min. The mixture was stirred at 0° C. for 20 min. Subsequently, the reaction solution was concentrated under reduced pressure and the residue was purified by means of preparative HPLC (eluent: methanol/aqueous 0.1% ammonia solution=65:35). The residue was stirred with acetonitrile and filtered with suction, and the solids were dried under high vacuum. 50 mg (19% of theory) of the title compound and 78 mg (30% of theory) of example 54 were obtained.

LC-MS (method 2): $R_t$=0.89 min; MS (EIpos): m/z=376 (M+H)$^+$.

¹H NMR (400 MHz, DMSO-d₆): δ [ppm]=4.48 (s, 3H) 5.88 (s, 2H), 7.13-7.28 (m, 3H), 7.34-7.40 (m, 1H), 7.45 (dd, 1H), 8.60 (s br, 1H), 8.68 (dd, 1H), 8.80 (s br, 1H), 9.04 (dd, 1H).

Example 56

5-[1-(2-Fluorobenzyl)-1H-pyrazolo[3,4-b]pyridin-3-yl]-3-(2,2,2-trifluoroethyl)-3H-[1,2,3]triazolo[4,5-d]pyrimidin-7-amine

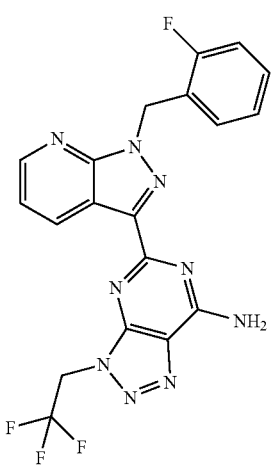 [SMILES: Nc1nc(-c2nn(Cc3ccccc3F)c3ncccc23)nc2c1nnn2CC(F)(F)F]

150 mg (0.415 mmol) of the compound from example 53 and 113 mg (0.0415 mmol) of BEMP were initially charged in 7 ml of dimethylformamide, and a solution of 117 mg (0.415 mmol) of 2,2,2-trifluoroethyl trichloromethanesulfonate in 2.5 ml of dimethylformamide was added dropwise at 0° C. within 10 min. The mixture was stirred at RT for 16 h. Subsequently, the reaction solution was concentrated under reduced pressure and the residue was purified by means of preparative HPLC (eluent: acetonitrile/water with 0.05% trifluoroacetic acid, gradient 10:90→90:10). 22 mg of the title compound were obtained (11% of theory).

LC-MS (method 2): $R_t$=1.04 min; MS (EIpos): m/z=444 (M+H)⁺.

¹H NMR (400 MHz, DMSO-d₆): δ [ppm]=5.73 (q, 2H), 5.88 (s, 2H), 7.11-7.16 (m, 2H), 7.22-7.26 (m, 1H), 7.33-7.39 (m, 1H), 7.45 (dd, 1H), 8.54 (s br, 1H), 8.67 (dd, 1H), 9.17 (dd, 1H).

Example 57

5-[1-(2-Fluorobenzyl)-1H-pyrazolo[3,4-b]pyridin-3-yl][1,2,5]thiadiazolo[3,4-d]pyrimidin-7-amine

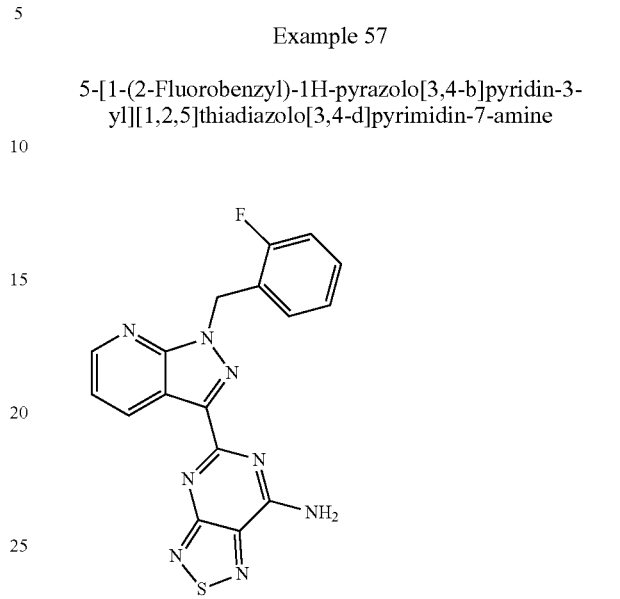

250 mg (0.714 mmol) of the compound from example 1A were dissolved in 4 ml of thionyl chloride. The mixture was heated to reflux for 5 h. The reaction mixture was concentrated on a rotary evaporator. Three times admixed with dichloromethane and concentrated. The residue was dissolved in methanol and precipitated with water, and the solids were filtered off with suction and dried under high vacuum. 192 mg of the title compound were obtained (71% of theory).

LC-MS (method 4): $R_t$=1.90 min; MS (EIpos): m/z=379 (M+H)⁺.

¹H NMR (400 MHz, DMSO-d₆): δ [ppm]=5.80 (s, 2H), 7.13-7.27 (m, 3H), 7.34-7.40 (m, 1H), 7.46 (dd, 1H), 8.68 (s br, 1H), 8.78 (s br, 1H), 9.10 (d, 1H).

Example 58

2-[1-(2-Fluorobenzyl)-1H-pyrazolo[3,4-b]pyridin-3-yl]-9H-purin-6-amine

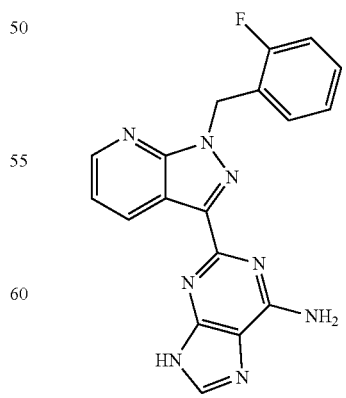

300 mg (0.856 mmol) of the compound from example 1A were admixed with 6 ml of formic acid and 600 mg (7.314 mmol) of anhydrous sodium acetate. The mixture was heated to reflux for 16 h. The reaction mixture was concentrated on a rotary evaporator. The residue was taken up in 10 ml of acetonitrile/water, 1 ml of trifluoroacetic acid was added, and the mixture was heated. A precipitate formed. After cooling, the precipitate was filtered off with suction, washed with 8 ml of acetonitrile and dried under high vacuum. 244 mg of the title compound were obtained (76% of theory).

LC-MS (method 4): $R_t$=1.60 min; MS (EIpos): m/z=361 (M+H)$^+$.

$^1$H NMR (400 MHz, DMSO-d$_6$): δ [ppm]=5.87 (s, 2H), 7.15 (t, 1H), 7.19-7.26 (m, 2H), 7.34-7.39 (m, 1H), 7.46 (dd, 1H), 7.98 (s br, 2H), 8.37 (s, 1H), 8.69 (dd, 1H), 9.00 (d, 1H).

Example 59

2-[1-(2-Fluorobenzyl)-1H-pyrazolo[3,4-b]pyridin-3-yl]-9-(2,2,2-trifluoroethyl)-9H-purin-6-amine

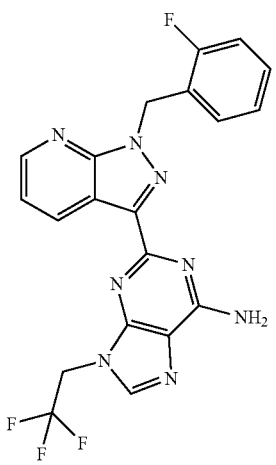 [SMILES: Nc1nc(-c2nn(Cc3ccccc3F)c3ncccc23)nc2c1ncn2CC(F)(F)F]

100 mg (0.278 mmol) of the compound from example 58 and 76 mg (0.278 mmol) of BEMP were initially charged in 3 ml of dimethylformamide, a solution of 78 mg (0.266 mmol) of 2,2,2-trifluoroethyl trichloromethanesulfonate in 2 ml of dimethylformamide was added dropwise at 0° C. within 10 min and the mixture was stirred at RT for 20 min The product was precipitated by adding water, filtered off with suction and purified by means of preparative HPLC (eluent: acetonitrile/water with 0.05% trifluoroacetic acid, gradient 20:80→50:50). 53 mg of the title compound were obtained (43% of theory).

LC-MS (method 3): $R_t$=1.11 min; MS (EIpos): m/z=443 (M+H)$^+$.

$^1$H NMR (400 MHz, DMSO-d$_6$): δ [ppm]=5.31 (q, 2H), 5.87 (s, 2H), 7.11-7.15 (m, 2H), 7.22-7.26 (m, 1H), 7.33-7.39 (m, 1H), 7.43 (dd, 1H), 7.80 (s br, 2H), 8.31 (s, 1H), 8.66 (dd, 1H), 9.12 (dd, 1H).

Example 60

2-[1-(2-Fluorobenzyl)-1H-pyrazolo[3,4-b]pyridin-3-yl]-7-(2,2,2-trifluoroethyl)-7H-purin-6-amine

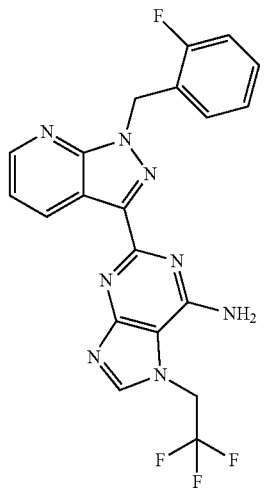 [SMILES: Nc1nc(-c2nn(Cc3ccccc3F)c3ncccc23)nc2ncn(CC(F)(F)F)c12]

68 mg (0.157 mmol) of the compound from example 17A were admixed with 1.1 ml of formic acid and 110 mg (1.343 mmol) of anhydrous sodium acetate. The mixture was heated to reflux for 3 days. The reaction mixture was concentrated on a rotary evaporator. The residue was stirred with 4 ml of acetonitrile/water (v/v=1:1), filtered off with suction and dried under high vacuum. 30 mg of the title compound were obtained (41% of theory).

LC-MS (method 2): $R_t$=1.60 min; MS (EIpos): m/z=361 (M+H)$^+$.

197

$^1$H NMR (400 MHz, DMSO-d$_6$): δ [ppm]=5.50 (q, 2H), 5.83 (s, 2H), 7.11-7.26 (m, 3H), 7.33-7.41 (m, 4H), 8.43 (s, 1H), 8.64 (dd, 1H), 9.09 (dd, 1H).

Example 61

2-[1-(2-Fluorobenzyl)-1H-pyrazolo[3,4-b]pyridin-3-yl]-7-(2,2,2-trifluoroethyl)-8-(trifluoromethyl)-7H-purin-6-amine

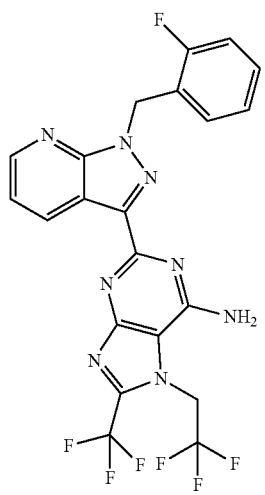 [SMILES: Nc1nc(-c2nn(Cc3ccccc3F)c3ncccc23)nc2nc(C(F)(F)F)n(CC(F)(F)F)c12]

194 mg (0.449 mmol) of the compound from example 17A were dissolved in 5 ml of tetrahydrofuran, and 141 mg (0.673 mmol) of trifluoroacetic anhydride were added. The mixture was stirred at 40° C. for 16 h. Subsequently, the reaction mixture was concentrated on a rotary evaporator, and 20 ml of pyridine and 521 mg (3.773 mmol) of potassium carbonate were added. The reaction mixture was stirred at RT for 16 h and concentrated under reduced pressure. The residue was purified by means of preparative HPLC (eluent: methanol/water, gradient 30:70→90:10). 45 mg of the title compound were obtained (20% of theory).

LC-MS (method 2): R$_t$=1.09 min; MS (EIpos): m/z=511 (M+H)$^+$.

198

$^1$H NMR (400 MHz, DMSO-d$_6$): δ [ppm]=5.62 (q, 2H), 5.85 (s, 2H), 7.12-7.26 (m, 3H), 7.34-7.39 (m, 1H), 7.42 (dd, 1H), 7.84 (s br, 2H), 8.66 (dd, 1H), 9.08 (dd, 1H).

Example 62

6-Amino-2-[5-fluoro-1-(2-fluorobenzyl)-1H-pyrazolo[3,4-b]pyridin-3-yl]-7-(2,2,2-trifluoroethyl)-7,9-dihydro-8H-purin-8-one

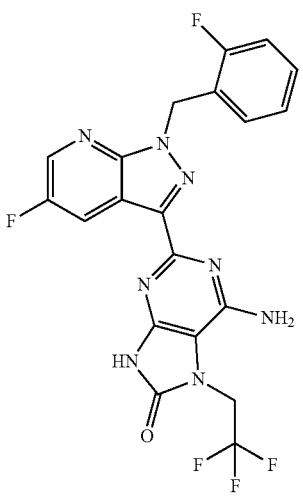 [SMILES: Nc1nc(-c2nn(Cc3ccccc3F)c3ncc(F)cc23)nc2[nH]c(=O)n(CC(F)(F)F)c12]

Under an argon atmosphere, 5.005 g (6.458 mmol) of the compound from example 32A were dissolved in 355 ml of tetrahydrofuran and cooled to 0° C., and 16.145 ml (16.145 mmol) of a 1N solution of bis(trimethylsilyl)sodium amide in tetrahydrofuran were added dropwise. The mixture was stirred at 0° C. for 2 h and then at RT for 16 h. 16.145 ml (16.145 mmol) of 1N hydrochloric acid were added and the mixture was concentrated on a rotary evaporator. The residue was taken up in ethyl acetate and the organic phase was washed twice with water, dried over sodium sulfate and concentrated on a rotary evaporator. 6.13 g of the title compound were obtained (purity by HPLC 61%). 500 mg of residue were purified by means of preparative HPLC (eluent: methanol/water, gradient 30:70→90:10). 93 mg of the title compound were obtained (36% of theory).

LC-MS (method 2): R$_t$=1.01 min; MS (EIpos): m/z=477 (M+H)$^+$.

¹H NMR (400 MHz, DMSO-d₆): δ [ppm]=4.91 (q, 2H), 5.80 (s, 2H), 7.01 (s br, 2H), 7.13-7.18 (m, 1H), 7.21-7.26 (m, 2H), 7.34-7.40 (m, 1H), 8.70 (dd, 1H), 8.87 (dd, 1H), 11.96 (s, 1H).

Example 63

Methyl 6-[1-(2-fluorobenzyl)-1H-pyrazolo[3,4-b]pyridin-3-yl]-3,4-dihydropyrido[2,3-b]pyrazine-1(2H)-carboxylate

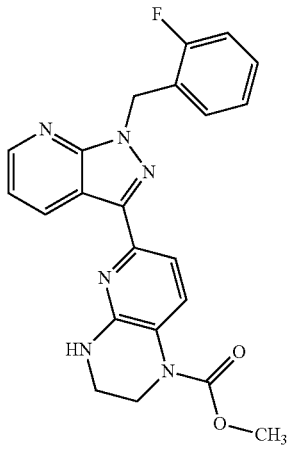 [SMILES: COC(=O)N1CCNc2nc(-c3nn(Cc4ccccc4F)c4ncccc34)ccc21]

Under argon, 78 mg (0.22 mmol) of the compound from example 142 were initially charged in tetrahydrofuran (3 ml) and cooled to 0° C. Subsequently, 17 mg (0.43 mmol) of sodium hydride (60% in mineral oil) were added and the mixture was stirred at 0° C. for a further 30 min. Thereafter, a solution of 20 µl (0.24 mmol) of methyl chloroformate in dichloromethane (1 ml) was added dropwise and the reaction mixture was stirred at RT overnight. The reaction mixture was admixed with saturated aqueous sodium hydrogencarbonate solution and extracted twice with ethyl acetate. The collected organic phases were dried over sodium sulfate, filtered and concentrated. The residue was separated by means of preparative HPLC (eluent: acetonitrile-water with 0.1% formic acid gradient) and the product fractions were concentrated. This gave 30 mg (32% of theory) of the title compound in solid form.

LC-MS (method 2): $R_t$=1.07 min
MS (ESIpos): m/z=419 (M+H)⁺

¹H NMR (400 MHz, DMSO-d₆): δ=3.41-3.46 (m, 2H), 3.74-3.75 (m, 5H), 5.79 (s, 2H), 7.11-7.19 (m, 2H), 7.20-7.25 (m, 2H), 7.28 (d, 1H), 7.31-7.36 (m, 2H), 7.81-7.86 (m, 1H), 8.61 (dd, 1H), 9.04 (dd, 1H).

Example 64

5-[6-Fluoro-3-(2-fluorobenzyl)-1H-pyrazolo[4,3-b]pyridin-1-yl]-1,3-dihydro-2H-imidazo[4,5-b]pyridin-2-one

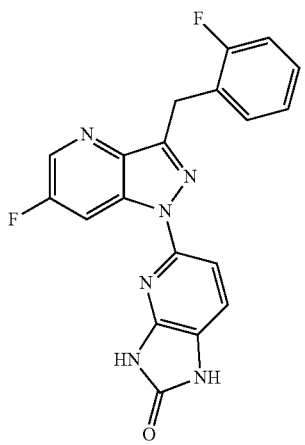 [SMILES: O=c1[nH]c2ccc(-n3nc(Cc4ccccc4F)c4ncc(F)cc43)nc2[nH]1]

70 mg (0.20 mmol) of the compound from example 40A were initially charged in dimethylformamide (5 ml), then 161 mg (0.993 mmol) of N,N-carbonyldiimidazole and 0.33 ml (2.38 mmol) of triethylamine were added and the mixture was stirred at 100° C. overnight. The reaction mixture was subsequently diluted with water and saturated aqueous sodium hydrogencarbonate solution and extracted twice with ethyl acetate. The collected organic phases were dried over sodium sulfate, filtered and concentrated by rotary evaporation. Preparative HPLC (eluent: acetonitrile-water with 0.1% formic acid gradient) of the residue gave 38 mg (48% of theory) of the desired title compound in solid form.

LC-MS (method 2): $R_t$=1.00 min
MS (ESIpos): m/z=379 (M+H)⁺

$^1$H NMR (400 MHz, DMSO-d$_6$): δ=4.45 (s, 2H), 7.11-7.16 (m, 1H), 7.16-7.23 (m, 1H), 7.26-7.33 (m, 1H), 7.39-7.50 (m, 3H), 8.67-8.71 (m, 2H), 10.98 (s, 1H), 11.51 (s, 1H).

Example 65

4-Amino-2-[1-(2-fluorobenzyl)-1H-pyrazolo[3,4-b]pyridin-3-yl]-7,8-dihydropteridine-5(6H)-sulfonamide

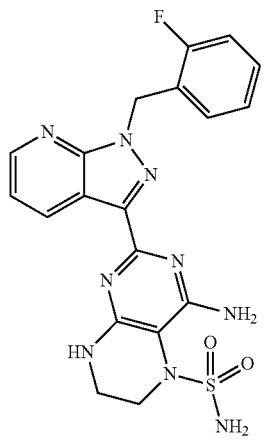 [SMILES: Nc1nc(-c2nn(Cc3ccccc3F)c3ncccc23)nc2c1N(S(N)(=O)=O)CCN2]

96 mg (0.17 mmol) of the compound from example 41A were initially charged in dichloromethane (5 ml), then 0.13 ml (1.73 mmol) of trifluoroacetic acid were added and the reaction mixture was stirred at RT overnight. The mixture was concentrated, the residue was separated by means of preparative HPLC (eluent: acetonitrile-water with 0.1% formic acid gradient) and the product fractions were concentrated. This gave 52 mg (66% of theory) of the title compound in solid form.

LC-MS (method 2): R$_t$=0.75 min

MS (ESIpos): m/z=456 (M+H)$^+$ $^1$H NMR (400 MHz, DMSO-d$_6$): δ=3.35-3.49 (m, 2H), 3.54-3.63 (m, 2H), 5.81 (s, 2H), 6.34-6.50 (m, 2H), 7.09-7.16 (m, 2H), 7.19-7.26 (m, 1H), 7.30-7.40 (m, 4H), 7.51-7.64 (m, 1H), 8.60-8.64 (m, 1H), 8.99-9.06 (m, 1H).

Example 66

6-[1-(2-Fluorobenzyl)-1H-pyrazolo[3,4-b]pyridin-3-yl]-2-methylpyrido[2,3-b]pyrazin-3(4H)-one

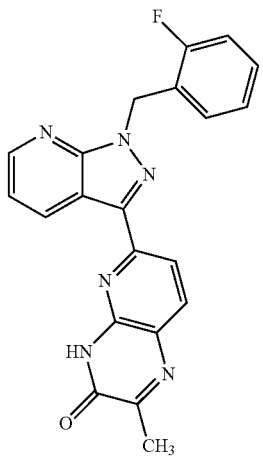 [SMILES: Cc1nc2ccc(-c3nn(Cc4ccccc4F)c4ncccc34)nc2[nH]c1=O]

146 mg (0.435 mmol) of the compound from example 43A were initially charged in ethanol (8 ml), then 56 mg (0.48 mmol) of ethyl 2-oxopropanoate were added and the reaction mixture was heated to reflux overnight. Thereafter, a catalytic amount of conc. sulfuric acid was added and the mixture was again heated to reflux overnight. Subsequently, the mixture was cooled to RT, and the solid formed was filtered off, washed with ethanol and dried under high vacuum. The crude product was dissolved in DMSO and separated by means of preparative HPLC (eluent: acetonitrile-water with 0.1% formic acid gradient), and the product fractions were concentrated. This gave 30 mg (18% of theory) of the title compound in solid form.

LC-MS (method 2): R$_t$=1.07 min

MS (ESIpos): m/z=387 (M+H)$^+$ $^1$H NMR (400 MHz, DMSO-d$_6$): δ=2.45 (s, 3H), 5.86 (s, 2H), 7.11-7.18 (m, 1H), 7.20-7.29 (m, 2H), 7.33-7.41 (m, 1H), 7.42-7.48 (m, 1H), 7.98-8.04 (m, 1H), 8.14-8.21 (m, 1H), 8.65-8.71 (m, 1H), 9.24-9.31 (m, 1H), 12.86-13.04 (m, 1H).

Example 67

6-[1-(2-Fluorobenzyl)-1H-pyrazolo[3,4-b]pyridin-3-yl]-2-isopropylpyrido[2,3-b]pyrazin-3 (4H)-one

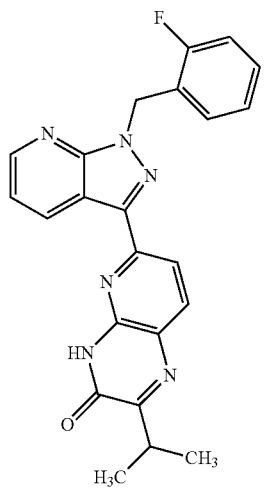 [SMILES: CC(C)c1nc2ccc(-c3nn(Cc4ccccc4F)c4ncccc34)nc2[nH]c1=O]

146 mg (0.435 mmol) of the compound from example 43A were initially charged in ethanol (8 ml), then 69 mg (0.48 mmol) of ethyl 3-methyl-2-oxobutanoate were added and the reaction mixture was heated to reflux overnight. Thereafter, a catalytic amount of conc. sulfuric acid was added and the mixture was again heated to reflux overnight. Subsequently, the mixture was cooled to RT, and the solid formed was filtered off, washed with methanol and dried under high vacuum. This gave 26 mg (14% of theory) of the title compound in solid form.

LC-MS (method 2): $R_t$=1.28 min

MS (ESIpos): m/z=415 (M+H)$^+$ $^1$H NMR (400 MHz, DMSO-d$_6$): δ=1.25 (d, 6H), 3.46-3.54 (m, 1H), 5.86 (s, 2H), 7.12-7.19 (m, 1H), 7.21-7.30 (m, 2H), 7.34-7.41 (m, 1H), 7.42-7.48 (m, 1H), 8.02 (d, 1H), 8.22 (d, 1H), 8.67-8.71 (m, 1H), 9.25-9.30 (m, 1H), 12.96 (s, 1H).

Example 68

6-[1-(2-Fluorobenzyl)-1H-pyrazolo[3,4-b]pyridin-3-yl]pyrido[2,3-b]pyrazine

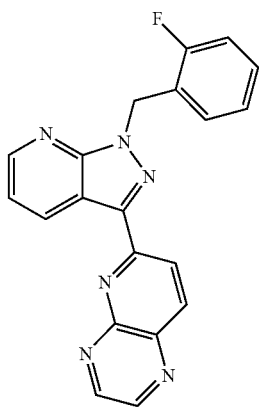 [SMILES: Fc1ccccc1Cn1nc(-c2ccc3nccnc3n2)c2cccnc21]

200 mg (0.598 mmol) of the compound from example 43A were initially charged in ethanol (10 ml), then 144 mg (1.20 mmol) of 2,3-dihydroxy-1,4-dioxane were added and the reaction mixture was stirred at RT for 5 h. The solid formed was filtered off, washed with ethanol and dried under high vacuum. This gave 90 mg (41% of theory) of the title compound in solid form.

LC-MS (method 2): $R_t$=1.09 min

MS (ESIpos): m/z=357 (M+H)$^+$

1H NMR (400 MHz, DMSO-d$_6$): δ=5.92 (s, 2H), 7.15-7.20 (m, 1H), 7.23-7.34 (m, 2H), 7.35-7.42 (m, 1H), 7.52-7.56 (m, 1H), 8.59-8.66 (m, 2H), 8.73-8.76 (m, 1H), 9.05-9.08 (m, 1H), 9.14-9.20 (m, 2H).

Example 69

Cyclopentyl 4-amino-2-[1-(2-fluorobenzyl)-1H-pyrazolo[3,4-b]pyridin-3-yl]-7,8-dihydropteridine-5(6H)-carboxylate

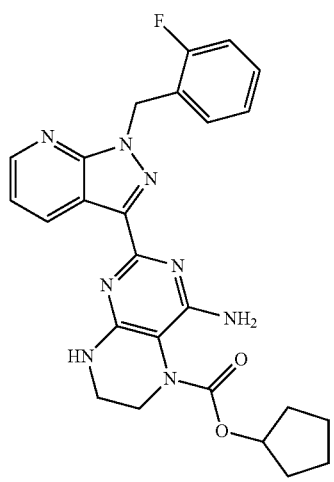 [SMILES: Nc1nc(-c2nn(Cc3ccccc3F)c3ncccc23)nc2c1N(C(=O)OC1CCCC1)CCN2]

200 mg (0.484 mmol) of the compound from example 81 were initially charged in tetrahydrofuran (6 ml) and cooled to 0° C. Subsequently, 38.8 mg (0.484 mmol) of sodium hydride (60% suspension in mineral oil) were added and the mixture was stirred at 0° C. for a further 30 min. Thereafter, a solution of 72.0 mg (0.484 mmol) of cyclopentyl chloroformate in dichloromethane (1 ml) was added dropwise and the reaction mixture was stirred at RT for a further 3 h. Subsequently, a further 72.0 mg (0.484 mmol) of cyclopentyl chloroformate in dichloromethane (1 ml) were added dropwise and the mixture was stirred at RT overnight. The reaction mixture was admixed with water and concentrated on a rotary evaporator. The residue was taken up in dimethylformamide and separated by means of preparative HPLC (eluent: acetonitrile-water with 0.1% formic acid gradient), and the product fractions were concentrated. The crude product was admixed with saturated aqueous sodium hydrogencarbonate solution and extracted twice with ethyl acetate. The collected organic phases were dried over magnesium sulfate, filtered and concentrated. The residue was stirred with tert-butyl methyl ether and the solids were filtered off. Lyophilization and further drying under high vacuum gave 42 mg (17% of theory) of the title compound in solid form.

LC-MS (method 2): $R_t$=0.94 min
MS (ESIpos): m/z=489 (M+H)$^+$ $^1$H NMR (400 MHz, DMSO-d$_6$): δ=1.42-1.85 (m, 8H), 3.27-3.40 (m., 4H), 5.08 (m, 1H), 5.79 (s, 2H), 6.15-6.29 (m, 2H), 7.13 (m, 2H), 7.19-7.27 (m, 1H), 7.35 (m, 3H), 8.57-8.63 (m, 1H), 9.00-9.08 (m, 1H).

Example 70

2-[1-(2-Fluorobenzyl)-1H-pyrazolo[3,4-b]pyridin-3-yl]pyrido[4,3-d]pyrimidin-5(6H)-one

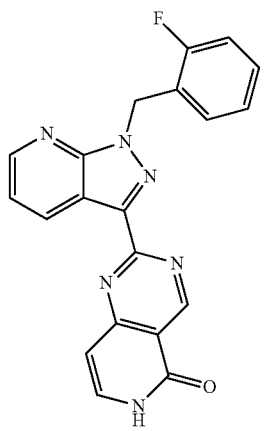 [SMILES: O=c1[nH]ccc2nc(-c3nn(Cc4ccccc4F)c4ncccc34)ncc12]

Under argon, 21 mg (0.522 mmol) of sodium hydride (60% suspension in mineral oil) were initially charged and washed repeatedly with hexane. Subsequently, dimethylformamide (0.18 ml) was added, and a solution of 158 mg (0.435 mmol) of the compound from example 46A in dimethylformamide (6.0 ml) was added to the suspension. The reaction mixture was stirred at 150° C. for two days, then diluted with acetonitrile at RT, then filtered, and the filtrate was concentrated. The residue was separated by means of preparative HPLC (eluent: acetonitrile-water with 0.1% formic acid gradient) and the product fractions were concentrated. This gave 31 mg (18% of theory) of the title compound in solid form.

LC-MS (method 3): $R_t$=1.02 min
MS (ESIpos): m/z=373 (M+H)$^+$ $^1$H NMR (400 MHz, DMSO-d$_6$): δ=5.91 (s, 2H), 6.72 (d, 1H), 7.12-7.20 (m, 1H), 7.21-7.29 (m, 2H), 7.34-7.42 (m, 1H), 7.49 (dd, 1H), 7.73-7.79 (m, 1H), 8.69-8.74 (m, 1H), 9.00-9.06 (m, 1H), 9.53 (s, 1H), 11.90 (br. s, 1H).

Example 71

5-[1-(2-Fluorobenzyl)-1H-pyrazolo[3,4-b]pyridin-3-yl]-1,3-dihydro-2H-imidazo[4,5-b]pyridin-2-one

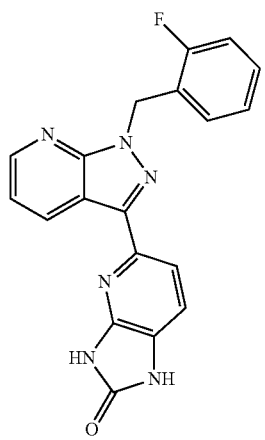 [SMILES: O=c1[nH]c2ccc(-c3nn(Cc4ccccc4F)c4ncccc34)nc2[nH]1]

23 mg (0.069 mmol) of example 43A and 12 mg (0.076 mmol) of N,N'-carbonylimidazole were combined in acetonitrile (4 ml) and heated to reflux overnight. This was followed by concentration and purification of the residue by means of preparative HPLC (eluent: acetonitrile/water with 0.05% formic acid, gradient). 13 mg of the title compound were obtained (52% of theory).

LC-MS (method 2): $R_t$=0.90 min

MS (ESIpos): m/z=361 (M+H)$^+$ $^1$H NMR (400 MHz, DMSO-$d_6$): δ=5.79 (s, 2H), 7.12-7.25 (m, 3H), 7.33-7.39 (m, 3H), 7.73 (d, 1H), 8.63 (dd, 1H), 8.87 (dd, 1H), 11.00 (s br, 1H), 11.46 (s br, 1H).

Example 72

2-[1-(2-Fluorobenzyl)-1H-pyrazolo[3,4-b]pyridin-3-yl]pyrido[3,4-d]pyrimidin-4-amine

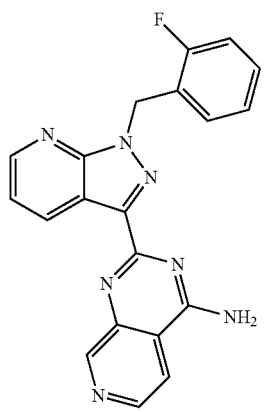 [SMILES: Nc1nc(-c2nn(Cc3ccccc3F)c3ncccc23)nc2cnccc12]

341 mg (1.35 mmol) of the compound from example 3A were initially charged in dimethylformamide (5.1 ml), then 177 mg (1.49 mmol) of 3-amino-4-cyanopyridine (prepared according to J. Org. Chem. Vol. 46, No. 21, 1981, 4179-4182) and 152 mg (1.35 mmol) of potassium tert-butoxide were added, and the reaction mixture was stirred at 200° C. in a microwave for 30 min. The reaction solution was added to sat. sodium hydrogencarbonate solution and extracted twice with ethyl acetate. The collected organic phases were washed with saturated aqueous sodium chloride solution, dried over magnesium sulfate, filtered and concentrated. The residue was separated by means of preparative HPLC (eluent: acetonitrile-water with 0.1% formic acid gradient) and the product fractions were concentrated. The crude product was admixed with methanol, and the solids were filtered off and dried under high vacuum at 50° C. for 2 h. This gave 194 mg (39% of theory) of the title compound in solid form.

LC-MS (method 2): $R_t$=0.88 min

MS (ESIpos): m/z=372 (M+H)$^+$

1H NMR (400 MHz, DMSO-$d_6$): δ=5.88 (s, 2H), 7.12-7.28 (m, 3H), 7.33-7.41 (m, 1H), 7.42-7.47 (m, 1H), 8.10-8.14 (m, 1H), 8.30-8.47 (m, 2H), 8.57-8.62 (m, 1H), 8.65-8.70 (m, 1H), 9.16-9.21 (m, 1H), 9.21-9.23 (m, 1H).

Example 73

2-[1-(2-Fluorobenzyl)-1H-pyrazolo[3,4-b]pyridin-3-yl]pyrimido[4,5-d]pyrimidin-4-ol

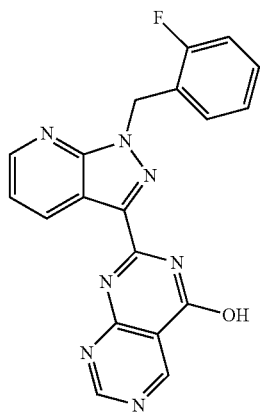 [SMILES: Oc1nc(-c2nn(Cc3ccccc3F)c3ncccc23)nc2ncncc12]

246 mg (0.629 mmol) of the compound from example 48A were initially charged in N,N-dimethylacetamide (22 ml) and stirred in a microwave at 220° C. for 30 min. The reaction mixture was poured onto ice-water and filtered. The filter residue was washed with water and dried under high vacuum at 50° C. overnight. This gave 142 mg (57% of theory) of the title compound in solid form.

LC-MS (method 2): $R_t$=0.89 min

MS (ESIpos): m/z=374 (M+H)$^+$

¹H NMR (400 MHz, DMSO-d₆): δ=5.92 (s, 2H), 7.15-7.20 (m, 1H), 7.22-7.28 (m, 1H), 7.34-7.45 (m, 2H), 7.54-7.60 (m, 1H), 8.76-8.79 (m, 1H), 8.88-8.93 (m, 1H), 9.42 (s, 1H), 9.46 (s, 1H), 13.16 (br. s, 1H).

1H), 7.76-7.81 (m, 1H), 8.05-8.11 (m, 1H), 8.15-8.20 (m, 1H), 8.20-8.25 (m, 1H), 8.70-8.73 (m, 1H), 9.10-9.16 (m, 1H), 9.75 (s, 1H).

Example 74

2-[1-(2-Fluorobenzyl)-1H-pyrazolo[3,4-b]pyridin-3-yl]quinazoline

Example 75

2-Methoxyethyl 4-amino-2-[1-(2-fluorobenzyl)-1H-pyrazolo[3,4-b]pyridin-3-yl]-7,8-dihydropteridine-5(6H)-carboxylate formate

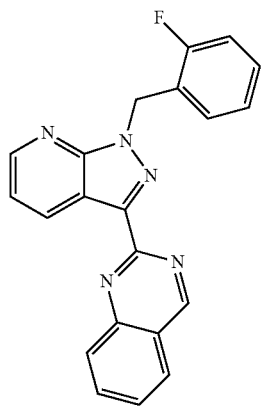 [SMILES: Fc1ccccc1Cn1nc(-c2ncc3ccccc3n2)c2cccnc21]

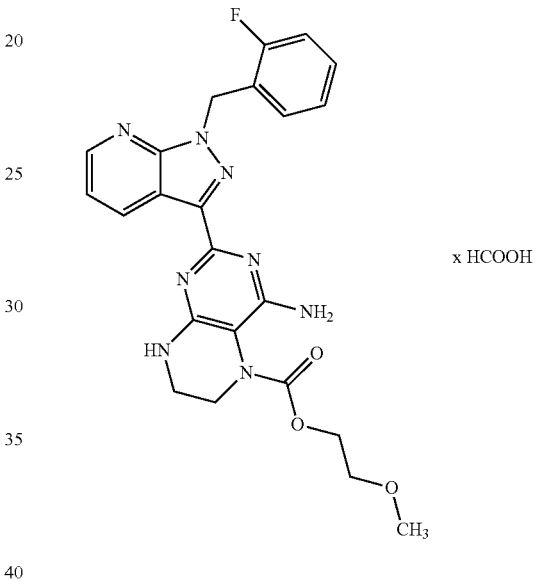

x HCOOH 200 mg (0.540 mmol) of the compound from example 5 were suspended in tetrahydrofuran (2.0 ml), then 145 μl (1.08 mmol) of isopentyl nitrite were added and the reaction mixture was heated to reflux for 30 min. Subsequently, dimethylformamide (1.0 ml) and 145 μl of isopentyl nitrite were added and the mixture was stirred at 95° C. for a further 5 h. The reaction mixture was subsequently separated directly by means of preparative HPLC (eluent: acetonitrile-water with 0.1% formic acid gradient) and the product-containing mixed fractions were concentrated. The crude product was subsequently further purified by means of HPLC (eluent: water/methanol/1% trifluoroacetic acid 28:65:7). This gave 30 mg (15% of theory) of the title compound in solid form.

LC-MS (method 3): $R_t$=1.28 min

MS (ESIpos): m/z=356 (M+H)±

¹H NMR (400 MHz, DMSO-d₆): δ=5.92 (s, 2H), 7.14-7.20 (m, 1H), 7.21-7.30 (m, 2H), 7.34-7.41 (m, 1H), 7.47-7.52 (m, 100 mg (0.242 mmol) of the compound from example 81 were initially charged in tetrahydrofuran (3 ml) and cooled to 0° C. Subsequently, 19.4 mg (0.484 mmol) of sodium hydride (60% in mineral oil) were added and the mixture was stirred at 0° C. for a further 30 min. Then 34 mg (0.24 mmol) of 2-methoxyethyl chlorocarbonate were added dropwise and the mixture was stirred at RT for 2 h. Subsequently, the mixture was diluted with saturated aqueous sodium hydrogencarbonate solution and extracted twice with ethyl acetate. The collected organic phases were dried over sodium sulfate, filtered and concentrated by rotary evaporation. The residue was separated by means of preparative HPLC (eluent: acetonitrile-water with 0.1% formic acid gradient) and the product fractions were concentrated. This gave 12 mg (9% of theory) of the title compound.

LC-MS (method 2): $R_t$=0.81 min

MS (ESIpos): m/z=479 (M+H)⁺

¹H NMR (400 MHz, DMSO-d₆): δ=3.27-3.41 (m, 7H), 3.52-3.58 (m, 2H), 4.23 (br. s, 2H), 5.79 (s, 2H), 6.24 (br. s,

2H), 7.09-7.16 (m, 2H), 7.19-7.26 (m, 1H), 7.31-7.42 (m, 3H), 8.23 (s, 0.5H), 8.58-8.63 (m, 1H), 9.02-9.07 (m, 1H).

Example 76

Ethyl 4-amino-2-[1-(2-fluorobenzyl)-1H-pyrazolo[3,4-b]pyridin-3-yl]-7,8-dihydropteridine-5(6H)-carboxylate formate

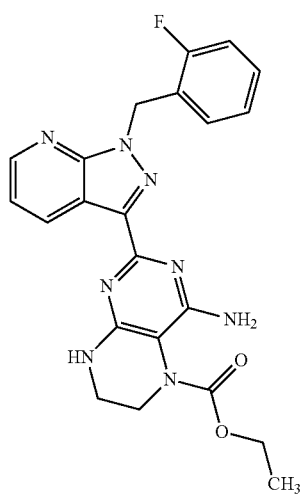

x HCOOH 200 mg (0.484 mmol) of the compound from example 81 were initially charged in tetrahydrofuran (6 ml) and cooled to 0° C. Subsequently, 38.8 mg (0.969 mmol) of sodium hydride were added and the mixture was stirred at 0° C. for a further 30 min. Thereafter, a solution of 51.0 µl (0.533 mmol) of ethyl chloroformate in dichloromethane (1.0 ml) was added dropwise and the reaction mixture was stirred at RT overnight. The reaction mixture was admixed with saturated aqueous sodium hydrogencarbonate solution and extracted twice with ethyl acetate. The collected organic phases were dried over sodium sulfate, filtered and concentrated by rotary evaporation. The residue was separated by means of preparative HPLC (eluent: acetonitrile-water with 0.1% formic acid gradient) and the product fractions were concentrated. This gave 110 mg (45% of theory) of the title compound.

LC-MS (method 2): $R_t$=0.82 min

MS (ESIpos): m/z=449 (M+H)$^+$ $^1$H NMR (400 MHz, DMSO-$d_6$): δ=1.20 (t, 2H), 3.27-3.41 (m, 7H), 4.13 (m, 2H), 4.23 (br. s, 2H), 6.24 (br. s, 2H), 7.09-7.16 (m, 2H), 7.19-7.26 (m, 1H), 7.31-7.42 (m, 3H), 8.23 (s, 0.5H), 8.58-8.63 (m, 1H), 9.02-9.07 (m, 1H), 12.72 (br. s, 0.5H).

Example 77

Isopropyl 4-amino-2-[1-(2-fluorobenzyl)-1H-pyrazolo[3,4-b]pyridin-3-yl]-7,8-dihydropteridine-5(6H)-carboxylate

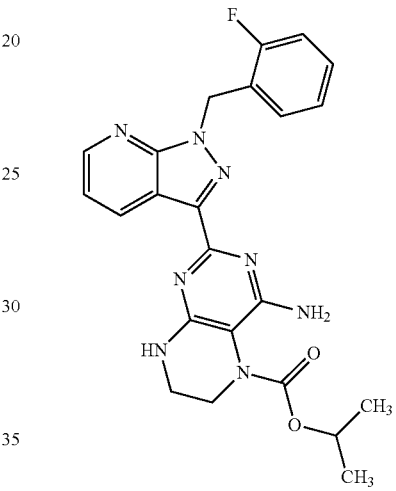

100 mg (0.242 mmol) of the compound from example 81 were initially charged in tetrahydrofuran (3 ml) and cooled to 0° C. Subsequently, 19.4 mg (0.484 mmol) of sodium hydride (60% in mineral oil) were added and the mixture was stirred at 0° C. for a further 30 min. Thereafter, 242 µl (0.242 mmol) of isopropyl chloroformate (1.0 M in toluene) were added dropwise and the reaction mixture was stirred at RT overnight. The reaction mixture was admixed with saturated aqueous sodium hydrogencarbonate solution and extracted twice with ethyl acetate. The collected organic phases were dried over sodium sulfate, filtered and concentrated by rotary evaporation. The residue was separated by means of preparative HPLC (eluent: acetonitrile-water with 0.1% formic acid gradient) and the product fractions were concentrated. The crude product was dissolved in ethyl acetate and washed once each with saturated aqueous sodium hydrogencarbonate solution and water, dried over sodium sulfate, filtered and concentrated. Further drying under high vacuum gave 29 mg (26% of theory) of the title compound in solid form.

LC-MS (method 2): $R_t$=0.89 min

MS (ESIpos): m/z=463 (M+H)$^+$ $^1$H NMR (400 MHz, DMSO-$d_6$): δ=1.16-1.26 (m, 6H), 3.32 (s, 4H), 4.83-4.92 (m, 1H), 5.79 (s, 2H), 6.22 (br. s, 2H), 7.09-7.16 (m, 2H), 7.19-7.26 (m, 1H), 7.31-7.40 (m, 3H), 8.58-8.63 (m, 1H), 9.01-9.07 (m, 1H).

Example 78

4-Amino-2-[1-(2-fluorobenzyl)-1H-pyrazolo[3,4-b]pyridin-3-yl]-6-(4-methylphenyl)pteridin-7(8H)-one

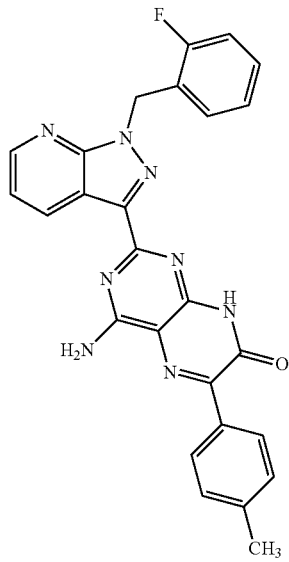 [SMILES: Cc1ccc(-c2nc3c(N)nc(-c4nn(Cc5ccccc5F)c5ncccc45)nc3[nH]c2=O)cc1]

200 mg (0.571 mmol) of the compound from example 1A were initially charged in ethanol (3.0 ml), then 121 mg (0.628 mmol) of ethyl 4-methylphenyl-2-oxoacetate were added and the reaction mixture was heated to reflux for 21 h. The reaction mixture was brought to RT and filtered. The solids were washed with ethanol, then suspended in dimethylformamide and filtered. The filtrate was separated by means of preparative HPLC (eluent: acetonitrile-water with 0.1% formic acid gradient) and the product fractions were concentrated. The crude product was stirred with dichloromethane/methanol, and the solids were filtered off and dried under high vacuum. This gave 17 mg (6% of theory) of the title compound in solid form.

LC-MS (method 2): $R_t$=1.09 min

MS (ESIpos): m/z=479 (M+H)$^+$ $^1$H NMR (400 MHz, DMSO-d$_6$): δ=2.39-2.61 (s, 3H), 5.76-5.93 (m, 2H), 7.06-7.30 (m, 3H), 7.31-7.50 (m, 4H), 7.57-7.80 (m, 2H), 8.32-8.46 (m, 2H), 8.61-8.71 (m, 1H), 9.02-9.14 (m, 1H), 12.25-12.37 (m, 1H).

Example 79

4-Amino-6-cyclopentyl-2-[1-(2-fluorobenzyl)-1H-pyrazolo[3,4-b]pyridin-3-yl]pteridin-7(8H)-one

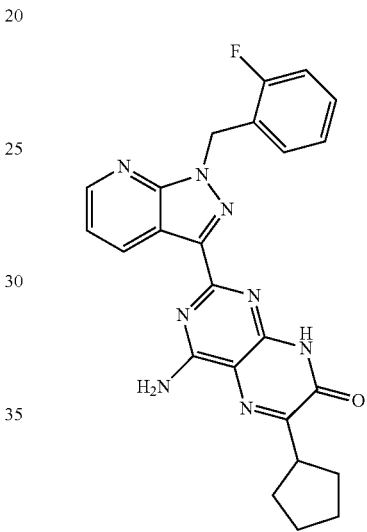

200 mg (0.571 mmol) of the compound from example 1A were initially charged in ethanol (3.0 ml), then 107 mg (0.628 mmol) of ethyl cyclopentyl(oxo)acetate were added and the reaction mixture was heated to reflux for 30 h. The reaction mixture was brought to RT and filtered. The solids were washed with ethanol, then dissolved in trifluoroacetic acid and basified with saturated aqueous sodium hydrogencarbonate solution. The resulting suspension was filtered and the filter residue was washed with dimethylformamide. The filtrate was separated by means of preparative HPLC (eluent: acetonitrile-water with 0.1% formic acid gradient) and the product fractions were concentrated. This gave 12 mg (90% purity, 4% of theory) of the title compound.

LC-MS (method 2): $R_t$=1.07 min

MS (ESIpos): m/z=457 (M+H)$^+$ $^1$H NMR (400 MHz, DMSO-d$_6$): δ=1.60-1.83 (m, 4H), 1.83-2.06 (m, 4H), 3.59-3.69 (m, 1H), 5.83 (s, 2H), 7.12-7.28

(m, 3H), 7.32-7.45 (m, 2H), 7.49-7.69 (m, 2H), 8.62-8.69 (m, 1H), 9.01-9.08 (m, 1H), 12.70 (m, 1H).

Example 80

Methyl 4-amino-2-[1-(2-fluorobenzyl)-1H-pyrazolo[3,4-b]pyridin-3-yl]-7,8-dihydropteridine-5(6H)-carboxylate

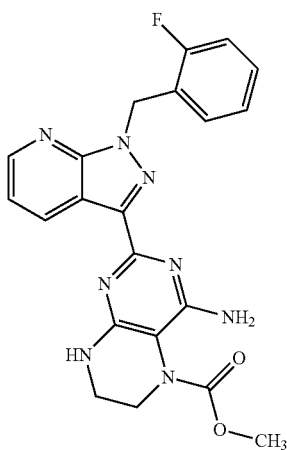 [SMILES: COC(=O)N1CCNc2nc(-c3nn(Cc4ccccc4F)c4ncccc34)nc(N)c21]

80.0 mg (0.194 mmol) of the compound from example 81 were initially charged in tetrahydrofuran (7 ml) and cooled to 0° C. Subsequently, 15.5 mg (0.388 mmol) of sodium hydride (60% in mineral oil) were added and the mixture was stirred at 0° C. for a further 30 min. Thereafter, a solution of 745 µl (0.194 mmol) of methyl chloroformate in dichloromethane (5.0 ml) was added dropwise and the reaction mixture was stirred at RT for a further 2 h. The reaction mixture was admixed with saturated aqueous sodium hydrogencarbonate solution and extracted twice with ethyl acetate. The collected organic phases were dried over sodium sulfate, filtered and concentrated by rotary evaporation. The residue was separated by means of preparative HPLC (eluent: acetonitrile-water with 0.1% formic acid gradient) and the product fractions were concentrated. The crude product was dissolved in ethyl acetate and washed once with saturated aqueous sodium hydrogencarbonate solution and twice with water, dried over sodium sulfate, filtered and concentrated. Further drying under high vacuum gave 39.8 mg (47% of theory) of the title compound in solid form.

LC-MS (method 2): $R_t$=0.78 min

MS (ESIpos): m/z=435 (M+H)$^+$ $^1$H NMR (400 MHz, DMSO-d$_6$): δ=3.32 (m, 4H), 3.67 (s, 3H), 5.79 (s, 2H), 6.32 (br. s, 2H), 7.09-7.16 (m, 2H), 7.19-7.26 (m, 1H), 7.31-7.38 (m, 3H), 8.58-8.62 (m, 1H), 9.02-9.06 (m, 1H).

Example 81

2-[1-(2-Fluorobenzyl)-1H-pyrazolo[3,4-b]pyridin-3-yl]-5,6,7,8-tetrahydropteridin-4-amine hydrochloride

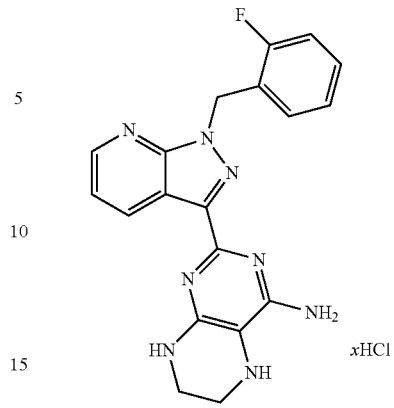

437 mg (1.17 mmol) of the compound from example 52 were initially charged in methanol (20.0 ml) and the suspension was blanketed with argon. Subsequently, 64 mg (0.24 mmol) of platinum(IV) oxide (83% w/w) were added and the reaction mixture was hydrogenated at standard hydrogen pressure overnight. The reaction mixture was filtered through Celite and the filtercake was washed with methanol The filtrate was admixed with conc. hydrochloric acid and concentrated by rotary evaporation. The residue was extracted by stirring with methanol/tert-butyl methyl ether and filtered off. The solids were washed with methanol/tert-butyl methyl ether and dried under high vacuum. This gave 451 mg (93% of theory) of the title compound in solid form.

LC-MS (method 3): $R_t$=0.87 min

MS (ESIpos): m/z=377 (M+H)$^+$ $^1$H NMR (400 MHz, DMSO-d$_6$): δ=3.23-3.30 (m, 2H), 3.46-3.53 (m, 2H), 4.20-4.63 (br. s, 1H), 5.90 (s, 2H), 7.11-7.20 (m, 2H), 7.21-7.30 (m, 2H), 7.31-7.41 (m, 1H), 7.47-7.54 (m, 1H), 8.32-8.47 (br. s, 1H), 8.72-8.76 (m, 1H), 8.86-8.92 (m, 1H).

Example 82

2-{4-Amino-6-[1-(2-fluorobenzyl)-1H-pyrazolo[3,4-b]pyridin-3-yl]-1H-pyrazolo[3,4-d]pyrimidin-1-yl}ethanol

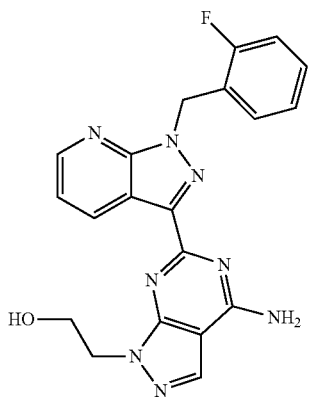 [SMILES: Nc1nc(-c2nn(Cc3ccccc3F)c3ncccc23)nc2c1cnn2CCO]

200 mg (0.793 mmol) of the compound from example 3A were initially charged in dimethylformamide (3.0 ml), then 133 mg (0.872 mmol) of 5-amino-1-(2-hydroxyethyl)-1H-pyrazole-4-carbonitrile and 89.0 mg (0.793 mmol) of potassium tert-butoxide were added and the reaction mixture was stirred in a microwave at 180° C. for 30 min. The reaction mixture was separated by means of preparative HPLC (eluent: acetonitrile-water with 0.1% formic acid gradient) and the product fractions were collected. This gave 126 mg (94%, 37% of theory) of the title compound in solid form.

LC-MS (method 2): $R_t$=0.81 min

MS (ESIpos): m/z=405 (M+H)$^+$ $^1$H NMR (400 MHz, DMSO-d$_6$): δ=3.84-3.92 (m, 2H), 4.44 (t, 2H), 4.87-4.95 (m, 1H), 5.86 (s, 2H), 7.10-7.17 (m, 2H), 7.21-7.28 (m, 1H), 7.32-7.39 (m, 1H), 7.40-7.45 (m, 1H), 7.84-7.91 (m, 2H), 8.12 (s, 1H), 8.62-8.67 (m, 1H), 9.08-9.14 (m, 1H).

Example 83

4-Amino-2-[1-(2-fluorobenzyl)-1H-pyrazolo[3,4-b]pyridin-3-yl]-6-isopropylpteridin-7(8H)-one

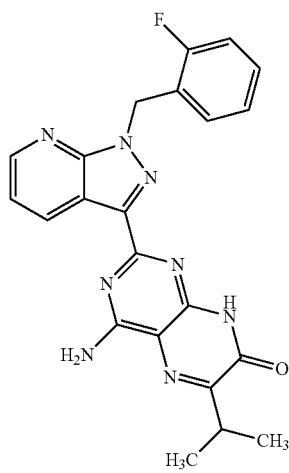 [SMILES: CC(C)c1nc2c(N)nc(-c3nn(Cc4ccccc4F)c4ncccc34)nc2[nH]c1=O]

1.00 g (2.85 mmol) of the compound from example 1A were initially charged in ethanol (50 ml), then 453 mg (3.14 mmol) of ethyl 3-methyl-2-oxobutanoate and a catalytic amount of conc. sulfuric acid were added and the reaction mixture was heated to reflux overnight. Subsequently, another 453 mg (3.14 mmol) of ethyl 3-methyl-2-oxobutanoate were added and heating of the mixture to reflux continued overnight. The reaction mixture was brought to RT and filtered. The solids were washed with ethanol and dried under high vacuum. This gave 592 mg (45% of theory) of the title compound.

LC-MS (method 1): $R_t$=2.13 min

MS (ESIpos): m/z=431 (M+H)$^+$ $^1$H NMR (400 MHz, DMSO-d$_6$): δ=1.23 (d, 6H), 3.35-3.39 (m, 1H), 5.84 (s, 2H), 7.12-7.28 (m, 3H), 7.33-7.45 (m, 3H), 7.87-7.97 (m, 1H), 8.63-8.68 (m, 1H), 9.15-9.20 (m, 1H), 12.73 (s, 1H).

Example 84

2-[1-(2-Fluorobenzyl)-1H-pyrazolo[3,4-b]pyridin-3-yl]pyrido[4,3-d]pyrimidin-4-amine

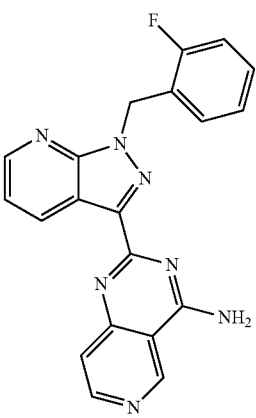 [SMILES: Nc1nc(-c2nn(Cc3ccccc3F)c3ncccc23)nc2ccncc12]

50 mg (0.16 mmol) of the compound from example 5A were initially charged in dimethylformamide (0.6 ml), then 41 mg (0.18 mmol) of 3-cyano-4-iodopyridine and 35 mg (0.33 mmol) of sodium carbonate were added and the mixture was stirred at 200° C. for 30 min. The reaction mixture was separated by means of preparative HPLC (eluent: acetonitrile-water with 0.1% formic acid gradient) and the product fractions were concentrated. This gave 9 mg (15% of theory) of the title compound in solid form.

LC-MS (method 1): $R_t$=1.62 min

MS (ESIpos): m/z=372 (M+H)$^+$

1H NMR (400 MHz, DMSO-d$_6$): δ=5.88 (s, 2H), 7.12-7.28 (m, 3H), 7.33-7.41 (m, 1H), 7.42-7.47 (m, 1H), 7.65-7.69 (m,

1H), 8.44-8.52 (m, 2H), 8.66-8.69 (m, 1H), 8.72-8.76 (m, 1H), 9.14-9.18 (m, 1H), 9.54 (s, 1H).

Example 85

2-[1-(2-Fluorobenzyl)-1H-pyrazolo[3,4-b]pyridin-3-yl]pyrido[3,2-d]pyrimidin-4-amine

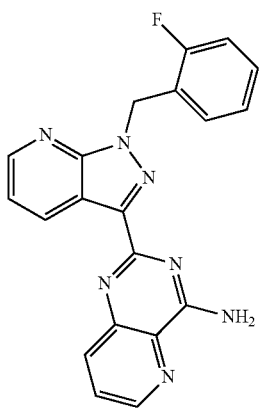 [SMILES: Nc1nc(-c2nn(Cc3ccccc3F)c3ncccc23)nc2cccnc12]

200 mg (0.793 mmol) of the compound from example 3A were initially charged in dimethylformamide (3.0 ml), then 104 mg (0.872 mmol) of 3-amino-3-cyanopyridine and 89.0 mg (0.793 mmol) of potassium tert-butoxide were added and the reaction mixture was stirred in a microwave at 200° C. for 30 min. The reaction solution was added to water and the solids formed were filtered off. The crude product thus obtained was dissolved in DMSO and precipitated with water. The solids were filtered off, washed with water and dried under high vacuum. This gave 17.8 mg (6% of theory) of the title compound in solid form.

LC-MS (method 3): $R_t$=0.98 min

MS (ESIpos): m/z=372 (M+H)$^+$ $^1$H NMR (400 MHz, DMSO-d$_6$): δ=5.87 (s, 2H), 7.11-7.30 (m, 3H), 7.33-7.40 (m, 1H), 7.41-7.47 (m, 1H), 7.82-7.89 (m, 1H), 8.00-8.09 (br. s, 1H), 8.23 (m, 2H), 8.63-8.70 (m, 1H), 8.77-8.83 (m, 1H), 9.13-9.21 (m, 1H).

Example 86

5-Fluoro-2-[1-(2-fluorobenzyl)-1H-pyrazolo[3,4-b]pyridin-3-yl]quinazolin-4-amine

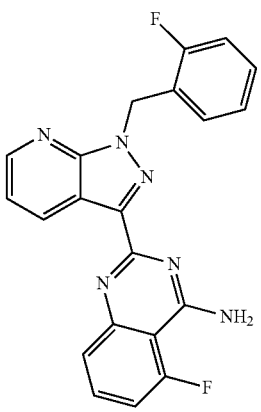 [SMILES: Nc1nc(-c2nn(Cc3ccccc3F)c3ncccc23)nc2cccc(F)c12]

300 mg (1.19 mmol) of the compound from example 3A were initially charged in dimethylformamide (4.5 ml), then 178 mg (1.31 mmol) of 2-amino-6-fluorobenzonitrile and 66.7 mg (0.595 mmol) of potassium tert-butoxide were added and the reaction mixture was stirred in a microwave at 200° C. for 1 h. Subsequently, another 66.7 mg (0.595 mmol) of potassium tert-butoxide were added and the mixture was stirred at 200° C. for a further 1 h. The reaction mixture was subsequently separated by means of preparative HPLC (eluent: acetonitrile-water with 0.1% formic acid gradient) and the product fractions were concentrated. The crude product was stirred with acetonitrile/DMSO, and the residue was filtered, washed with acetonitrile and dried under high vacuum. This gave 10 mg (2% of theory) of the title compound in solid form.

LC-MS (method 3): $R_t$=1.02 min

MS (ESIpos): m/z=389 (M+H)$^+$

¹H NMR (400 MHz, DMSO-d₆): δ=5.87 (s, 2H), 7.12-7.17 (m, 2H), 7.21-7.32 (m, 2H), 7.33-7.47 (m, 3H), 7.63-7.70 (m, 1H), 7.74-7.84 (m, 1H), 8.34 (br. s, 1H), 8.60-8.71 (m, 1H), 9.20 (m, 1H).

Example 87

2-[1-(2-Fluorobenzyl)-1H-pyrazolo[3,4-b]pyridin-3-yl]pyrido[2,3-d]pyrimidin-4-amine

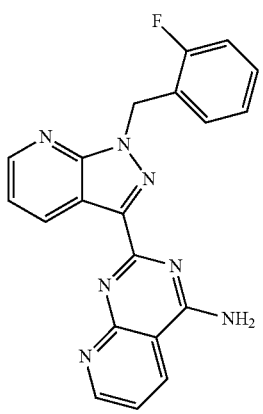 [SMILES: Nc1nc(-c2nn(Cc3ccccc3F)c3ncccc23)nc2ncccc12]

100 mg (0.396 mmol) of the compound from example 3A were initially charged in dimethylformamide (1.5 ml), then 51.9 mg (0.436 mmol) of 2-amino-3-cyanopyridine and 44.5 mg (0.396 mmol) of potassium tert-butoxide were added and the reaction mixture was stirred in a microwave at 200° C. for 1 h. The reaction solution was subsequently separated by means of preparative HPLC (eluent: acetonitrile-water with 0.1% formic acid gradient) and the product fractions were concentrated. This gave 36.2 mg (25% of theory) of the title compound in solid form.

LC-MS (method 2): R$_t$=0.79 min

MS (ESIpos): m/z=372 (M+H)⁺

¹H NMR (400 MHz, DMSO-d₆): δ=5.87 (s, 2H), 7.12-7.18 (m, 1H), 7.19-7.28 (m, 2H), 7.33-7.41 (m, 1H), 7.42-7.48 (m, 1H), 7.49-7.55 (m, 1H), 8.29 (br. s, 2H), 8.65-8.71 (m, 2H), 9.00-9.04 (m, 1H), 9.13-9.18 (m, 1H).

Example 88

6-Amino-7-ethyl-2-[3-(2-fluorobenzyl)-1H-pyrazolo[4,3-b]pyridin-1-yl]-7,9-dihydro-8H-purin-8-one

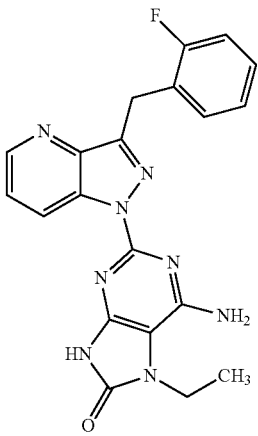 [SMILES: CCn1c(=O)[nH]c2nc(-n3nc(Cc4ccccc4F)c4ncccc43)nc(N)c21]

200 mg (0.392 mmol) of 2-[3-(2-fluorobenzyl)-1H-pyrazolo[4,3-b]pyridin-1-yl]pyrimidine-4,5,6-triamine (example 2A) were initially charged in tetrahydrofuran (11.1 ml) and the suspension was cooled to 0° C. Subsequently, 0.43 ml (0.43 mmol) of bis(trimethylsilyl)sodium amide solution (1.0 M in tetrahydrofuran) was added and the mixture was stirred at 0° C. for a further 30 min Thereafter, 31.3 μl (0.392 mmol) of iodoethane were added dropwise and the reaction mixture was stirred at RT overnight. The reaction mixture was cooled again to 0° C. and a further 0.47 ml (0.47 mmol) of bis(trimethylsilyl)sodium amide solution was added. Thereafter, the reaction mixture was stirred at RT overnight and heated to reflux for a further 2 days. Subsequently, the reaction mixture was diluted with ethyl acetate and washed twice with saturated aqueous sodium hydrogencarbonate solution. The organic phase was dried over magnesium sulfate, filtered and concentrated by rotary evaporation. The residue was separated by means of preparative HPLC (eluent: acetonitrile-water with 0.1% formic acid gradient) and the product fractions were concentrated. The crude product was extracted by stirring in methyl tert-butyl ether, and the solids were filtered off and dried under high vacuum. This gave 4.6 mg (2.9% of theory) of the title compound in solid form.

LC-MS (method 2): R$_t$=0.85 min

MS (ESIpos): m/z=405 (M+H)⁺

¹H NMR (400 MHz, DMSO-d₆): δ=1.17 (t, 3H), 3.98 (q, 2H), 4.44 (s, 2H), 6.98 (s, 2H), 7.09-7.15 (m, 1H), 7.15-7.22

(m, 1H), 7.24-7.32 (m, 1H), 7.35-7.42 (m, 1H), 7.51-7.58 (m, 1H), 8.60-8.66 (m, 1H), 9.10-9.16 (m, 1H), 11.70 (s, 1H).

7.34-7.43 (m, 1H), 7.50-7.60 (m, 1H), 8.59-8.68 (m, 1H), 9.08-9.16 (m, 1H), 11.69 (s, 1H).

Example 89

6-Amino-2-[3-(2-fluorobenzyl)-1H-pyrazolo[4,3-b]pyridin-1-yl]-7-methyl-7,9-dihydro-8H-purin-8-one Example 90

6-Amino-2-[3-(2-fluorobenzyl)-1H-pyrazolo[4,3-b]pyridin-1-yl]-7,9-dihydro-8H-purin-8-one

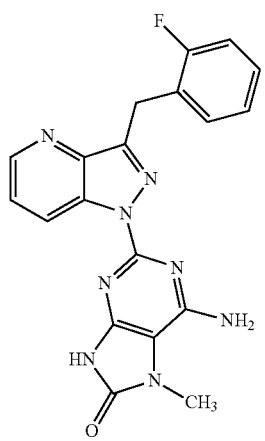 [SMILES: Cn1c(=O)[nH]c2nc(-n3nc(Cc4ccccc4F)c4ncccc43)nc(N)c21]

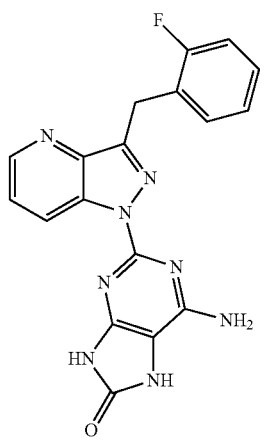 [SMILES: Nc1nc(-n2nc(Cc3ccccc3F)c3ncccc32)nc2[nH]c(=O)[nH]c12]

200 mg (0.392 mmol) of 2-[3-(2-fluorobenzyl)-1H-pyrazolo[4,3-b]pyridin-1-yl]pyrimidine-4,5,6-triamine (example 2A) were initially charged in tetrahydrofuran (11.1 ml) and the suspension was cooled to 0° C. Subsequently, 0.43 ml of a 1M solution of bis(trimethylsilyl)sodium amide in tetrahydrofuran was added and the mixture was stirred at 0° C. for a further 30 min. Thereafter, 24.4 µl (0.392 mmol) of iodomethane were added dropwise and the reaction mixture was stirred at RT overnight. The reaction mixture was again cooled to 0° C. and a further 12.2 µl (0.196 mmol) of iodomethane (dissolved in 1.0 ml of tetrahydrofuran) were added. Thereafter, the mixture was stirred at 0° C. for 1 h and then heated to reflux overnight. The reaction mixture was diluted with ethyl acetate and washed twice with saturated aqueous sodium hydrogencarbonate solution. The organic phase was dried over magnesium sulfate, filtered and concentrated by rotary evaporation. The residue was chromatographed on silica gel (eluent: dichloromethane/methanol 40:1) and the product fractions were concentrated. This gave 15.6 mg (10% of theory) of the title compound in solid form.

LC-MS (method 2): $R_t$=0.81 min

MS (ESIpos): m/z=391 (M+H)$^+$ $^1$H NMR (400 MHz, DMSO-d$_6$): δ=3.46 (s, 3H), 4.44 (s, 2H), 6.98 (s, 2H), 7.08-7.23 (m, 2H), 7.23-7.32 (m, 1H), 235 mg (0.540 mmol) of the compound from example 49A were initially charged in tetrahydrofuran (4.7 ml), 23.8 mg (0.594 mmol) of sodium hydride (60% in mineral oil) were added and the mixture was stirred at 65° C. for 15 min. The reaction mixture was diluted with ethyl acetate and washed with saturated aqueous sodium hydrogencarbonate solution. The organic phase was dried over magnesium sulfate, filtered and concentrated by rotary evaporation. The residue was separated by means of preparative HPLC (eluent: acetonitrile-water with 0.1% formic acid gradient) and the product fractions were concentrated. This gave 11.3 mg (5% of theory) of the title compound in solid form.

LC-MS (method 4): $R_t$=1.66 min

MS (ESIpos): m/z=377 (M+H)$^+$.

¹H NMR (400 MHz, DMSO-d₆): δ=4.43 (s, 2H), 6.79 (br. s, 1H), 7.09-7.15 (m, 1H), 7.15-7.22 (m, 1H), 7.24-7.32 (m, 1H), 7.35-7.42 (m, 1H), 7.51-7.57 (m, 1H), 8.59-8.64 (m, 1H), 9.02-9.08 (m, 1H).

Example 91

6-Amino-7-(4-fluorobenzyl)-2-[3-(2-fluorobenzyl)-1H-pyrazolo[4,3-b]pyridin-1-yl]-7,9-dihydro-8H-purin-8-one

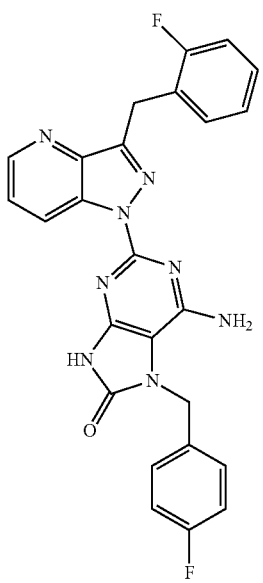 [SMILES: Nc1nc(-n2nc(Cc3ccccc3F)c3ncccc32)nc2[nH]c(=O)n(Cc3ccc(F)cc3)c12]

21 mg (0.04 mmol) of the compound from example 50A were initially charged in tetrahydrofuran (1.0 ml), 1.8 mg (0.04 mmol) of sodium hydride (60% in mineral oil) were added and the mixture was stirred at 65° C. for 30 min. The reaction mixture was admixed with saturated aqueous sodium hydrogencarbonate solution and extracted twice with ethyl acetate. The combined organic phases were dried over sodium sulfate, filtered and concentrated by rotary evaporation. The residue was separated by means of preparative HPLC (eluent: acetonitrile-water with 0.1% formic acid gradient) and the product fractions were concentrated. This gave 8.5 mg (44% of theory) of the title compound in solid form.

LC-MS (method 2): $R_t$=1.00 min

MS (ESIpos): m/z=485 (M+H)⁺

¹H NMR (400 MHz, DMSO-d₆): δ=4.43 (s, 2H), 5.20 (s, 2H), 6.92 (s, 2H), 7.08-7.22 (m, 4H), 7.24-7.32 (m, 3H), 7.35-7.41 (m, 1H), 7.51-7.56 (m, 1H), 8.60-8.65 (m, 1H), 9.07-9.13 (m, 1H), 11.90 (s, 1H).

Example 92

6-Amino-2-[3-(2-fluorobenzyl)-1H-pyrazolo[4,3-b]pyridin-1-yl]-7-(2-hydroxyethyl)-7,9-dihydro-8H-purin-8-one

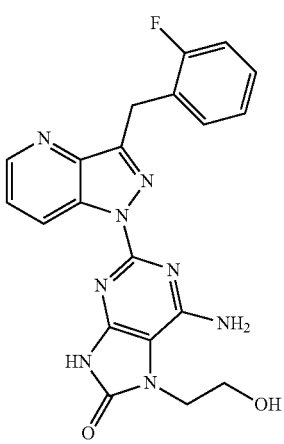 [SMILES: Nc1nc(-n2nc(Cc3ccccc3F)c3ncccc32)nc2[nH]c(=O)n(CCO)c12]

120 mg (0.263 mmol) of the carbamate from example 51A were initially charged in methanol (5.0 ml), 100 μl (0.525 mmol) of sodium methoxide solution (25% w/w in methanol) were added and the mixture was stirred at 65° C. for 30 min. The solvent was removed under reduced pressure, the residue was separated by means of preparative HPLC and the product fractions were concentrated. This gave 53.1 mg (48% of theory) of the title compound in solid form.

LC-MS (method 2): $R_t$=0.80 min

MS (ESIpos): m/z=421 (M+H)⁺

¹H NMR (400 MHz, DMSO-d₆): δ=3.59-3.66 (m, 2H), 3.93-3.99 (m, 2H), 4.44 (s, 2H), 5.32-5.36 (m, 1H), 7.00 (s, 2H), 7.09-7.15 (m, 1H), 7.16-7.22 (m, 1H), 7.25-7.32 (m,

1H), 7.36-7.42 (m, 1H), 7.53-7.58 (m, 1H), 8.62-8.65 (m, 1H), 9.09-9.14 (m, 1H), 11.74 (s, 1H).

Example 93

4-Amino-2-[1-(2-fluorobenzyl)-1H-pyrazolo[3,4-b]pyridin-3-yl]-6-propylpteridin-7(8H)-one

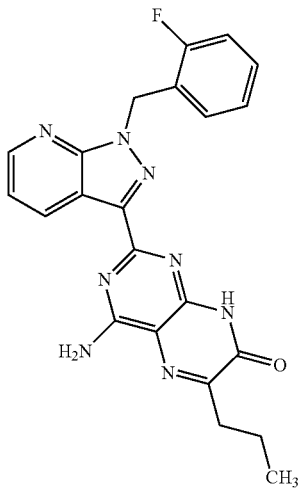 [SMILES: CCCc1nc2c(N)nc(-c3nn(Cc4ccccc4F)c4ncccc34)nc2[nH]c1=O]

250 mg (0.714 mmol) of the compound from example 1A were initially charged in ethanol (3.0 ml), then 113 mg (0.785 mmol) of ethyl 2-oxopentanoate were added and the reaction mixture was heated to reflux for two days. The reaction mixture was brought to RT and filtered. The solids were washed with ethanol, then suspended in dimethylformamide, and the mixture was left to stand overnight. Thereafter, the supernatant solution was decanted and discarded. The remaining residue was stirred repeatedly with methanol and the supernatant solution was discarded each time. The residue was dried under high vacuum and, after lyophilization, 69 mg (22% of theory) of the title compound were obtained in solid form.

LC-MS (method 2): $R_t$=1.02 min

MS (ESIpos): m/z=431 (M+H)$^+$ $^1$H NMR (400 MHz, DMSO-$d_6$): δ=0.97 (t, 3H), 1.70-1.81 (m, 2H), 2.69-2.76 (m, 2H), 5.84 (s, 1H), 7.11-7.27 (m, 3H), 7.33-7.45 (m, 3H), 7.88 (br. s, 1H), 8.63-8.68 (m, 1H), 9.14-9.20 (m, 1H), 12.73 (s, 1H).

Example 94

4-Amino-6-ethyl-2-[1-(2-fluorobenzyl)-1H-pyrazolo[3,4-b]pyridin-3-yl]pteridin-7(8H)-one

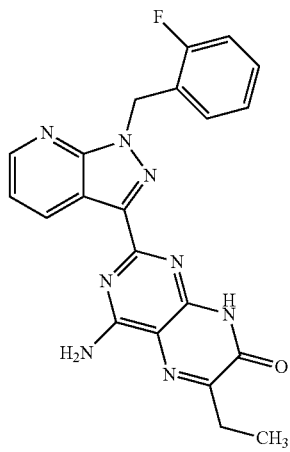 [SMILES: CCc1nc2c(N)nc(-c3nn(Cc4ccccc4F)c4ncccc34)nc2[nH]c1=O]

250 mg (0.714 mmol) of the compound from example 1A were initially charged in ethanol (3.8 ml), then 102 mg (0.785 mmol) of methyl 3-oxopentanoate were added and the reaction mixture was heated to reflux for two days. The reaction mixture was brought to RT and filtered. The solids were washed with ethanol, then suspended in dimethylformamide, and the mixture was left to stand overnight. Thereafter, the supernatant solution was decanted and discarded. The remaining residue was stirred repeatedly with methanol and the supernatant solution was discarded each time. The residue was dried under high vacuum and, after lyophilization, 77 mg (25% of theory) of the title compound were obtained in solid form.

LC-MS (method 2): $R_t$=0.96 min

MS (ESIpos): m/z=417 (M+H)$^+$

¹H NMR (400 MHz, DMSO-d₆): δ=1.24 (t, 3H), 2.76 (q, 2H), 5.84 (s, 2H), 7.12-7.28 (m, 3H), 7.32-7.47 (m, 3H), 7.89 (br. s, 1H), 8.63-8.68 (m, 1H), 9.14-9.20 (m, 1H), 12.72 (s, 1H).

Example 95

2-[5-Fluoro-1-(2-fluorobenzyl)-1H-pyrazolo[3,4-b]pyridin-3-yl]-7-methyl-7,9-dihydro-8H-purin-8-one

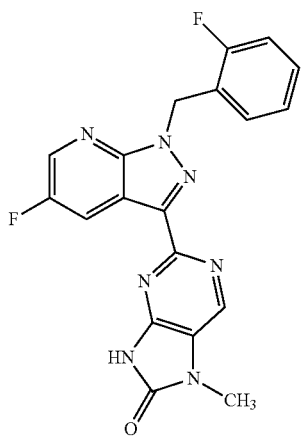 [SMILES: Cn1c(=O)[nH]c2nc(-c3nn(Cc4ccccc4F)c4ncc(F)cc34)ncc21]

In analogy to the method described in example 1, 417 mg (0.686 mmol, purity approx. 70%) of example 75A were converted. This gave 213 mg (79% of theory) of the title compound.

LC-MS (method 2): R$_t$=0.96 min; MS (ESIpos): m/z=394 (M+H)⁺

¹H NMR (400 MHz, DMSO-d₆): δ [ppm]=3.37 (s, 3H), 5.83 (s, 2H), 7.15-7.30 (m, 3H), 7.34-7.40 (m, 1H), 8.51 (s, 1H), 8.58 (dd, 1H), 8.72 (dd, 1H), 12.16 (s br, 1H).

Example 96

5-[1-(2-Fluorobenzyl)-1H-pyrazolo[3,4-b]pyridin-3-yl]-1,3-dihydro-2H-imidazo[4,5-b]pyrazin-2-one

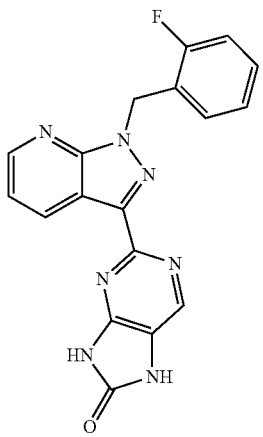 [SMILES: O=c1[nH]c2cnc(-c3nn(Cc4ccccc4F)c4ncccc34)nc2[nH]1]

40 mg (0.12 mmol) of the compound from example 52A were initially charged in pyridine (5.0 ml), then 39 mg (0.13 mmol) of bis(trichloromethyl) carbonate were added and the mixture was stirred at 100° C. for 1 h. The reaction mixture was concentrated, admixed with saturated aqueous sodium hydrogencarbonate solution and extracted twice with ethyl acetate. The collected organic phases were dried over sodium sulfate, filtered and concentrated by rotary evaporation. The residue was separated by means of preparative HPLC (eluent: acetonitrile-water with 0.1% formic acid gradient) and the product fractions were concentrated. This gave 9 mg (20% of theory) of the title compound in solid form.

LC-MS (method 2): R$_t$=0.87 min

MS (ESIpos): m/z=362 (M+H)⁺

¹H NMR (400 MHz, DMSO-d₆): δ=5.82 (s, 2H), 7.11-7.17 (m, 1H), 7.18-7.27 (m, 2H), 7.32-7.42 (m, 2H), 8.55 (s, 1H), 8.64-8.67 (m, 1H), 8.74-8.78 (m, 1H), 11.89 (br. s, 1H).

Example 97

5-Fluoro-1-(2-fluorobenzyl)-3-(7H-pyrrolo[2,3-d]pyrimidin-2-yl)-1H-pyrazolo[3,4-b]pyridine

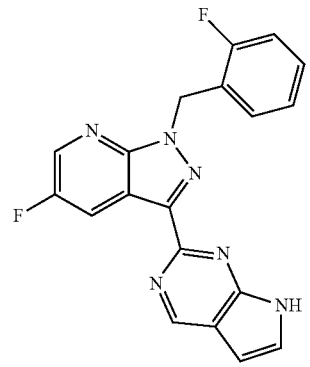 [SMILES: Fc1cnc2c(c1)c(-c1ncc3cc[nH]c3n1)nn2Cc1ccccc1F]

Under an argon atmosphere, 2.000 g (5.389 mmol) of the compound from example 24A were dissolved in 200 ml of 1,4-dioxane, and 9.378 g (16.167 mmol) of hexabutyldistannane were added. Added to the mixture were 2.000 g (1.731 mmol) of tetrakis(triphenylphosphine)palladium(0) and 0.910 g (5.928 mmol) of 2-chloro-7H-pyrrolo[2,3-d]pyrimidine (described in Bioorg. Med. Chem. 17(19), 6926-6936; 2009). The mixture was heated to reflux for 60 h. After cooling, the reaction mixture was filtered through Celite and the filtrate was concentrated on a rotary evaporator. The residue was stirred successively with ethyl acetate, acetonitrile and dimethyl sulfoxide. Subsequently, the residue was dissolved in trifluoroacetic acid, and acetonitrile and water were added until slight turbidity. The mixture was filtered and the filtrate was concentrated on a rotary evaporator and the residue was dried under high vacuum. 161 mg (8% of theory) of the title compound were obtained.

LC-MS (method 3): R$_t$=1.20 min; MS (EIpos): m/z=362 (M+H)±.

¹H NMR (400 MHz, DMSO-d₆): δ [ppm]=5.88 (s, 2H), 6.74-6.75 (m, 1H), 7.18 (t, 1H), 7.23-7.27 (m, 1H), 7.31 (dt, 1H), 7.36-7.41 (m, 1H), 7.74-7.76 (m, 1H), 8.72 (dd, 1H), 8.77-8.78 (m, 1H), 9.21 (s, 1H), 12.51 (s br, 1H).

Example 98

Methyl 4-amino-2-[1-(2-fluorobenzyl)-1H-pyrazolo[3,4-b]pyridin-3-yl]-7-oxo-7,8-dihydropteridine-5(6H)-carboxylate

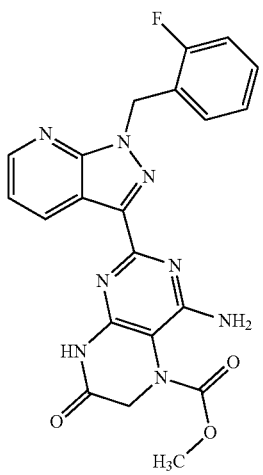 [SMILES: COC(=O)N1CC(=O)Nc2nc(-c3nn(Cc4ccccc4F)c4ncccc34)nc(N)c21]

3.5 g (7.285 mmol) of the crude compound from example 55A were dissolved in ethanol (25 ml) and water (25 ml), and 174 mg (7.285 mmol) of lithium hydroxide were added. After stirring at RT for 30 min, the mixture was adjusted to pH=6 with dilute hydrochloric acid and extracted with ethyl acetate. After separation of the phases, the organic phase was washed with saturated aqueous sodium chloride solution and then dried with sodium sulfate, filtered and concentrated to dryness. The residue was slurried in acetonitrile and ethyl acetate, and insoluble constituents were filtered off. The filtrate was concentrated and the residue was purified by means of preparative HPLC (acetonitrile:water (+0.05% formic acid) gradient). 38 mg of the title compound were obtained (1% of theory).

LC-MS (method 2): $R_t$=0.88 min; MS (ESIpos): m/z=449 (M+H)$^+$ $^1$H NMR (400 MHz, DMSO-d$_6$): δ [ppm]=3.30 (s, 2H), 3.69 (s, 3H), 5.82 (s, 2H), 7.12-7.16 (m, 2H), 7.20-7.25 (m, 1H), 7.33-7.40 (m, 2H), 8.63 (dd, 1H), 9.10 (dd, 1H), 11.17 (s, 1H).

Example 99

2-[1-(2-Fluorobenzyl)-1H-pyrazolo[3,4-b]pyridin-3-yl]-7-(3,3,3-trifluoro-2-hydroxypropyl)-7,9-dihydro-8H-purin-8-one

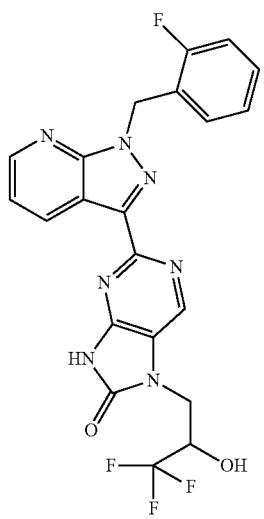 [SMILES: O=c1[nH]c2nc(-c3nn(Cc4ccccc4F)c4ncccc34)ncc2n1CC(O)C(F)(F)F]

In analogy to the synthesis of example 3, example 99 was prepared from 597 mg (1.261 mmol) of example 77A. 42 mg of the title compound were obtained (7% of theory).

LC-MS (method 2): $R_t$=0.96 min; MS (EIpos): m/z=474 (M+H)$^+$.

$^1$H NMR (400 MHz, DMSO-d$_6$): δ [ppm]=4.04-4.16 (m, 2H), 4.42-4.46 (m, 1H), 5.84 (s, 2H), 6.77 (d, 1H), 7.16 (t, 1H), 7.22-7.26 (m, 2H), 7.34-7.44 (m, 2H), 8.59 (s, 1H), 8.66 (dd, 1H), 8.87 (dd, 1H), 12.34 (s, 1H).

Example 100

7-(2,2-Difluoroethyl)-2-[1-(2-fluorobenzyl)-1H-pyrazolo[3,4-b]pyridin-3-yl]-6-iodo-7,9-dihydro-8H-purin-8-one

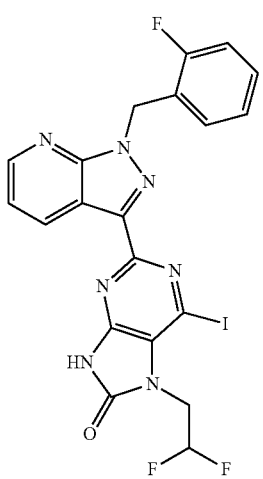 [SMILES: O=c1[nH]c2nc(-c3nn(Cc4ccccc4F)c4ncccc34)nc(I)c2n1CC(F)F]

603 mg (1.369 mmol) of example 4 were initially charged in isopentyl nitrite (3.96 ml) and diiodomethane (10.53 ml) and then heated to 85° C. while stirring for 1 h. Then the mixture was concentrated to dryness and admixed with acetonitrile. The insoluble residue was filtered off, washed with acetonitrile and dried. 227 mg of the title compound were obtained (30% of theory).

LC-MS (method 2): $R_t$=1.12 min; MS (ESIpos): m/z=552 (M+H)$^+$ $^1$H NMR (400 MHz, DMSO-d$_6$): δ [ppm]=4.55 (m, 2H), 5.86 (s, 2H), 6.29-6.57 (m, 1H), 7.13-7.39 (m, 4H), 7.45-7.49 (m, 1H), 8.68 (dd, 1H), 8.81 (dd, 1H), 12.67 (s, 1H).

Example 101

4-Amino-6-[1-(2-fluorobenzyl)-1H-pyrazolo[3,4-b]pyridin-3-yl]-1H-pyrazolo[3,4-d]pyrimidin-3-ol

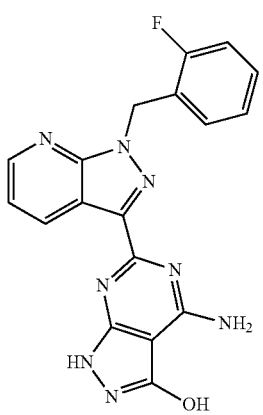 [SMILES: Nc1nc(-c2nn(Cc3ccccc3F)c3ncccc23)nc2[nH]nc(O)c12]

150 mg (0.357 mmol) of example 21 were admixed with an excess of pyridine hydrochloride (approx. 1 g) and stirred overnight at 155° C. in the melt. After cooling, the residue was admixed with water and acetonitrile, treated briefly in an ultrasound bath and then filtered off. The residue was washed with water and acetonitrile, and dried under reduced pressure. 136 mg of the title compound were obtained (91% of theory, 90% purity).

LC-MS (method 2): $R_t$=0.76 min; MS (ESIpos): m/z=377 (M+H)$^+$ $^1$H NMR (400 MHz, DMSO-d$_6$): δ [ppm]=5.90 (s, 2H), 7.14-7.27 (m, 3H), 7.35-7.40 (m, 1H), 7.48-7.52 (m, 1H), 8.72 (dd, 1H), 8.91 (dd, 1H).

Example 102

7-(2,2-Difluoroethyl)-2-[1-(2-fluorobenzyl)-1H-pyrazolo[3,4-b]pyridin-3-yl]-7,9-dihydro-8H-purin-8-one

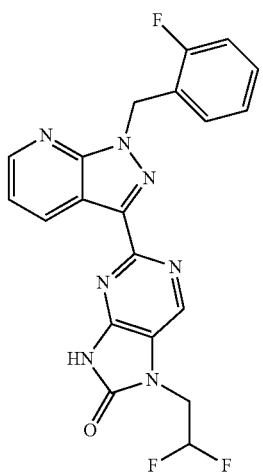 [SMILES: O=c1[nH]c2nc(-c3nn(Cc4ccccc4F)c4ncccc34)ncc2n1CC(F)F]

100 mg (0.181 mmol) of example 100 in dimethylformamide (10 ml) were admixed with 40 mg of palladium on charcoal (10%) and hydrogenated at standard hydrogen pressure for 4 h. This was followed by filtration and concentration to dryness. The residue was purified by means of preparative HPLC (acetonitrile:water (+0.05% formic acid) gradient). 47 mg of the title compound were obtained (68% of theory).

LC-MS (method 2): $R_t$=0.95 min; MS (ESIpos): m/z=426 (M+H)$^+$

¹H NMR (400 MHz, DMSO-d₆): δ [ppm]=4.39 (m, 2H), 5.84 (s, 2H), 6.26-6.56 (m, 1H), 7.14-7.44 (m, 5H), 8.57 (s, 1H), 8.66 (dd, 1H), 8.87 (dd, 1H), 12.47 (s br, 1H).

Example 103

7-(2,2-Difluoroethyl)-2-[1-(2-fluorobenzyl)-1H-pyrazolo[3,4-b]pyridin-3-yl]-6-(methylamino)-7,9-dihydro-8H-purin-8-one

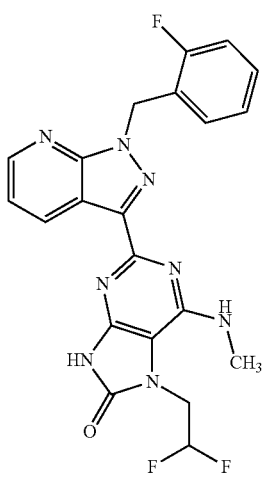 [SMILES: CNc1nc(-c2nn(Cc3ccccc3F)c3ncccc23)nc2[nH]c(=O)n(CC(F)F)c12]

166 mg (0.301 mmol) of example 100 in DMSO (13 ml) were admixed with 2.5 ml of a 2M solution of methylamine in methanol and heated in a microwavable flask with septum in a microwave at 150° C. for 2.5 h. This was followed by addition of ethyl acetate and water and separation of the phases. The aqueous phase was extracted twice with ethyl acetate and the combined organic phases were washed with water and saturated aqueous sodium chloride solution. They were dried with sodium sulfate, filtered and concentrated to dryness. The residue was purified by means of preparative HPLC (acetonitrile:water (+0.05% formic acid) gradient). 33 mg of the title compound were obtained (22% of theory) are.

LC-MS (method 2): $R_t$=0.92 min; MS (ESIpos): m/z=455 (M+H)⁺

¹H NMR (400 MHz, DMSO-d₆): δ [ppm]=3.10 (d, 3H), 4.50 (m, 2H), 5.82 (s, 2H), 6.09-6.38 (m, 1H), 6.67 (m, 1H), 7.12-7.25 (m, 3H), 7.31-7.42 (m, 2H), 8.64 (dd, 1H), 8.90 (dd, 1H), 11.85 (s br, 1H).

Example 104

7-(1-Cyclopropylpiperidin-4-yl)-2-[1-(2-fluorobenzyl)-1H-pyrazolo[3,4-b]pyridin-3-yl]-7,9-dihydro-8H-purin-8-one

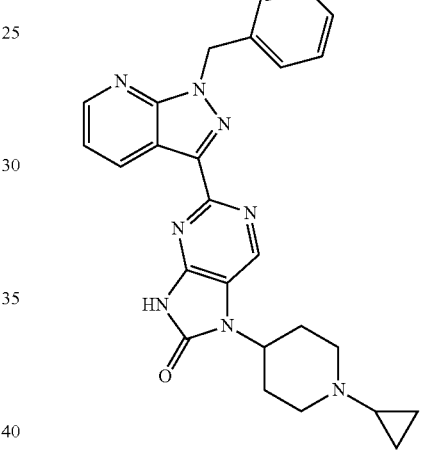

55 mg (0.12 mmol) of example 34A and 27 mg (0.092 mmol) of bis(trichloromethyl) carbonate were initially charged in dichloromethane (1.5 ml) and pyridine (1.5 ml) was added at 0° C. After stirring at 0° C. for 30 min, saturated aqueous sodium hydrogencarbonate solution was added, and the mixture was briefly stirred vigorously and then extracted three times with dichloromethane. The combined organic phases were dried over sodium sulfate, filtered, concentrated and then purified by means of preparative HPLC (acetonitrile:water (+0.05% formic acid) gradient). 22 mg of the title compound were obtained (37% of theory).

LC-MS (method 2): $R_t$=0.76 min; MS (EIpos): m/z=485 [M+H]⁺.

¹H NMR (400 MHz, DMSO-d₆): δ [ppm]=0.86 (m, 2H), 1.12 (m, 2H), 2.05 (m, 2H), 2.59-2.89 (m, 5H covered by solvent), 3.65 (m, 2H), 4.63 (m, 1H), 5.84 (s, 2H), 7.15 (t, 1H), 7.21-7.26 (m, 2H), 7.35-7.38 (m, 1H), 7.42 (dd, 1H), 8.66 (dd, 1H), 8.80-8.87 (m, 2H), 12.31 (s br, 1H).

Example 105

Methyl 8-amino-6-[1-(2-fluorobenzyl)-1H-pyrazolo[3,4-b]pyridin-3-yl]-3-oxo-3,4-dihydropyrimido[4,5-e][1,2,4]triazine-1(2H)-carboxylate

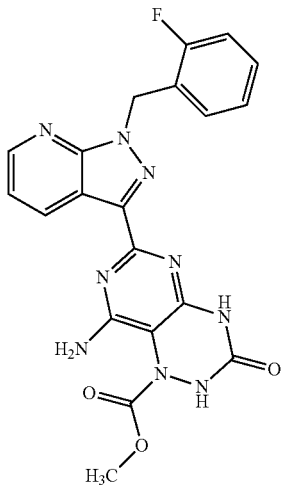 [SMILES: COC(=O)N1NC(=O)Nc2nc(-c3nn(Cc4ccccc4F)c4ncccc34)nc(N)c21]

56 mg (0.132 mmol) of the compound obtained in example 56A were initially charged in 3 ml of dimethylformamide, and 27.6 μl (0.159 mmol) of N,N-diisopropylethylamine and 25.7 mg (0.159 mmol) of carbonyldiimidazole were added. After 5 h at RT, another 27.6 μl (0.159 mmol) of N,N-diisopropylethylamine and 25.7 mg (0.159 mmol) of carbonyldiimidazole were added and the mixture was heated to 60° C. The next day, another 27.6 μl (0.159 mmol) of N,N-diisopropylethylamine and 25.7 mg (0.159 mmol) of carbonyldiimidazole were added and the mixture was heated to 60° C. for 2 further days. The reaction mixture was purified by means of preparative HPLC (acetonitrile:water (+0.05% formic acid) gradient). 25 mg of the title compound were obtained (42% of theory).

LC-MS (method 2): $R_t$=0.84 min; MS (ESIpos): m/z=450 (M+H)$^+$ $^1$H NMR (400 MHz, DMSO-d$_6$): δ [ppm]=3.72 (s, 3H), 5.82 (s, 2H), 7.11-7.25 (m, 5H), 7.33-7.40 (m, 2H), 8.63 (dd, 1H), 9.07 (dd, 1H), 10.01 (s br, 1H), 10.36 (s br, 1H).

Example 106

7-Amino-5-[1-(2-fluorobenzyl)-1H-pyrazolo[3,4-b]pyridin-3-yl][1,3]oxazolo[4,5-d]pyrimidin-2(3H)-one

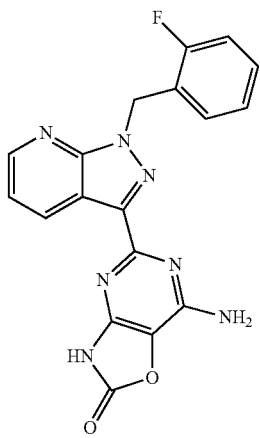 [SMILES: Nc1nc(-c2nn(Cc3ccccc3F)c3ncccc23)nc2[nH]c(=O)oc12]

159 mg (0.453 mmol) of the compound prepared in example 58A in dimethylformamide (10 ml) were admixed with 94 μl (0.543 mmol) of N,N-diisopropylethylamine and 88 mg (0.543 mmol) of carbonyldiimidazole, and the mixture was stirred at RT overnight. The mixture was filtered, the filtrate was concentrated and the residue was purified by means of preparative HPLC (acetonitrile:water (+0.05% formic acid) gradient). 90 mg of the title compound were obtained (52% of theory).

LC-MS (method 2): $R_t$=0.87 min; MS (ESIpos): m/z=378 (M+H)$^+$ $^1$H NMR (400 MHz, DMSO-d$_6$): δ [ppm]=5.81 (s, 2H), 7.12-7.25 (m, 3H), 7.33-7.41 (m, 4H), 8.64 (dd, 1H), 8.97 (dd, 1H), 12.38 (s br, 1H).

Example 107

2-[1-(2-Fluorobenzyl)-1H-pyrazolo[3,4-b]pyridin-3-yl]-6-iodo-7-methyl-7,9-dihydro-8H-purin-8-one

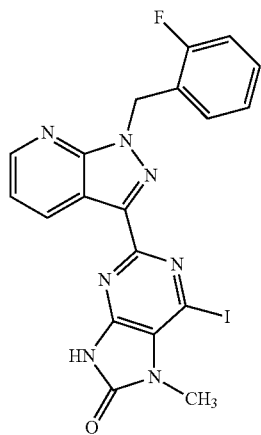 [SMILES: Cn1c(=O)[nH]c2nc(-c3nn(Cc4ccccc4F)c4ncccc34)nc(I)c21]

7.634 g (19.554 mmol) of the compound obtained in example 41 were converted in analogy to example 100. 5.63 g of the title compound were obtained (57% of theory).

LC-MS (method 2): R$_t$=1.08 min; MS (EIpos): m/z=502 (M+H)$^+$.

$^1$H NMR (400 MHz, DMSO-d$_6$): δ [ppm]=3.54 (s, 3H), 5.85 (s, 2H), 7.13-7.26 (m, 3H), 7.34-7.39 (m, 1H), 7.47 (dd, 1H), 8.67 (dd, 1H), 8.79 (dd, 1H), 12.41 (s, 1H).

Example 108

2-[1-(2-Fluorobenzyl)-1H-pyrazolo[3,4-b]pyridin-3-yl]-6-[(2-hydroxyethyl)amino]-7-methyl-7,9-dihydro-8H-purin-8-one

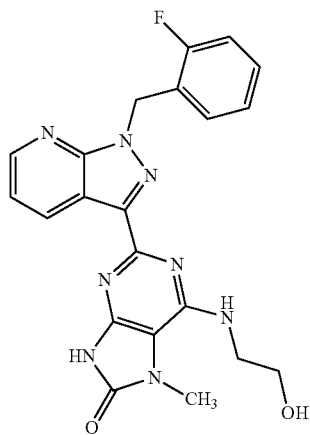 [SMILES: Cn1c(=O)[nH]c2nc(-c3nn(Cc4ccccc4F)c4ncccc34)nc(NCCO)c21]

200 mg (0.399 mmol) of the compound obtained in example 107 were dissolved in N-methylpyrrolidone (4 ml) and admixed with 2-aminoethanol (1.5 ml), and then heated in a microwavable flask with septum in a microwave at 150° C. for 5 h. The reaction mixture was purified by means of preparative HPLC (acetonitrile:water (+0.05% formic acid) gradient). 31 mg of the title compound were obtained (18% of theory).

LC-MS (method 2): R$_t$=0.83 min; MS (EIpos): m/z=435 (M+H)$^+$.

$^1$H NMR (400 MHz, DMSO-d$_6$): δ [ppm]=3.51 (s, 3H), 3.69 (m, 4H), 4.87 (m, 1H), 5.81 (s, 2H), 6.61 (m, 1H), 7.12-7.25 (m, 3H), 7.33-7.40 (m, 2H), 8.63 (dd, 1H), 8.84 (dd, 1H), 11.53 (br s, 1H).

Example 109

2-[1-(2-Fluorobenzyl)-1H-pyrazolo[3,4-b]pyridin-3-yl]-6-isopropoxy-7-methyl-7,9-dihydro-8H-purin-8-one

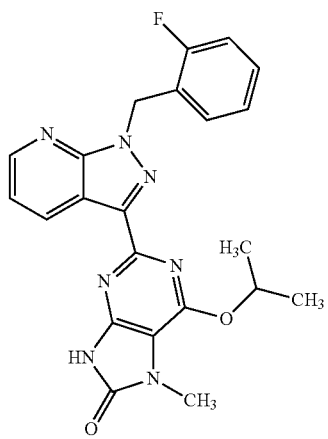 [SMILES: CC(C)Oc1nc(-c2nn(Cc3ccccc3F)c3ncccc23)nc2[nH]c(=O)n(C)c12]

200 mg (0.399 mmol) of the compound obtained in example 107 were admixed in a microwavable flask with isopropanol (3 ml), 260 mg (0.798 mmol) of cesium carbonate, 8 mg (0.04 mmol) of copper(I) iodide and 19 mg (0.08 mmol) of 3,4,7,8-tetramethyl-1,10-phenanthroline. The flask was purged with argon while being treated with ultrasound for 5 min, and then closed with an appropriate septum. Then it was heated in a microwave at 140° C. for 2 h. Reaction monitoring showed low conversion. For that reason, N-methylpyrrolidone (1 ml) was added and the mixture was once again heated in a microwave at 140° C. for 2 h and then at 180° C. for 8 h. After cooling, the reaction mixture was filtered and concentrated, and the residue was purified by means of preparative HPLC (acetonitrile:water (+0.05% formic acid) gradient). 21 mg of the title compound were obtained (12% of theory).

LC-MS (method 2): R$_t$=1.13 min; MS (EIpos): m/z=434 (M+H)±.

$^1$H NMR (400 MHz, DMSO-d$_6$): δ [ppm]=1.47 (d, 6H), 3.44 (s, 3H), 5.59 (sep, 1H), 5.84 (s, 2H), 7.15 (t, 1H), 7.20-

7.26 (m, 2H), 7.33-7.39 (m, 1H), 7.43 (dd, 1H), 8.66 (dd, 1H), 8.80 (dd, 1H), 11.98 (s br, 1H).

Example 110

2-[1-(2-Fluorobenzyl)-1H-pyrazolo[3,4-b]pyridin-3-yl]-7-methyl-8-oxo-8,9-dihydro-7H-purine-6-carbonitrile

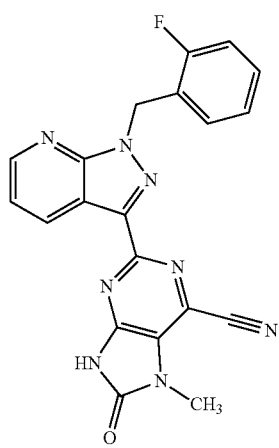 [SMILES: Cn1c(=O)[nH]c2nc(-c3nn(Cc4ccccc4F)c4ncccc34)nc(C#N)c21]

200 mg (0.399 mmol) of the compound obtained in example 107 in pyridine (3 ml) were admixed with 37 mg (0.419 mmol) of copper(I) cyanide and heated to reflux overnight. After cooling, the reaction mixture was filtered and concentrated, and the residue was purified by means of preparative HPLC (acetonitrile:water (+0.05% formic acid) gradient). 31 mg of the title compound were obtained (18% of theory).

LC-MS (method 2): $R_t$=0.99 min; MS (EIpos): m/z=401 (M+H)$^+$.

$^1$H NMR (400 MHz, DMSO-d$_6$): δ [ppm]=3.55 (s, 3H), 5.85 (s, 2H), 7.15 (t, 1H), 7.20-7.26 (m, 2H), 7.33-7.39 (m, 1H), 7.45 (dd, 1H), 8.67 (dd, 1H), 8.82 (dd, 1H), 12.88 (s br, 1H).

Example 111

2-[1-(2-Fluorobenzyl)-1H-pyrazolo[3,4-b]pyridin-3-yl]-6-methoxy-7-methyl-7,9-dihydro-8H-purin-8-one

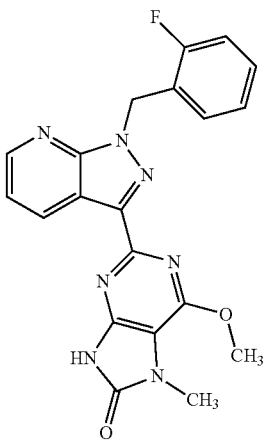 [SMILES: COc1nc(-c2nn(Cc3ccccc3F)c3ncccc23)nc2[nH]c(=O)n(C)c12]

200 mg (0.399 mmol) of the compound obtained in example 107 were admixed in a microwavable flask with methanol (3 ml), N-methylpyrrolidone (1 ml), 260 mg (0.798 mmol) of cesium carbonate, 8 mg (0.04 mmol) of copper(I) iodide and 19 mg (0.08 mmol) of 3,4,7,8-tetramethyl-1,10-phenanthroline. The flask was purged with argon while being treated with ultrasound for 5 min, and then closed with an appropriate septum. Then it was heated in a microwave at 180° C. for 8 h. After cooling, the reaction mixture was filtered and concentrated, and the residue was purified by means of preparative HPLC (acetonitrile:water (+0.05% formic acid) gradient). 17 mg of the title compound were obtained (10% of theory).

LC-MS (method 2): $R_t$=0.98 min; MS (EIpos): m/z=406 (M+H)$^+$.

$^1$H NMR (400 MHz, DMSO-d$_6$): δ [ppm]=3.44 (s, 3H), 4.19 (s, 3H), 5.84 (s, 2H), 7.13-7.26 (m, 3H), 7.33-7.39 (m, 1H), 7.42 (dd, 1H), 8.66 (dd, 1H), 8.90 (dd, 1H), 12.02 (s br, 1H).

Example 112

6-(Azetidin-1-yl)-2-[1-(2-fluorobenzyl)-1H-pyrazolo[3,4-b]pyridin-3-yl]-7-methyl-7,9-dihydro-8H-purin-8-one

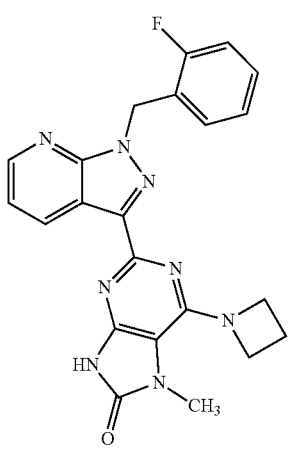 [SMILES: Cn1c(=O)[nH]c2nc(-c3nn(Cc4ccccc4F)c4ncccc34)nc(N3CCC3)c21]

200 mg (0.399 mmol) of the compound obtained in example 107 were dissolved in N-methylpyrrolidone (3 ml) and admixed with 1.00 g (17.514 mmol) of azetidine, and then heated in a microwavable flask with septum in a microwave at 150° C. for 5 h. The mixture was purified by means of preparative HPLC (acetonitrile:water (+0.05% formic acid) gradient). 9 mg of the title compound were obtained (5% of theory).

LC-MS (method 2): R$_t$=1.00 min; MS (EIpos): m/z=431 (M+H)$^+$.

$^1$H NMR (400 MHz, DMSO-d$_6$): δ [ppm]=2.42 (m, 2H), 3.38 (s, 3H), 4.37 (t, 4H), 5.81 (s, 2H), 7.12-7.25 (m, 3H), 7.33-7.40 (m, 2H), 8.63 (dd, 1H), 8.86 (dd, 1H), 11.66 (br s, 1H).

Example 113

2-[1-(2-Fluorobenzyl)-1H-pyrazolo[3,4-b]pyridin-3-yl]-7-(2-hydroxyethyl)-7,9-dihydro-8H-purin-8-one

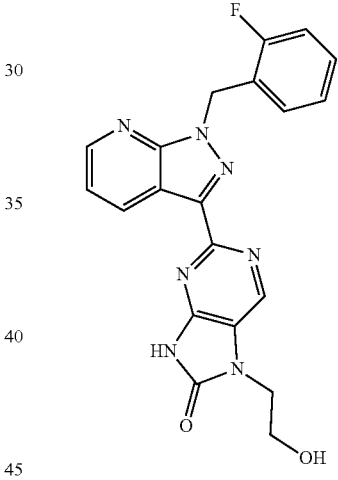

232 mg (0.359 mmol) of the compound obtained in example 60A were hydrogenated analogously to example 102. The reaction mixture was purified by means of preparative HPLC (acetonitrile:water (+0.05% formic acid) gradient). 14 mg of the title compound were obtained (9% of theory).

LC-MS (method 2): R$_t$=0.81 min; MS (ESIpos): m/z=406 (M+H)$^+$ $^1$H NMR (400 MHz, DMSO-d$_6$): δ [ppm]=3.69 (br signal, 2H), 3.92 (t, 2H), 4.96 (br signal, 1H), 5.83 (s, 2H), 7.15 (t, 1H), 7.21-7.26 (m, 2H), 7.34-7.43 (m, 2H), 8.52 (s, 1H), 8.65 (dd, 1H), 8.88 (dd, 1H).

Example 114

2-[1-(2-Fluorobenzyl)-1H-pyrazolo[3,4-b]pyridin-3-yl]-6-(hydroxymethyl)-7,9-dihydro-8H-purin-8-one

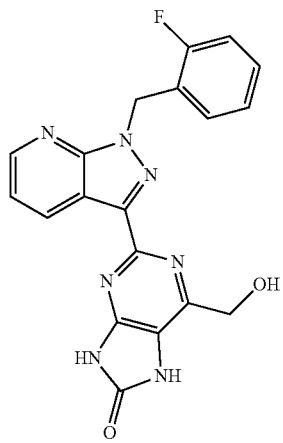 [SMILES: O=c1[nH]c2nc(-c3nn(Cc4ccccc4F)c4ncccc34)nc(CO)c2[nH]1]

Under an argon atmosphere, 76 mg (0.18 mmol) of the compound from example 118 were initially charged in tetrahydrofuran (1.8 ml). At 0° C., 0.26 ml of a 1M solution of lithium aluminum hydride in tetrahydrofuran was subsequently added dropwise and the mixture was stirred at 0° C. for a further 30 min. Dropwise addition of water was followed by final addition of sodium hydroxide solution (1.0 M) to the reaction mixture. Thereafter, the mixture was warmed to RT and stirred for a further 30 min. Subsequently, saturated aqueous sodium chloride solution was added, and the precipitate formed was filtered off and washed with water. Further drying under high vacuum gave 51 mg (71% of theory) of the title compound in solid form.

LC-MS (method 3): R$_t$=0.90 min
MS (ESIpos): m/z=392 (M+H)$^+$ $^1$H NMR (400 MHz, DMSO-d$_6$): δ [ppm]=4.60 (s, 2H), 5.21 (br. s, 1H), 5.80 (s, 2H), 7.08-7.18 (m, 2H), 7.19-7.28 (m, 1H), 7.29-7.41 (m, 2H), 8.54-8.63 (m, 1H), 8.96-9.06 (m, 1H).

Example 115

6-Amino-2-[1-(2-fluorobenzyl)-1H-pyrazolo[3,4-b]pyridin-3-yl]-7-isopropyl-7,9-dihydro-8H-purin-8-one

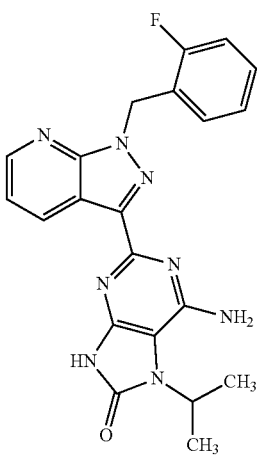 [SMILES: CC(C)n1c(=O)[nH]c2nc(-c3nn(Cc4ccccc4F)c4ncccc34)nc(N)c21]

520 mg (1.33 mmol) of the compound from example 61A were initially charged in dimethylformamide (5 ml), then 1.07 g (6.63 mmol) of N,N-carbonyldiimidazole and 2.31 ml (1.68 mmol) of triethylamine were added and the mixture was stirred at 100° C. overnight. The reaction mixture was then diluted with water and ethyl acetate, the phases were separated and the aqueous phase was extracted with ethyl acetate. The collected organic phases were dried over sodium sulfate, filtered and concentrated. The crude product (540 mg, 84% purity) was not purified any further.

LC-MS (method 2): R$_t$=0.90 min
MS (ESIpos): m/z=419 (M+H)$^+$ $^1$H NMR (400 MHz, DMSO-d$_6$): δ [ppm]=1.48 (d, 6H), 4.55-4.65 (m, 1H), 5.80 (s, 2H), 6.66-6.71 (m, 2H), 7.11-7.27 (m, 3H), 7.34-7.39 (m, 2H), 8.61-8.65 (m, 1H), 9.05-9.09 (m, 1H), 11.51-11.57 (m, 1H).

Example 116

2-[1-(2-Fluorobenzyl)-1H-pyrazolo[3,4-b]pyridin-3-yl]-6-iodo-7-isopropyl-7,9-dihydro-8H-purin-8-one

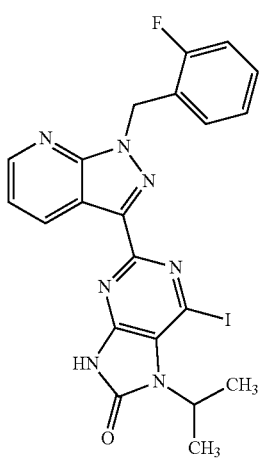 [SMILES: CC(C)n1c(=O)[nH]c2nc(-c3nn(Cc4ccccc4F)c4ncccc34)nc(I)c21]

To a mixture of 2.59 ml (32.20 mmol) of diiodomethane and 2.78 ml (20.61 mmol) of isoamyl nitrite were added 539 mg (approx. 1.08 mmol) of the compound from example 115, and the reaction mixture was stirred at 85° C. overnight. The mixture was concentrated, and the residue was stirred with dichloromethane and filtered. The solids were washed with dichloromethane and dried under high vacuum. 330 mg of the title compound were obtained (92% purity; 53% of theory).

LC-MS (method 2): $R_t$=1.21 min
MS (ESIpos): m/z=530 (M+H)$^+$
$^1$H NMR (400 MHz, DMSO-d$_6$): δ [ppm]=1.55 (d, 6H), 5.22-5.32 (m, 1H), 5.85 (s, 2H), 7.11-7.28 (m, 3H), 7.32-7.40 (m, 1H), 7.43-7.51 (m, 1H), 8.65-8.71 (m, 1H), 8.77-8.83 (m, 1H), 12.29-12.35 (m, 1H).

Example 117

2-[1-(2-fluorobenzyl)-1H-pyrazolo[3,4-b]pyridin-3-yl]-7-isopropyl-7,9-dihydro-8H-purin-8-one

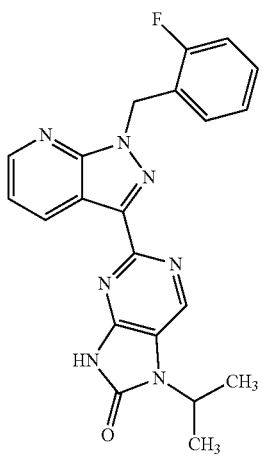 [SMILES: CC(C)n1c(=O)[nH]c2nc(-c3nn(Cc4ccccc4F)c4ncccc34)ncc21]

330 mg (0.57 mmol) of the compound from example 116 were initially charged in dimethylformamide (10.0 ml), then 66 mg of palladium (10% w/w on charcoal) were added and the mixture was hydrogenated at standard hydrogen pressure for two days. Subsequently, another 66 mg of palladium (10% w/w on charcoal) were added and hydrogenation was continued overnight.

Thereafter, the mixture was filtered through Celite and washed through with methanol, and the filtrate was concentrated. Preparative HPLC (eluent: acetonitrile-water with 0.1% formic acid gradient) of the residue gave 23 mg (90% purity, 9% of theory) of the title compound in solid form.

LC-MS (method 2): $R_t$=1.00 min
MS (ESIpos): m/z=404 (M+H)$^+$
$^1$H NMR (400 MHz, DMSO-d$_6$): δ [ppm]=1.48 (d, 6H), 4.57-4.65 (m, 1H), 5.82-5.86 (m, 2H), 7.12-7.18 (m, 1H), 7.20-7.27 (m, 2H), 7.33-7.40 (m, 1H), 7.40-7.44 (m, 1H), 8.65-8.67 (m, 1H), 8.70 (s, 1H), 8.85-8.89 (m, 1H), 12.16-12.20 (m, 1H).

Example 118

Ethyl 2-[1-(2-fluorobenzyl)-1H-pyrazolo[3,4-b]pyridin-3-yl]-8-oxo-8,9-dihydro-7H-purine-6-carboxylate

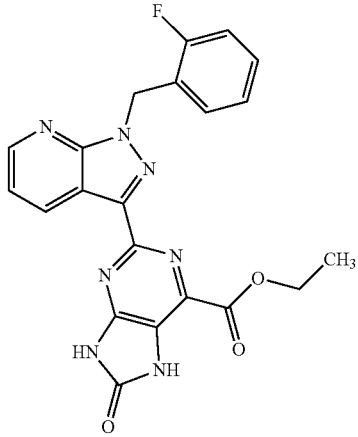 [SMILES: CCOC(=O)c1nc(-c2nn(Cc3ccccc3F)c3ncccc23)nc2[nH]c(=O)[nH]c12]

225 mg (0.55 mmol) of the compound from example 63A were initially charged in dimethylformamide (2.5 ml), then 448 mg (2.76 mmol) of N,N-carbonyldiimidazole and 0.96 ml (6.90 mmol) of triethylamine were added and the mixture was stirred at 100° C. overnight. The reaction mixture was subsequently diluted with water and ethyl acetate, and filtered. The solids were washed with water and, after drying under high vacuum, gave 112 mg (46% of theory) of the title compound.

LC-MS (method 2): $R_t$=0.95 min
MS (ESIpos): m/z=434 (M+H)$^+$
$^1$H NMR (400 MHz, DMSO-d$_6$): δ [ppm]=1.40 (t, 3H), 4.48 (q, 2H), 5.82-5.88 (m, 2H), 7.12-7.18 (m, 1H), 7.19-7.27

(m, 2H), 7.33-7.40 (m, 1H), 7.45 (dd, 1H), 8.65-8.69 (m, 1H), 8.99-9.03 (m, 1H), 11.54 (br. s, 1H), 12.32 (br. s, 1H).

Example 119

2-[1-(2-Fluorobenzyl)-1H-pyrazolo[3,4-b]pyridin-3-yl]-6-methyl-7,9-dihydro-8H-purin-8-one

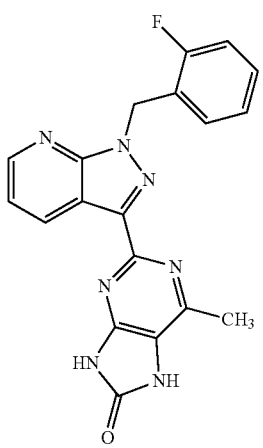 [SMILES: Cc1nc(-c2nn(Cc3ccccc3F)c3ncccc23)nc2[nH]c(=O)[nH]c12]

$^1$H NMR (400 MHz, DMSO-$d_6$): δ [ppm]=2.48 (s, 3H), 5.81 (s, 2H), 7.10-7.27 (m, 3H), 7.32-7.41 (m, 2H), 8.60-8.64 (m, 1H), 8.90-8.96 (m, 1H), 11.25 (br. s, 2H).

Example 120

6-Amino-7-(2,2-dimethylpropyl)-2-[1-(2-fluorobenzyl)-1H-pyrazolo[3,4-b]pyridin-3-yl]-7,9-dihydro-8H-purin-8-one

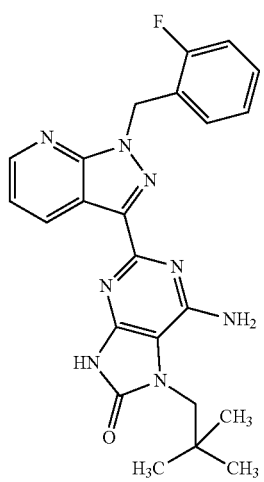 [SMILES: CC(C)(C)Cn1c(=O)[nH]c2nc(-c3nn(Cc4ccccc4F)c4ncccc34)nc(N)c21]

Under an argon atmosphere, 245 mg (0.60 mmol) of the compound from example 69A were initially charged in tetrahydrofuran (2.6 ml) and cooled to 0° C., and 0.90 ml (0.90 mmol) of bis(trimethylsilyl)sodium amide (1.0 M in tetrahydrofuran) was added dropwise. The mixture was stirred at 0° C. for 1 h and then at RT overnight. Subsequently, the mixture was stirred at 60° C. for 8 h. Thereafter, water was added and the reaction mixture was concentrated. The residue was extracted twice with ethyl acetate, and the collected organic phases were washed with water and saturated aqueous sodium chloride solution, dried over magnesium sulfate, filtered and concentrated. This gave 110 mg (85% purity, 41% of theory) of the title compound in solid form. A solid likewise precipitated out of the aqueous phase, which was filtered off, washed with water and dried under high vacuum. This gave a further 100 mg (44% of theory) of the title compound.

LC-MS (method 2): R$_t$=0.87 min; MS (EIpos): m/z=376 (M+H)$^+$.

447 mg (0.94 mmol) of the compound from example 64A were initially charged in dimethylformamide (5 ml), then 758 mg (4.68 mmol) of N,N-carbonyldiimidazole and 1.57 ml (11.23 mmol) of triethylamine were added and the mixture was stirred at 100° C. overnight. The reaction mixture was purified directly by means of preparative HPLC (eluent: methanol/water with 0.1% formic acid gradient). This gave 163 mg (39% of theory) of the title compound in solid form.

LC-MS (method 2): R$_t$=0.99 min
MS (ESIpos): m/z=447 (M+H)$^+$

¹H NMR (400 MHz, DMSO-d₆): δ [ppm]=0.94 (s, 9H), 3.83 (s, 2H), 5.80 (s, 2H), 6.73 (s, 2H), 7.11-7.26 (m, 3H), 7.32-7.41 (m, 2H), 8.61-8.65 (m, 1H), 9.04-9.08 (m, 1H), 11.65 (s, 1H).

Example 121

6-Amino-7-cyclobutyl-2-[1-(2-fluorobenzyl)-1H-pyrazolo[3,4-b]pyridin-3-yl]-7,9-dihydro-8H-purin-8-one

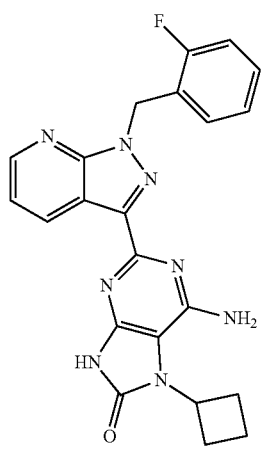 [SMILES: Nc1nc(-c2nn(Cc3ccccc3F)c3ncccc23)nc2[nH]c(=O)n(C3CCC3)c12]

133 mg (0.26 mmol) of the compound from example 65A were initially charged in dimethylformamide (1.4 ml), then 213 mg (1.32 mmol) of N,N-carbonyldiimidazole and 0.44 ml (3.16 mmol) of triethylamine were added and the mixture was stirred at 100° C. overnight. Thereafter, another 200 mg (1.23 mmol) of N,N-carbonyldiimidazole were added and the mixture was again stirred at 100° C. overnight. The reaction mixture was purified directly by means of preparative HPLC (eluent: acetonitrile/water with 0.1% formic acid gradient). This gave 79 mg (68% of theory) of the title compound in solid form.

LC-MS (method 2): $R_t$=0.94 min
MS (ESIpos): m/z=431 (M+H)⁺
¹H NMR (400 MHz, DMSO-d₆): δ [ppm]=1.63-1.81 (m, 2H), 2.20-2.30 (m, 2H), 2.92-3.04 (m, 2H), 4.78-4.88 (m, 1H), 5.80 (s, 2H), 6.74 (s, 2H), 7.11-7.26 (m, 3H), 7.32-7.39 (m, 2H), 8.61-8.64 (m, 1H), 9.03-9.08 (m, 1H), 11.58 (s, 1H).

Example 122

7-(2,2-Dimethylpropyl)-2-[1-(2-fluorobenzyl)-1H-pyrazolo[3,4-b]pyridin-3-yl]-7,9-dihydro-8H-purin-8-one

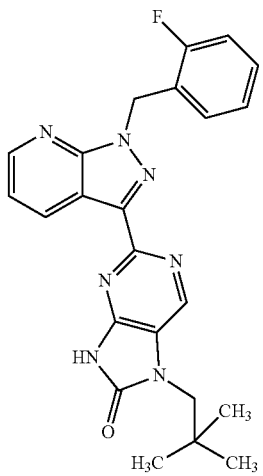 [SMILES: CC(C)(C)Cn1c(=O)[nH]c2nc(-c3nn(Cc4ccccc4F)c4ncccc34)ncc21]

100 mg (0.22 mmol) of the compound from example 120 were initially charged in tetrahydrofuran (10 ml), then 0.21 ml (1.57 mmol) of isoamyl nitrite and 6.0 mg (0.05 mmol) of copper(II) chloride were added, and the mixture was stirred at RT overnight. The reaction mixture was admixed with saturated aqueous sodium hydrogencarbonate solution and extracted twice with ethyl acetate. The collected organic phases were dried over sodium sulfate, filtered and concentrated. The residue was purified by means of preparative HPLC (eluent: acetonitrile/water with 0.1% formic acid gradient). This gave 34 mg (34% of theory) of the title compound in solid form.

LC-MS (method 2): $R_t$=1.12 min
MS (ESIpos): m/z=432 (M+H)⁺
¹H NMR (400 MHz, DMSO-d₆): δ [ppm]=0.99 (s, 9H), 3.66 (s, 2H), 5.84 (s, 2H), 7.12-7.18 (m, 1H), 7.20-7.26 (m, 2H), 7.33-7.39 (m, 1H), 7.39-7.44 (m, 1H), 8.56 (s, 1H), 8.64-8.67 (m, 1H), 8.86-8.90 (m, 1H), 12.21 (br. s, 1H).

Example 123

6-Amino-7-(2-fluorobenzyl)-2-[1-(2-fluorobenzyl)-1H-pyrazolo[3,4-b]pyridin-3-yl]-7,9-dihydro-8H-purin-8-one

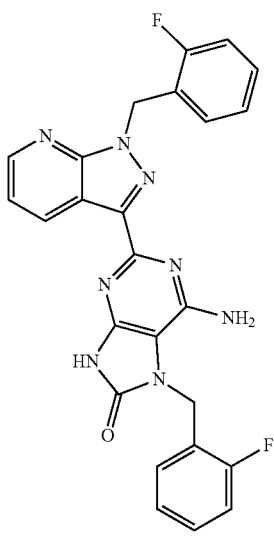 [SMILES: Nc1nc(-c2nn(Cc3ccccc3F)c3ncccc23)nc2[nH]c(=O)n(Cc3ccccc3F)c12]

268 mg (0.48 mmol) of the compound from example 66A were initially charged in dimethylformamide (2.6 ml), then 389 mg (2.40 mmol) of N,N-carbonyldiimidazole and 0.80 ml (5.75 mmol) of triethylamine were added and the mixture was stirred at 100° C. overnight. Subsequently, 380 mg (2.34 mmol) of N,N-carbonyldiimidazole were added and the mixture was stirred again at 100° C. overnight. The reaction mixture was purified directly by means of preparative HPLC (eluent: acetonitrile/water with 0.1% formic acid gradient). This gave 130 mg (56% of theory) of the title compound.

LC-MS (method 4): $R_t$=2.05 min; MS (ESIpos): m/z=485 [M+H]$^+$.

Example 124

7-(2-fluorobenzyl)-2-[1-(2-fluorobenzyl)-1H-pyrazolo[3,4-b]pyridin-3-yl]-7,9-dihydro-8H-purin-8-one

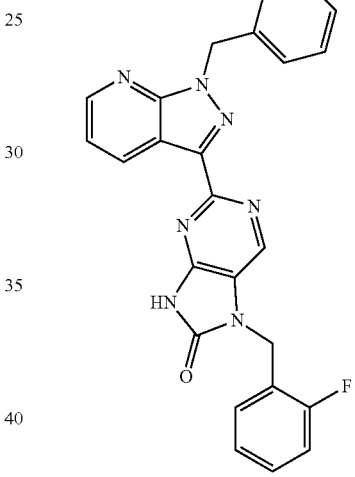

80 mg (0.17 mmol) of the compound from example 124 were initially charged in tetrahydrofuran (7 ml), then 0.16 ml (1.16 mmol) of isoamyl nitrite and 4 mg (0.03 mmol) of copper(II) chloride were added, and the mixture was stirred at RT overnight. The reaction mixture was admixed with saturated aqueous sodium hydrogencarbonate solution and extracted twice with ethyl acetate. The collected organic phases were dried over sodium sulfate, filtered and concentrated. The residue was purified by means of preparative HPLC (eluent: acetonitrile/water with 0.1% formic acid gradient). This gave 15 mg (19% of theory) of the title compound in solid form.

LC-MS (method 2): $R_t$=1.10 min

MS (ESIpos): m/z=470 (M+H)$^+$

¹H NMR (400 MHz, DMSO-d₆): δ [ppm]=5.16 (s, 2H), 5.83 (s, 2H), 7.12-7.18 (m, 1H), 7.19-7.28 (m, 4H), 7.32-7.42 (m, 4H), 8.40 (s, 1H), 8.64-8.67 (m, 1H), 8.84-8.88 (m, 1H), 12.35 (br. s, 1H).

Example 125

7-Cyclobutyl-2-[1-(2-fluorobenzyl)-1H-pyrazolo[3,4-b]pyridin-3-yl]-7,9-dihydro-8H-purin-8-one

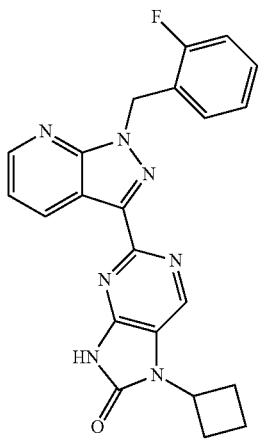 [SMILES: O=c1[nH]c2nc(-c3nn(Cc4ccccc4F)c4ncccc34)ncc2n1C1CCC1]

50 mg (0.12 mmol) of the compound from example 121 were initially charged in tetrahydrofuran (5 ml), then 0.11 ml (0.81 mmol) of isoamyl nitrite and 3 mg (0.02 mmol) of copper(II) chloride were added, and the mixture was stirred at RT overnight. The reaction mixture was admixed with saturated aqueous sodium hydrogencarbonate solution and extracted twice with ethyl acetate. The collected organic phases were dried over sodium sulfate, filtered and concentrated. The residue was purified by means of preparative HPLC (eluent: acetonitrile/water with 0.1% formic acid gradient). This gave 7 mg (13% of theory) of the title compound in solid form.

LC-MS (method 2): R$_t$=1.05 min

MS (ESIpos): m/z=416 (M+H)⁺

¹H NMR (400 MHz, DMSO-d₆): δ [ppm]=1.74-1.87 (m, 1H), 1.87-1.97 (m, 1H), 2.28-2.38 (m, 2H), 2.69-2.82 (m, 2H), 4.79-4.90 (m, 1H), 5.84 (s, 2H), 7.13-7.18 (m, 1H), 7.21-7.27 (m, 2H), 7.33-7.40 (m, 1H), 7.40-7.45 (m, 1H), 8.65-8.68 (m, 1H), 8.75 (s, 1H), 8.86-8.90 (m, 1H), 12.20 (br. s, 1H).

Example 126

6-Chloro-7-ethyl-2-[1-(2-fluorobenzyl)-1H-pyrazolo[3,4-b]pyridin-3-yl]-7,9-dihydro-8H-purin-8-one

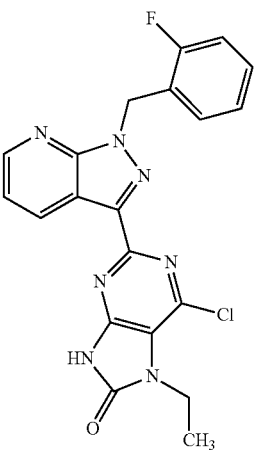 [SMILES: CCn1c(=O)[nH]c2nc(-c3nn(Cc4ccccc4F)c4ncccc34)nc(Cl)c21]

428 mg (1.06 mmol) of the compound from example 42 were initially charged in tetrahydrofuran (20 ml), then 1.0 ml (7.41 mmol) of isoamyl nitrite and 28 mg (0.21 mmol) of copper(II) chloride were added, and the mixture was stirred at RT overnight. Subsequently, another 1.0 ml (7.41 mmol) of isoamyl nitrite and 28 mg (0.21 mmol) of copper(II) chloride were added and stirring of the mixture continued at RT overnight. The reaction mixture was admixed with saturated aqueous sodium hydrogencarbonate solution and extracted twice with ethyl acetate. The collected organic phases were dried over sodium sulfate, filtered and concentrated. The residue was chromatographed on silica gel (eluent: dichloromethane/methanol 40:1, 20:1) and purified further by means of preparative HPLC (eluent: acetonitrile-water with 0.1% formic acid gradient). This gave 195 mg (57% purity, 25% of theory) of the title compound, which were converted without further purification.

LC-MS (method 3): R$_t$=1.23 min

MS (ESIpos): m/z=424 (M+H)⁺

Example 127

7-Ethyl-2-[1-(2-fluorobenzyl)-1H-pyrazolo[3,4-b]pyridin-3-yl]-7,9-dihydro-8H-purin-8-one

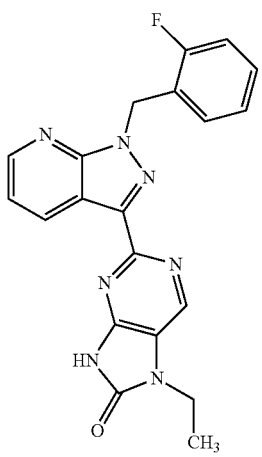 [SMILES: CCn1c(=O)[nH]c2nc(-c3nn(Cc4ccccc4F)c4ncccc34)ncc21]

195 mg (0.22 mmol) of the compound from example 126 were initially charged in pyridine (2.4 ml), then 24 mg (0.02 mmol) of palladium (10% on charcoal) were added and the mixture was hydrogenated at RT under standard hydrogen pressure overnight. The reaction mixture was filtered through Celite, the filtercake was washed with methanol, and the filtrate was concentrated. The residue was taken up again in pyridine (5.0 ml), 59 mg (0.06 mmol) of palladium (10% on charcoal) were added and the mixture was hydrogenated at RT under standard hydrogen pressure overnight. Thereafter, the reaction mixture was filtered through Celite, the filter residue was washed with methanol, and the filtrate was concentrated. The residue was separated by means of preparative HPLC (eluent: acetonitrile-water with 0.1% formic acid gradient) and the product fractions were concentrated. The crude product thus obtained was stirred with dichloromethane, and the solids were filtered off and dried under high vacuum. This gave 18 mg (21% of theory) of the title compound in solid form.

LC-MS (method 2): $R_t$=0.95 min
MS (ESIpos): m/z=390 (M+H)$^+$ $^1$H NMR (400 MHz, DMSO-d$_6$): δ [ppm]=1.28 (t, 3H), 3.90 (q, 2H), 5.83 (s, 2H), 7.12-7.29 (m, 3H), 7.32-7.46 (m, 2H), 8.58 (s, 1H), 8.63-8.69 (m, 1H), 8.88 (d, 1H), 12.11 (br. s, 1H).

Example 128

6-[1-(2-Fluorobenzyl)-1H-pyrazolo[3,4-b]pyridin-3-yl]-2H-pyrazolo[3,4-b]pyrazin-3-ol

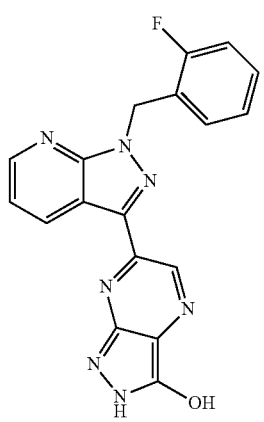 [SMILES: Oc1[nH]nc2nc(-c3nn(Cc4ccccc4F)c4ncccc34)cnc12]

500 mg (1.291 mmol) of the compound from example 68A were admixed with 7 ml of acetic acid and 273 mg (1.291 mmol) of 3,4-diamino-1H-pyrazol-5-ol sulfate. The mixture was stirred at RT for 16 h and then concentrated on a rotary evaporator. Water and ethyl acetate were added, and the mixture was stirred. The organic phase was removed and extracted once with a 1N sodium hydroxide solution, dried over sodium sulfate and concentrated on a rotary evaporator. The residue was purified by preparative HPLC (eluent: water/acetonitrile/water with 1% trifluoroacetic acid, ratio 80:15:5). 142 mg of the title compound were obtained (29% of theory).

LC-MS (method 3): $R_t$=1.03 min; MS (EIpos): m/z=362 (M+H)$^+$.

$^1$H NMR (400 MHz, DMSO-d$_6$): δ [ppm]=5.86 (s, 2H), 7.14-7.18 (m, 1H), 7.23-7.28 (m, 2H), 7.33-7.39 (m, 1H), 7.45 (dd, 1H), 8.70 (dd, 1H), 9.04 (dd, 1H), 9.20 (s, 1H), 11.39 (s br, 1H), 12.83 (s, 1H).

Example 129

2-[1-(2-Fluorobenzyl)-1H-pyrazolo[3,4-b]pyridin-3-yl]-6-iodo-7-methyl-7,9-dihydro-8H-purin-8-one

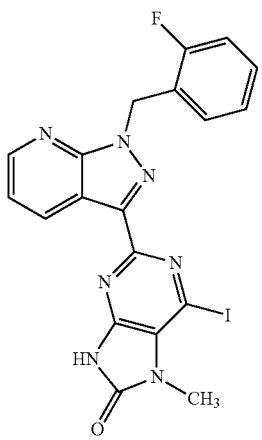 [SMILES: Cn1c(=O)[nH]c2nc(-c3nn(Cc4ccccc4F)c4ncccc34)nc(I)c21]

1.725 g (3.358 mmol) of the compound from example 41 were dissolved in 7 ml of diiodomethane and admixed with 7.19 ml (53.732 mmol) of isopentyl nitrite. The reaction mixture was heated to 85° C. for 16 h and, after cooling, concentrated on a rotary evaporator. The residue was by means of preparative HPLC (eluent: water/acetonitrile/water with 1% trifluoroacetic acid, gradient 55:40:5→0:95:5). 64 mg of the title compound were obtained (4% of theory).

LC-MS (method 3): R$_t$=1.22 min; MS (EIpos): m/z=502 (M+H)$^+$.

$^1$H NMR (400 MHz, DMSO-d$_6$): δ [ppm]=3.54 (s, 3H), 5.85 (s, 2H) 7.13-7.17 (m, 1H), 7.17-7.26 (m, 2H), 7.34-7.39 (m, 1H), 7.46 (dd, 1H), 8.68 (dd, 1H), 8.80 (dd, 1H), 12.41 (s, 1H).

Example 130

2-[1-(2-Fluorobenzyl)-1H-pyrazolo[3,4-b]pyridin-3-yl]-7-methyl-7,9-dihydro-8H-purin-8-one

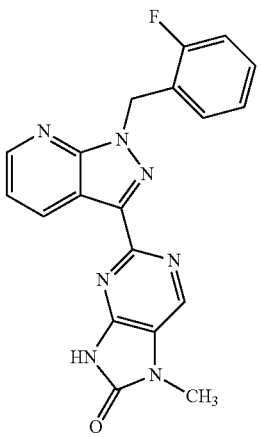 [SMILES: Cn1c(=O)[nH]c2nc(-c3nn(Cc4ccccc4F)c4ncccc34)ncc21]

Under an argon atmosphere, 225 mg (approx. 0.112 mmol) of the compound from example 107 were dissolved in 15 ml of dimethylformamide, admixed with 150 mg of 10% palladium on charcoal and hydrogenated under standard hydrogen pressure overnight. The reaction mixture was filtered through Celite and concentrated, and the residue was purified by means of preparative HPLC (eluent: water/acetonitrile/water with 1% trifluoroacetic acid, gradient 60:35:5→35:60:5). 33 mg of the title compound were obtained (76% of theory).

LC-MS (method 2): R$_t$=0.88 min; MS (EIpos): m/z=376 (M+H)$^+$.

¹H NMR (400 MHz, DMSO-d₆): δ [ppm]=3.38 (s, 3H), 5.84 (s, 2H) 7.13-7.17 (m, 1H), 7.21-7.26 (m, 2H), 7.34-7.39 (m, 1H), 7.42 (dd, 1H), 8.53 (s, 1H), 8.66 (dd, 1H), 8.88 (dd, 1H), 12.21 (s, 1H).

Example 131

2-[5-Fluoro-1-(2-fluorobenzyl)-1H-pyrazolo[3,4-b]pyridin-3-yl]-6-iodo-7-(2,2,2-trifluoro ethyl)-7,9-dihydro-8H-purin-8-one

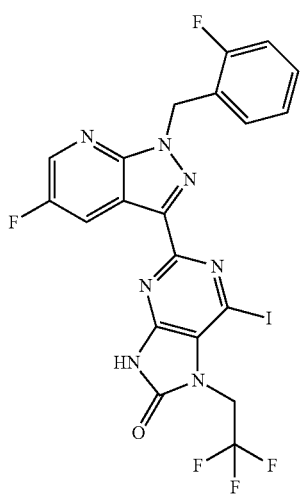 [SMILES: O=c1[nH]c2nc(-c3nn(Cc4ccccc4F)c4ncc(F)cc34)nc(I)c2n1CC(F)(F)F]

4.650 g (5.954 mmol) of the compound from example 62 were dissolved in 12 ml of diiodomethane and admixed with 12.76 ml (95.270 mmol) of isopentyl nitrite. The reaction mixture was heated to 85° C. for 16 h and, after cooling, concentrated on a rotary evaporator. 5 g of the crude product (purity 54%) were obtained. 1.2 g of the residue were by means of preparative HPLC (eluent: acetonitrile/water with 0.05% formic acid, gradient 40:60→95:5). 128 mg of the title compound were obtained (15% of theory).

LC-MS (method 2): R$_t$=1.23 min; MS (EIpos): m/z=588 (M+H)⁺.

¹H NMR (400 MHz, DMSO-d₆): δ [ppm]=4.95 (q, 2H), 5.86 (s, 2H), 7.14-7.18 (m, 1H), 7.21-7.27 (m, 2H), 7.35-7.41 (m, 1H), 8.47 (dd, 1H), 8.76 (dd, 1H), 12.79 (s, 1H).

Example 132

2-[5-Fluoro-1-(2-fluorobenzyl)-1H-pyrazolo[3,4-b]pyridin-3-yl]-7-(2,2,2-trifluoro ethyl)-7,9-dihydro-8H-purin-8-one

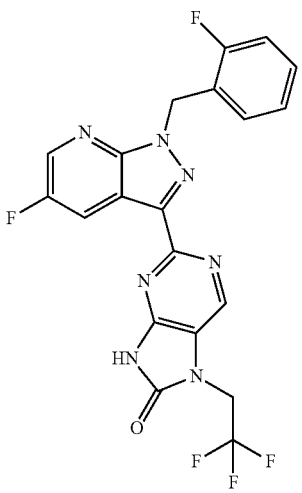 [SMILES: O=c1[nH]c2nc(-c3nn(Cc4ccccc4F)c4ncc(F)cc34)ncc2n1CC(F)(F)F]

Under an argon atmosphere, 161 mg (0.275 mmol) of the compound from example 131 were dissolved in 15 ml of dimethylformamide, admixed with 100 mg of 10% palladium on charcoal and hydrogenated under standard hydrogen pressure overnight. The reaction mixture was filtered through Celite and concentrated, and the residue was purified by means of preparative HPLC (eluent: water/acetonitrile/water with 1% trifluoroacetic acid, gradient 65:30:5→0:95:5). 41 mg of the title compound were obtained (33% of theory).

LC-MS (method 2): R$_t$=1.08 min; MS (EIpos): m/z=462 (M+H)⁺.

¹H NMR (400 MHz, DMSO-d₆): δ [ppm]=4.87 (q, 2H), 5.84 (s, 2H) 7.15-7.19 (m, 1H), 7.21-7.30 (m, 2H), 7.35-7.41 (m, 1H), 8.60 (dd, 1H), 8.64 (s, 1H), 8.74 (dd, 1H), 12.53 (s, 1H).

Example 133

5-[1-(2-Fluorobenzyl)-1H-pyrazolo[3,4-b]pyridin-3-yl]-3H-[1,2,3]triazolo[4,5-d]pyrimidine

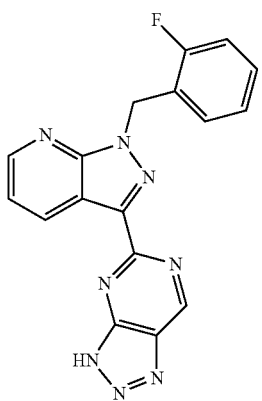 [SMILES: Fc1ccccc1Cn1nc(-c2ncc3nn[nH]c3n2)c2cccnc21]

570 mg (5.535 mmol) of tert-butyl nitrite were dissolved in 20 ml of dry dimethylformamide, and 1000 mg (2.767 mmol) of the compound from example 53 suspended in 15 ml of dimethylformamide were added at 65° C. by means of a syringe pump within 1 h. After stirring at 65° C. for a further hour, 100 ml of water were added, forming a precipitate. The precipitate was filtered off and purified by means of preparative HPLC (eluent: water/acetonitrile/water with 1% trifluoroacetic acid, gradient 64:20:16→0:100:0). 10 mg of the title compound were obtained (1% of theory).

LC-MS (method 3): $R_t$=1.02 min; MS (EIpos): m/z=347 (M+H)⁺.

Example 134

6-Acetyl-2-[1-(2-fluorobenzyl)-1H-pyrazolo[3,4-b]pyridin-3-yl]-7-methyl-7,9-dihydro-8H-purin-8-one

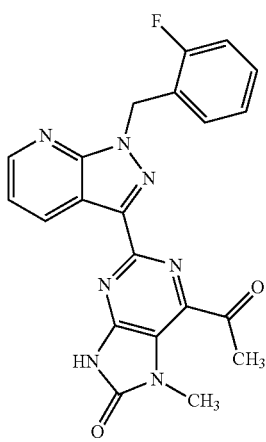 [SMILES: CC(=O)c1nc(-c2nn(Cc3ccccc3F)c3ncccc23)nc2[nH]c(=O)n(C)c12]

1.20 g (1.798 mmol, 60% purity) of the compound obtained in example 110 in tetrahydrofuran (70 ml) were admixed with 2.997 ml (8.992 mmol) of methylmagnesium bromide (3.0 M in diethyl ether) and heated to reflux for 7 h. After cooling, first ice and then 4N hydrochloric acid (20 ml) were added and the mixture was stirred vigorously. The mixture was then extracted three times with ethyl acetate and the combined organic phases were washed with saturated aqueous sodium chloride solution. After drying over sodium sulfate, the mixture was filtered and concentrated, and the residue was purified by means of preparative HPLC (acetonitrile:water (+0.05% formic acid) gradient). 236 mg of the title compound were obtained (31% of theory).

LC-MS (method 2): $R_t$=1.05 min; MS (EIpos): m/z=418 (M+H)⁺.

¹H NMR (400 MHz, DMSO-d₆): δ [ppm]=2.84 (s, 3H), 3.45 (s, 3H), 5.86 (s, 2H), 7.15 (t, 1H), 7.21-7.26 (m, 2H), 7.34-7.38 (m, 1H), 7.46 (dd, 1H), 8.68 (dd, 1H), 8.91 (dd, 1H), 12.62 (s br, 1H).

Example 135

2-[1-(2-Fluorobenzyl)-1H-pyrazolo[3,4-b]pyridin-3-yl]-6-(3-hydroxy-3-methylbut-1-yn-1-yl)-7-methyl-7,9-dihydro-8H-purin-8-one

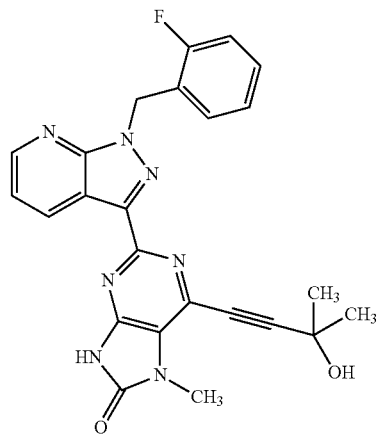 [SMILES: Cn1c(=O)[nH]c2nc(-c3nn(Cc4ccccc4F)c4ncccc34)nc(C#CC(C)(C)O)c21]

0.5 g (0.997 mmol) of the compound obtained in example 107 in tetrahydrofuran (10 ml) was admixed under argon with 251 mg (2.992 mmol) of 2-methyl-3-butyn-2-ol, 0.419 ml (2.992 mmol) of diisopropylamine, 57 mg (0.299 mmol) of copper(I) iodide and 140 mg (0.199 mmol) of dichlorobis(triphenylphosphine)palladium(II). Subsequently, the mixture was stirred at RT overnight and then heated to reflux for 10 h. After cooling, the mixture was filtered. The filtrate was concentrated, slurried in acetonitrile, water and a small amount of dimethylformamide, and filtered once again. The filtrate thus obtained was admixed with ethyl acetate and cyclohexane and stirred briefly, the precipitated residue was filtered off, and the filtrate was concentrated and purified by means of preparative HPLC (acetonitrile: water+5% trifluoroacetic acid)–gradient. 110 mg of the title compound were obtained (23% of theory).

LC-MS (method 2): $R_t$=0.94 min; MS (EIpos): m/z=458 (M+H)⁺.

¹H NMR (400 MHz, DMSO-d₆): δ [ppm]=1.55 (s, 6H), 3.56 (s, 3H), 5.80 (s, 1H), 5.84 (s, 2H), 7.15 (t, 1H), 7.21-7.26 (m, 2H), 7.34-7.39 (m, 1H), 7.44 (dd, 1H), 8.67 (dd, 1H), 8.82 (dd, 1H), 12.36 (s br, 1H).

Example 136

2-[1-(2-Fluorobenzyl)-1H-pyrazolo[3,4-b]pyridin-3-yl]-6-(2-hydroxypropan-2-yl)-7-methyl-7,9-dihydro-8H-purin-8-one ¹H NMR (400 MHz, DMSO-d₆): δ [ppm]=1.70 (s, 6H), 3.69 (s, 3H), 5.78 (s, 1H), 5.84 (s, 2H), 7.15 (t, 1H), 7.19-7.25 (m, 2H), 7.33-7.39 (m, 1H), 7.44 (dd, 1H), 8.66 (dd, 1H), 8.86 (dd, 1H), 12.26 (s br, 1H).

Example 137

2-[1-(2-Fluorobenzyl)-1H-pyrazolo[3,4-b]pyridin-3-yl]-7-(2-methoxyethyl)-7,9-dihydro-8H-purin-8-one

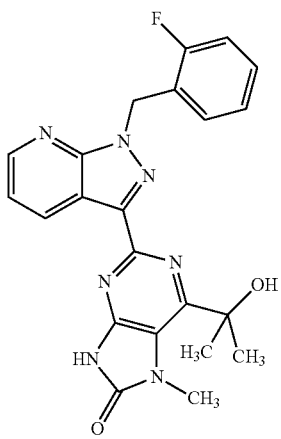 [SMILES: Cn1c(=O)[nH]c2nc(-c3nn(Cc4ccccc4F)c4ncccc34)nc(C(C)(C)O)c21]

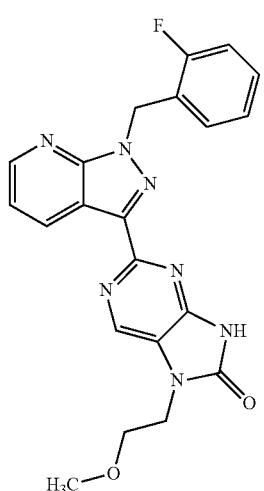 [SMILES: COCCn1c(=O)[nH]c2nc(-c3nn(Cc4ccccc4F)c4ncccc34)ncc21]

237 mg (0.568 mmol) of the compound obtained in example 134 in tetrahydrofuran were cooled to 0° C. and admixed with 0.568 ml of a 3M solution of methylmagnesium bromide in diethyl ether, and the mixture was stirred at this temperature for 1 h and then at RT overnight. Then 2 portions, each of 0.379 ml, of a 3M solution of methylmagnesium bromide in diethyl ether were added and the mixture was stirred at RT for a further night. After cooling, first ice and then 4N hydrochloric acid (20 ml) were added and the mixture was stirred vigorously. The mixture was then extracted three times with ethyl acetate and the combined organic phases were washed with saturated aqueous sodium chloride solution. After drying over sodium sulfate, the mixture was filtered and concentrated, and the residue was purified by means of preparative HPLC (acetonitrile:water (+0.05% formic acid) gradient). 29 mg of the title compound were obtained (10% of theory).

LC-MS (method 3): $R_t$=1.09 min; MS (EIpos): m/z=434 (M+H)⁺.

317 mg (0.501 mmol) of the compound from example 83A were dissolved in 15 ml of trifluoroacetic acid, 582 mg (5.009 mmol) of triethylsilane were added and the mixture was heated to reflux for 18 h. The reaction mixture was partitioned between water and ethyl acetate, and neutralized with saturated aqueous sodium hydrogencarbonate solution. The organic phase was dried over sodium sulfate and concentrated on a rotary evaporator. The residue was dried under high vacuum. and purified by means of preparative HPLC (eluent: methanol/water with 0.1% trifluoroacetic acid, gradient 30:70→90:10). 167 mg of the title compound were obtained (79% of theory).

LC-MS (method 3): $R_t$=1.07 min; MS (ESIpos): m/z=420 (M+H)⁺

¹H NMR (400 MHz, DMSO-d₆): δ [ppm]=3.26 (s, 3H), 3.64 (t, 2H), 4.05 (t, 2H), 5.84 (s, 2H), 7.15 (dt, 1H), 7.21-7.26

(m, 2H), 7.34-7.40 (m, 1H), 7.42 (dd, 1H), 8.55 (s, 1H), 8.66 (dd, 1H), 8.88 (dd, 1H), 12.25 (s br, 1H).

Example 138

6-[1-(2-Fluorobenzyl)-1H-pyrazolo[3,4-b]pyridin-3-yl]-1,2,3,4-tetrahydropyrido[2,3-b]pyrazine

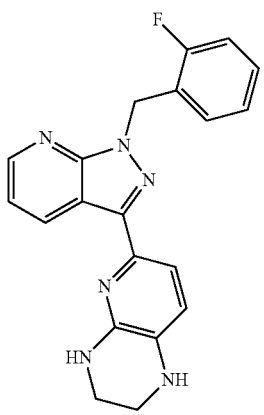 [SMILES: Fc1ccccc1Cn1nc(-c2ccc3c(n2)NCCN3)c2cccnc21]

80 mg (0.22 mmol) of the compound from example 68 were initially charged in methanol (4 ml), then 12 mg (0.045 mmol) of platinum(IV) oxide were added and the reaction mixture was hydrogenated at standard pressure overnight. The reaction mixture was filtered through Celite and the filtercake was washed with methanol. The filtrate was concentrated to give 79 mg (92% purity, 90% of theory) of the title compound, which were converted without further purification.

LC-MS (method 2): $R_t$=0.79 min
MS (ESIpos): m/z=361 (M+H)$^+$.

Example 139

7-(Cyclopropylmethyl)-2-[1-(2-fluorobenzyl)-1H-pyrazolo[3,4-b]pyridin-3-yl]-7,9-dihydro-8H-purin-8-one

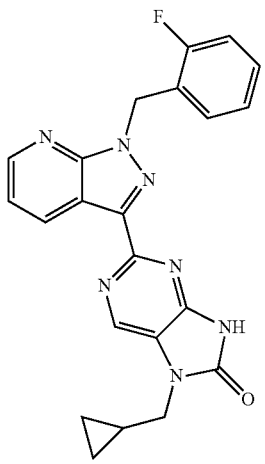 [SMILES: O=c1[nH]c2nc(-c3nn(Cc4ccccc4F)c4ncccc34)ncc2n1CC1CC1]

482 mg (0.70 mmol) of the compound from example 84A were dissolved in 21 ml of trifluoroacetic acid, 817 mg (7.02 mmol) of triethylsilane were added and the mixture was heated to reflux for 18 h. The reaction mixture was admixed with water and ethyl acetate, and neutralized with saturated aqueous sodium hydrogencarbonate solution. The organic phase was dried over sodium sulfate and concentrated on a rotary evaporator. The residue was dried under high vacuum, and purified by means of preparative HPLC (eluent: methanol/water with 0.1% trifluoroacetic acid, gradient 30:70→90:10). 156 mg of the title compound were obtained (53% of theory).

LC-MS (method 2): $R_t$=1.02 min; MS (ESIpos): m/z=416 (M+H)$^+$ $^1$H NMR (400 MHz, DMSO-d$_6$): δ [ppm]=0.40-0.44 (m, 2H), 0.50-0.55 (m, 2H), 1.20-1.27 (m, 1H), 3.76 (d, 2H), 5.84 (s, 2H), 7.16 (t, 1H), 7.21-7.27 (m, 2H), 7.34-7.40 (m, 1H), 7.42 (dd, 1H), 8.65 (s, 1H), 8.66 (dd, 1H), 8.88 (dd, 1H), 12.24 (s br, 1H).

Example 140

2-[1-(2-Fluorobenzyl)-1H-pyrazolo[3,4-b]pyridin-3-yl]-7-(2,2,3,3,3-pentafluoropropyl)-7,9-dihydro-8H-purin-8-one

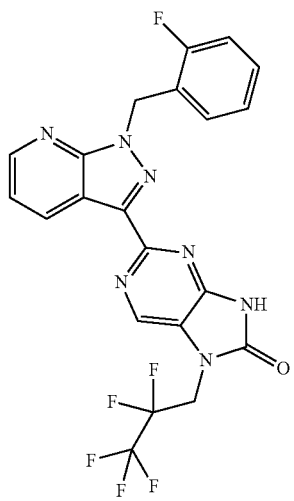 [SMILES: O=c1[nH]c2nc(-c3nn(Cc4ccccc4F)c4ncccc34)ncc2n1CC(F)(F)C(F)(F)F]

471 mg (0.60 mmol) of the compound from example 85A were dissolved in 15 ml of trifluoroacetic acid, 698 mg (6.01 mmol) of triethylsilane were added and the mixture was heated to reflux for 18 h. The reaction mixture was admixed with water and ethyl acetate, and neutralized with saturated aqueous sodium hydrogencarbonate solution. The organic phase was dried over sodium sulfate and concentrated on a rotary evaporator. The residue was dried under high vacuum, and purified by means of preparative HPLC (eluent: methanol/water with 0.1% trifluoroacetic acid, gradient 30:70→90:10). 252 mg of the title compound were obtained (85% of theory).

LC-MS (method 3): $R_t$=1.29 min; MS (ESIpos): m/z=494 (M+H)$^+$ $^1$H NMR (400 MHz, DMSO-d$_6$): δ [ppm]=4.92 (t, 2H), 5.85 (s, 2H), 7.16 (dt, 1H), 7.21-7.26 (m, 2H), 7.34-7.40 (m, 1H), 7.43 (dd, 1H), 8.63 (s, 1H), 8.67 (dd, 1H), 8.88 (dd, 1H), 12.60 (s br, 1H).

Example 141

2-[1-(2-Fluorobenzyl)-1H-pyrazolo[3,4-b]pyridin-3-yl]-7-(oxetan-2-ylmethyl)-7,9-dihydro-8H-purin-8-one

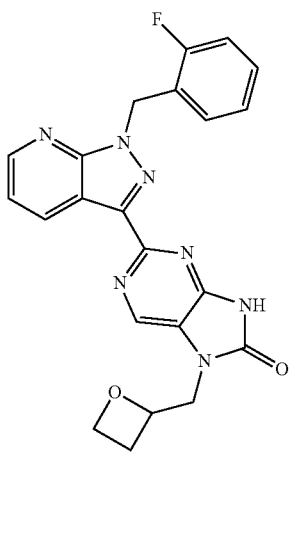 [SMILES: O=c1[nH]c2nc(-c3nn(Cc4ccccc4F)c4ncccc34)ncc2n1CC1CCO1]

476 mg (0.82 mmol) of the compound from example 86A were dissolved in 15 ml of trifluoroacetic acid, 953 mg (8.20 mmol) of triethylsilane were added and the mixture was heated to reflux for 18 h. The reaction mixture was admixed with water and ethyl acetate, and neutralized with saturated aqueous sodium hydrogencarbonate solution. The organic phase was dried over sodium sulfate and concentrated on a rotary evaporator. The residue was dried under high vacuum, and purified by means of preparative HPLC (eluent: methanol/water with 0.1% trifluoroacetic acid, gradient 30:70→90:10). 173 mg of the title compound were obtained (49% of theory).

LC-MS (method 2): R$_t$=0.91 min; MS (ESIpos): m/z=432 (M+H)$^+$ $^1$H NMR (400 MHz, DMSO-d$_6$): δ [ppm]=2.09-2.18 (m, 1H), 2.37-4.46 (m, 1H), 3.71 (q, 1H), 3.85 (dd, 1H), 4.07 (dd, 1H), 4.20-4.25 (m, 1H), 5.09-5.15 (m, 1H), 5.84 (dt, 1H), 5.84 (s, 2H), 7.15 (dt, 1H), 7.21-7.26 (m, 2H), 7.34-7.39 (m, 1H), 7.42 (dd, 1H), 8.51 (s, 1H), 8.66 (dd, 1H), 8.89 (dd, 1H), 12.27 (s br, 1H).

Example 142

2-[1-(2-Fluorobenzyl)-1H-pyrazolo[3,4-b]pyridin-3-yl]-7-[2-(morpholin-4-yl)ethyl]-7,9-dihydro-8H-purin-8-one

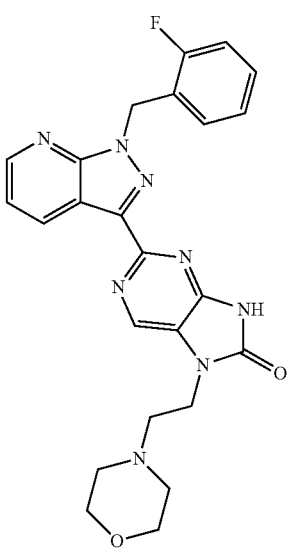 [SMILES: O=c1[nH]c2nc(-c3nn(Cc4ccccc4F)c4ncccc34)ncc2n1CCN1CCOCC1]

101 mg (0.16 mmol) of the compound from example 87A were dissolved in 10 ml of trifluoroacetic acid, 188 mg (1.62 mmol) of triethylsilane were added and the mixture was heated to reflux for 18 h. The reaction mixture was admixed with water and ethyl acetate, and neutralized with saturated aqueous sodium hydrogencarbonate solution. The organic phase was dried over sodium sulfate and concentrated on a rotary evaporator. The residue was dried under high vacuum, and purified by means of preparative HPLC (eluent: methanol/water with 0.1% trifluoroacetic acid, gradient 30:70→90:10). 53 mg of the title compound were obtained (69% of theory).

LC-MS (method 2): R$_t$=0.72 min; MS (ESIpos): m/z=475 (M+H)$^+$

¹H NMR (400 MHz, DMSO-d₆): δ [ppm]=3.19-4.30 (m, 12H), 5.85 (s, 2H), 7.16 (t, 1H), 7.22-7.28 (m, 2H), 7.35-7.40 (m, 1H), 7.44 (dd, 1H), 8.67 (s, 1H), 8.68 (dd, 1H), 8.88 (dd, 1H), 12.40 (s br, 1H).

Example 143

2-[1-(2-Fluorobenzyl)-1H-pyrazolo[3,4-b]pyridin-3-yl]-7-[1-(2,2,2-trifluoroethyl)piperidin-4-yl]-7,9-dihydro-8H-purin-8-one

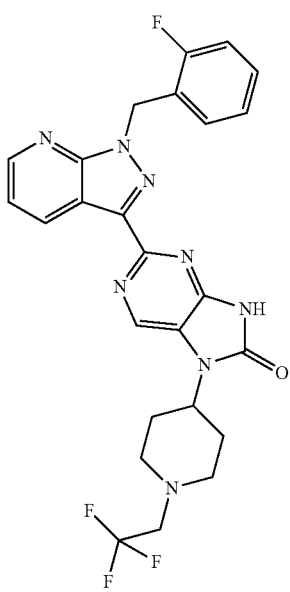 [SMILES: O=c1[nH]c2nc(-c3nn(Cc4ccccc4F)c4ncccc34)ncc2n1C1CCN(CC(F)(F)F)CC1]

30 mg (0.06 mmol) of example 88A were initially charged in acetonitrile (5 ml) and admixed with 12.6 mg (0.078 mmol) of N,N'-carbonyldiimidazole, and then heated to reflux for 4 h. In parallel, 70 mg (0.14 mmol) of example 88A were initially charged in acetonitrile (10 ml) and admixed with 29.5 mg (0.182 mmol) of N,N'-carbonyldiimidazole, and then heated to reflux for 4 h. The two mixtures were then combined, freed of the solvent and then treated with a little acetonitrile. A solid separated out, which was filtered off and washed with a little acetonitrile. After drying under high vacuum, 17 mg of the title compound were obtained (23% of theory).

LC-MS (method 2): R$_t$=1.04 min; MS (EIpos): m/z=527 [M+H]⁺.

¹H NMR (400 MHz, DMSO-d₆): δ [ppm]=1.76-1.79 (m, 2H), 2.24-2.33 (m, 2H), 3.06 (d, 2H), 4.19-4.25 (m, 1H), 5.84 (s, 2H), 7.15 (t, 1H), 7.21-7.26 (m, 2H), 7.34-7.39 (m, 1H), 7.42 (dd, 1H), 8.65-8.67 (m, 2H), 8.87 (d, 1H), 12.24 (s br, 1H), 4H under solvent peak.

Example 144

2-[1-(2-Fluorobenzyl)-1H-pyrazolo[3,4-b]pyridin-3-yl]-7-[1-(2,2,2-trifluoroethyl)pyrrolidin-3-yl]-7,9-dihydro-8H-purin-8-one

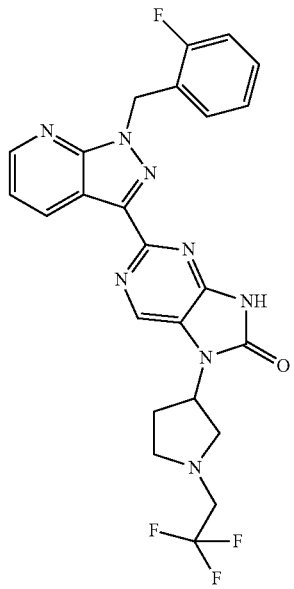 [SMILES: O=c1[nH]c2nc(-c3nn(Cc4ccccc4F)c4ncccc34)ncc2n1C1CCN(CC(F)(F)F)C1]

240 mg (0.493 mmol) of Example 89A were converted in analogy to the method in Example 143. After purification by means of preparative HPLC (acetonitrile:water (+0.05% formic acid) gradient), this gave 73 mg of the title compound (29% of theory).

LC-MS (method 2): R$_t$=1.11 min; MS (EIpos): m/z=513 (M+H)⁺.

¹H NMR (400 MHz, DMSO-d₆): δ [ppm]=2.00-2.08 (m, 1H), 2.30-2.35 (m, 1H), 2.87 (dd, 1H), 3.18 (dd, 1H), 5.03-5.09 (m, 1H), 5.84 (s, 2H), 7.15 (t, 1H), 7.20-7.26 (m, 2H), 7.34-7.39 (m, 1H), 7.43 (dd, 1H), 8.66 (dd, 1H), 8.78 (s, 1H), 8.86 (dd, 1H), 12.22 (s br, 1H), 4H under solvent peak.

Example 145

7-[1-(2,2-Difluoroethyl)piperidin-4-yl]-2-[1-(2-fluorobenzyl)-1H-pyrazolo[3,4-b]pyridin-3-yl]-7,9-dihydro-8H-purin-8-one

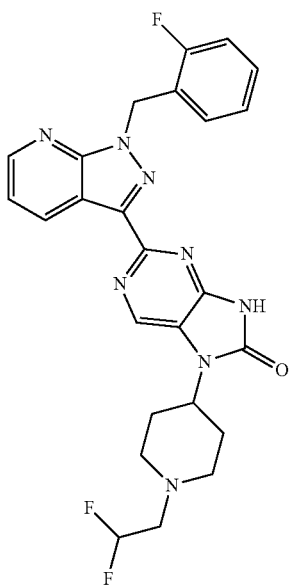 [SMILES: O=c1[nH]c2nc(-c3nn(Cc4ccccc4F)c4ncccc34)ncc2n1C1CCN(CC(F)F)CC1]

110 mg (0.228 mmol) of Example 90A were converted in analogy to the method in Example 143. After purification by means of preparative HPLC (acetonitrile:water (+0.05% formic acid) gradient), this gave 18 mg of the title compound (15% of theory, 94% purity).

LC-MS (method 2): $R_t$=0.81 min; MS (EIpos): m/z=509 [M+H]$^+$.

$^1$H NMR (400 MHz, DMSO-d$_6$): δ [ppm]=2.01 (m, 2H), 4.48 (m, 1H), 5.84 (s, 2H), 6.30-6.70 (m, 1H), 7.15 (t, 1H), 7.22-7.26 (m, 2H), 7.34-7.40 (m, 1H), 7.43 (dd, 1H), 8.67 (m, 2H), 8.86 (d, 1H), 12.32 (s br, 1H), 8H under solvent peak.

Example 146

2-[5-Fluoro-1-(2-fluorobenzyl)-1H-pyrazolo[3,4-b]pyridin-3-yl]-7-[2-(methylsulfonyl)ethyl]-7,9-dihydro-8H-purin-8-one

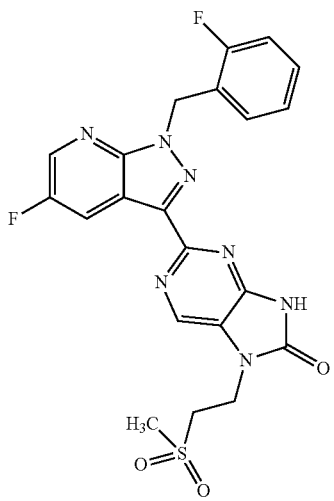 [SMILES: CS(=O)(=O)CCn1c(=O)[nH]c2nc(-c3nn(Cc4ccccc4F)c4ncc(F)cc34)ncc21]

490 mg (0.567 mmol, 73% purity) of the compound from example 94A were converted in analogy to the method in example 142. 89 mg (30% of theory, 95% purity) of the title compound were obtained.

LC-MS (method 2): $R_t$=0.86 min; MS (EIpos): m/z=486 [M+H]$^+$.

$^1$H NMR (400 MHz, DMSO-d$_6$): δ [ppm]=3.09 (s, 3H), 3.64 (t, 2H), 4.33 (t, 2H), 5.84 (s, 2H), 7.16 (t, 1H), 7.21-7.29 (m, 2H), 7.35-7.40 (m, 1H), 8.58 (dd, 1H), 8.62 (s, 1H), 8.74 (dd, 1H), 12.30 (s br, 1H).

Example 147

7-(Azetidin-3-yl)-2-[1-(2-fluorobenzyl)-1H-pyrazolo[3,4-b]pyridin-3-yl]-7,9-dihydro-8H-purin-8-one hydrochloride

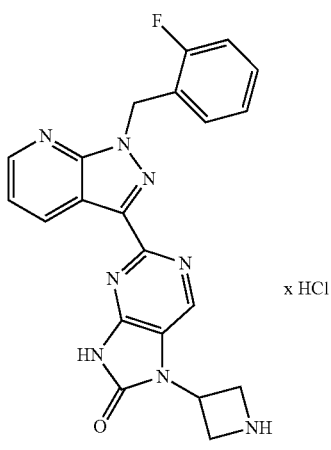 [SMILES: O=c1[nH]c2nc(-c3nn(Cc4ccccc4F)c4ncccc34)ncc2n1C1CNC1]

579 mg (approx. 0.887 mmol, 79% purity) of the compound from example 98A were dissolved 10 ml of dioxane and then admixed with 4 ml of a 4N solution of hydrogen chloride in dioxane and stirred at RT for 0.5 h. This was followed by concentration to dryness. After purification by means of preparative HPLC (acetonitrile:water (+0.05% formic acid) gradient), this gave 168 mg (41% of theory) of the title compound.

LC-MS (method 2): R$_t$=0.66 min; MS (EIpos): m/z=417 [M+H]$^+$.

$^1$H NMR (400 MHz, DMSO-d$_6$): δ [ppm]=4.03 (t, 2H), 4.23 (t, 2H), 5.21-5.29 (m, 1H), 5.84 (s, 2H), 7.16 (t, 1H), 7.22-7.26 (m, 2H), 7.34-7.40 (m, 1H), 7.42 (dd, 1H), 8.22 (s, 1H), 8.66 (dd, 1H), 8.88 (dd, 1H), 8.90 (s, 1H).

Example 148

5-[5-Fluoro-1-(2-fluorobenzyl)-1H-pyrazolo[3,4-b]pyridin-3-yl]-1-methyl-1,3-dihydro[1,2,5]thiadiazolo[3,4-d]pyrimidine 2,2-dioxide

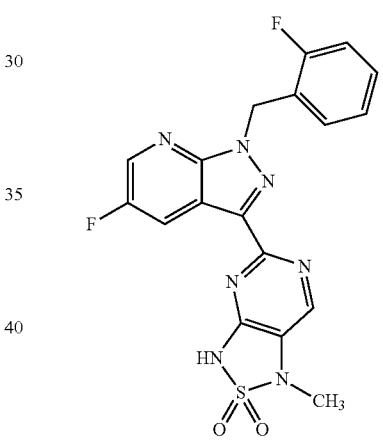

28 mg (0.050 mmol) of the compound from example 100A were dissolved in 1.5 ml of trifluoroacetic acid and then admixed with 79 μl (0.495 mmol) of triethylsilane, and the mixture was heated to reflux overnight. This was followed by concentration to dryness. After purification by means of preparative HPLC (acetonitrile:water (+0.05% formic acid) gradient), this gave 10.4 mg (48% of theory) of the title compound.

LC-MS (method 2): R$_t$=0.92 min; MS (EIpos): m/z=430 [M+H]$^+$.

$^1$H NMR (400 MHz, DMSO-d$_6$): δ [ppm]=3.24 (s, 3H), 5.91 (s, 2H), 7.16 (t, 1H), 7.22-7.28 (m, 2H), 7.35-7.40 (m, 1H), 7.49 (s, 1H), 8.48 (dd, 1H), 8.83 (dd, 1H), 13.80 (s br, 1H).

$^1$H NMR (400 MHz, DMSO-d$_6$): δ [ppm]=4.72 (q, 2H), 5.91 (s, 2H), 7.17 (t, 1H), 7.21-7.31 (m, 2H), 7.38 (m, 1H), 7.52 (dd, 1H), 8.73 (dd, 1H), 9.07 (dd, 1H), 9.28 (s, 1H), 12.86 (s, 1H).

Example 149

7-[1-(2-Fluorobenzyl)-1H-pyrazolo[3,4-b]pyridin-3-yl]-3-(2,2,2-trifluoroethyl)pyrimido[4,5-d]pyrimidine-2,4(1H,3H)-dione Example 150

7-[1-(2-Fluorobenzyl)-1H-pyrazolo[3,4-b]pyridin-3-yl]pyrimido[4,5-d]pyrimidine-2,4(1H,3H)-dione

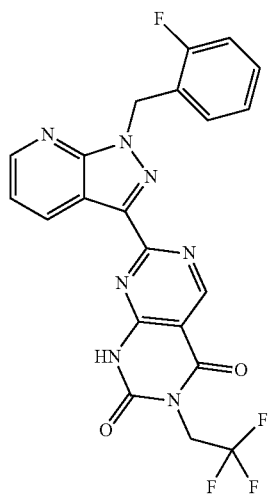 [SMILES: O=c1[nH]c2nc(-c3nn(Cc4ccccc4F)c4ncccc34)ncc2c(=O)n1CC(F)(F)F]

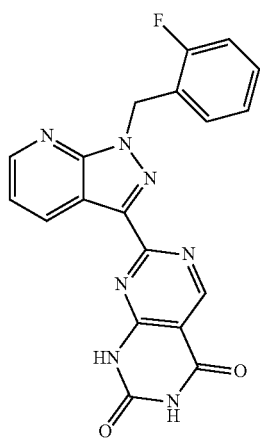 [SMILES: O=c1[nH]c(=O)c2cnc(-c3nn(Cc4ccccc4F)c4ncccc34)nc2[nH]1]

50 mg (0.11 mmol) of 4-amino-2-[1-(2-fluorobenzyl)-1H-pyrazolo[3,4-b]pyridin-3-yl]-N-(2,2,2-trifluoroethyl)pyrimidine-5-carboxamide (example 103A) were initially charged in 5 ml of THF and, while cooling with ice, 18.0 mg (0.45 mmol) of sodium hydride (60% in mineral oil) were added over a period of 5 min. The mixture was stirred for 25 min, then 27.3 mg (0.17 mmol) of 1,1'-carbonyldiimidazole were added with ice cooling over 5 min. Conversion was effected at room temperature for 1 h and at reflux temperature for 90 min. After cooling, the mixture was hydrolyzed and then the organic phase was diluted with 10 ml of THF. After drying with sodium sulfate, the volatile components were removed by means of a rotary evaporator. Then the crude material was purified by means of preparative HPLC [column: Reprosil C18, 10 μm, 250*30 mm; flow rate: 40 ml/min; eluent: methanol/0.05% formic acid; gradient: 50% methanol→95% methanol]. The volatile components of the product fractions were removed on the rotary evaporator. Thus, 26 mg (48% of theory) of the target compound were obtained.

LC-MS (method 2): R$_t$=1.02 min; MS (ESIpos): m/z=472 (M+H)$^+$ 70 mg (0.19 mmol) of 4-amino-2-[1-(2-fluorobenzyl)-1H-pyrazolo[3,4-b]pyridin-3-yl]pyrimidine-5-carboxamide (example 104A) were initially charged in 7 ml of THF and, while cooling with ice, 30.8 mg (0.77 mmol) of sodium hydride (60% in mineral oil) were added over a period of 5 min. The mixture was stirred for 25 min, then 46.9 mg (0.29 mmol) of 1,1'-carbonyldiimidazole were added with ice cooling over 5 min. Conversion was effected at room temperature for 1 h and at reflux temperature for 90 min. After cooling, the mixture was hydrolyzed with 2 ml of water. The precipitate formed was filtered off and then stirred in 7 ml of methanol/water (5/2). The remaining precipitate was filtered off and dried under high vacuum. Thus, 26 mg (35% of theory) of the target compound were obtained.

LC-MS (method 2): R$_t$=0.80 min; MS (ESIpos): m/z=390 (M+H)$^+$ $^1$H NMR (400 MHz, DMSO-d$_6$): δ [ppm]=5.85 (s, 2H), 7.15 (t, 1H), 7.19-7.28 (m, 2H), 7.36 (t, 1H), 7.41 (dd, 1H), 8.65 (d, 1H), 8.78 (s, 1H), 8.97 (d, 1H), 10.10 (s br, 1H), 1×NH not assigned.

Example 151

7-[1-(2-Fluorobenzyl)-1H-pyrazolo[3,4-b]pyridin-3-yl]pyrimido[4,5-d]pyrimidin-4(1H)-one

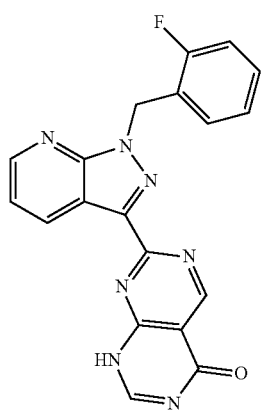 [SMILES: O=c1nc[nH]c2nc(-c3nn(Cc4ccccc4F)c4ncccc34)ncc12]

150 mg (0.38 mmol) of methyl 4-chloro-2-[1-(2-fluorobenzyl)-1H-pyrazolo[3,4-b]pyridin-3-yl]pyrimidine-5-carboxylate (example 106A) and 78.5 mg (0.75 mmol) of formamidine hydrochloride were initially charged in 1.5 ml of DMF. Subsequently, 260 μl (1.89 mmol) of triethylamine were added and conversion was effected at 80° C. overnight. After cooling, the precipitated solid was filtered off and the mother liquor was then purified by means of preparative HPLC [column: Reprosil C18, 10 μm, 250*40 mm; eluent: acetonitrile/0.05% formic acid; gradient: 10% acetonitrile→>90% acetonitrile]. Thus, 65 mg (46% of theory) of the target compound were obtained.

LC-MS (method 2): R$_t$=0.83 min; MS (ESIpos): m/z=374 (M+H)$^+$ $^1$H NMR (400 MHz, DMSO-d$_6$): δ [ppm]=5.92 (s, 2H), 7.17 (dt, 1H), 7.21-7.32 (m, 2H), 7.38 (m, 1H), 7.51 (dd, 1H), 8.56 (s, 1H), 8.73 (dd, 1H), 8.98 (dd, 1H), 9.56 (s, 1H), 12.94 (s br, 1H).

Example 152

7-[1-(2-Fluorobenzyl)-1H-pyrazolo[3,4-b]pyridin-3-yl]-2-methylpyrimido[4,5-d]pyrimidin-4(1H)-one

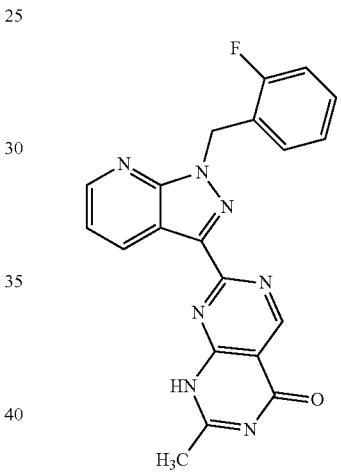

In analogy to the preparation process for 7-[1-(2-fluorobenzyl)-1H-pyrazolo[3,4-b]pyridin-3-yl]pyrimido[4,5-d]pyrimidin-4(1H)-one (example 152), proceeding from 100 mg (0.25 mmol) of methyl 4-chloro-2-[1-(2-fluorobenzyl)-1H-pyrazolo[3,4-b]pyridin-3-yl]pyrimidine-5-carboxylate (example 106A), 47.5 mg (0.50 mmol) of acetamidine hydrochloride and 175 μl (1.26 mmol) of triethylamine, 32 mg (31% of theory) of the target compound were obtained.

LC-MS (method 2): R$_t$=0.85 min; MS (ESIpos): m/z=388 (M+H)$^+$ $^1$H NMR (400 MHz, DMSO-d$_6$): δ [ppm]=2.47 (s, 3H), 5.91 (s, 2H), 7.17 (t, 1H), 7.24 (t, 1H), 7.30 (dt, 1H), 7.38 (m, 1H), 7.51 (dd, 1H), 8.72 (dd, 1H), 8.98 (dd, 1H), 9.49 (s, 1H), 12.85 (s br, 1H).

Example 153

2-Ethyl-7-[1-(2-fluorobenzyl)-1H-pyrazolo[3,4-b]pyridin-3-yl]pyrimido[4,5-d]pyrimidin-4(1H)-one

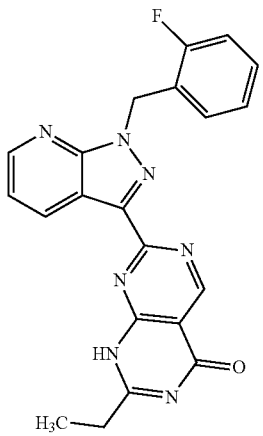 [SMILES: CCc1nc(=O)c2cnc(-c3nn(Cc4ccccc4F)c4ncccc34)nc2[nH]1]

In analogy to the preparation process for 7-[1-(2-fluorobenzyl)-1H-pyrazolo[3,4-b]pyridin-3-yl]pyrimido[4,5-d]pyrimidin-4(1H)-one (example 152), proceeding from 150 mg (0.38 mmol) of methyl 4-chloro-2-[1-(2-fluorobenzyl)-1H-pyrazolo[3,4-b]pyridin-3-yl]pyrimidine-5-carboxylate (example 106A), 81.9 mg (0.75 mmol) of propionamidine hydrochloride and 260 ml (1.89 mmol) of triethylamine, 42 mg (25% of theory) of the target compound were obtained.

LC-MS (method 5): R$_t$=0.89 min; MS (ESIpos): m/z=402 (M+H)$^+$ $^1$H NMR (400 MHz, DMSO-d$_6$): δ [ppm]=1.29 (t, 3H), 2.70 (q, 2H), 5.90 (s, 2H), 7.17 (t, 1H), 7.21-7.33 (m, 2H), 7.38 (m, 1H), 7.50 (dd, 1H), 8.72 (dd, 1H), 8.99 (dd, 1H), 9.45 (s, 1H), 12.81 (s br, 1H).

B. ASSESSMENT OF PHARMACOLOGICAL EFFICACY

The pharmacological action of the inventive compounds can be shown in the following assays:
B-1. Vasorelaxant Action In Vitro Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each mM): sodium chloride 119; potassium chloride: 4.8; calcium chloride dihydrate: 1; magnesium sulfate heptahydrate: 1.4; potassium dihydrogenphosphate: 1.2; sodium hydrogencarbonate: 25; glucose: 10. The contractile force is determined with Statham UC$_2$ cells, amplified and digitalized using A/D transducers (DAS-1802 HC, Keithley Instruments Munich), and recorded in parallel on linear recorders. To obtain a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% (IC$_{50}$ value). The standard administration volume is 5 μl; the DMSO content in the bath solution corresponds to 0.1%.

Representative IC$_{50}$ values for the inventive compounds are shown in the table below (table 1):

TABLE 1

| Example No. | IC$_{50}$ [nM] |
|---|---|
| 2 | 49 |
| 7 | 1090 |
| 12 | 284 |
| 13 | 246 |
| 15 | 730 |
| 21 | 233 |
| 23 | 197 |
| 28 | 800 |
| 29 | 31 |
| 44 | 83 |
| 45 | 41 |
| 50 | 1390 |
| 52 | 126 |
| 53 | 424 |
| 57 | 39 |
| 60 | 199 |
| 61 | 759 |
| 62 | 114 |
| 63 | 139 |
| 71 | 86 |
| 74 | 713 |
| 76 | 23 |
| 83 | 27 |
| 84 | 155 |
| 85 | 164 |
| 89 | 146 |
| 90 | 5980 |
| 91 | 475 |
| 92 | 535 |
| 95 | 44 |
| 97 | 464 |
| 98 | 71 |
| 103 | 658 |
| 104 | 40 |
| 105 | 402 |
| 112 | 1350 |
| 119 | 735 |
| 122 | 42 |
| 124 | 87 |
| 135 | 264 |
| 136 | 114 |
| 142 | 98 |
| 145 | 171 |
| 146 | 421 |
| 147 | 580 |
| 149 | 462 |
| 150 | 479 |
| 153 | 1300 |

B-2. Effect on a Recombinant Guanylate Cyclase Reporter Cell Line

The cellular action of the inventive compounds is determined on a recombinant guanylate cyclase reporter cell line as described in F. Wunder et al., *Anal. Biochem.* 339, 104-112 (2005).

Representative values (MEC=minimal effective concentration) for the inventive compounds are shown in the table below (table 2):

TABLE 2

| Example No. | IC$_{50}$ [μM] |
|---|---|
| 1 | 0.003 |
| 2 | 0.01 |
| 3 | 0.01 |
| 4 | 0.03 |
| 5 | 1.0 |
| 6 | 10.0 |
| 7 | 3.0 |
| 8 | 10.0 |
| 9 | 10.0 |
| 10 | 0.3 |
| 11 | 3.0 |
| 12 | 0.3 |
| 13 | 0.3 |
| 14 | 0.3 |
| 15 | 0.1 |
| 16 | 0.03 |
| 17 | 1.0 |
| 18 | 0.03 |
| 19 | 0.01 |
| 20 | 0.01 |
| 21 | 0.1 |
| 22 | 0.01 |
| 23 | 0.1 |
| 24 | 0.1 |
| 25 | 0.03 |
| 26 | 0.1 |
| 27 | 0.1 |
| 28 | 0.03 |
| 29 | 0.01 |
| 30 | 1.0 |
| 31 | 0.003 |
| 32 | 0.003 |
| 33 | 0.03 |
| 34 | 10.0 |
| 35 | 1.0 |
| 36 | 0.1 |
| 37 | 0.1 |
| 38 | 0.3 |
| 39 | 1.0 |
| 40 | 10.0 |
| 41 | 0.03 |
| 42 | 0.01 |
| 43 | 0.01 |
| 44 | 0.0003 |
| 45 | 0.003 |
| 46 | 0.3 |
| 47 | 0.003 |
| 48 | 0.03 |
| 49 | 0.01 |
| 50 | 0.001 |
| 51 | 0.3 |
| 52 | 0.03 |
| 53 | 0.03 |
| 54 | 0.3 |
| 55 | 0.3 |
| 56 | 0.3 |
| 57 | 10.0 |
| 58 | 0.003 |
| 59 | 1.0 |
| 60 | 0.3 |
| 61 | 0.3 |
| 62 | 0.003 |
| 63 | 0.1 |
| 64 | 0.3 |
| 65 | 1.0 |
| 66 | 3.0 |
| 67 | 1.0 |
| 68 | 3.0 |
| 69 | 0.03 |
| 70 | 1.0 |
| 71 | 0.01 |
| 72 | 0.3 |
| 73 | 1.0 |
| 74 | 1.0 |
| 75 | 0.03 |
| 76 | 0.03 |
| 77 | 0.03 |
| 78 | 1.0 |
| 79 | 0.1 |
| 80 | 0.03 |
| 81 | 0.3 |
| 82 | 1.0 |
| 83 | 0.01 |
| 84 | 0.3 |
| 85 | 0.3 |
| 86 | 0.1 |
| 87 | 0.3 |
| 88 | 0.03 |
| 89 | 0.1 |
| 90 | 0.1 |
| 91 | 0.03 |
| 92 | 0.03 |
| 93 | 0.03 |
| 94 | 0.01 |
| 95 | 0.1 |
| 96 | 0.01 |
| 97 | 0.1 |
| 98 | 0.1 |
| 99 | 0.03 |
| 100 | 0.3 |
| 101 | 0.3 |
| 103 | 0.1 |
| 105 | 0.1 |
| 106 | 0.3 |
| 108 | 0.3 |
| 109 | 0.3 |
| 110 | 0.1 |
| 111 | 3.0 |
| 112 | 0.3 |
| 113 | 0.1 |
| 114 | 0.3 |
| 117 | 0.01 |
| 118 | 0.3 |
| 119 | 0.1 |
| 120 | 0.01 |
| 121 | 0.003 |
| 122 | 0.03 |
| 124 | 0.03 |
| 125 | 0.1 |
| 127 | 0.01 |
| 128 | 0.3 |
| 129 | 0.1 |
| 130 | 0.1 |
| 131 | 0.3 |
| 132 | 0.03 |
| 133 | 0.3 |
| 134 | 1.0 |
| 136 | 0.03 |
| 137 | 0.03 |
| 139 | 0.03 |
| 140 | 0.03 |
| 141 | 0.1 |
| 142 | 0.3 |
| 143 | 0.1 |
| 144 | 0.1 |
| 145 | 0.03 |
| 146 | 0.3 |
| 147 | 3.0 |
| 148 | 1.0 |
| 149 | 0.1 |
| 150 | 0.3 |
| 151 | 1.0 |
| 152 | 3.0 |
| 153 | 3.0 |

B-3. Radiotelemetry Measurement of Blood Pressure in Conscious, Spontaneously Hypertensive Rats A commercially available telemetry system from DATA SCIENCES INTERNATIONAL DSI, USA, is used for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963, were a cross of male Wistar Kyoto rats with greatly elevated blood pressure and female rats having slightly elevated blood pressure, and were handed over at F13 to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The TA11 PA—C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is used as a control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute values are corrected in the diagram with the currently measured barometric pressure (Ambient Pressure Reference Monitor; APR-1) and stored as individual data. Further technical details are given in the extensive documentation from the manufacturer company (DSI).

Unless stated otherwise, the test substances are administered at 9.00 am on the day of the experiment. Following the administration, the parameters described above are measured over 24 hours.

Evaluation

After the end of the experiment, the acquired individual data are sorted using the analysis software (Dataquest™ A.R.T.™ ANALYSIS). The blank value is assumed to be the time 2 hours before administration, and so the selected data set encompasses the period from 7.00 am on the day of the experiment to 9.00 am the following day.

The data are smoothed over a predefinable period by determination of the average (15-minute average) and transferred as a text file to a storage medium. The measured values presorted and compressed in this way are transferred to Excel templates and tabulated. For each day of the experiment, the data obtained are stored in a dedicated file bearing the experiment number. Results and test protocols are filed in paper form sorted by numbers.

Literature

Klaus Witte, Kai Hu, Johanna Swiatek, Claudia Müssig, Georg Ertl and Björn Lemme: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

C. WORKING EXAMPLES OF PHARMACEUTICAL COMPOSITIONS

The inventive compounds can be converted to pharmaceutical formulations as follows:

Tablet:
Composition:

100 mg of the compound according to the invention, 50 mg of lactose (monohydrate), 50 mg of maize starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:

The mixture of inventive compound, lactose and starch is granulated with a 5% solution (w/w) of the PVP in water. The granules are dried and then mixed with the magnesium stearate for 5 minutes. This mixture is pressed with a conventional tableting press (for tablet dimensions see above). The guide value used for the pressing is a pressing force of 15 kN.

Suspension for Oral Administration:
Composition:

1000 mg of the inventive compound, 1000 mg of ethanol (96%), 400 mg of Rhodigel xanthan gum from FMC, Pennsylvania, USA) and 99 g of water.

A single dose of 100 mg of the inventive compound corresponds to 10 ml of oral suspension.

Production:

The Rhodigel is suspended in ethanol and the inventive compound is added to the suspension. The water is added while stirring. The mixture is stirred for approx. 6 h until swelling of the Rhodigel has ended.

Solution for Oral Administration:

Composition:

500 mg of the inventive compound, 2.5 g of polysorbate and 97 g of polyethylene glycol 400. A single dose of 100 mg of the inventive compound corresponds to 20 g of oral solution.

Production:

The inventive compound is suspended in the mixture of polyethylene glycol and polysorbate while stirring. The stirring operation is continued until dissolution of the inventive compound is complete.

i.v. Solution:

The inventive compound is dissolved in a concentration below the saturation solubility in a physiologically acceptable solvent (e.g. isotonic saline, 5% glucose solution and/or 30% PEG 400 solution). The solution is subjected to sterile filtration and dispensed into sterile and pyrogen-free injection vessels.

The invention claimed is:

1. A compound of the formula (I)

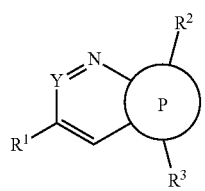

(I)

in which
the ring P is a group of the formula

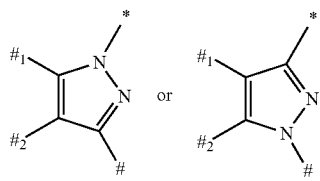

where
\* is the attachment site to $R^2$,
\# is the attachment site to $R^3$,
$\#_1$ is the attachment site to the nitrogen atom,
$\#_2$ is the attachment site to the carbon atom,
Y is CH or N,
$R^1$ is hydrogen or fluorine,
$R^2$ is $(C_1-C_6)$-alkyl or benzyl,
where $(C_1-C_6)$-alkyl is substituted by one trifluoromethyl substituent, where $(C_1-C_6)$-alkyl may be substituted by 1 to 3 fluorine substituents, and
where benzyl is substituted by 1 to 3 fluorine substituents, $R^3$ is a group of the formula

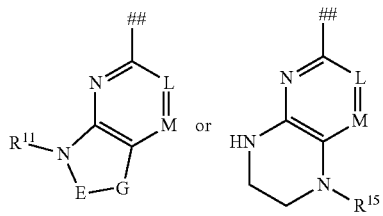

where
\#\# is the attachment site to the ring P,
L is N or CH,
M is N or $CR^4$,
in which
$R^4$ is hydrogen or amino,
with the proviso that only one of the L and M groups is N,
E is C=O,
G is $NR^{12}$,
in which
$R^{12}$ is trideuteromethyl, $(C_1-C_6)$-alkyl, cyclopropyl, cyclobutyl, azetidin-3-yl, pyrrolidin-3-yl or piperidin-4-yl,
in which $(C_1-C_6)$-alkyl may itself be substituted by 1 to 3 substituents each independently selected from the group of fluorine, trifluoromethyl, cyclopropyl, cyclobutyl, hydroxyl, oxetanyl and morpholin-1-yl,
and
in which azetidin-3-yl, pyrrolidin-3-yl and piperidin-4-yl are themselves substituted by 1 or 2 substituents each independently selected from the group of fluorine, trifluoromethyl, 2,2-difluoroethyl, 2,2,2-trifluoroethyl, methyl and ethyl, cyclopropyl and cyclobutyl,
$R^{11}$ is hydrogen,
$R^{15}$ is hydrogen or $(C_1-C_3)$-alkoxycarbonyl,
in which $(C_1-C_3)$-alkoxycarbonyl may be substituted by 1 or 2 substituents each independently selected from the group of fluorine, trifluoromethyl, hydroxyl, methoxy and ethoxy,
the N-oxides and salts thereof.

2. The compound of claim 1, in which
the ring P is a group of the formula

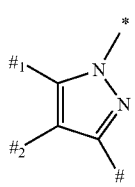

where
\* is the attachment site to $R^2$,
\# is the attachment site to $R^3$,
$\#_1$ is the attachment site to the nitrogen atom,
$\#_2$ is the attachment site to the carbon atom,
Y is CH,
$R^1$ is hydrogen or fluorine, and
$R^2$ is 2-fluorobenzyl,

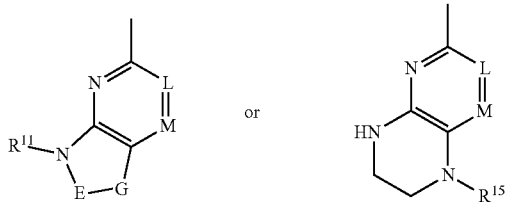

salts and solvates thereof.
3. The compound of claim 1, in which
the ring P is a group of the formula

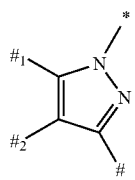

where
* is the attachment site to $R^2$,
# is the attachment site to $R^3$,
$\#_1$ is the attachment site to the nitrogen atom,
$\#_2$ is the attachment site to the carbon atom,
Y is CH,
$R^1$ is hydrogen or fluorine,
$R^2$ is 2-fluorobenzyl,
$R^3$ is a group of the formula

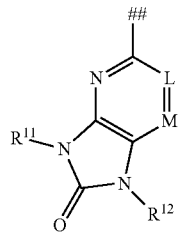

where
## is the attachment site to the ring P,
L is CH or N,
M is N or $CR^4$,
  where
  $R^4$ is hydrogen or amino,
with the proviso that only one of the L and M groups is N,
$R^{11}$ is hydrogen,
$R^{12}$ is trideuteromethyl, $(C_1-C_6)$-alkyl, cyclopropyl, cyclobutyl, azetidin-3-yl, pyrrolidin-3-yl or piperidin-4-yl,
  in which $(C_1-C_6)$-alkyl may itself be substituted by 1 to 3 substituents each independently selected from the group of fluorine, trifluoromethyl, cyclopropyl, cyclobutyl, hydroxyl, oxetanyl and morpholin-1-yl,
  and
  in which azetidin-3-yl, pyrrolidin-3-yl and piperidin-4-yl are themselves substituted by 1 or 2 substituents each independently selected from the group of fluorine, trifluoromethyl, 2,2-difluoroethyl, 2,2,2-trifluoroethyl, methyl and ethyl, cyclopropyl and cyclobutyl, salts and solvates thereof.

4. A pharmaceutical composition comprising a compound of claim 1 in combination with an inert, nontoxic, pharmaceutically suitable excipient.

5. The pharmaceutical composition of claim 4, further comprising an active ingredient selected from the group consisting of organic nitrates, NO donors, cGMP-PDE inhibitors, antithrombotic agents, hypotensive agents and lipid metabolism modifiers.

6. A process for preparing compounds of formula (I) as defined in claim 1 comprising,

[A] reacting a compound of the formula (II-1) or (II-2)

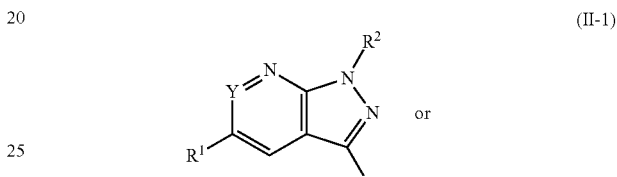

(II-1)

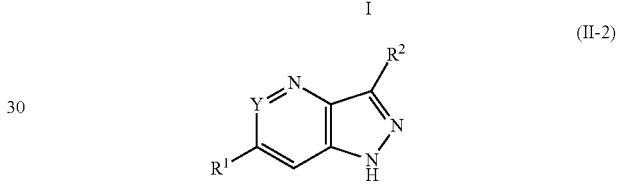

(II-2)

in which Y, $R^1$ and $R^2$ are each as defined in claim 1, in an inert solvent in the presence of a suitable transition metal catalyst with a compound of the formula (III)

(III)

in which $R^3$ is as defined in claim 1 and $X^1$ is a suitable leaving group, for example halogen, mesylate, tosylate or triflate, to give a compound of the formula (I-A-1) or (I-A-2)

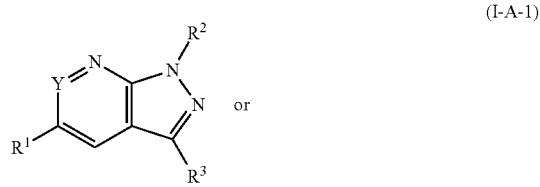

(I-A-1)

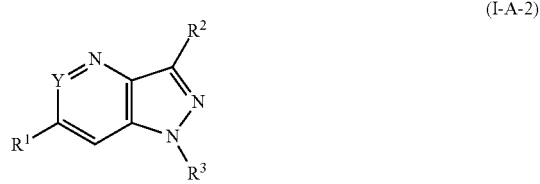

(I-A-2)

in which Y, R¹ and R² are each as defined in claim 1, or

[B] converting a compound of the formula (IV)

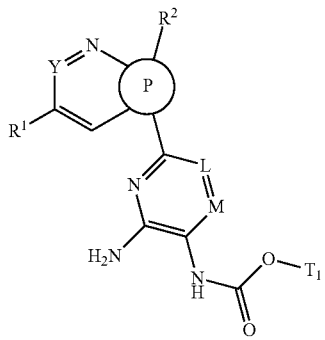
(IV)

in which L, M, P, Y, R¹ and R² are each as defined in claim 1 and

T¹ is $(C_1-C_4)$-alkyl in an inert solvent in the presence of a suitable base into a compound of the formula (I-B)

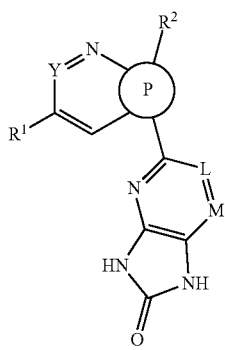
(I-B)

in which L, M, P, Y, R¹ and R² are each as defined in claim 1, or

[C] reacting a compound of the formula (IV) in an inert solvent in the presence of a suitable base with a compound of the formula (V)

$$R^{12A}-X^2 \quad (V)$$

in which

R$^{12A}$ is trideuteromethyl, $(C_1-C_6)$-alkyl, $(C_2-C_6)$-alkenyl, $(C_3-C_7)$-cycloalkyl, azetidinyl, pyrrolidinyl, piperidinyl or benzyl, in which $(C_1-C_6)$-alkyl may itself be substituted by 1 to 3 substituents each independently selected from the group of fluorine, trifluoromethyl, cyclopropyl, cyclobutyl, hydroxyl, methoxy, ethoxy, methylsulfonyl, ethylsulfonyl, azetidinyl, oxetanyl, pyrrolidinyl, piperidinyl and morpholinyl, in which azetidinyl, oxetanyl, pyrrolidinyl, piperidinyl and morpholinyl in turn may themselves be substituted by 1 or 2 substituents each independently selected from the group of fluorine, trifluoromethyl, 2,2-difluoroethyl, 2,2,2-trifluoroethyl, methyl and ethyl, in which azetidinyl, pyrrolidinyl and piperidinyl may themselves be substituted by 1 or 2 substituents each independently selected from the group of fluorine, trifluoromethyl, methyl, ethyl, cyclopropyl and cyclobutyl, in which methyl and ethyl in turn may themselves be substituted by 1 or 2 substituents each independently selected from the group of fluorine, trifluoromethyl, cyclopropyl, cyclobutyl, hydroxyl, methoxy and ethoxy, and in which benzyl may itself be substituted by 1 or 2 fluorine, chlorine, trifluoromethyl, methyl, ethyl, methylsulfonyl and ethylsulfonyl substituents, and X² is a suitable leaving group, for example halogen, especially chlorine or bromine, mesylate or tosylate, to give a compound of the formula (VI)

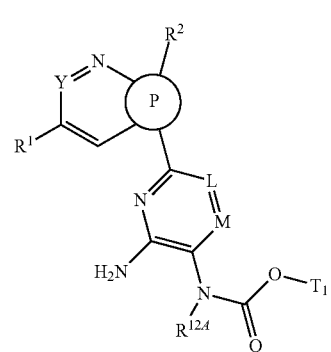
(VI)

in which L, M, P, Y, R¹, and R² are each as defined in claim 1, and cyclizing the compound of formula VI in an inert solvent, in the presence of a suitable base, to give a compound of the formula (I-C)

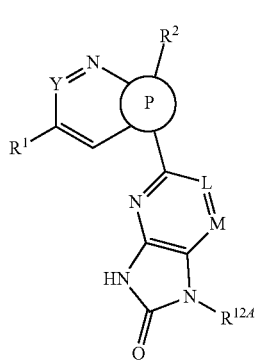
(I-C)

in which L, M, P, Y, $R^1$, and $R^2$ are each as defined in claim 1, or

[D] reductively aminating a compound of the formula (VII)

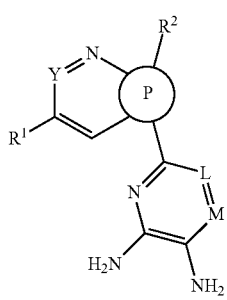

(VII)

in which L, M, P, Y, $R^1$ and $R^2$ are each as defined in claim 1, with a compound of the formula (VIII)

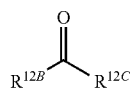

(VIII)

in which $R^{12B}$ is trifluoromethyl, $(C_1-C_5)$-alkyl, $(C_2-C_6)$-alkenyl, cyclopropyl, cyclobutyl or phenyl, in which $(C_1-C_5)$-alkyl may itself be substituted by 1 or 2 substituents each independently selected from the group of fluorine, trifluoromethyl, hydroxyl, methoxy and ethoxy, and in which phenyl may itself be substituted by 1 or 2 fluorine, chlorine, trifluoromethyl, methyl, ethyl, methylsulfonyl and ethylsulfonyl substituents, $R^{12C}$ is hydrogen or $(C_1-C_5)$-alkyl, in which $(C_1-C_5)$-alkyl may itself be substituted by 1 or 2 substituents each independently selected from the group of fluorine, trifluoromethyl, cyclopropyl, cyclobutyl, hydroxyl, methoxy and ethoxy, or where $R^{12B}$ and $R^{12C}$ together with the carbon atom to which they are bonded form a cyclobutyl, azetidinyl, pyrrolidinyl or piperidinyl ring, in which the azetidinyl, pyrrolidinyl and piperidinyl ring may itself be substituted by 1 or 2 substituents each independently selected from the group of fluorine, trifluoromethyl, methyl, ethyl, cyclopropyl and cyclobutyl, in which methyl and ethyl may themselves be substituted by 1 or 2 substituents each independently selected from the group of fluorine, trifluoromethyl, cyclopropyl, cyclobutyl, hydroxyl, methoxy and ethoxy, to give a compound of the formula (IX)

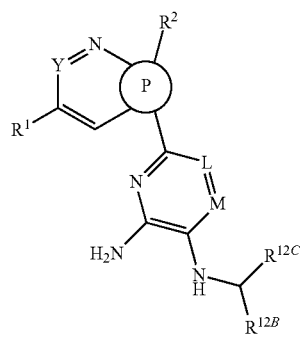

(IX)

in which L, M, P, Y, $R^1$, and $R^2$ are each as defined in claim 1, and cyclizing the compound of formula (IX) in an inert solvent in the presence of a suitable base with phosgene, a phosgene derivative or a phosgene equivalent to give a compound of the formula (I-D)

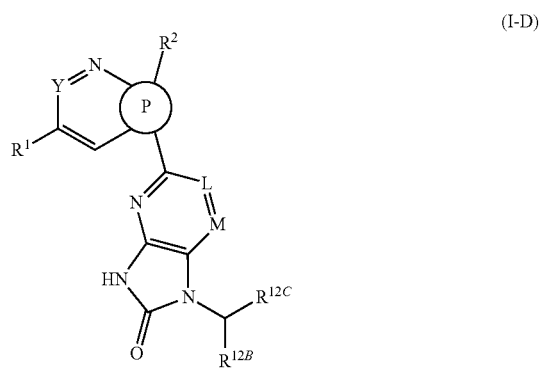

(I-D)

in which L, M, P, Y, $R^1$, and $R^2$ are each as defined in claim 1, or

[E] cyclizing a compound of the formula (X)

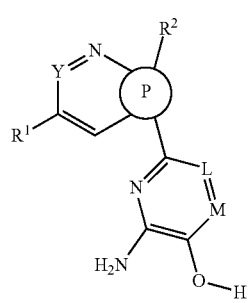

(X)

in which L, M, P, Y, $R^1$ and $R^2$ are each as defined in claim 1, in an inert solvent in the presence of a suitable base with phosgene, a phosgene derivative or a phosgene equivalent to give a compound of the formula (I-E)

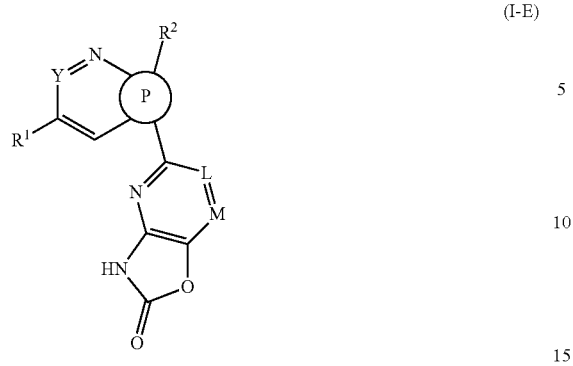
(I-E)
in which L, M, P, Y, $R^1$ and $R^2$ are each as defined in claim 1.
* * * * *